(12) United States Patent
Miller et al.

(10) Patent No.: US 9,493,440 B2
(45) Date of Patent: Nov. 15, 2016

(54) COMPOUNDS INHIBITING LEUCINE-RICH REPEAT KINASE ENZYME ACTIVITY

(71) Applicant: Merck Sharp & Dohme Corp., Rahway, NJ (US)

(72) Inventors: Michael Miller, Scotch Plains, NJ (US); Kallol Basu, Hillsborough, NJ (US); Duane DeMong, Somerset, NJ (US); Jack Scott, Scotch Plains, NJ (US); Wei Li, Audubon, PA (US); Andrew Stamford, Chatham, NJ (US); Marc Poirer, Stewartsville, NJ (US); Paul Tempest, Shanghai (CN)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/772,295

(22) PCT Filed: Feb. 27, 2014

(86) PCT No.: PCT/US2014/018888
§ 371 (c)(1),
(2) Date: Sep. 2, 2015

(87) PCT Pub. No.: WO2014/137723
PCT Pub. Date: Sep. 12, 2014

(65) Prior Publication Data
US 2016/0009689 A1    Jan. 14, 2016

(30) Foreign Application Priority Data

Mar. 4, 2013 (WO) ............... PCT/CN2013/072130

(51) Int. Cl.
| | | |
|---|---|---|
| *C07D 403/04* | (2006.01) |
| *C07D 401/14* | (2006.01) |
| *C07D 405/14* | (2006.01) |
| *C07D 413/14* | (2006.01) |
| *C07D 403/14* | (2006.01) |
| *C07D 409/14* | (2006.01) |
| *C07D 417/14* | (2006.01) |
| *C07D 471/04* | (2006.01) |
| *C07D 471/10* | (2006.01) |
| *C07D 487/04* | (2006.01) |
| *C07D 487/08* | (2006.01) |
| *C07D 487/10* | (2006.01) |
| *C07D 491/107* | (2006.01) |
| *C07D 498/04* | (2006.01) |
| *C07D 498/08* | (2006.01) |
| *C07D 498/10* | (2006.01) |

(52) U.S. Cl.
CPC ........... *C07D 403/04* (2013.01); *C07D 401/14* (2013.01); *C07D 403/14* (2013.01); *C07D 405/14* (2013.01); *C07D 409/14* (2013.01); *C07D 413/14* (2013.01); *C07D 417/14* (2013.01); *C07D 471/04* (2013.01); *C07D 471/10* (2013.01); *C07D 487/04* (2013.01); *C07D 487/08* (2013.01); *C07D 487/10* (2013.01); *C07D 491/107* (2013.01); *C07D 498/04* (2013.01); *C07D 498/08* (2013.01); *C07D 498/10* (2013.01)

(58) Field of Classification Search
None
See application file for complete search history.

(56) References Cited

U.S. PATENT DOCUMENTS

| | | |
|---|---|---|
| 7,776,890 B2 | 8/2010 | Oinuma et al. |
| 2004/0127536 A1 | 7/2004 | Bhagwat et al. |
| 2006/0079564 A1 | 4/2006 | Jansen et al. |
| 2009/0203690 A1 | 8/2009 | Akritopoulou-Zanze et al. |
| 2009/0221602 A1 | 9/2009 | Charrier et al. |
| 2012/0329780 A1 | 12/2012 | Thormann et al. |
| 2014/0031360 A1 * | 1/2014 | Wang .................. C07D 401/14 514/252.11 |

FOREIGN PATENT DOCUMENTS

| | | |
|---|---|---|
| EP | 1380576 B1 | 1/2004 |
| EP | 1510516 | 3/2005 |
| WO | 0153268 A2 | 7/2001 |
| WO | 0210137 | 2/2002 |
| WO | 02083648 | 10/2002 |
| WO | 03035005 | 5/2003 |
| WO | 2006081230 | 8/2006 |
| WO | 2008068171 | 6/2008 |
| WO | 2008137105 | 11/2008 |
| WO | 2008154241 | 12/2008 |
| WO | 2009054984 | 4/2009 |
| WO | 2010017046 A1 | 2/2010 |
| WO | 2010083145 A1 | 7/2010 |
| WO | 2011141756 | 11/2011 |
| WO | 2012038743 | 3/2012 |
| WO | 2012058193 | 5/2012 |
| WO | 2012078777 | 6/2012 |
| WO | 2014137719 A1 | 9/2014 |
| WO | 2014137723 A1 | 9/2014 |
| WO | 2014137725 A1 | 9/2014 |
| WO | 2014137728 | 9/2014 |
| WO | 2015026683 A1 | 2/2015 |
| WO | 2015073344 A1 | 5/2015 |
| WO | 2016036586 A1 | 3/2016 |

OTHER PUBLICATIONS

Deng et al., Nature Chemical Biology, 2011, vol. 7 Issue 4, p. 203-205.*
Bonifati et al., European Journal of Human Genetics, (2006), 14, 1061-1062.*

* cited by examiner

*Primary Examiner* — Karl J Puttlitz
(74) *Attorney, Agent, or Firm* — Keith D. MacMillan; John C. Todaro

(57) ABSTRACT

The present invention is directed to indazole compounds which are potent inhibitors of LRRK2 kinase and useful in the treatment or prevention of diseases in which the LRRK2 kinase is involved, such as Parkinson's Disease. The invention is also directed to pharmaceutical compositions comprising these compounds and the use of these compounds and compositions in the prevention or treatment of such diseases in which LRRK-2 kinase is involved.

18 Claims, No Drawings

COMPOUNDS INHIBITING LEUCINE-RICH REPEAT KINASE ENZYME ACTIVITY

CROSS-REFERENCE TO RELATED APPLICATIONS

This Application is a U.S. National Stage Application under 35 U.S.C. 371 of PCT Application No. PCT/US2014/018888, filed Feb. 27, 2014, which claims priority under 35 U.S.C. 119(e) to PCT/CN2013/072130, filed Mar. 4, 2013, incorporated herein by reference.

BACKGROUND OF THE INVENTION

Parkinson's disease (PD) is a common neurodegenerative disease caused by progressive loss of mid-brain dopaminergic neurons leading to abnormal motor symptoms such as bradykinesia, rigidity and resting tremor. Many PD patients also experience a variety of non-motor symptoms including cognitive dysfunction, autonomic dysfunction, emotional changes and sleep disruption. The combined motor and non-motor symptoms of Parkinson's disease severely impact patient quality of life.

While the majority of PD cases are idiopathic, there are several genetic determinants such as mutations in SNCA, Parkin, PINK1, DJ-1 and LRRK2. Linkage analysis studies have demonstrated that multiple missense mutations in the Leucine-Rich Repeat Kinase 2 (LRRK2) gene lead to an autosomal late onset form of PD. LRRK2 is a 286 kDa cytoplasmic protein containing kinase and GTPase domains as well as multiple protein-protein interaction domains. See for example, Aasly et al., Annals of Neurology, Vol. 57(5), May 2005, pp. 762-765; Adams et al., Brain, Vol. 128, 2005, pp. 2777-85; Gilks et al., Lancet, Vol. 365, Jan. 29, 2005, pp. 415-416, Nichols et al., Lancet, Vol. 365, Jan. 29, 2005, pp. 410-412, and U. Kumari and E. Tan, FEBS journal 276 (2009) pp. 6455-6463.

In vitro biochemical studies have demonstrated that LRRK2 proteins harboring the PD associated proteins generally confer increased kinase activity and decreased GTP hydrolysis compared to the wild type protein (Guo et al., Experimental Cell Research, Vol, 313, 2007, pp. 3658-3670) thereby suggesting that small molecule LRRK2 kinase inhibitors may be able to block aberrant LRRK2-dependent signaling in PD. In support of this notion, it has been reported that inhibitors of LRRK2 are protective in models of PD (Lee et al., Nature Medicine, Vol 16, 2010, pp. 998-1000).

LRRK2 protein has also been demonstrated to be associated with Lewy bodies, a pathological hallmark of PD as well as other neurodegenerative diseases such as Lewy body dementia (Zhu et al., Molecular Neurodegeneration, Vol 30, 2006, pp. 1-17) thereby suggesting that LRRK2 may be associated with the pathogenesis of these diseases.

A growing body of evidence also suggests a role for LRRK2 in immune cell function in the brain with LRRK2 inhibition demonstrated to attenuate microglial inflammatory responses (Moehle et al., The Journal of Neuroscience Vol 32, 2012, pp. 1602-1611). Neuroinflammation is a hallmark of a number of neurodegenerative diseases such as PD and Alzheimer's disease, thereby suggesting that LRRK2 inhibitors may have utility in the treatment of neuroinflammation in these disorders.

Genome-wide association studies also highlight LRRK2 in the modification of susceptibility to the chronic autoimmune Crohn's disease and leprosy (Zhang et al., The New England Jopuranl of Medicine, Vol 361, 2009, pp. 2609-2618; Umeno et al., Inflammatory Bowel Disease Vol 17, 2011, pp. 2407-2415). LRRK2 is also associated with certain types of cancer, e.g. melanoma as well as renal and thyroid carcinomas (Saunders-Pullman et al., Movement Disorders, Vol 25, 2010, pp. 2536-2541; Looyenga, et al., Proceedings of the National Academy of Sciences, USA, Vol 108, 2011, pp. 1439-1444).

Accordingly, compounds and compositions effective at modulating LRRK2 activity may provide a treatment for neurodegenerative diseases such as Parkinson's disease, Lewy body dementia, neuroinflammation, and for disease such as Crohn's disease, leprosy and cancer.

SUMMARY OF THE INVENTION

The present invention is directed to indazole compounds which are potent inhibitors of LRRK2 kinase and may be useful in the treatment or prevention of diseases in which the LRRK2 kinase is involved, such as Parkinson's Disease. The invention is also directed to pharmaceutical compositions comprising these compounds and the use of these compounds and compositions in the prevention or treatment of such diseases in which LRRK-2 kinase is involved.

DETAILED DESCRIPTION OF THE INVENTION

The present invention is directed to compounds of Formula I:

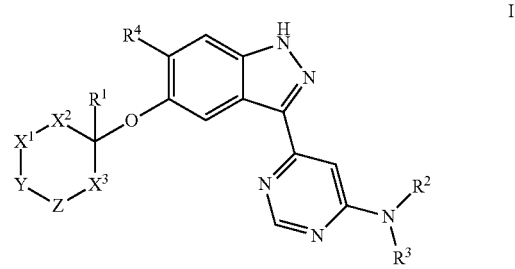

or a pharmaceutically acceptable salt thereof, wherein:
$X^1$, $X^2$ and $X^3$ are each independently selected from the group consisting of a bond or $CR^eR^f$;
Y is O, $CR^aR^b$ or $NR^e$;
Z is O, $CR^aR^b$ or $NR^e$;
$R^1$ is selected from the group consisting of hydrogen and $C_{1-6}$ alkyl, which is optionally substituted with one to three substitutents independently selected from the group consisting of halo, cyano, hydroxyl, $NR^cR^d$, $OR^5$ and $(C=O)OR^5$;
$R^2$ is selected from the group consisting of hydrogen and $C_{1-6}$ alkyl, which is optionally substituted with one to three substitutents independently selected from the group consisting of:
  a) halo,
  b) cyano,
  c) $R^5$,
  d) $R^7$,
  e) $OR^5$, and
  f) $NR^cR^d$;
$R^3$ is selected from the group consisting of:
  a) hydrogen,
  b) $C_{1-6}$ alkyl, which is optionally substituted with one to three substitutents independently selected from the group consisting of halo, cyano, $OR^5$ and $NR^cR^d$, c) cycloalkyl, which is optionally substituted with one to three substituents independently selected from the group consisting of halo, cyano, $OR^5$ and $NR^cR^d$,
d) heterocyclyl, which is optionally substituted with one to three substitutents independently selected from the group consisting of halo, cyano, oxo, $R^5$, $OR^5$ and $NR^cR^d$,
e) heteroaryl, which is optionally substituted with one to three substituents independently selected from the group consisting of halo, cyano, oxo, $R^5$, $OR^5$ and $NR^cR^d$,
f) $C_{4-8}$ cycloalkenyl, which is optionally substituted with one to three substituents independently selected from the group consisting of halo, cyano, $OR^5$ and $NR^cR^d$,
g) $(C=O)R^7$,
h) $(C=O)R^5$,
i) $S(O)_mR^5$, and
j) $S(O)_mR^7$;

or $R^2$ and $R^3$ can be taken together with the atoms to which they are attached to form a 3 to 8 membered heterocyclic ring, wherein said ring may contain from one to three heteroatoms selected from N, O and S, wherein the sulfur is optionally oxidized to the sulfone or sulfoxide, and which ring is optionally substituted with one to four substituents each independently selected from the group consisting of:
a) halo,
b) oxo,
c) cyano,
d) $OR^5$,
e) $NR^cR^d$,
f) $SO_3H$,
g) $S(O)_mR^5$,
h) $S(O)_mR^7$
i) $R^5$,
j) $R^6$,
k) $R^7$,
l) $(C=O)R^5$,
m) $(C=O)OR^5$,
n) $(C=O)R^7$, and
o) $(C=O)NR^cR^d$;

$R^4$ is selected from the group consisting of: hydrogen, halo, cyano, $OR^5$, aryl, heteroaryl, $C_{3-8}$ cycloalkyl, $C_{4-8}$ cycloalkenyl, $C_{4-8}$ heterocyclyl and $C_{1-6}$ alkyl, which is optionally substituted with one to three substituents independently selected from the group consisting of halo, cyano, $OC_{1-3}$ alkyl, $NR^cR^d$ and hydroxyl;

$R^5$ is selected from the group consisting of hydrogen and $C_{1-6}$ alkyl, which is optionally substituted with one to three substituents independently selected from the group consisting of:
a) halo,
b) hydroxyl,
c) $OC_{1-6}$ alkyl,
d) $NR^cR^d$,
e) $(C=O)NR^cR^d$,
f) $S(O)_m$,
g) $S(O)_mR^8$,
h) $S(O)_mR^7$,
i) $R^7$, and
j) $OR^7$;

$R^6$ is $C_{1-6}$ alkyl, which is optionally substituted with one to three substituents independently selected from the group consisting of halo and hydroxyl;

or $R^5$ and $R^6$ can be taken together with the atoms to which they are attached to form a 4 to 8 membered heterocyclic, 3 to 8 membered carbocyclic, aryl or heteroaryl ring, wherein said heterocyclic and heteroaryl rings may contain from one to three heteroatoms selected from N, O and S, wherein said heterocyclic, carbocyclic, aryl and heteroaryl rings are optionally substituted with one to three substituents independently selected from the group consisting of:
a) halo,
b) oxo,
c) cyano,
d) hydroxyl,
e) $C_{1-3}$ alkyl, which is optionally substituted with one to three halo,
f) cycloalkyl,
g) $OC_{1-3}$ alkyl, which is optionally substituted with one to three halo, and
h) $OC_{3-8}$ cycloalkyl;

$R^7$ is selected from the group consisting of $C_{4-8}$ heterocyclyl, $C_{3-8}$ cycloalkyl, $C_{4-8}$ cycloalkenyl, aryl or heteroaryl, wherein said heterocyclyl, cycloalkyl, cycloalkenyl, aryl and heteroaryl groups are optionally substituted with one to three substituents independently selected from the group consisting of:
a) halo,
b) cyano,
c) hydroxyl,
d) oxo,
e) $C_{1-3}$ alkyl, which is optionally substituted with one to four substituents independently selected from the group consisting of hydroxyl, halo, cyano, heterocyclyl, $OC_{1-3}$ alkyl and $NR^cR^d$,
f) $OC_{1-3}$ alkyl, which is optionally substituted with one to four substituents independently selected from the group consisting of hydroxyl, halo, cyano, heterocyclyl, $OC_{1-3}$ alkyl $NR^cR^d$ and aryl,
g) $C_{3-8}$ cycloalkyl, which is optionally substituted with one to four substituents independently selected from the group consisting of hydroxyl, halo, cyano, heterocyclyl, $OC_{1-3}$ alkyl and $NR^cR^d$,
h) aryl, which is optionally substituted with one to four substituents independently selected from the group consisting of hydroxyl, halo, cyano, heterocyclyl, $OC_{1-3}$ alkyl, $S(O)_mNR^cR^d$, $C(O)NR^cR^d$ and $NR^cR^d$,
i) heteroaryl, which is optionally substituted with one to four substituents independently selected from the group consisting of hydroxyl, halo, cyano, heterocyclyl, $OC_{1-3}$ alkyl, $S(O)_mNR^cR^d$, $C(O)NR^cR^d$ and $NR^cR^d$,
j) heterocyclyl, which is optionally substituted with one to four substituents independently selected from the group consisting of hydroxyl, halo, cyano, $OC_{1-3}$ alkyl and $NR^cR^d$,
k) $C_{4-8}$ cycloalkenyl, which is optionally substituted with one to four substituents independently selected from the group consisting of hydroxyl, halo, cyano, heterocyclyl, $OC_{1-3}$ alkyl and $NR^cR^d$;

$R^8$ is hydrogen or $C_{1-6}$ alkyl, which is optionally substituted with one to three substituents independently selected from the group consisting of:
a) halo,
b) cyano,
c) hydroxyl,
d) $OC_{1-3}$ alkyl, which is optionally substituted with one to four substituents independently selected from the group consisting of hydroxyl, halo and $NR^cR^d$, and
e) $C_{3-8}$ cycloalkyl;

$R^a$ is selected from the group consisting of hydrogen and $C_{1-6}$ alkyl;
$R^b$ is selected from the group consisting of hydrogen and $C_{1-6}$ alkyl;
$R^c$ is selected from the group consisting of:

a) hydrogen and
b) $C_{1-3}$ alkyl, which is optionally substituted with one to three substituents independently selected from the group consisting of halo, hydroxyl, cyano, heteroaryl, aryl, $NH(C_{1-3}$ alkyl), $N(C_{1-3}$ alkyl)$_2$, $OC_{1-6}$ alkyl, and $C_{3-8}$ cycloalkyl;

$R^d$ is selected from the group consisting of:
a) hydrogen,
b) $C_{3-8}$ cycloalkyl,
c) $C_{3-6}$ heterocyclyl,
d) $C_{1-3}$ alkyl,
e) $(C=O)C_{1-3}$ alkyl,
f) aryl, and
g) heteroaryl;
wherein said cycloalkyl, heterocyclyl, alkyl, aryl and heteroaryl groups are each optionally substituted with one to three substituents independently selected from the group consisting of halo, hydroxyl, cyano, $R^8$, $SO_2R^8$, $OC_{1-6}$ alkyl and $C_{3-8}$ cycloalkyl;

or $R^e$ and $R^d$ can be taken together with the atoms to which they are attached to form a 3 to 8 membered heterocyclic ring, wherein said ring may contain from one to three heteroatoms selected from N, O and S, wherein the sulfur is optionally oxidized to the sulfone or sulfoxide, and which ring is optionally substituted with one to four substituents each independently selected from the group consisting of halo, cyano, hydroxyl, $C_{1-3}$ alkyl and $OC_{1-3}$ alkyl;

$R^e$ is selected from the group consisting of hydrogen and $C_{1-3}$ alkyl;

$R^f$ is selected from the group consisting of hydrogen and $C_{1-3}$ alkyl; and m is an integer from zero to two.

In a class of the invention, $X^1$ is a bond. In another class of the invention, $X^1$ is $CR^eR^f$.

In a class of the invention, $X^2$ is a bond. In another class of the invention, $X^2$ is $CR^eR^f$.

In a class of the invention, $X^3$ is a bond. In another class of the invention, $X^3$ is $CR^eR^f$.

In a class of the invention, Y is O. In another class of the invention, Y is $CR^aR^b$. In another class of the invention, Y is $NR^e$.

In a class of the invention, Z is O. In another class of the invention, Z is $CR^aR^b$. In another class of the invention, Z is $NR^e$.

In a class of the invention, $R^1$ is selected from the group consisting of: hydrogen and $C_{1-3}$ alkyl. In a subclass of the invention, $R^1$ is hydrogen. In another subclass of the invention, $R^1$ is methyl.

In a class of the invention, $R^2$ and $R^3$ are taken together with the atoms to which they are attached to form a 3 to 8 membered heterocyclic ring, wherein said ring may contain from one to three heteroatoms selected from N, O and S, wherein the sulfur is optionally oxidized to the sulfone or sulfoxide, and which ring is optionally substituted with one to four substituents each independently selected from the group consisting of:
a) halo,
b) oxo,
c) cyano,
d) $OR^5$,
e) $NR^cR^d$,
f) $SO_3H$
g) $S(O)_mR^5$,
h) $S(O)_mR^7$,
i) $R^5$,
j) $R^6$,
k) $R^7$,
l) $(C=O)R^5$,
m) $(C=O)OR^5$,
n) $(C=O)R^7$, and
o) $(C=O)NR^cR^d$.

In a subclass of the invention, $R^2$ and $R^3$ can be taken together with the atoms to which they are attached to form a 6 membered heterocyclic ring, wherein said ring may contain from one to three heteroatoms selected from N, O and S, wherein the sulfur is optionally oxidized to the sulfone or sulfoxide, and which ring is optionally substituted with one to four substituents each independently selected from the group consisting of:
a) halo,
b) oxo,
c) $OR^5$,
d) $NR^cR^d$,
e) $S(O)_mR^5$,
f) $R^5$,
g) $R^6$,
h) $R^7$,
i) $(C=O)R^5$,
j) $(C=O)OR^5$, and
k) $(C=O)R^7$.

In a further subclass of the invention, $R^2$ and $R^3$ can be taken together with the atoms to which they are attached to form a morpholinyl group, which is optionally substituted with $C_{1-6}$ alkyl or $C_{1-6}$ alkylhydroxyl. In a further subclass of the invention, $R^2$ and $R^3$ can be taken together with the atoms to which they are attached to form a piperazinyl group, which is optionally substituted with $C_{1-6}$ alkyl or $C_{1-6}$ alkyl-$SO_2$. In a further subclass of the invention, $R^2$ and $R^3$ can be taken together with the atoms to which they are attached to form a piperazinone group.

In a class of the invention, $R^4$ is selected from the group consisting of: hydrogen and halo. In a subclass of the invention, $R^4$ is hydrogen.

In a class of the invention, $R^5$ is hydrogen.
In a class of the invention, $R^6$ is hydrogen.
In a class of the invention, $R^7$ is heterocyclyl.
In a class of the invention, $R^a$ is hydrogen.
In a class of the invention, $R^b$ is hydrogen.
In a class of the invention, $R^c$ is hydrogen.
In a class of the invention, $R^d$ is hydrogen.
In a class of the invention, $R^e$ is hydrogen.
In a class of the invention, $R^f$ is hydrogen.

Reference to the preferred classes and subclasses set forth above is meant to include all combinations of particular and preferred groups unless stated otherwise.

Specific embodiments of the present invention include, but are not limited to the compounds identified herein as Examples 1 to 237, or pharmaceutically acceptable salts thereof.

The invention also encompasses a pharmaceutical composition which comprises an inert carrier and the compound of Formula I, or a pharmaceutically acceptable salt thereof.

The invention may also encompass a method of treating Parkinson's Disease in a mammalian patient in need of such treatment, which comprises administering to the patient a therapeutically effective amount of the compound of Formula I, or a pharmaceutically acceptable salt thereof.

The invention may also encompass the use of a compound of Formula I, or a pharmaceutically acceptable salt thereof, and a pharmaceutically acceptable carrier, for the manufacture of a medicament for the treatment of Parkinson's Disease.

The invention is also directed to medicaments or pharmaceutical compositions which may be useful for treating diseases or disorders in which LRRK2 is involved, such as Parkinson's Disease, which comprise a compound of Formula I, or a pharmaceutically acceptable salt thereof, and a pharmaceutically acceptable carrier.

The invention is also directed to the use of a compound of Formula I which may be useful for treating diseases or disorders in which LRRK2 is involved, such as Parkinson's Disease.

The invention is further directed to a method for the manufacture of a medicament or a composition which may be useful for treating diseases or disorders in which LRRK2 is involved, such as Parkinson's Disease, comprising combining a compound of Formula I with one or more pharmaceutically acceptable carriers.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. Unless a specific stereochemistry is indicated, the present invention is meant to comprehend all such isomeric forms of these compounds.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

In the compounds of Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium (1H) and deuterium (2H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

Tautomers of compounds defined in Formula I are also included within the scope of the present invention. For example, compounds including carbonyl —CH2C(O)— groups (keto forms) may undergo tautomerism to form hydroxyl —CH=C(OH)— groups (enol forms). Both keto and enol forms are included within the scope of the present invention.

When any variable (e.g. $R^5$, etc.) occurs more than one time in any constituent, its definition on each occurrence is independent at every other occurrence. Also, combinations of substituents and variables are permissible only if such combinations result in stable compounds. Lines drawn into the ring systems from substituents represent that the indicated bond may be attached to any of the substitutable ring atoms. If the ring system is bicyclic, it is intended that the bond be attached to any of the suitable atoms on either ring of the bicyclic moiety.

It is understood that one or more silicon (Si) atoms can be incorporated into the compounds of the instant invention in place of one or more carbon atoms by one of ordinary skill in the art to provide compounds that are chemically stable and that can be readily synthesized by techniques known in the art from readily available starting materials. Carbon and silicon differ in their covalent radius leading to differences in bond distance and the steric arrangement when comparing analogous C-element and Si-element bonds. These differences lead to subtle changes in the size and shape of silicon-containing compounds when compared to carbon. One of ordinary skill in the art would understand that size and shape differences can lead to subtle or dramatic changes in potency, solubility, lack of off-target activity, packaging properties, and so on. (Diass, J. O. et al. Organometallics (2006) 5:1188-1198; Showell, G. A. et al. Bioorganic & Medicinal Chemistry Letters (2006) 16:2555-2558).

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted with one or more substituents" should be understood as meaning that the group in question is either unsubstituted or may be substituted with one or more substituents.

As used herein, "alkyl" is intended to mean linear or branched structures having no carbon-to-carbon double or triple bonds. Thus, $C_{1-4}$ alkyl is defined to identify the group as having 1, 2, 3 or 4 carbons in a linear or branched arrangement, such that $C_{1-4}$ alkyl specifically includes, but is not limited to, methyl, ethyl, n-propyl, iso-propyl, n-butyl, iso-butyl and tert-butyl.

As appreciated by those of skill in the art, "halo" or "halogen" as used herein is intended to include chloro (Cl), fluoro (F), bromo (Br) and iodo (I).

The term "cycloalkyl" shall mean cyclic rings of alkanes of three to eight total carbon atoms, unless otherwise indicated, or any number within this range (i.e., cyclopropyl, cyclobutyl, cyclopentyl, cyclohexyl, cycloheptyl, methylcyclopropyl, 2,2-dimethyl-cyclobutyl, 2-ethyl-cyclopentyl or cyclooctyl) and also includes bicyclic or fused spirocyclic compounds.

The term "cycloalkenyl" shall mean cyclic rings of four to eight total carbon atoms, unless otherwise indicated, or any number within this range where one or two degrees of unsaturation are present. Non-limiting examples of said cycloalkenyl groups are: cyclohexenyl, cyclopentenyl, cyclooctadienyl.

The term "carbocycle" shall mean cyclic rings of three to eight total carbon atoms, unless otherwise indicated, or any number within this range, where zero, one or two degrees of unsaturation are present and where said "carbocycle" can be bicyclic or fused spirocyclic in nature. Non-limiting examples of said carbocyclyl groups are: cyclohexenyl, cyclopentenyl, cyclooctadienyl, cyclohexyl or cyclopropyl.

If no number of carbon atoms is specified, the term "alkenyl" refers to a non-aromatic hydrocarbon radical, straight or branched, containing from 2 to 10 carbon atoms and at least 1 carbon to carbon double bond. Preferably 1 carbon to carbon double bond is present, and up to 4 non-aromatic carbon-carbon double bonds may be present. Thus, "C2-C6 alkenyl" means an alkenyl radical having from 2 to 6 carbon atoms. Alkenyl groups include ethenyl, propenyl, butenyl and cyclohexenyl. As described above with respect to alkyl, the straight, branched or cyclic portion of the alkenyl group may contain double bonds and may be substituted if a substituted alkenyl group is indicated.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

The term "heteroaryl", as used herein, represents a stable monocyclic, bicyclic or tricyclic ring of up to 10 atoms in each ring, wherein at least one ring is aromatic and contains from 1 to 4 heteroatoms selected from the group consisting of O, N and S. Heteroaryl groups within the scope of this definition include but are not limited to: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, pyranyl, pyrazinyl, pyrazolyl, pyridazinyl, pyridopyridinyl, pyridyl, pyrimidinyl, pyrrolyl, quinazolinyl, quinolyl, quinoxalinyl, tetrazolyl, tetrazolopyridyl, thiadiazolyl, thiazolyl, thienyl, triazolyl, dihydrobenzoimidazolyl, dihydrobenzofuranyl, dihydrobenzothiophenyl, dihydrobenzoxazolyl, dihydroindolyl, dihydroquinolinyl, methylenedioxybenzene, benzothiazolyl, benzothienyl, quinolinyl, isoquinolinyl, oxazolyl, and tetra-hydroquinoline. In cases where the heteroaryl substituent is bicyclic and one ring is non-aromatic or contains no heteroatoms, it is understood that attachment is via the aromatic ring or via the heteroatom containing ring, respectively. If the heteroaryl contains nitrogen atoms, it is understood that the corresponding N-oxides thereof are also encompassed by this definition.

The term "heterocycle" or "heterocyclyl" as used herein is intended to mean a 5- to 10-membered nonaromatic ring, unless otherwise specified, containing from 1 to 4 heteroatoms selected from the group consisting of O, N, S, SO, or $SO_2$ and includes bicyclic groups. The heterocyclyl group also includes rings that possess one or two degrees of unsaturation. "Heterocyclyl" therefore includes, but is not limited to the following: piperazinyl, piperidinyl, pyrrolidinyl, morpholinyl, thiomorpholinyl, tetrahydropyranyl, dihydropiperidinyl, tetrahydrothiophenyl and the like. If the heterocycle contains a nitrogen, it is understood that the corresponding N-oxides thereof are also emcompassed by this definition.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives wherein the parent compound is modified by making acid or base salts thereof. Salts in the solid form may exist in more than one crystal structure, and may also be in the form of hydrates. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. Salts derived from inorganic bases include aluminum, ammonium, calcium, copper, ferric, ferrous, lithium, magnesium, manganic salts, manganous, potassium, sodium, zinc, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. In one aspect of the invention the salts are citric, hydrobromic, hydrochloric, maleic, phosphoric, sulfuric, fumaric, and tartaric acids. It will be understood that, as used herein, references to the compounds of Formula I are meant to also include the pharmaceutically acceptable salts.

Exemplifying the invention is the use of the compounds disclosed in the Examples and herein. Specific compounds within the present invention include a compound which may be selected from the group consisting of the compounds disclosed in the following Examples and pharmaceutically acceptable salts thereof and individual diastereomers thereof.

The subject compounds are useful in a method of inhibition of LRRK2 receptors in a patient such as a mammal in need of such antagonism comprising the administration of an effective amount of the compound. The present invention is directed to the use of the compounds disclosed herein as inhibitors of LRRK2 receptors. In addition to primates, especially humans, a variety of other mammals can be treated according to the method of the present invention.

Another embodiment of the present invention is directed to a method for the treatment, control, amelioration, or reduction of risk of a disease or disorder in which the LRRK2 kinase is involved in a patient that comprises administering to the patient a therapeutically effective amount of a compound that is an inhibitor of LRRK2 kinase.

The present invention is further directed to a method for the manufacture of a medicament for inhibition of LRRK2 receptors activity in humans and animals comprising combining a compound of the present invention with a pharmaceutical carrier or diluent.

The subject treated in the present methods is generally a mammal, for example a human being, male or female, in whom inhibition of LRRK2 kinase activity is desired. The term "therapeutically effective amount" means the amount of the subject compound that will elicit the biological or medical response of a tissue, system, animal or human that is being sought by the researcher, veterinarian, medical doctor or other clinician.

The terms "treating" or "treatment" of a disease as used herein includes: inhibiting the disease, i.e., arresting or reducing the development of the disease or its clinical symptoms; or relieving the disease, i.e., causing regression of the disease or its clinical symptoms. The term "preventing" or "prevention" of a disease as used herein includes: causing the clinical symptoms of the disease not to develop in a mammal that may be exposed to or predisposed to the disease but does not yet experience or display symptoms of the disease, and the like.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The present invention includes within its scope prodrugs of the compounds of this invention. In general, such prodrugs will be functional derivatives of the compounds of this invention which are readily convertible in vivo into the required compound. Thus, in the methods of treatment of the present invention, the terms "administration of" or "administering a" compound shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985. Metabolites of these compounds include active species produced upon introduction of compounds of this invention into the biological milieu.

The ability of the compounds of the present invention to act as LRRK2 kinase inhibitors makes them useful pharmacological agents for disorders that involve LRRK2 kinase in humans and animals, but particularly in humans.

In another embodiment the invention provides a method of inhibiting LRRK2 Kinase activity (this is to say, inhibiting the kinase activity associated with Leucine-Rich Repeat Kinase 2 [LRRK2], a multidomain protein containing kinase and GTPase enzymatic activities) in a patient in need of therapy for a condition amenable to treatment by such kinase activity inhibition, for example, treatment or prevention of neurologic damage associated with Parkinson's disease, for example, improvement in dopaminergic tone and in providing symptomatic benefit, for example, in treating, alleviating, ameliorating, or managing motor and non-motor symptoms of Parkinson's disease, and other conditions that may be treated or prevented by inhibition of LRRK2 kinase. Of particular importance is the acute or prophylactic treatment of Parkinson's Disease.

The subject compounds may be further useful in a method for the prevention, treatment, control, amelioration, or reduction of risk of the diseases, disorders and conditions noted herein.

The subject compounds may be further useful in a method for the prevention, treatment, control, amelioration, or reduction of risk of the aforementioned diseases, disorders and conditions in combination with other agents.

The compounds of the present invention may be used in combination with one or more other drugs in the treatment, prevention, control, amelioration, or reduction of risk of diseases or conditions for which compounds of Formula I or the other drugs may have utility, where the combination of the drugs together are safer or more effective than either drug alone. Such other drug(s) may be administered, by a route and in an amount commonly used therefore, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy may also include therapies in which the compound of Formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I.

For example, the present compounds may be used in conjunction with one or more additional therapeutic agents, for example: L-DOPA; dopaminergic agonists such as quinpirole, ropinirole, pramipexole, pergolide and bromocriptine; MAO-B inhibitors such as rasagiline, deprenyl and selegiline; DOPA decarboxylase inhibitors such as carbidopa and benserazide; and COMT inhibitors such as tolcapone and entacapone; or potential therapies such as an adenosine A2a antagonists, metabotropic glutamate receptor 4 modulators, or growth factors such as brain derived neurotrophic factor (BDNF), and a pharmaceutically acceptable carrier.

The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the present invention to the other active ingredient(s) may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, or from about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s), and via the same or different routes of administration.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, buccal or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, solutions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release. Oral tablets may also be formulated for immediate release, such as fast melt tablets or wafers, rapid dissolve tablets or fast dissolve films.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or *arachis* oil, or a mineral oil, for example liquid paraffin or mixtures of these. Suitable emulsifying agents may be naturally-occurring gums, for example gum *acacia* or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions and the like, containing the compounds of the present invention are employed. Similarly, transdermal patches may also be used for topical administration.

The pharmaceutical composition and method of the present invention may further comprise other therapeutically active compounds as noted herein which are usually applied in the treatment of the above mentioned pathological conditions.

In the treatment, prevention, control, amelioration, or reduction of risk of conditions which require inhibition of LRRK2 kinase activity an appropriate dosage level will generally be about 0.01 to 500 mg per kg patient body weight per day which can be administered in single or multiple doses. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are may be provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, or may be administered once or twice per day.

When treating, preventing, controlling, ameliorating, or reducing the risk of Parkinson's Disease, or other diseases for which compounds of the present invention are indicated, generally satisfactory results are obtained when the compounds of the present invention are administered at a daily dosage of from about 0.1 milligram to about 100 milligram per kilogram of animal body weight, given as a single daily dose or in divided doses two to six times a day, or in sustained release form. For most large mammals, the total daily dosage is from about 1.0 milligrams to about 1000 milligrams, or from about 1 milligrams to about 50 milligrams. In the case of a 70 kg adult human, the total daily dose will generally be from about 7 milligrams to about 350 milligrams. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Methods for preparing the compounds of this invention are illustrated in the following Schemes and Examples. Starting materials are made according to procedures known in the art or as illustrated herein.

The compounds of the present invention can be prepared readily according to the following Schemes and specific examples, or modifications thereof, using readily available starting materials, reagents and conventional synthesis procedures. In these reactions, it is also possible to make use of variants which are themselves known to those of ordinary skill in this art but are not mentioned in greater detail. The general procedures for making the compounds claimed in this invention can be readily understood and appreciated by one skilled in the art from viewing the following Schemes.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

General Schemes

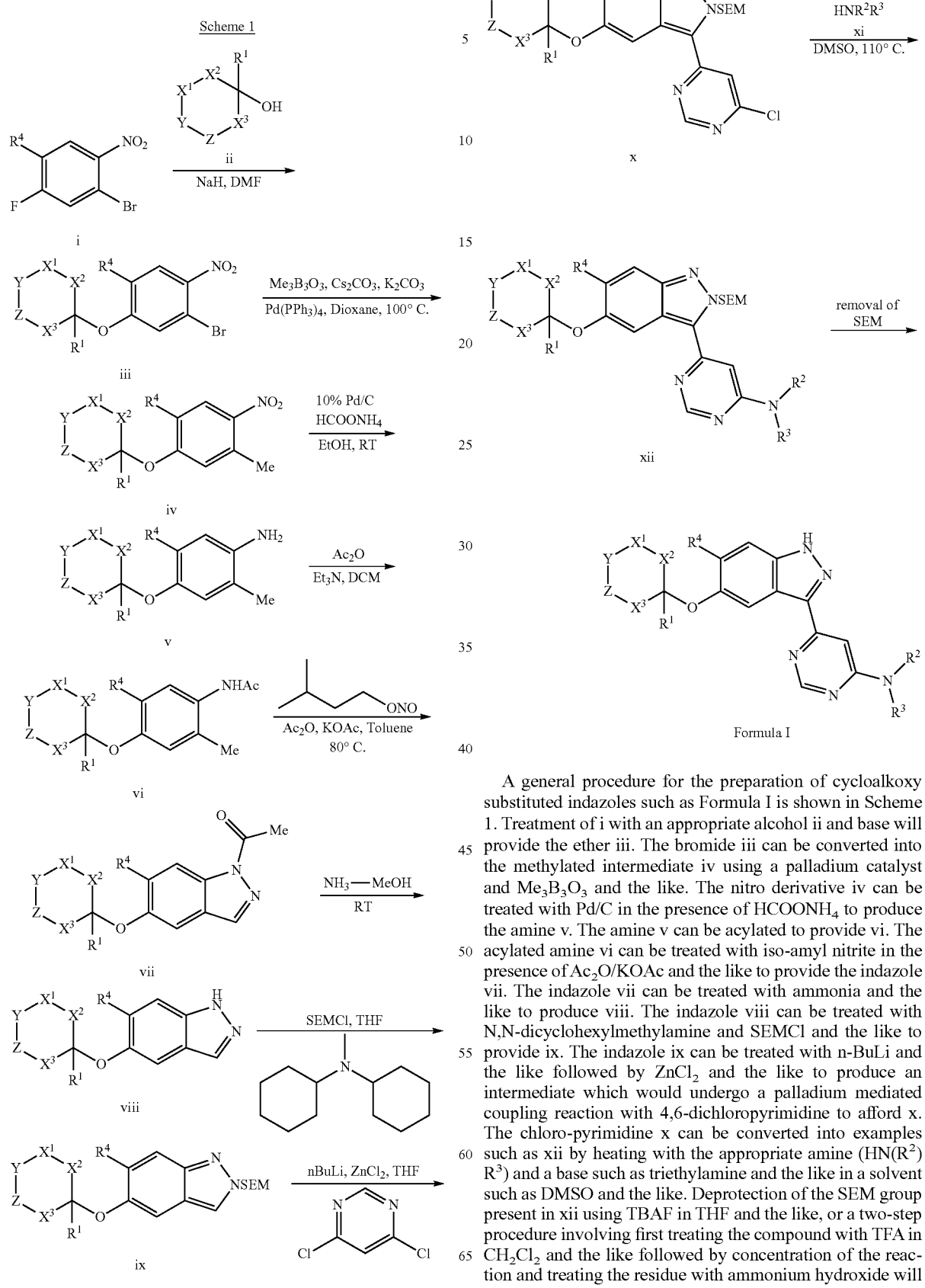

A general procedure for the preparation of cycloalkoxy substituted indazoles such as Formula I is shown in Scheme 1. Treatment of i with an appropriate alcohol ii and base will provide the ether iii. The bromide iii can be converted into the methylated intermediate iv using a palladium catalyst and $Me_3B_3O_3$ and the like. The nitro derivative iv can be treated with Pd/C in the presence of $HCOONH_4$ to produce the amine v. The amine v can be acylated to provide vi. The acylated amine vi can be treated with iso-amyl nitrite in the presence of $Ac_2O/KOAc$ and the like to provide the indazole vii. The indazole vii can be treated with ammonia and the like to produce viii. The indazole viii can be treated with N,N-dicyclohexylmethylamine and SEMCl and the like to provide ix. The indazole ix can be treated with n-BuLi and the like followed by $ZnCl_2$ and the like to produce an intermediate which would undergo a palladium mediated coupling reaction with 4,6-dichloropyrimidine to afford x. The chloro-pyrimidine x can be converted into examples such as xii by heating with the appropriate amine ($HN(R^2)R^3$) and a base such as triethylamine and the like in a solvent such as DMSO and the like. Deprotection of the SEM group present in xii using TBAF in THF and the like, or a two-step procedure involving first treating the compound with TFA in $CH_2Cl_2$ and the like followed by concentration of the reaction and treating the residue with ammonium hydroxide will afford examples such as Formula I.

Scheme 2

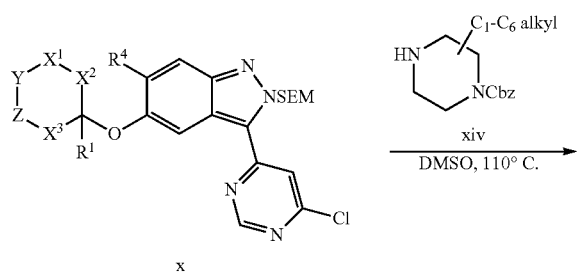

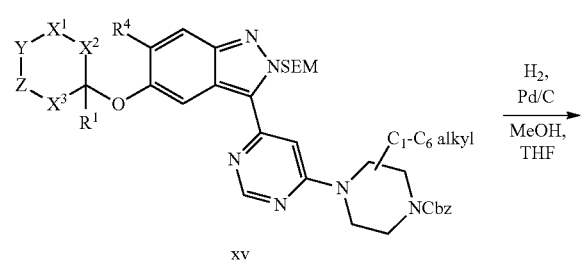

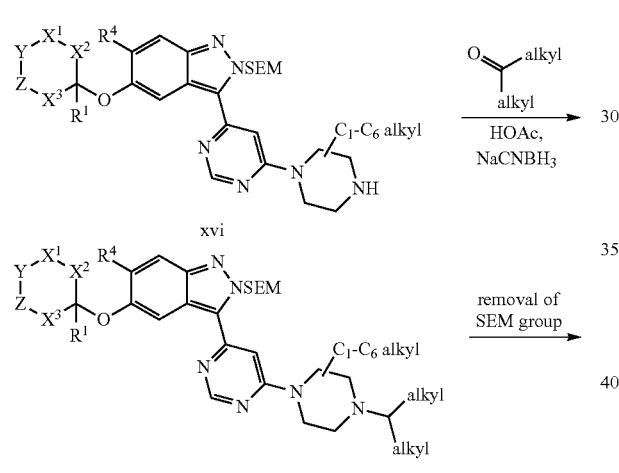

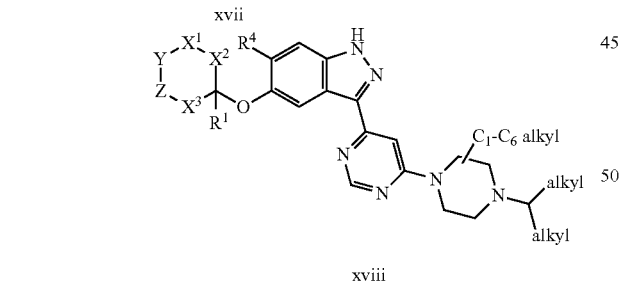

A general procedure for the preparation of cycloalkoxy substituted indazoles containing a substituted piperizine such as xviii is shown in Scheme 2. Heating of chloropyrimidine x with an appropriate piperizine xiv would form the adduct xv. The Cbz group in xv can be removed under palladium catalyzed hydrogenation to provide xvi. The piperizine xvi can be converted into examples such as xviii by treatment with appropriate carbonyl compound ((alkyl)(alkyl)C(O)) in presence of NaCNBH₃ and the like and AcOH and the like followed by deprotection of the SEM group using standard conditions.

Scheme 3

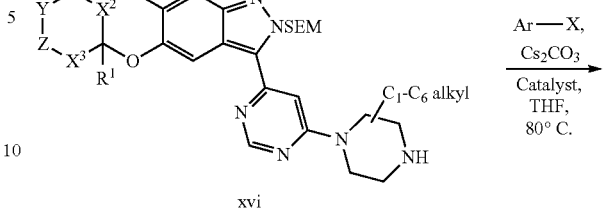

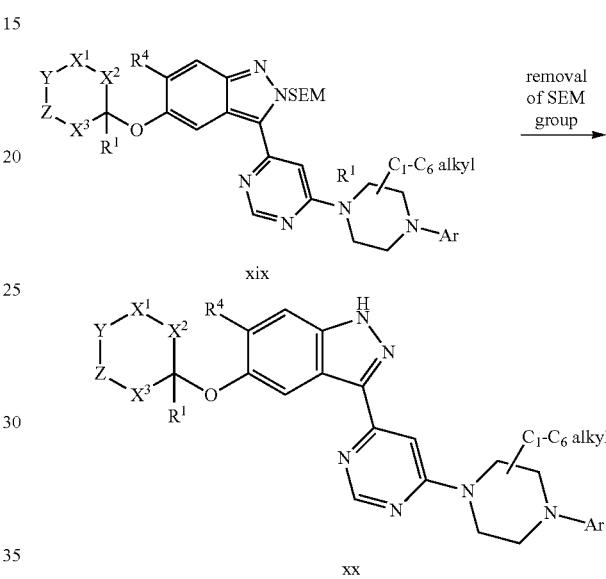

A general procedure for the preparation of cycloalkoxy substituted indazoles containing an aryl-substituted piperizine such as xx is shown in Scheme 3. Piperizine xvi can be converted into example xx by Pd-mediated direct arylation with aryl halides/triflates followed by deprotection of the SEM group using standard conditions.

Scheme 4

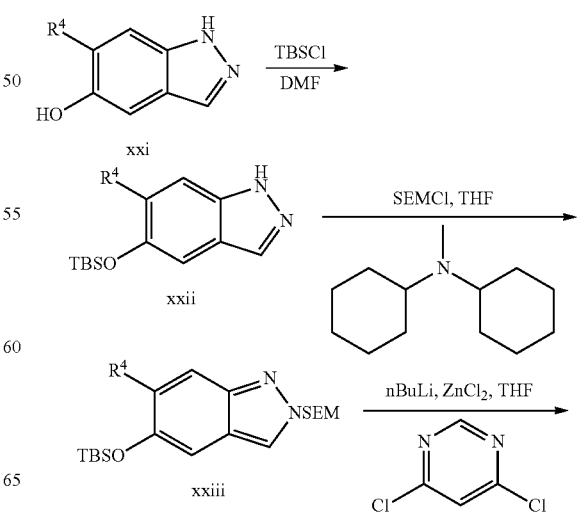

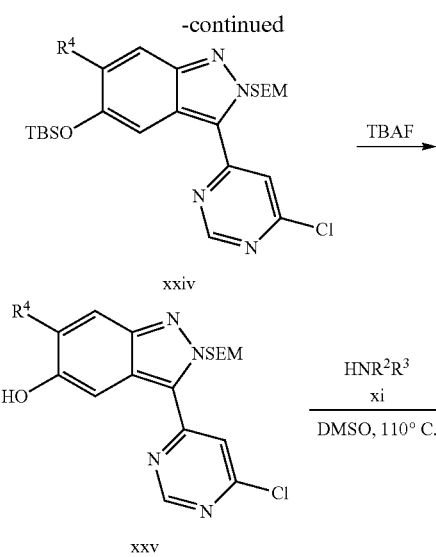
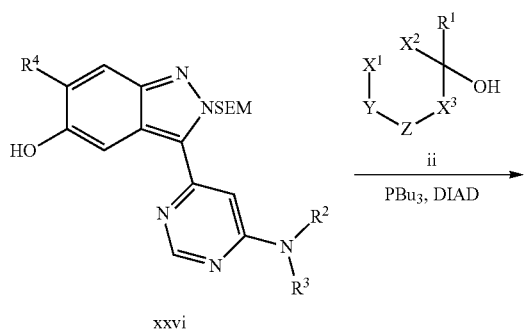
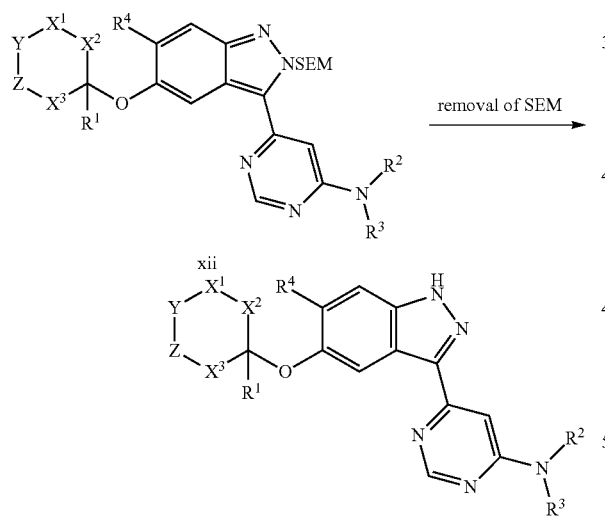

with the appropriate amine HN(R²)R³ and base will produce xxvi. The hydroxyindazole will then undergo a Mitsunobu reaction with alcohol ii in presence of PBu₃ and the like and DIAD and the like to produce xii which upon SEM deprotection will produce examples such as Formula 1.

Scheme 5

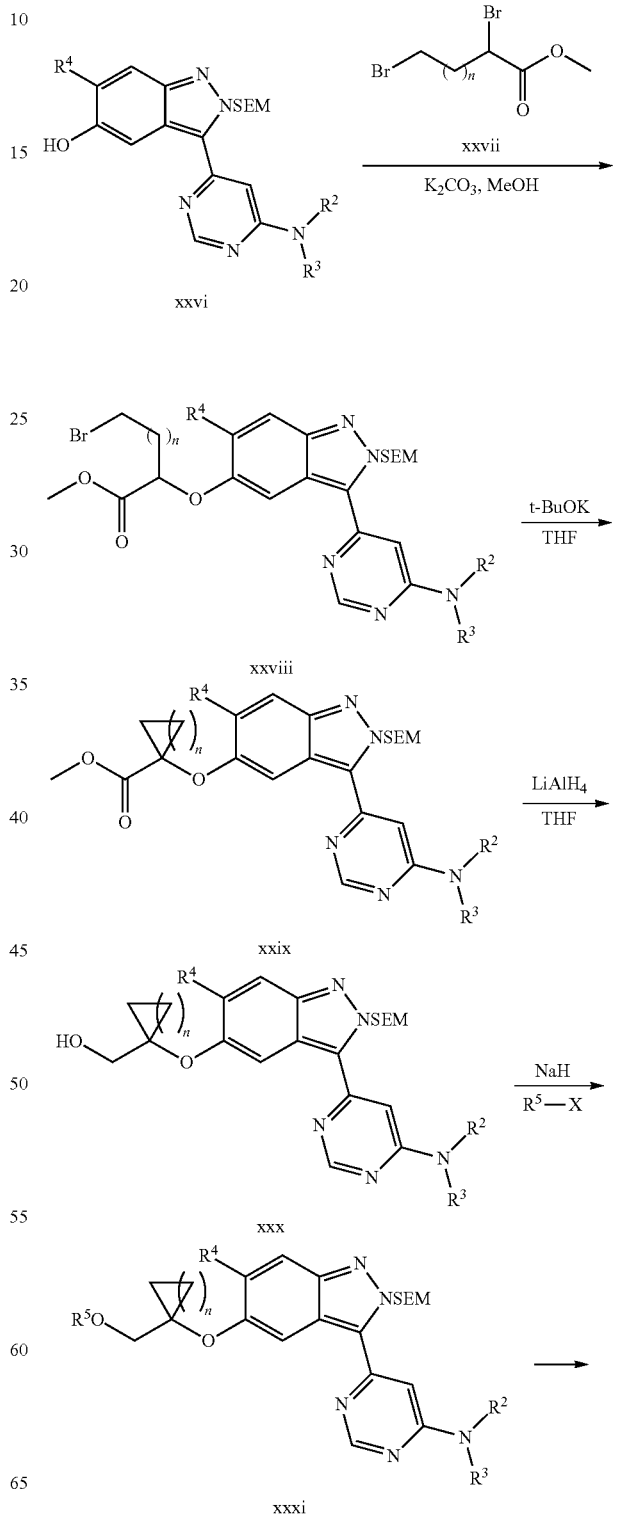

A general procedure for the preparation of cycloalkoxy substituted indazoles such as Formula I is shown in Scheme 4. Treatment of an appropriate hydroxyindazole xxi with TBSCl in the presence of an appropriate base will provide the ether xxii. The indazole xxii can be treated with N,N-dicyclohexylmethylamine and SEM-Cl and the like to provide xxiii. The indazole xxiii can be treated with n-BuLi and the like followed by ZnCl₂ and the like to produce a zinc intermediate which would undergo a palladium mediated coupling reaction with 4,6-dichloropyrimidine to afford xxiv. The TBS group can be removed with TBAF and the like to afford the hydroxyindazole xxv which upon heating

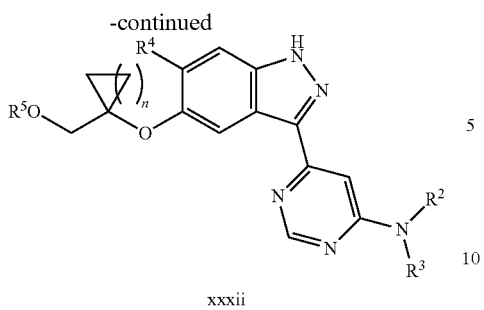

xxxii

A general procedure for the preparation of cycloalkoxy substituted indazoles such as xxxi is shown in Scheme 5.

Treatment of hydroxyindazole xxvi with bromide xxvii in presence of a base will furnish compound xxviii which will subsequently undergo cyclization in presence of $^t$BuOK and the like to form ester xxix. Reduction of the ester with LiAlH$_4$ and the like will produce the alcohol xxx which can be converted to example xxxii by treatment with an R$_5$-LG (LG=Leaving Group (e.g. I, Br, OTs, OMs)) in presence of NaH and the like followed by deprotection of SEM group under standard conditions.

EXPERIMENTALS

Abbreviations used in the experimentals may include the following:

| | | | |
|---|---|---|---|
| ACN | Acetonitrile | AcOH | Acetic acid |
| Ac$_2$O | Acetic anhydride | Bn | Benzyl |
| Aq | Aqueous | BOC$_2$O | BOC Anhydride |
| BOC | tert-Butoxycarbonyl | C (or ° C.) | degrees Celsius |
| Bu | Butyl | DBU | 1,8-Diazabicyclo[5.4.0]undec-7-ene |
| Cbz | benzyloxycarbonyl | DIPEA | Diisopropylethylamine |
| DCM | Dichloromethane | DMAP | 4-Dimethylaminopyridine |
| DMA | N,N-Dimethylacetamide | DMF | Dimethylformamide |
| DME | 1,2-dimethoxyethane | DPPF | 1,1'-(bis-diphenylphosphino) ferrocene |
| DMSO | Dimethyl sulfoxide | EDC | 1-(3-Dimethylaminopropyl)-3-ethylcarbodiimide hydrochloride |
| EDCI | 1-(3-Dimethylaminopropyl)-3-ethylcarbodiimide hydrochloride | Eq | Equivalents |
| EI | Electron ionization | EtOAc | Ethyl acetate |
| Et | Ethyl | g | grams |
| EtOH | Ethanol | $^1$H | proton |
| h, hr | hours | Hex | hexanes |
| HATU | N,N,N',N'-Tetramethyl-O-(7-Azabenzotriazol-1-yl)uronium hexafluorophosphate | HOBT•H$_2$O | 1-Hydroxybenzotriazole hydrate |
| HOBT | 1-Hydroxybenzotriazole | HOTS•H$_2$O | para-toluene sulfonic acid hydrate (see also TsOH•H$_2$O) |
| HOTS | para-toluene sulfonic acid (see also TsOH) | HPLC | High pressure liquid chromatography |
| HMPA | hexamethylphosphoramide | LDA | lithium diisopropylamide |
| KOAc | Potassium acetate | mmol | milimolar |
| IPA | isopropanol, 2-propanol | Me | Methyl |
| M | Molar | MeOH | Methanol |
| mCPBA | meta-Chloroperoxy benzoic acid | mg | Milligrams |
| MeCN | Acetonitrile | mL (or ml) | Milliliter |
| min | Minutes | N | normal |
| MHZ | Megahertz | MS | Mass Spectroscopy |
| Mol sieves | molecular sieves | NMM | N-Methylmorpholine |
| NMR | Nuclear Magnetic Resonance | ON | Overnight |
| NBS | N-Bromosuccinimide | PyBrOP | Bromo-tris-pyrrolidino-phosphonium hexafluorophosphate |
| NMP | 1-methyl-2-pyrrolidone | RT or rt | Room temperature |
| PTLC | Preparative thin layer chromatography | SFC | supercritical fluid chromatography |
| PyBOP | (Benzotriazol-1-yloxy)tripyrrolidinophosphonium hexa-fluorophosphate | SEMC1 | 2-(trimethylsilyl)ethoxymethyl chloride |
| Quant | quantitative | SiO$_2$ | Silica gel |
| sat (or sat. or sat'd.) | Saturated | t-Bu | tert-butyl |
| SEM | 2-(trimethylsilyl)ethoxymethyl | Tf | Trifluoromethane sulfonyl |
| sgc | Silica gel 60 chromatography | THF | Tetrahydrofuran |

| | | | |
|---|---|---|---|
| tBOC | tert-Butoxycarbonyl | Ts | p-toluene sulfonyl |
| TEA | Triethylamine | TsOH•H$_2$O | para-toluene sulfonic acid hydrate |
| TFA | Trifluoroacetic acid | TBAF | Tetrabutylammonium fluoridepara-toluene |
| TLC | Thin layer chromatography | | |
| TsOH | para-toluene sulfonic acid | | |
| PE | Petroleum ether | | |

General Experimental Information:

Unless otherwise noted, all reactions are magnetically stirred.

Unless otherwise noted, when ethyl acetate, hexanes, dichloromethane, 2-propanol, and methanol are used in the experiments described below, they are Fisher Optima grade solvents.

Unless otherwise noted, when diethyl ether is used in the experiments described below, it is Fisher ACS certified material and is stabilized with BHT.

Unless otherwise noted, "concentrated to dryness" means evaporating the solvent from a solution or mixture using a rotary evaporator.

Unless otherwise noted, flash chromatography is carried out on an Isco, Analogix, or Biotage automated chromatography system using a commercially available cartridge as the column. Columns may be purchased from Isco, Analogix, Biotage, Varian, or Supelco and are usually filled with silica gel as the stationary phase.

Unless otherwise noted, all LRRK2 IC$_{50}$ data presented in tables refers to the LRRK K$_m$ ATP LanthaScreen™ Assay that is described in the Biological Assay section.

Experimental Procedures:

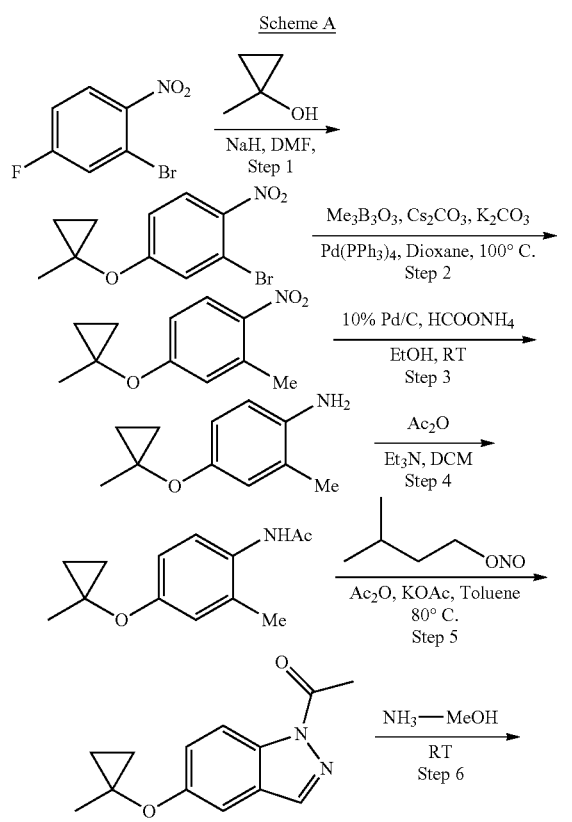

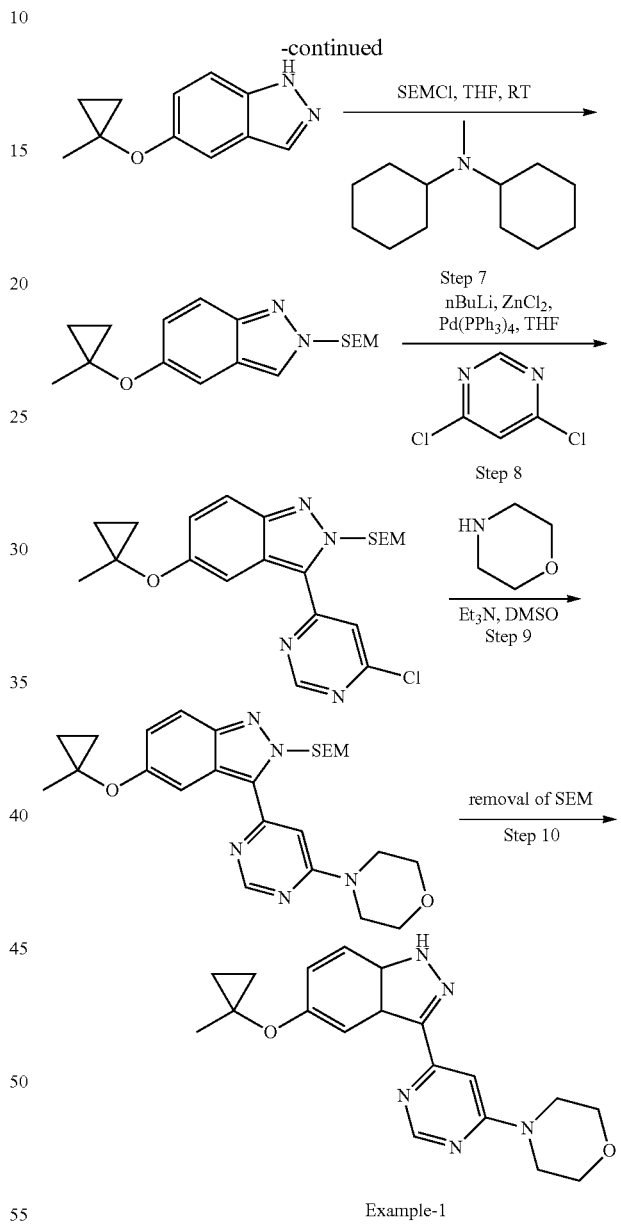

Example-1

Step 1:

To a cold (0° C.), stirred mixture of 2-bromo-4-fluoronitrobenzene (10.0 g, 45.5 mmol) and 1-methylcyclopropanol (3.61 g, 50.0 mmol) in DMF (200 ml) was added NaH (2.36 g of 60% in oil, 59.1 mmol) in portions. Once the addition was complete, the cold bath was removed and the mixture was stirred at room temperature for 5 h. The reaction was quenched with water and extracted with EtOAc (×3). The combined organic layers were washed with water (×3), brine (×2), dried, filtered and concentrated to leave an oil which was purified by column chromatography (SiO$_2$:gradient elution with 100:0 to 20:1 hexane:EtOAc) to yield the desired product.

Step 2:

A stirred mixture of the ether (2.0 g, 7.35 mmol), K$_2$CO$_3$ (2.03 g, 14.70 mmol) and Cs$_2$CO$_3$ (2.39 g, 7.35 mmol) in dioxane (110 ml) was purged Ar for 15 min. Then trimethylboraxine (2.26 ml, 16.17 mmol) and Pd(Ph$_3$P)$_4$ (0.85 g, 0.74 mmol) were added and the mixture was heated at 100° C. overnight. The reaction was cooled to room temperature and concentrated under vacuum. To this residue was added 10:1 hex:EtOAc (500 mL). The mixture was filtered through a pad of silica. The filter cake was washed with a mixture of hexane:EtOAc (1 L of 10:1 hexane:EtOAc) solution. The filtrate was concentrated under vacuum to yield the desired compound, which was used in the next step without further purification.

Step 3:

The crude nitro derivative from Step 2 (~7.35 mmol) was dissolved in absolute EtOH (110 mL). To this solution were added 10% Pd/C (0.782 g, 0.735 mmol) and ammonium formate (5.56 g, 88.0 mmol) and the mixture was stirred at room temperature for 5 h. To this solution was added a solution containing 5:1 hexane:EtOAc (500 mL) and the mixture was filtered through a pad of silica. The filtrate was concentrated and the residue was purified by column chromatography (SiO$_2$:gradient elution with 10:1 to 5:1 hexane:EtOAc) to yield the desired amine. LCMS 178.2 [M+H]$^+$ Step 4:

To a cold (0° C.), stirred mixture of amine (1.4 g, 7.90 mmol) and triethylamine (2.20 ml, 15.80 mmol) in CH$_2$Cl$_2$ (12 ml) was added Ac$_2$O (1.12 ml, 11.85 mmol). The mixture was slowly warmed to room temperature and stirred overnight. Silica gel was added and the mixture was evaporated to leave a slurry which was then purified by column chromatography (SiO$_2$: eluted with 1:1 hexane:EtOAc) to yield the desired acetamide. LCMS 220.2 [M+H]$^+$ Step 5:

To a stirred solution of acetamide (1.76 g, 8.03 mmol) in toluene (42 ml) was added KOAc (1.182 g, 12.04 mmol) and Ac$_2$O (3.48 ml, 36.9 mmol). Then the mixture was heated to 80° C. after which isoamyl nitrite (4.49 ml, 32.1 mmol) was added dropwise and the resulting mixture was heated at 80° C. overnight. The insoluble material was filtered through a pad of celite and the filtrate was concentrated to leave a residue which was purified by column chromatography (SiO$_2$: eluted with 20:1 hexane:EtOAc) to yield the desired product. LCMS 231.2 [M+H]$^+$ Step 6:

To a stirred suspension of the N-acetyl indazole (6.5 g, 28.2 mmol) in MeOH (20 mL) was added NH$_3$ (20.16 ml of 7M solution, 141.0 mmol) and the mixture was stirred at room temperature for 2 h. The reaction was concentrated and the residue was purified by column chromatography (SiO$_2$: gradient elution with 5:1 to 1:1 hexane:EtOAc) to yield the desired indazole. LCMS 189.3 [M+H]$^+$ Step 7:

To a stirred solution of the indazole (3.36 g, 17.85 mmol) in THF (50 mL) were added N,N-dicyclohexylmethylamine (4.97 ml, 23.21 mmol) and SEMCl (3.78 ml, 21.42 mmol). The mixture was stirred at room temperature overnight. The reaction was quenched with water and extracted with CH$_2$Cl$_2$ (×3). The combined organic layers were washed with 1N HCl (×2) and 1N NaOH (×2), brine, dried, filtered and concentrated to leave a residue which was purified by column chromatography (SiO$_2$: eluted with 10:1 hexane:EtOAc) to yield the desired product. LCMS 319.2 [M+H]$^+$ Step 8:

To a cold (−78° C.), stirred solution of the SEM protected indazole (1.7 g, 5.34 mmol) in THF (10 ml) was added n-BuLi (4.34 ml of 1.6 M solution in hexane, 6.94 mmol). After the addition was complete the mixture was stirred at −78° C. for 15 min and then warmed to −20° C. for 5 min. The mixture was cooled to −78° C. after which time a freshly prepared solution of ZnCl$_2$ (16.01 ml of 0.5 M solution in THF, 8.01 mmol) was added. The mixture was then raised to −20° C. and stirred for 10 min at −20° C., afterwards a mixture of 4,6-dichloropyrimidine (0.88 g, 5.87 mmol) and Pd(PPh$_3$)$_4$ (0.31 g, 0.27 mmol) was added. The cold bath was removed and the mixture was stirred at room temperature for 5 h before being quenched by a saturated aqueous solution of NH$_4$Cl. The mixture was then extracted with CH$_2$Cl$_2$ (×3). The combined organic layers were dried over MgSO$_4$, filtered and concentrated under vacuum to leave a residue which was purified by column chromatography (SiO$_2$: eluted with 10:1 hexane:EtOAc) to yield the desired chloropyrimidine. LCMS 431.2 [M+H]$^+$.

Step 9:

A mixture of the chloropyrimidine (0.20 g, 0.46 mmol), morpholine (0.12 g, 1.39 mmol) and triethylamine (0.4 mL, 2.87 mmol) in DMSO (2 mL) was heated at 110° C. overnight. The reaction was cooled to room temperature and diluted with water. The layer was then extracted with EtOAc (×3). The combined organic layers were washed with water, brine, dried over MgSO$_4$, filtered and concentrated under vacuum to leave a residue which was purified by column chromatography (SiO$_2$: eluted with 2:1 hexane:EtOAc) to yield the desired morpholine adduct: LCMS 482.3 [M+H]$^+$.

Step 10: Method 1:

To a stirred solution of the morpholine adduct (0.19 g, 0.38 mmol) in CH$_2$Cl$_2$ (3 ml) was added trifluoroacetic acid (3 ml, 38.9 mmol) and the mixture was stirred at room temperature for 5 h. The reaction was carefully quenched with a saturated aqueous solution of NaHCO$_3$ and extracted with DCM (×2). The combined organic layers were dried over MgSO$_4$, filtered and concentrate to leave a residue. The residue was then dissolved in DCM (2 mL) and MeOH (2 mL) followed by the addition of NH$_4$OH (2 mL) and the mixture was stirred at room temperature overnight. The reaction was quenched with water and extracted with DCM (×3). The combined organic layers were dried, filtered and concentrated to leave a residue which was purified by column (SiO$_2$: eluted with 20:1 DCM:MeOH) to yield Example 1 which was further purified by reverse phase chromatography (Analogix 55 g C18 column, gradient elution 0% to 100% MeCN in water w/0.1% TFA). LCMS 352.2 [M+H]$^+$.

Method 2:

(An alternative method for the removal of SEM group, Example 37): To a stirred solution of SEM-protected indazole (0.464 mmol) in MeOH (4.00 ml) was added HCl (4.64 ml of 4M solution in 1,4-dioxane, 18.56 mmol) followed by heating at 65° C. for 30 min. The mixture was cooled to RT and diluted with EtOAc. The resulting layer was washed with a saturated aqueous solution of NaHCO$_3$, dried over MgSO$_4$, filtered and concentrated under reduced pressure to leave a residue which was purified by flash column chromatography on silica (elution with 0-30% MeOH in EtOAc) to afford Example 37.

TABLE 1

The folowing exampleswere prepared by treating the chloropyrimidine core (Scheme A) with the appropriate amine using conditions similiar to those described in Scheme A steps 1 to 9 followed by deprotection of SEM group (Step 10).

| Ex | Structure | LRRK2 IC$_{50}$ (nM) | m/z | RT (min) | Method |
|---|---|---|---|---|---|
| 1 | 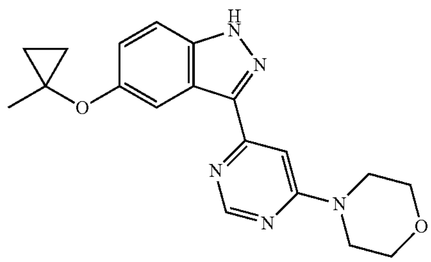 [SMILES: CC1(Oc2ccc3[nH]nc(-c4cc(N5CCOCC5)ncn4)c3c2)CC1] | 1.88 | 352.0 | 1.78 | B |
| 2 | 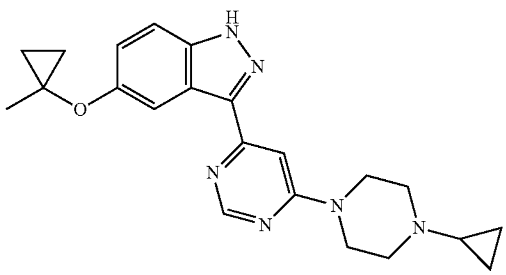 [SMILES: CC1(Oc2ccc3[nH]nc(-c4cc(N5CCN(C6CC6)CC5)ncn4)c3c2)CC1] | 2.77 | 391.0 | 1.68 | B |
| 3 | 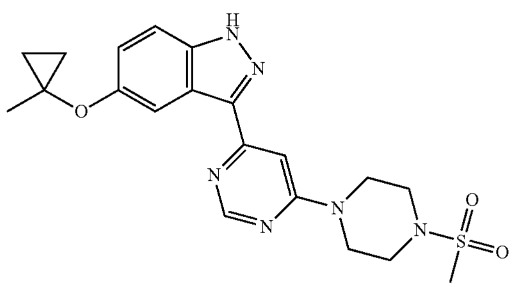 [SMILES: CC1(Oc2ccc3[nH]nc(-c4cc(N5CCN(S(C)(=O)=O)CC5)ncn4)c3c2)CC1] | 2.26 | 429.0 | 1.78 | B |
| 4 | 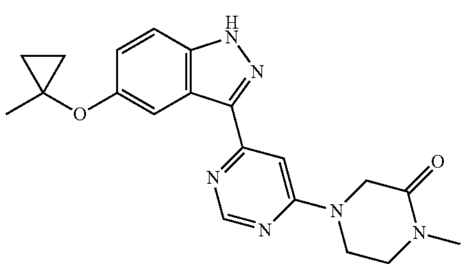 | 2.47 | 379.0 | 1.75 | B |
| 5 | 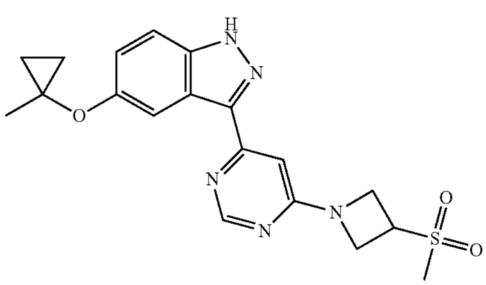 [SMILES: CC1(Oc2ccc3[nH]nc(-c4cc(N5CC(S(C)(=O)=O)C5)ncn4)c3c2)CC1] | 2.15 | 400.0 | 1.77 | B |

TABLE 1-continued

The folowing exampleswere prepared by treating the chloropyrimidine core (Scheme A) with the appropriate amine using conditions similiar to those described in Scheme A steps 1 to 9 followed by deprotection of SEM group (Step 10).

| Ex | Structure | LRRK2 IC$_{50}$ (nM) | LCMS data m/z | RT (min) | Method |
|---|---|---|---|---|---|
| 6 | 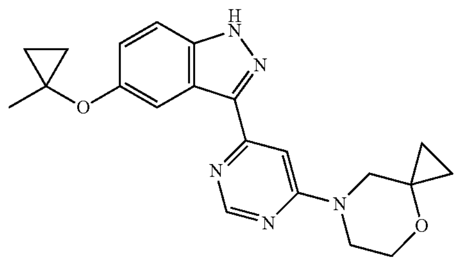 [SMILES: CC1(Oc2ccc3[nH]nc(-c4cc(N5CCOC6(CC6)C5)ncn4)c3c2)CC1] | 1.51 | 378.0 | 1.88 | B |
| 7 | 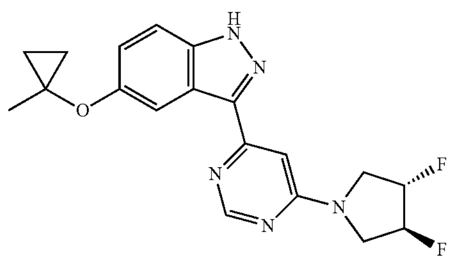 [SMILES: CC1(Oc2ccc3[nH]nc(-c4cc(N5C[C@H](F)[C@@H](F)C5)ncn4)c3c2)CC1] | 3.92 | 372.0 | 1.85 | B |
| 8 | 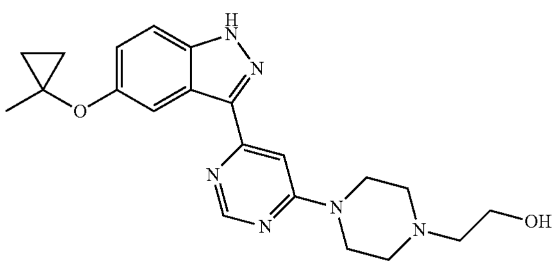 [SMILES: CC1(Oc2ccc3[nH]nc(-c4cc(N5CCN(CCO)CC5)ncn4)c3c2)CC1] | 1.17 | 395.2 | 1.68 | C1 |
| 10 | 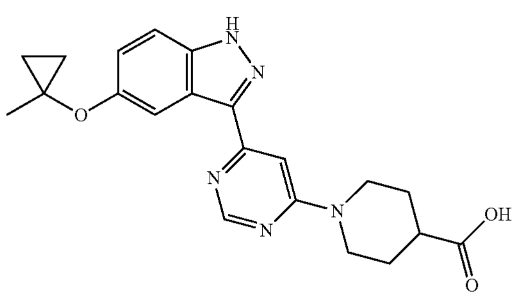 [SMILES: CC1(Oc2ccc3[nH]nc(-c4cc(N5CCC(C(=O)O)CC5)ncn4)c3c2)CC1] | 1.30 | 394.2 | 1.02 | A |
| 11 | 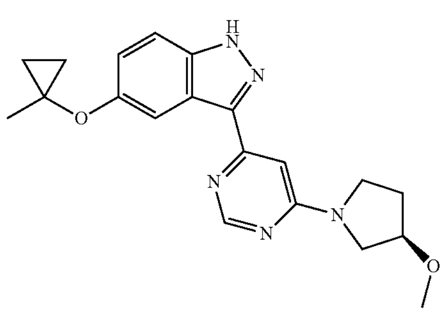 [SMILES: CO[C@@H]1CCN(c2cc(-c3n[nH]c4ccc(OC5(C)CC5)cc34)ncn2)C1] | 1.85 | 366.2 | 1.04 | A |

TABLE 1-continued

The folowing exampleswere prepared by treating the chloropyrimidine core (Scheme A) with the appropriate amine using conditions similiar to those described in Scheme A steps 1 to 9 followed by deprotection of SEM group (Step 10).

| Ex | Structure | LRRK2 IC$_{50}$ (nM) | LCMS data m/z | RT (min) | Method |
|---|---|---|---|---|---|
| 12 | 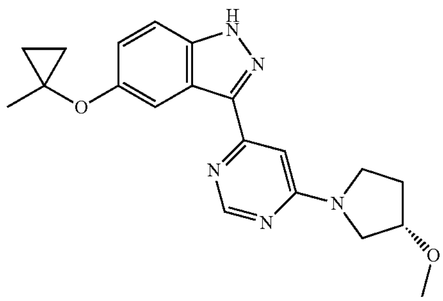 [SMILES: CO[C@H]1CCN(c2cc(-c3n[nH]c4ccc(OC5(C)CC5)cc34)ncn2)C1] | 1.42 | 366.2 | 1.03 | A |
| 13 | 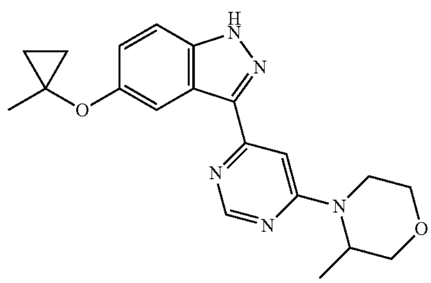 [SMILES: CC1COCCN1c1cc(-c2n[nH]c3ccc(OC4(C)CC4)cc23)ncn1] | 2.29 | 366.2 | 1.34 | C6 |
| 14 | 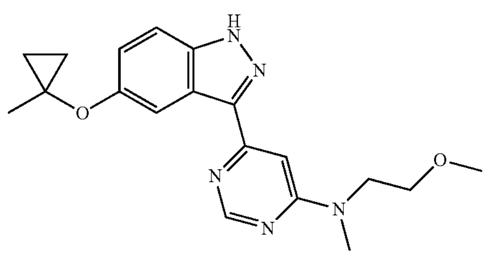 | 4.44 | 354.2 | 1.34 | C6 |
| 15 | 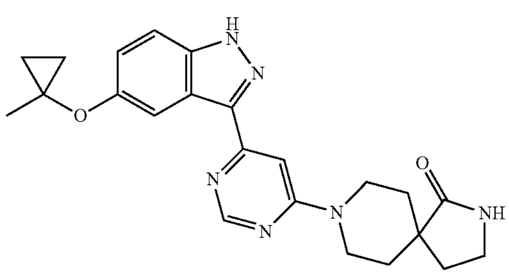 [SMILES: CC1(Oc2ccc3[nH]nc(-c4cc(N5CCC6(CCNC6=O)CC5)ncn4)c3c2)CC1] | 0.86 | 419.2, | 1.02 | A |
| 16 | 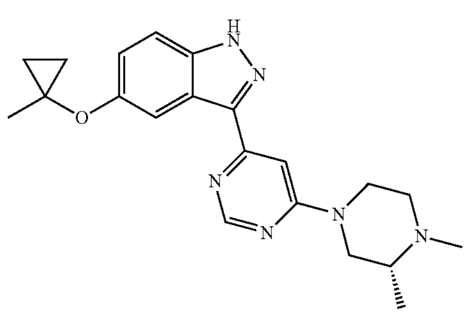 | <0.6 | 379.1 | 0.98 | A |

TABLE 1-continued

The folowing exampleswere prepared by treating the chloropyrimidine core (Scheme A) with the appropriate amine using conditions similiar to those described in Scheme A steps 1 to 9 followed by deprotection of SEM group (Step 10).

| Ex | Structure | LRRK2 IC$_{50}$ (nM) | LCMS data m/z | RT (min) | Method |
|---|---|---|---|---|---|
| 18 | 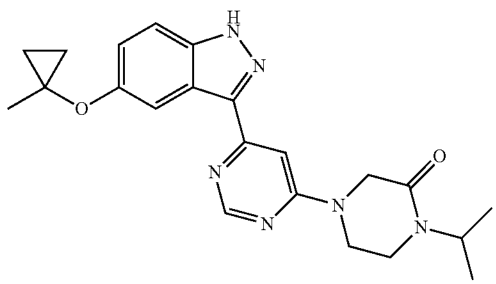 [SMILES: CC(C)N1CCN(c2cc(-c3n[nH]c4ccc(OC5(C)CC5)cc34)ncn2)CC1=O] | 1.50 | 407.2 | 1.08 | C3 |
| 19 | 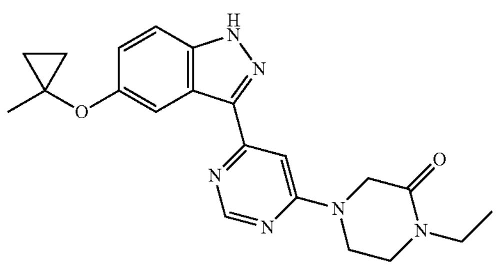 [SMILES: CCN1CCN(c2cc(-c3n[nH]c4ccc(OC5(C)CC5)cc34)ncn2)CC1=O] | 1.08 | 393.2 | 1.75 | C2 |
| 20 | 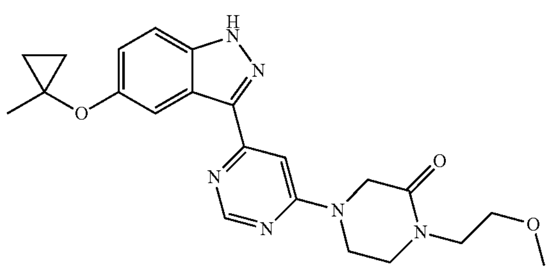 | 1.01 | 423.1 | 1.74 | C1 |
| 21 | 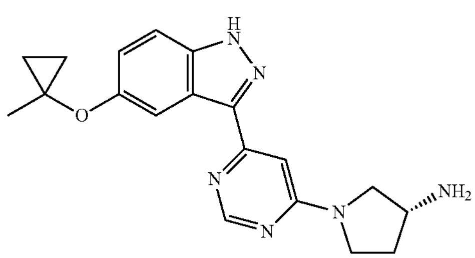 [SMILES: CC1(Oc2ccc3[nH]nc(-c4cc(N5CC[C@@H](N)C5)ncn4)c3c2)CC1] | 1.99 | 351.2 | 1.62 | C1 |
| 22 | 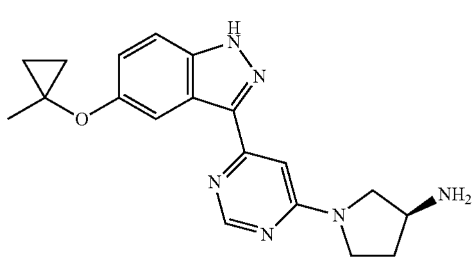 [SMILES: CC1(Oc2ccc3[nH]nc(-c4cc(N5CC[C@H](N)C5)ncn4)c3c2)CC1] | 2.19 | 351.1 | 1.69 | C1 |

TABLE 1-continued

The folowing exampleswere prepared by treating the chloropyrimidine core (Scheme A) with the appropriate amine using conditions similiar to those described in Scheme A steps 1 to 9 followed by deprotection of SEM group (Step 10).

| Ex | Structure | LRRK2 IC$_{50}$ (nM) | LCMS data m/z | RT (min) | Method |
|----|-----------|----------------------|----------------|----------|--------|
| 23 | 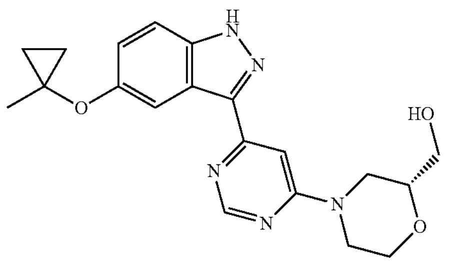 [SMILES: CC1(Oc2ccc3[nH]nc(-c4cc(N5CCO[C@@H](CO)C5)ncn4)c3c2)CC1] | 0.75 | 382.2 | 0.79 | A |
| 24 | 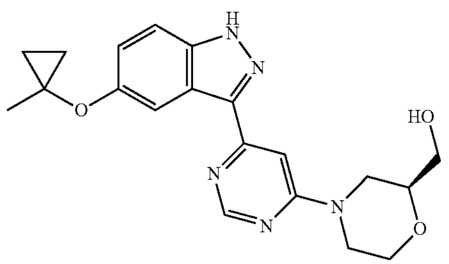 [SMILES: CC1(Oc2ccc3[nH]nc(-c4cc(N5CCO[C@H](CO)C5)ncn4)c3c2)CC1] | 0.78 | 382.1 | 0.84 | A |
| 25 | 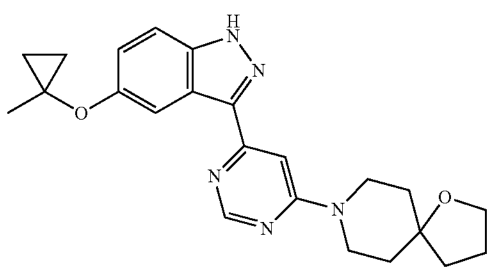 [SMILES: CC1(Oc2ccc3[nH]nc(-c4cc(N5CCC6(CCCO6)CC5)ncn4)c3c2)CC1] | 1.21 | 406.2 | 1.08 | A |
| 26 | 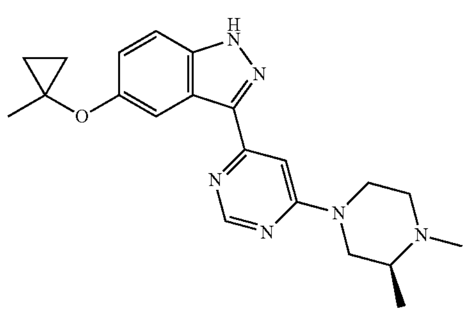 | <0.6 | 379.2 | 0.93 | A |
| 29 | 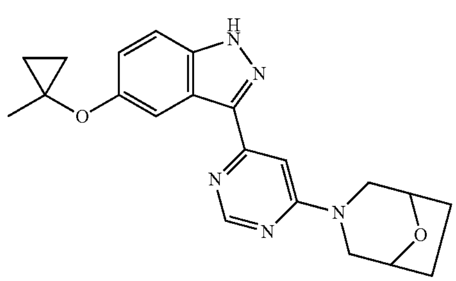 [SMILES: CC1(Oc2ccc3[nH]nc(-c4cc(N5CC6CCC(C5)O6)ncn4)c3c2)CC1] | 1.59 | 378.2 | 1.04 | A |

TABLE 1-continued

The folowing exampleswere prepared by treating the chloropyrimidine core (Scheme A) with the appropriate amine using conditions similiar to those described in Scheme A steps 1 to 9 followed by deprotection of SEM group (Step 10).

| Ex | Structure | LRRK2 IC$_{50}$ (nM) | LCMS data m/z | RT (min) | Method |
|---|---|---|---|---|---|
| 30 | 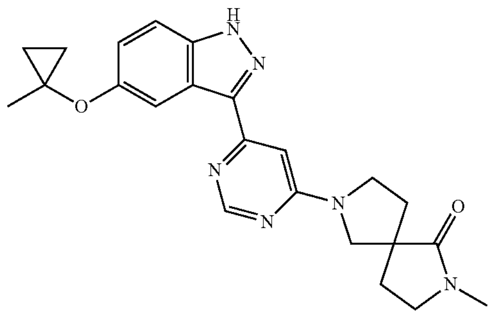 | 0.95 | 419.1 | 1.01 | A |
| 31 | 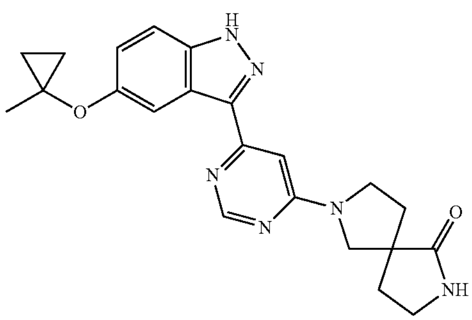 [SMILES: CC1(Oc2ccc3[nH]nc(-c4cc(N5CCC6(CCNC6=O)C5)ncn4)c3c2)CC1] | 1.29 | 405.2 | 0.96 | A |
| 32 | 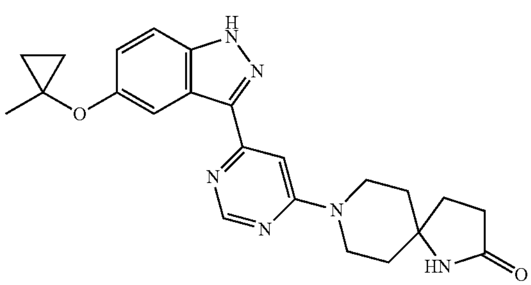 [SMILES: CC1(Oc2ccc3[nH]nc(-c4cc(N5CCC6(CCC(=O)N6)CC5)ncn4)c3c2)CC1] | 0.86 | 419.2 | 1.0 | A |
| 33 | 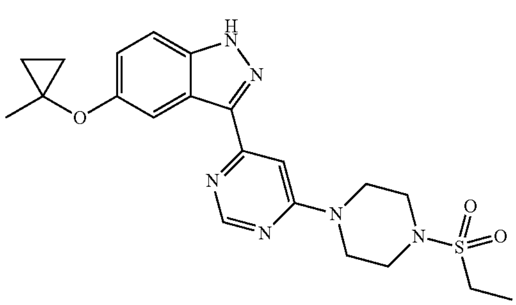 [SMILES: CCS(=O)(=O)N1CCN(c2cc(-c3n[nH]c4ccc(OC5(C)CC5)cc34)ncn2)CC1] | 0.63 | 443.2 | 1.83 | C2 |

TABLE 1-continued

The folowing exampleswere prepared by treating the chloropyrimidine core (Scheme A) with the appropriate amine using conditions similiar to those described in Scheme A steps 1 to 9 followed by deprotection of SEM group (Step 10).

| Ex | Structure | LRRK2 IC$_{50}$ (nM) | m/z | RT (min) | Method |
|----|-----------|----------------------|-----|----------|--------|
| 34 | 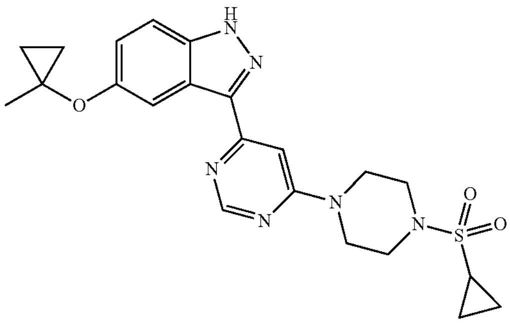 [SMILES: CC1(Oc2ccc3[nH]nc(-c4cc(N5CCN(S(=O)(=O)C6CC6)CC5)ncn4)c3c2)CC1] | 0.99 | 455.2 | 1.85 | C2 |
| 35 | 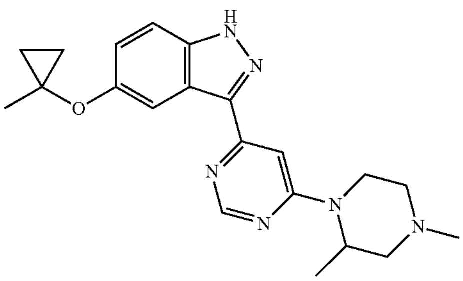 | 1.03 | 379.3 | 0.95 | A |
| 36 | 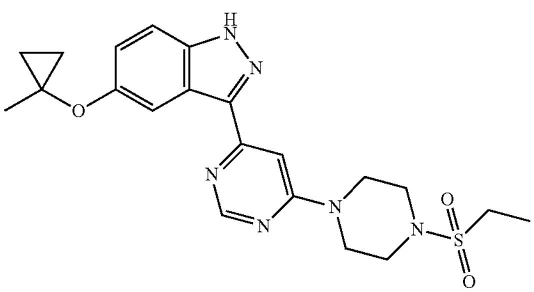 [SMILES: CCS(=O)(=O)N1CCN(c2cc(-c3n[nH]c4ccc(OC5(C)CC5)cc34)ncn2)CC1] | 0.63 | 443.2 | 1.83 | C2 |
| 37 | 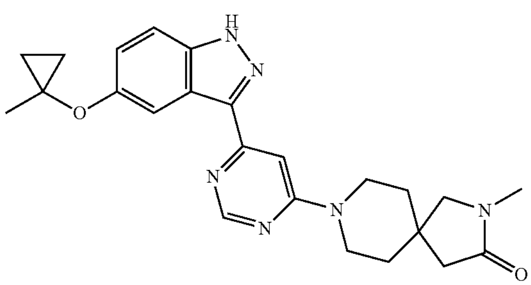 [SMILES: CN1CC2(CCN(c3cc(-c4n[nH]c5ccc(OC6(C)CC6)cc45)ncn3)CC2)CC1=O] | 0.70 | 433.3 | 1.02 | A |
| 38 | 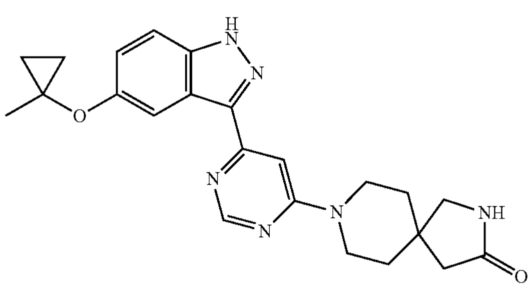 [SMILES: CC1(Oc2ccc3[nH]nc(-c4cc(N5CCC6(CC5)CNC(=O)C6)ncn4)c3c2)CC1] | <0.6 | 419.2 | 1.0 | A |

TABLE 1-continued

The folowing exampleswere prepared by treating the chloropyrimidine core (Scheme A) with the appropriate amine using conditions similiar to those described in Scheme A steps 1 to 9 followed by deprotection of SEM group (Step 10).

| Ex | Structure | LRRK2 IC$_{50}$ (nM) | m/z | RT (min) | Method |
|----|-----------|----------------------|-----|----------|--------|
| 39 | 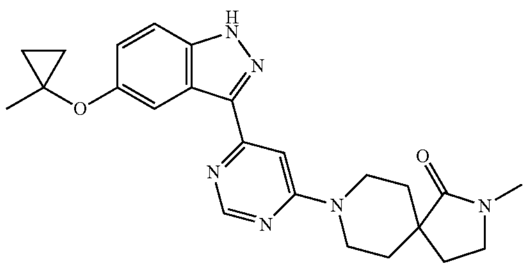 | 0.71 | 433.2 | 1.03 | A |
| 40 | 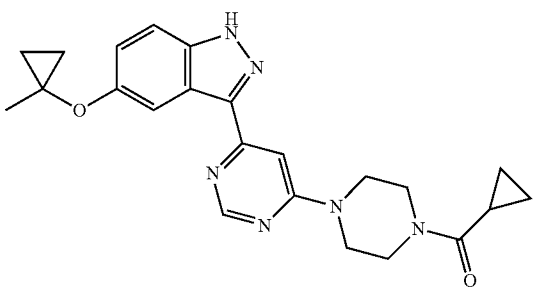 [SMILES: CC1(Oc2ccc3[nH]nc(-c4cc(N5CCN(C(=O)C6CC6)CC5)ncn4)c3c2)CC1] | 1.07 | 419.2 | 1.78 | C2 |
| 41 | 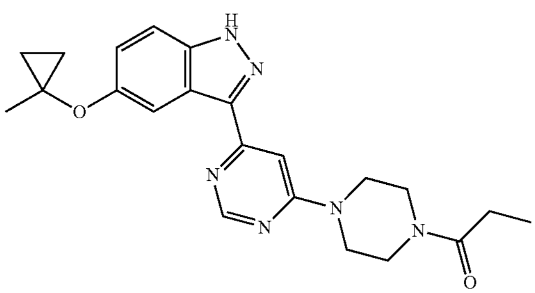 [SMILES: CCC(=O)N1CCN(c2cc(-c3n[nH]c4ccc(OC5(C)CC5)cc34)ncn2)CC1] | 0.87 | 407.3 | 1.79 | C2 |
| 42 | 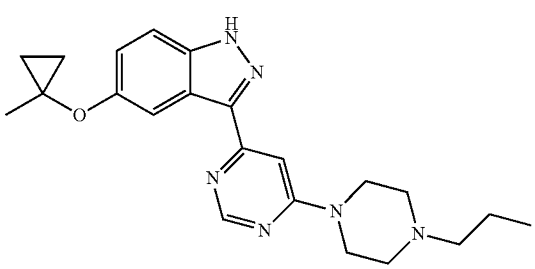 [SMILES: CCCN1CCN(c2cc(-c3n[nH]c4ccc(OC5(C)CC5)cc34)ncn2)CC1] | 1.41 | 393.1 | 2.03 | C1 |

In examples 21 and 22 the primary amines are protected with a Boc which was removed during the final SEM deprotection.

Scheme B

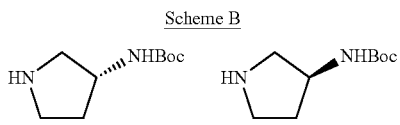

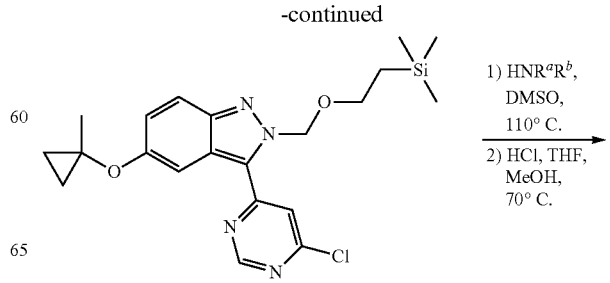

1) HNR$^a$R$^b$, DMSO, 110° C.
2) HCl, THF, MeOH, 70° C.

-continued

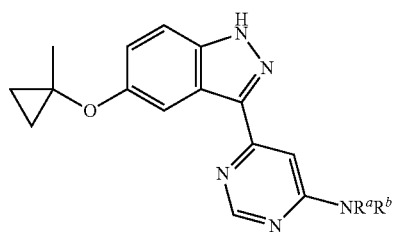

Examples 43-70

Parallel preparation of Examples 43-70: To a set of vials containing the chloropyridine from Scheme A (30 mg, 0.070 mmol) in DMSO (0.3 mL) was individually added the requisite amine (0.084 mmol) and diisopropylethylamine (0.049 mL, 0.280 mmol). The vials were capped and the mixtures were heated to 110° C. with stirring for 3 hours. The mixtures were cooled to RT. Water (2 mL) was added to each vial. The aqueous phase in each vial was extracted with DCM (2×1 mL). The organic layers from each vial were transferred to a clean vial and the solvent was removed in vacuo. To each vial was then added THF:MeOH (1:3, 1 mL) followed by HCl (4 N in dioxane, 0.20 mL, 0.80 mmol). The vials were capped and the solutions were heated to 70° C. for 0.5 h. The solutions were allowed to cool to RT and the solvent was then removed from the vials in vacuo. Each crude product was redissolved in 1 mL of DMSO and filtered. The crude products were purified by mass triggered HPLC. Example 43 was purified using the following conditions: [Waters Sunfire C18 column, 5 μm, 19×100 mm, gradient 10% to 24% MeCN (0.1% formic acid) in water (0.1% formic acid) 50 mL/min, 8 min run time] to provide the Example 43. Examples 44-70 were purified using the following conditions: [Waters XBridge C18 column, 5 μm, 19×100 mm, gradient ranges from 10-35% initial to 49-75% MeCN (0.1% NH$_4$OH) in water (0.1% NH$_4$OH) 50 mL/min, 8 min run time] to provide the Examples 44-70.

TABLE 2

Examples 43-70.

| Ex | Structure | LCMS m/z | RT (min) | Method | LRRK2 IC$_{50}$ (nM) |
|---|---|---|---|---|---|
| 43 | | 395.20 | 0.83 | D | 1.2 |
| 44 | | 350.23 | 1.14 | D | 3.1 |
| 45 | | 322.19 | 0.92 | D | 3.9 |

TABLE 2-continued
Examples 43-70.
| Ex | Structure | LCMS m/z | RT (min) | Method | LRRK2 IC$_{50}$ (nM) |
|---|---|---|---|---|---|
| 46 | 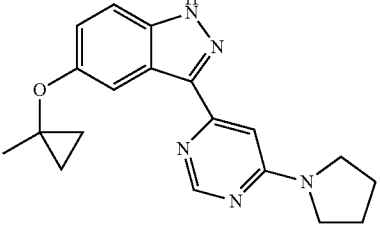 | 336.21 | 1.00 | D | 3.5 |
| 47 | 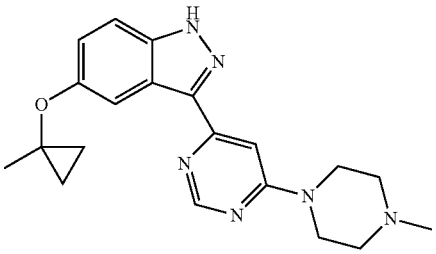 | 365.22 | 0.93 | D | 1.2 |
| 48 | 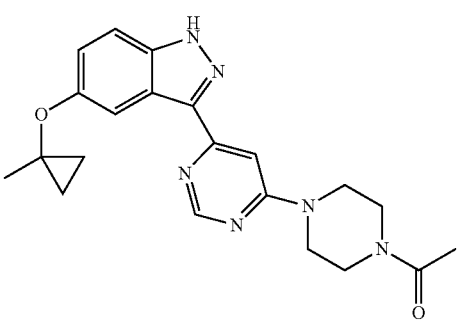 [SMILES: CC(=O)N1CCN(c2cc(-c3n[nH]c4ccc(OC5(C)CC5)cc34)ncn2)CC1] | 393.23 | 0.86 | D | 1.2 |
| 49 | 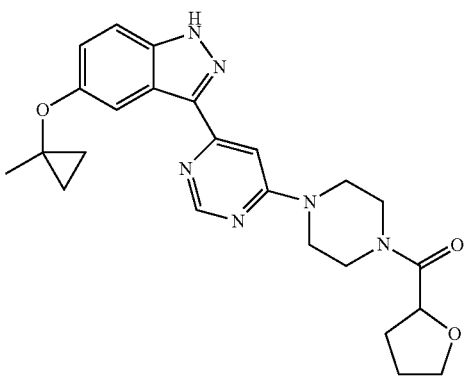 [SMILES: CC1(Oc2ccc3[nH]nc(-c4cc(N5CCN(C(=O)C6CCCO6)CC5)ncn4)c3c2)CC1] | 449.25 | 0.91 | D | 3 |
| 50 | 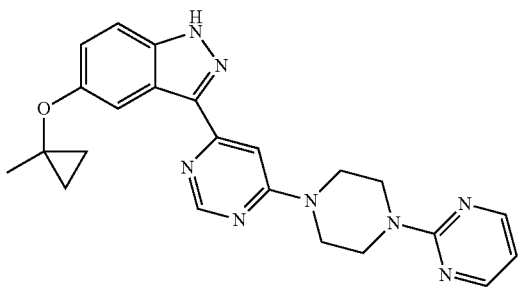 [SMILES: CC1(Oc2ccc3[nH]nc(-c4cc(N5CCN(c6ncccn6)CC5)ncn4)c3c2)CC1] | 429.25 | 1.08 | D | 4.3 |

TABLE 2-continued

Examples 43-70.

| Ex | Structure | LCMS m/z | RT (min) | Method | LRRK2 IC$_{50}$ (nM) |
|---|---|---|---|---|---|
| 51 | | 380.22 | 1.10 | D | 1 |
| 52 | | 409.22 | 0.96 | D | 1.5 |
| 53 | | 395.22 | 0.79 | D | 2.7 |
| 54 | | 380.22 | 1.10 | D | 4.6 |

TABLE 2-continued

Examples 43-70.

| Ex | Structure | LCMS m/z | RT (min) | Method | LRRK2 IC$_{50}$ (nM) |
|---|---|---|---|---|---|
| 55 | 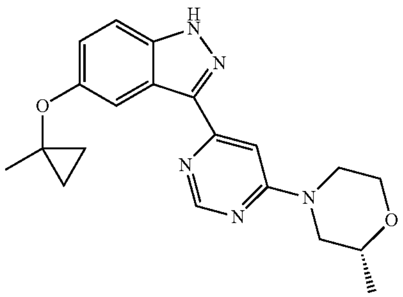 [SMILES: C[C@@H]1CN(c2cc(-c3n[nH]c4ccc(OC5(C)CC5)cc34)ncn2)CCO1] | 409.22 | 0.96 | D | 2 |
| 56 | 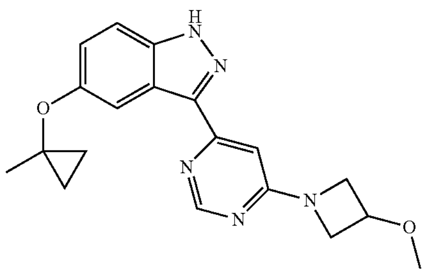 | 395.22 | 0.79 | D | 2.5 |
| 57 | 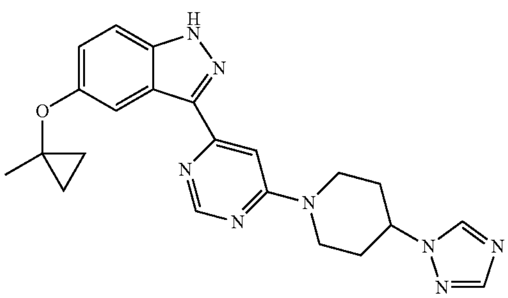 [SMILES: CC1(Oc2ccc3[nH]nc(-c4cc(N5CCC(n6cncn6)CC5)ncn4)c3c2)CC1] | 380.22 | 1.10 | D | 2.1 |
| 58 | 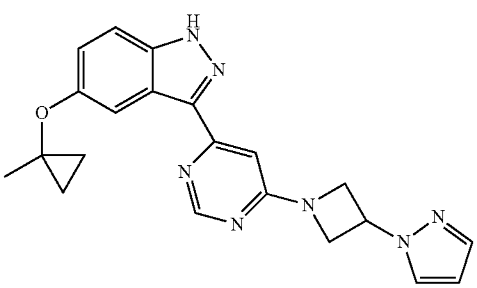 [SMILES: CC1(Oc2ccc3[nH]nc(-c4cc(N5CC(n6cccn6)C5)ncn4)c3c2)CC1] | 388.23 | 0.90 | D | 5 |
| 59 | 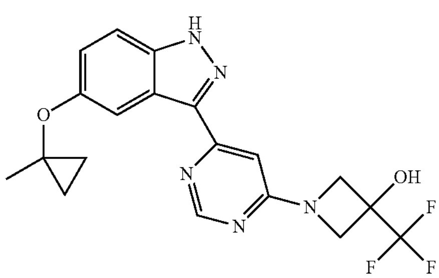 [SMILES: CC1(Oc2ccc3[nH]nc(-c4cc(N5CC(O)(C(F)(F)F)C5)ncn4)c3c2)CC1] | 406.19 | 0.96 | D | 3.3 |

TABLE 2-continued
Examples 43-70.
| Ex | Structure | LCMS m/z | RT (min) | Method | LRRK2 IC$_{50}$ (nM) |
|---|---|---|---|---|---|
| 60 | 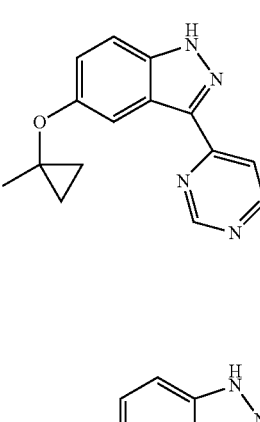 | 429.25 | 1.12 | D | 7.7 |
| 61 | | 431.26 | 0.93 | D | 1.4 |
| 62 | 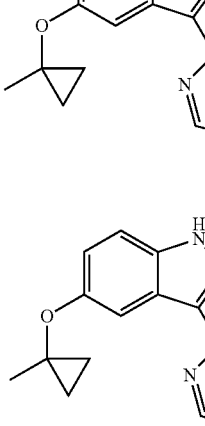 | 386.20 | 1.12 | D | 5.5 |
| 63 | 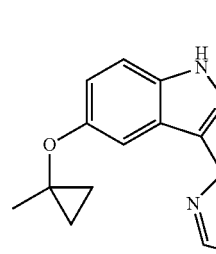 | 338.19 | 0.77 | D | 2 |
| 64 |  | 340.20 | 0.80 | D | 13.8 |

TABLE 2-continued

Examples 43-70.

| Ex | Structure | LCMS m/z | RT (min) | Method | LRRK2 IC$_{50}$ (nM) |
|---|---|---|---|---|---|
| 65 | 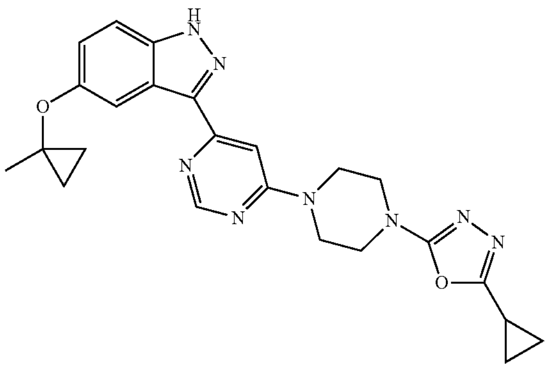 [SMILES: CC1(Oc2ccc3[nH]nc(-c4cc(N5CCN(c6nnc(C7CC7)o6)CC5)ncn4)c3c2)CC1] | 459.23 | 0.99 | D | 4.1 |
| 66 | 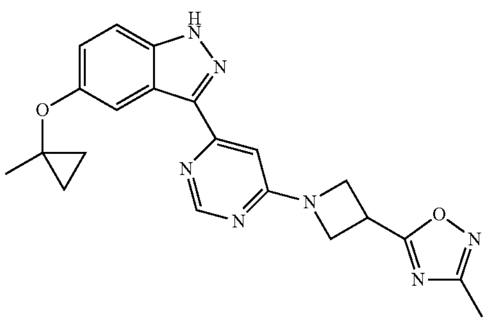 | 404.20 | 0.93 | D | 3 |
| 67 | 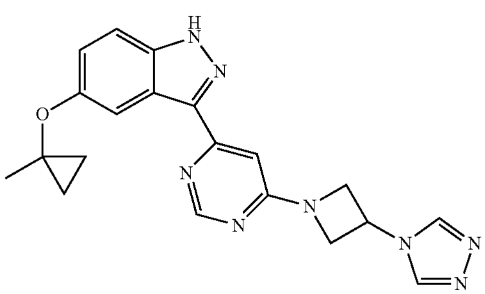 [SMILES: CC1(Oc2ccc3[nH]nc(-c4cc(N5CC(n6cnnc6)C5)ncn4)c3c2)CC1] | 389.20 | 0.80 | D | 3.3 |
| 68 | 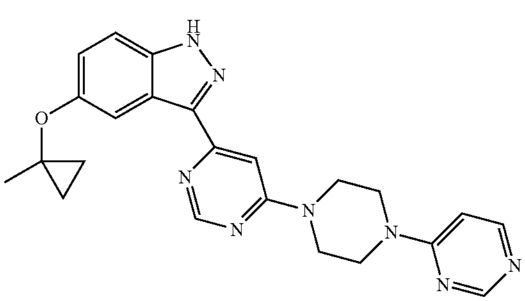 [SMILES: CC1(Oc2ccc3[nH]nc(-c4cc(N5CCN(c6ccncn6)CC5)ncn4)c3c2)CC1] | 429.26 | 0.94 | D | 3 |

TABLE 2-continued

Examples 43-70.

| Ex | Structure | LCMS m/z | RT (min) | Method | LRRK2 IC$_{50}$ (nM) |
|---|---|---|---|---|---|
| 69 | | 354.20 | 0.95 | D | 3.3 |
| 70 | | 354.20 | 0.95 | D | 2.7 |

TABLE 3

The following compounds were prepared using a procedure similiar to that described in Scheme B using the requisite amine. The crude products were purified by mass triggered HPLC [Waters Sunfire C18 column, 5 μm, 19 × 100 mm, gradient 8-15% initial to 22-65% final MeCN (0.1% formic acid) in water (0.1% formic acid) 50 mL/min, 8 min run time] to provide Example 71-90.

| Ex | Structure | LCMS m/z | RT (min) | Method | LRRK2 IC$_{50}$ (nM) |
|---|---|---|---|---|---|
| 71 | | 366.20 | 0.89 | D | 3.5 |
| 72 | | 338.20 | 1.10 | D | 18.3 |

TABLE 3-continued

The following compounds were prepared using a procedure similiar to that described in Scheme B using the requisite amine. The crude products were purified by mass triggered HPLC [Waters Sunfire C18 column, 5 μm, 19 × 100 mm, gradient 8-15% initial to 22-65% final MeCN (0.1% formic acid) in water (0.1% formic acid) 50 mL/min, 8 min run time] to provide Example 71-90.

| Ex | Structure | LCMS m/z | RT (min) | Method | LRRK2 IC$_{50}$ (nM) |
|---|---|---|---|---|---|
| 73 | | 391.20 | 1.04 | D | 1.9 |
| 74 | | 380.20 | 1.05 | D | 5.7 |
| 75 | | 393.20 | 1.08 | D | 1.6 |
| 76 | | 409.20 | 0.99 | D | 2.4 |
| 77 | | 407.20 | 0.84 | D | 6.4 |

TABLE 3-continued

The following compounds were prepared using a procedure similiar to that described in Scheme B using the requisite amine. The crude products were purified by mass triggered HPLC [Waters Sunfire C18 column, 5 μm, 19 × 100 mm, gradient 8-15% initial to 22-65% final MeCN (0.1% formic acid) in water (0.1% formic acid) 50 mL/min, 8 min run time] to provide Example 71-90.

| Ex | Structure | LCMS m/z | RT (min) | Method | LRRK2 IC$_{50}$ (nM) |
|---|---|---|---|---|---|
| 78 | | 402.20 | 0.83 | D | 2.6 |
| 79 | | 434.20 | 1.05 | D | 2.9 |
| 80 | | 416.20 | 1.01 | D | 5 |
| 81 | | 442.20 | 1.00 | D | 2.1 |

TABLE 3-continued

The following compounds were prepared using a procedure similiar to that described in Scheme B using the requisite amine. The crude products were purified by mass triggered HPLC [Waters Sunfire C18 column, 5 μm, 19 × 100 mm, gradient 8-15% initial to 22-65% final MeCN (0.1% formic acid) in water (0.1% formic acid) 50 mL/min, 8 min run time] to provide Example 71-90.

| Ex | Structure | LCMS m/z | RT (min) | Method | LRRK2 IC$_{50}$ (nM) |
|---|---|---|---|---|---|
| 82 | | 364.20 | 0.88 | D | 6.3 |
| 83 | | 429.20 | 0.96 | D | 4.2 |
| 84 | | 391.20 | 0.92 | D | 8.2 |
| 85 | | 366.20 | 1.01 | D | 5.8 |

TABLE 3-continued

The following compounds were prepared using a procedure similiar to that described in Scheme B using the requisite amine. The crude products were purified by mass triggered HPLC [Waters Sunfire C18 column, 5 µm, 19 × 100 mm, gradient 8-15% initial to 22-65% final MeCN (0.1% formic acid) in water (0.1% formic acid) 50 mL/min, 8 min run time] to provide Example 71-90.

| Ex | Structure | LCMS m/z | RT (min) | Method | LRRK2 IC$_{50}$ (nM) |
|---|---|---|---|---|---|
| 86 | 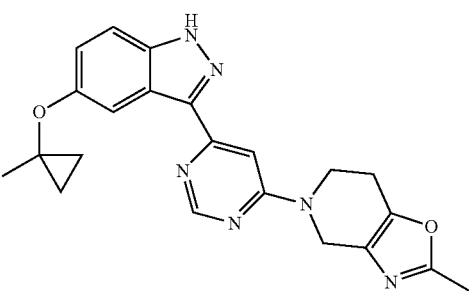 | 403.20 | 1.03 | D | 3.1 |
| 87 | 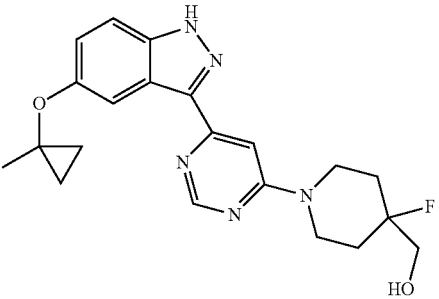 [SMILES: CC1(Oc2ccc3[nH]nc(-c4cc(N5CCC(F)(CO)CC5)ncn4)c3c2)CC1] | 398.20 | 0.91 | D | 1.9 |
| 88 | 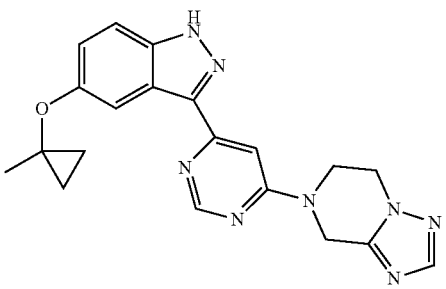 [SMILES: CC1(Oc2ccc3[nH]nc(-c4cc(N5CCn6ncnc6C5)ncn4)c3c2)CC1] | 389.20 | 0.86 | D | 3.9 |
| 89 | 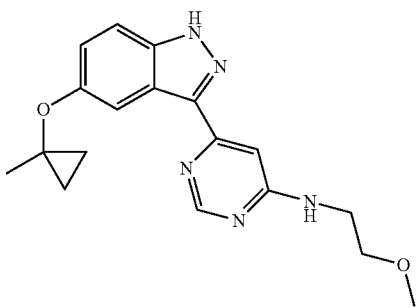 | 340.20 | 0.88 | D | 4.2 |

TABLE 3-continued

The following compounds were prepared using a procedure similiar to that described in Scheme B using the requisite amine. The crude products were purified by mass triggered HPLC [Waters Sunfire C18 column, 5 μm, 19 × 100 mm, gradient 8-15% initial to 22-65% final MeCN (0.1% formic acid) in water (0.1% formic acid) 50 mL/min, 8 min run time] to provide Example 71-90.

| Ex | Structure | LCMS m/z | RT (min) | Method | LRRK2 IC$_{50}$ (nM) |
|---|---|---|---|---|---|
| 90 | 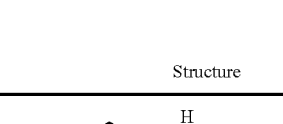 | 326.20 | 0.75 | D | 6.3 |

TABLE 4

The following compounds were prepared using a procedure similiar to that described in Scheme B. The crude products were purified by mass triggered HPLC [Waters Sunfire C18 column, 5 μm, 19 × 100 mm, initial gradient 5-25% to 30-60% MeCN (0.1% formic acid) in water (0.1% formic acid) 25 mL/min, 8 min run time] to provide Examples 91-116. Example 117 was purified using the following condition: [Waters XBridge C18 column, 5 μm, 19 × 100 mm, gradient range from 30%-65% MeCN (0.1% NH$_4$OH) in water (0.1% NH$_4$OH) 25 mL/min, 8 min run time] to provide Example 117.

| Example | Structure | LCMS data m/z | Ret time (min) | method | LRRK2 IC$_{50}$ (nM) |
|---|---|---|---|---|---|
| 91 | 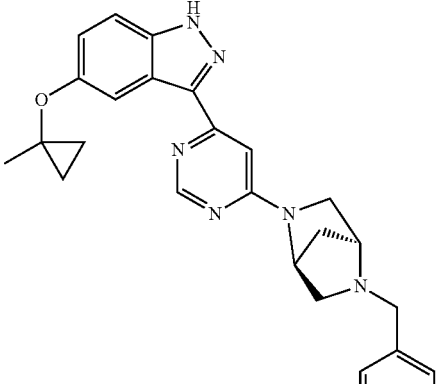 | 453.23 | 1.14 | D | 5.8 |
| 92 | 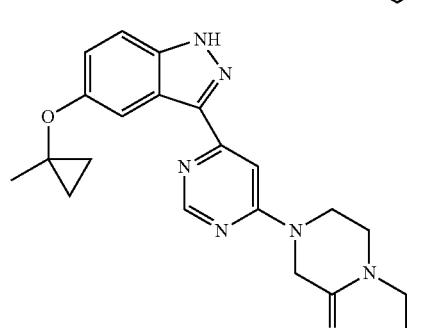 | 419.21 | 0.98 | D | 1.5 |

TABLE 4-continued

The following compounds were prepared using a procedure similiar to that described in Scheme B. The crude products were purified by mass triggered HPLC [Waters Sunfire C18 column, 5 μm, 19 × 100 mm, initial gradient 5-25% to 30-60% MeCN (0.1% formic acid) in water (0.1% formic acid) 25 mL/min, 8 min run time] to provide Examples 91-116. Example 117 was purified using the following condition: [Waters XBridge C18 column, 5 μm, 19 × 100 mm, gradient range from 30%-65% MeCN (0.1% NH$_4$OH) in water (0.1% NH$_4$OH) 25 mL/min, 8 min run time] to provide Example 117.

| Example | Structure | m/z | Ret time (min) | method | LRRK2 IC$_{50}$ (nM) |
|---|---|---|---|---|---|
| 93 | | 409.19 | 0.82 | D | 1.3 |
| 94 | | 423.21 | 0.85 | D | 1.6 |
| 95 | | 428.20 | 1.21 | D | 6 |
| 96 | | 423.21 | 0.87 | D | 2 |

TABLE 4-continued

The following compounds were prepared using a procedure similiar to that described in Scheme B. The crude products were purified by mass triggered HPLC [Waters Sunfire C18 column, 5 μm, 19 × 100 mm, initial gradient 5-25% to 30-60% MeCN (0.1% formic acid) in water (0.1% formic acid) 25 mL/min, 8 min run time] to provide Examples 91-116. Example 117 was purified using the following condition: [Waters XBridge C18 column, 5 μm, 19 × 100 mm, gradient range from 30%-65% MeCN (0.1% NH$_4$OH) in water (0.1% NH$_4$OH) 25 mL/min, 8 min run time] to provide Example 117.

| Example | Structure | LCMS data m/z | Ret time (min) | method | LRRK2 IC$_{50}$ (nM) |
|---|---|---|---|---|---|
| 97 | 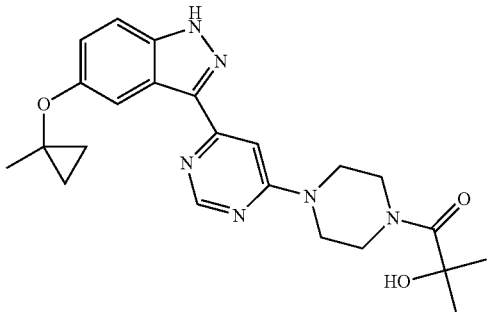 [SMILES: CC1(Oc2ccc3[nH]nc(-c4cc(N5CCN(C(=O)C(C)(C)O)CC5)ncn4)c3c2)CC1] | 437.22 | 0.90 | D | 1.1 |
| 98 | 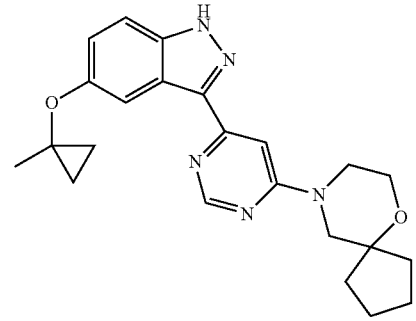 [SMILES: CC1(Oc2ccc3[nH]nc(-c4cc(N5CCOC6(CCCC6)C5)ncn4)c3c2)CC1] | 406.22 | 1.17 | D | 1.6 |
| 99 | 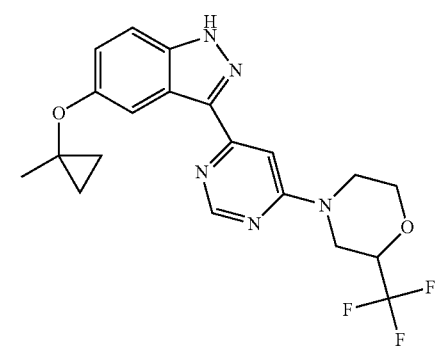 [SMILES: CC1(Oc2ccc3[nH]nc(-c4cc(N5CCOC(C(F)(F)F)C5)ncn4)c3c2)CC1] | 420.16 | 1.15 | D | 3.2 |
| 100 | 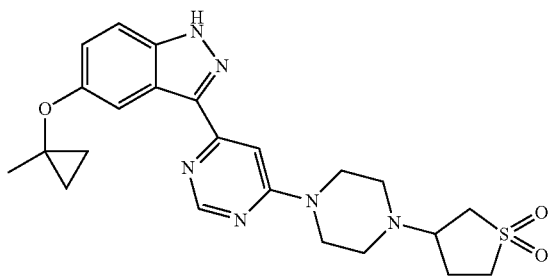 [SMILES: CC1(Oc2ccc3[nH]nc(-c4cc(N5CCN(C6CCS(=O)(=O)C6)CC5)ncn4)c3c2)CC1] | 469.19 | 0.88 | D | 0.8 |

TABLE 4-continued

The following compounds were prepared using a procedure similiar to that described in Scheme B. The crude products were purified by mass triggered HPLC [Waters Sunfire C18 column, 5 μm, 19 × 100 mm, initial gradient 5-25% to 30-60% MeCN (0.1% formic acid) in water (0.1% formic acid) 25 mL/min, 8 min run time] to provide Examples 91-116. Example 117 was purified using the following condition: [Waters XBridge C18 column, 5 μm, 19 × 100 mm, gradient range from 30%-65% MeCN (0.1% NH$_4$OH) in water (0.1% NH$_4$OH) 25 mL/min, 8 min run time] to provide Example 117.

| Example | Structure | LCMS data m/z | Ret time (min) | method | LRRK2 IC$_{50}$ (nM) |
|---|---|---|---|---|---|
| 101 | | 458.21 | 1.20 | D | 2.8 |
| 102 | | 485.20 | 1.09 | D | 5.5 |
| 103 | | 378.18 | 0.99 | D | 2.2 |
| 104 | | 447.24 | 1.09 | D | 1.2 |

TABLE 4-continued

The following compounds were prepared using a procedure similiar to that described in Scheme B. The crude products were purified by mass triggered HPLC [Waters Sunfire C18 column, 5 μm, 19 × 100 mm, initial gradient 5-25% to 30-60% MeCN (0.1% formic acid) in water (0.1% formic acid) 25 mL/min, 8 min run time] to provide Examples 91-116. Example 117 was purified using the following condition: [Waters XBridge C18 column, 5 μm, 19 × 100 mm, gradient range from 30%-65% MeCN (0.1% NH$_4$OH) in water (0.1% NH$_4$OH) 25 mL/min, 8 min run time] to provide Example 117.

| Example | Structure | LCMS data m/z | Ret time (min) | method | LRRK2 IC$_{50}$ (nM) |
|---|---|---|---|---|---|
| 105 | | 396.20 | 0.99 | D | 0.8 |
| 106 | | 408.23 | 1.24 | D | 6.6 |
| 107 | | 380.20 | 1.05 | D | 39.1 |
| 108 | | 377.20 | 0.86 | D | 10.3 |

TABLE 4-continued

The following compounds were prepared using a procedure similiar to that described in Scheme B. The crude products were purified by mass triggered HPLC [Waters Sunfire C18 column, 5 μm, 19 × 100 mm, initial gradient 5-25% to 30-60% MeCN (0.1% formic acid) in water (0.1% formic acid) 25 mL/min, 8 min run time] to provide Examples 91-116. Example 117 was purified using the following condition: [Waters XBridge C18 column, 5 μm, 19 × 100 mm, gradient range from 30%-65% MeCN (0.1% NH$_4$OH) in water (0.1% NH$_4$OH) 25 mL/min, 8 min run time] to provide Example 117.

| Example | Structure | LCMS data m/z | Ret time (min) | method | LRRK2 IC$_{50}$ (nM) |
|---|---|---|---|---|---|
| 109 | 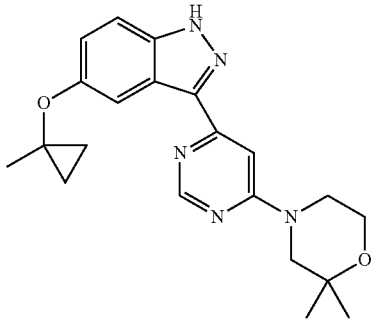 [SMILES: CC1(C)CN(c2cc(-c3n[nH]c4ccc(OC5(C)CC5)cc34)ncn2)CCO1] | 380.20 | 1.06 | D | 1.8 |
| 110 | 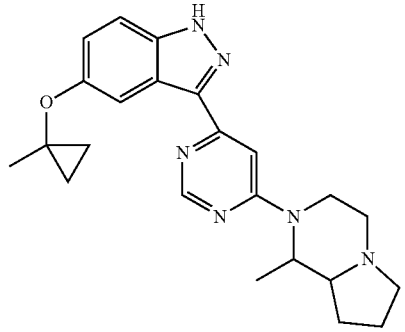 [SMILES: CC1C2CCCN2CCN1c1cc(-c2n[nH]c3ccc(OC4(C)CC4)cc23)ncn1] | 405.23 | 1.13 | D | 2.8 |
| 111 | 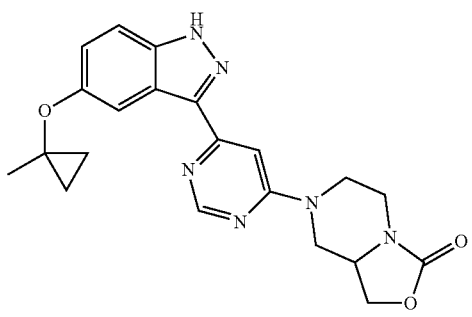 [SMILES: CC1(Oc2ccc3[nH]nc(-c4cc(N5CCN6C(=O)OCC6C5)ncn4)c3c2)CC1] | 407.17 | 0.90 | D | 1.6 |
| 112 | 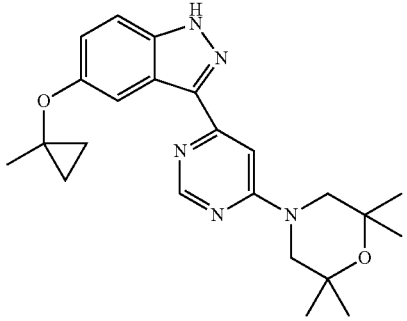 | 408.23 | 1.19 | D | 6.8 |

TABLE 4-continued

The following compounds were prepared using a procedure similiar to that described in Scheme B. The crude products were purified by mass triggered HPLC [Waters Sunfire C18 column, 5 μm, 19 × 100 mm, initial gradient 5-25% to 30-60% MeCN (0.1% formic acid) in water (0.1% formic acid) 25 mL/min, 8 min run time] to provide Examples 91-116. Example 117 was purified using the following condition: [Waters XBridge C18 column, 5 μm, 19 × 100 mm, gradient range from 30%-65% MeCN (0.1% NH$_4$OH) in water (0.1% NH$_4$OH) 25 mL/min, 8 min run time] to provide Example 117.

| Example | Structure | LCMS data m/z | Ret time (min) | method | LRRK2 IC$_{50}$ (nM) |
|---|---|---|---|---|---|
| 113 | | 435.21 | 0.85 | D | 0.9 |
| 114 | | 423.21 | 1.06 | D | 2.1 |
| 115 | | 435.24 | 1.04 | D | 0.7 |
| 116 | | 366.18 | 1.02 | D | 3.3 |

TABLE 4-continued

The following compounds were prepared using a procedure similiar to that described in Scheme B. The crude products were purified by mass triggered HPLC [Waters Sunfire C18 column, 5 μm, 19 × 100 mm, initial gradient 5-25% to 30-60% MeCN (0.1% formic acid) in water (0.1% formic acid) 25 mL/min, 8 min run time] to provide Examples 91-116. Example 117 was purified using the following condition: [Waters XBridge C18 column, 5 μm, 19 × 100 mm, gradient range from 30%-65% MeCN (0.1% NH₄OH) in water (0.1% NH₄OH) 25 mL/min, 8 min run time] to provide Example 117.

| Example | Structure | LCMS data m/z | Ret time (min) | method | LRRK2 IC$_{50}$ (nM) |
|---|---|---|---|---|---|
| 117 | 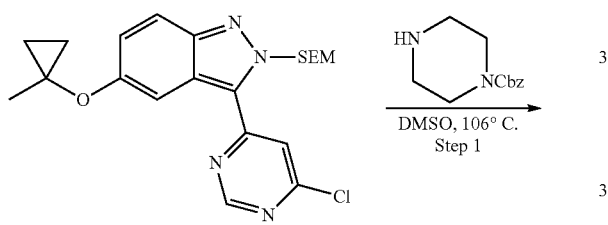 | 366.18 | 1.01 | D | 2.2 |

Scheme C:

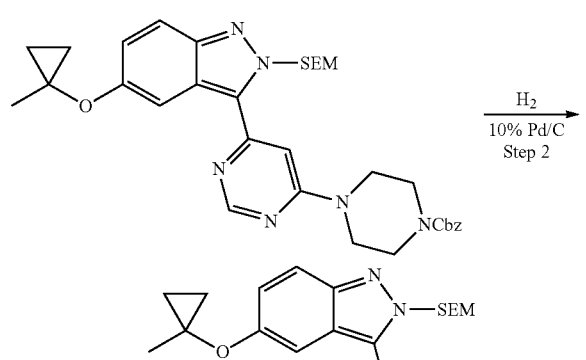

Step 1:
To a stirred solution of the chloropyrimidine from Scheme A (2.0 g, 4.64 mmol) in DMSO (23.20 ml) were added Et₃N (3.23 ml, 23.20 mmol) and benzyl piperizine-1-carboxylate (2.04 g, 9.28 mmol). The mixture was then heated in a sealed vial at 106° C. for 60 h. The mixture was cooled to room temperature and diluted with water (300 mL). The layer was then extracted with EtOAc (×3). The combined organic layers were dried over MgSO₄, filtered, and concentrated under vacuum to leave a residue which was purified by column chromatography on silica gel (elution with 2:1 hexane:EtOAc) to yield the desired product. LCMS 614.97 [M+H]⁺.

Step 2:
To a stirred solution of Cbz-piperazine adduct (2.7 g, 4.39 mmol) in MeOH (14 mL) and THF (1 mL) was added 10% Pd/C (0.47 g, 0.44 mmol) and the mixture was evacuated and backfilled with H₂ (×2). After being stirred overnight under H₂ atmosphere at room temperature, the mixture was filtered through a pad of silica. The filtrate was concentrated to leave a residue which was purified by column chromatography on silica gel (elution with 4:1 DCM:MeOH) to yield the desired amine. LCMS 481.31 [M+H]⁺.

The following two intermediates were prepared utilizing the same sequence of steps from Scheme C using the appropriately substituted methyl piperazine in step 1.

Figure 1:

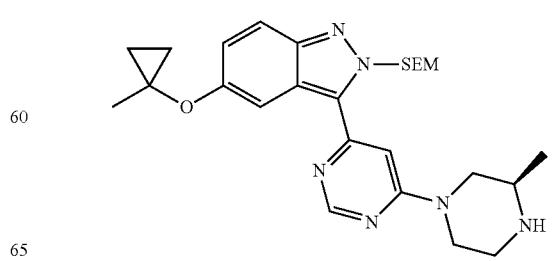

83

-continued

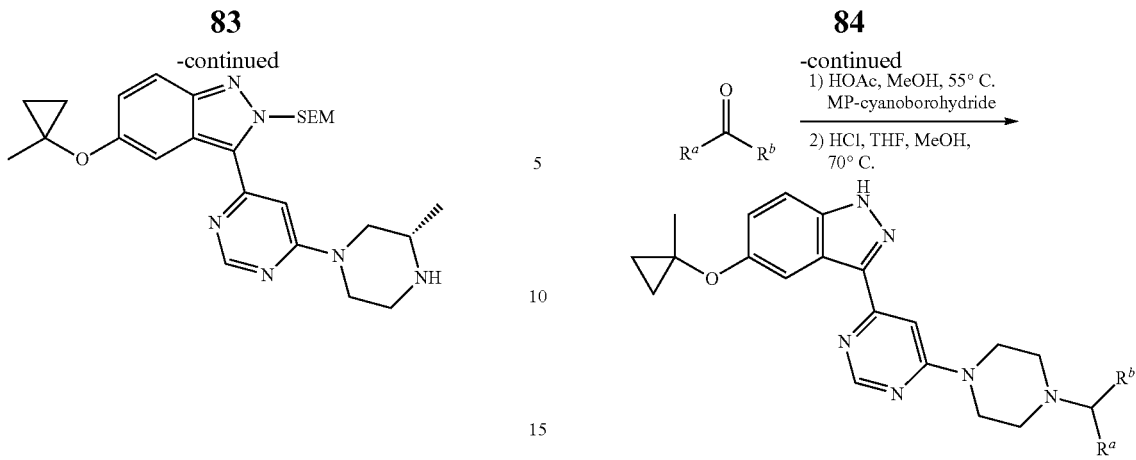

Scheme D:

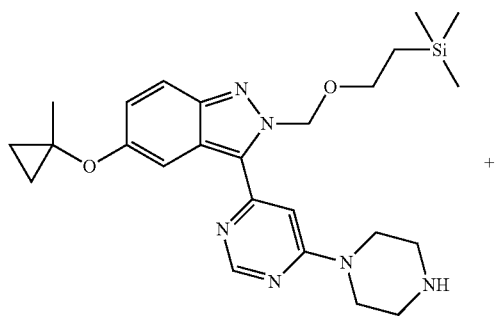

+

84

-continued
1) HOAc, MeOH, 55° C.
   MP-cyanoborohydride
2) HCl, THF, MeOH,
   70° C.

Example 118-127

Parallel preparation of Examples 118-127: To a set of vials containing a solution of the piperazine from Scheme C (25 mg, 0.052 mmol) in MeOH (1 mL) was added the requesite ketone or aldehyde (0.52 mmol) and acetic acid (0.012 mL, 0.21 mmol). The solutions were shaken at RT for 10 min. To each of the vials was added MP-cyanoborohydride (Biotage) (48 mg, 0.10 mmol) and the mixtures were heated at 55° C. for 1 hour. The solutions were removed by pipette and transferred to a new set of vials. The solvent was removed in vacuo. To each vial was then added THF:MeOH (1:3, 1 mL) followed by HCl (4 N in dioxane, 0.20 mL, 0.80 mmol). The vials were capped and the solutions were heated to 70° C. for 0.5 h. The solutions were allowed to cool to RT and the solvent was then removed in vacuo. Each crude product was redissolved in 1 mL of DMSO and filtered. The crude products were purified by mass triggered HPLC using the following conditions: [Waters XBridge C18 column, 5 μm, 19×100 mm, gradient ranges from 21-51% initial to 56-86% MeCN (0.1% NH$_4$OH) in water (0.1% NH$_4$OH) 25 mL/min, 8 min run time] to provide Examples 118-127.

TABLE 5

Parallel preparation of Examples 118-127.

| | | LCMS data | | | LRRK2 |
| --- | --- | --- | --- | --- | --- |
| Example | Structure | m/z | Ret time (min) | method | IC$_{50}$ (nM) |
| 118 | | 431.51 | 1.08 | D | 1.7 |

TABLE 5-continued
Parallel preparation of Examples 118-127.
| Example | Structure | LCMS data m/z | Ret time (min) | method | LRRK2 IC$_{50}$ (nM) |
|---|---|---|---|---|---|
| 119 | 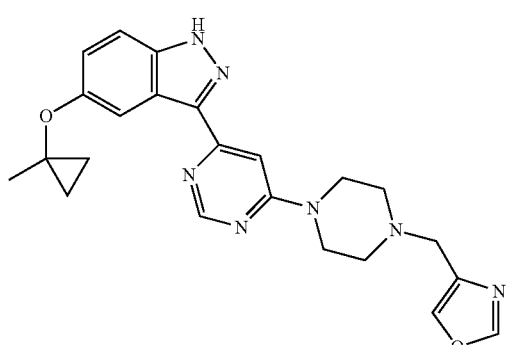 | 432.50 | 0.90 | D | 1.9 |
| 120 | 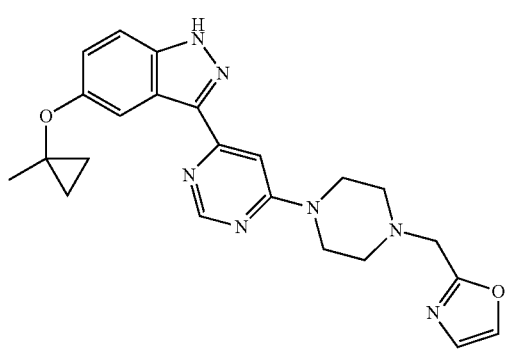 [SMILES: CC1(Oc2ccc3[nH]nc(-c4cc(N5CCN(Cc6ncco6)CC5)ncn4)c3c2)CC1] | 432.5 | 0.92 | D | 1.2 |
| 121 | 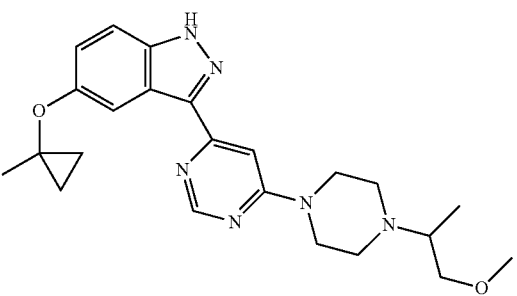 | 423.53 | 1.02 | D | 1.1 |
| 122 | 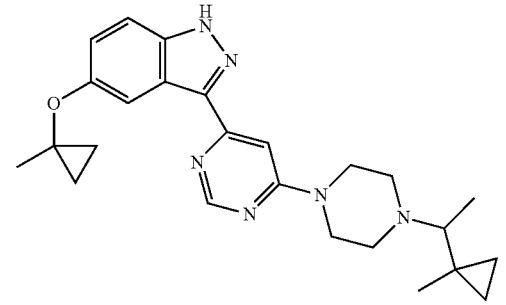 [SMILES: CC(N1CCN(c2cc(-c3n[nH]c4ccc(OC5(C)CC5)cc34)ncn2)CC1)C1(C)CC1] | 433.57 | 1.28 | D | 2.8 |

TABLE 5-continued

Parallel preparation of Examples 118-127.

| Example | Structure | LCMS data m/z | Ret time (min) | method | LRRK2 IC$_{50}$ (nM) |
|---|---|---|---|---|---|
| 123 | | 433.57 | 1.31 | D | 1.1 |
| 124 | | 429.49 | 1.11 | D | 0.9 |
| 125 | | 433.57 | 1.26 | D | 1 |

TABLE 5-continued

Parallel preparation of Examples 118-127.

| Example | Structure | LCMS data m/z | Ret time (min) | method | LRRK2 IC$_{50}$ (nM) |
|---|---|---|---|---|---|
| 126 | | 379.48 | 0.99 | D | 1.9 |
| 127 | | 447.48 | 1.12 | D | 1 |

Scheme E:

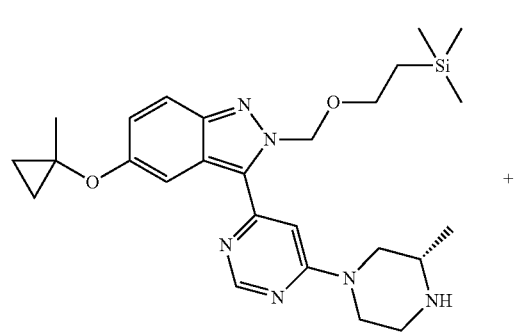

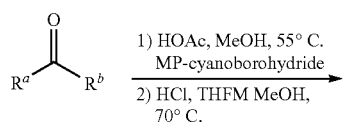

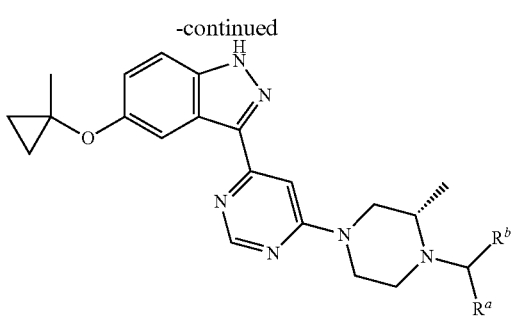

Examples 128-135

Examples 128-135 were prepared using a procedure similar to that described in Scheme D starting with the appropriate piperazine from FIG. 1 and the requisite amine. The crude products were purified by mass triggered HPLC using the following conditions: [Waters XBridge C18 column, 5 μm, 19×100 mm, gradient ranges from 23-50% initial to 58-85% MeCN (0.1% NH$_4$OH) in water (0.1% NH$_4$OH) 25 mL/min, 8 min run time] to provide the Examples 128-135.

TABLE 6

Parallel preparation of Examples 128-135

| Example | Structure | LCMS data | | | LRRK2 |
| | | m/z | Ret time (min) | method | IC$_{50}$ (nM) |
| --- | --- | --- | --- | --- | --- |
| 128 | | 445.54 | 1.11 | D | 0.7 |
| 129 | | 446.53 | 0.96 | D | 0.6 |
| 130 | | 446.53 | 0.94 | D | 0.7 |
| 131 | | 437.56 | 1.08 | D | 0.6 |

TABLE 6-continued
Parallel preparation of Examples 128-135
| Example | Structure | LCMS data m/z | Ret time (min) | method | LRRK2 IC$_{50}$ (nM) |
|---|---|---|---|---|---|
| 132 | 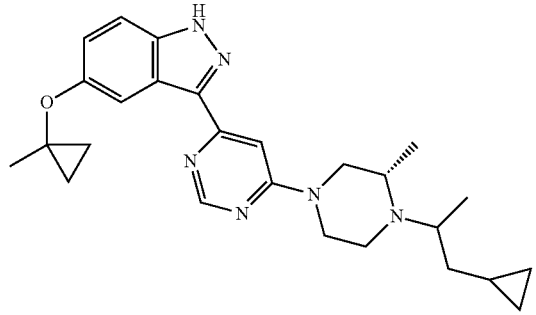 [SMILES: CC(CC1CC1)N1CCN(c2cc(-c3n[nH]c4ccc(OC5(C)CC5)cc34)ncn2)C[C@@H]1C] | 447.60 | 1.34 | D | 1.5 |
| 133 | 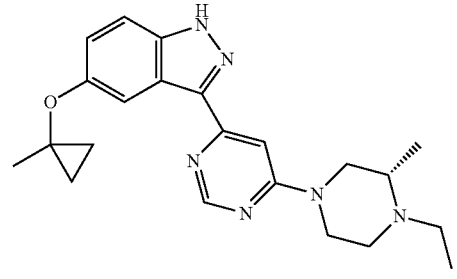 [SMILES: CCN1CCN(c2cc(-c3n[nH]c4ccc(OC5(C)CC5)cc34)ncn2)C[C@@H]1C] | 393.51 | 1.03 | D | 0.6 |
| 134 | 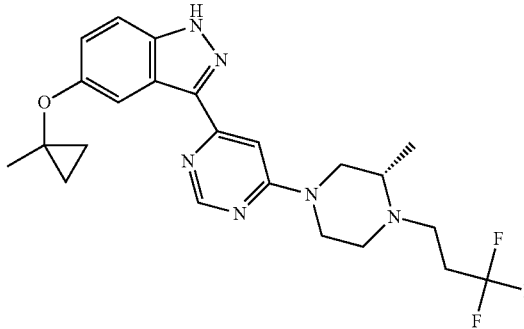 | 461.51 | 1.16 | D | 0.8 |
| 135 | 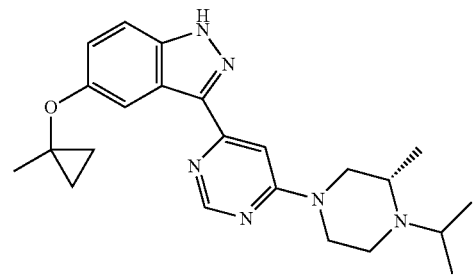 [SMILES: CC(C)N1CCN(c2cc(-c3n[nH]c4ccc(OC5(C)CC5)cc34)ncn2)C[C@@H]1C] | 407.54 | 1.11 | D | 1.5 |

Scheme F:

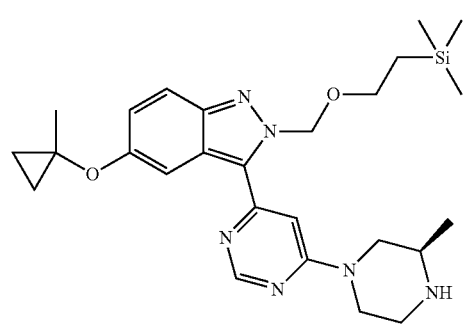

+

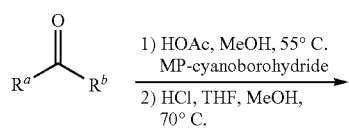

1) HOAc, MeOH, 55° C.
MP-cyanoborohydride
2) HCl, THF, MeOH, 70° C.

→

-continued

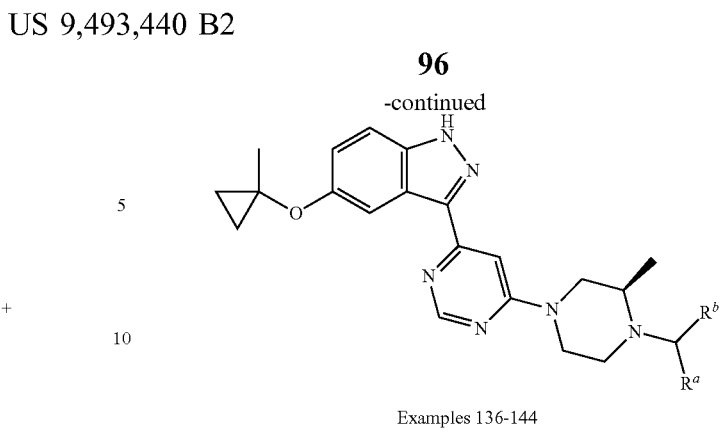

Examples 136-144

Examples 136-144 were prepared using a procedure similar to that described in Scheme D using the appropriate piperazine from FIG. 1 and the requisite amine. The crude products were purified by mass triggered HPLC using the following conditions: [Waters XBridge C18 column, 5 μm, 19×100 mm, gradient ranges from 10-25% initial to 85-95% MeCN (0.1% NH$_4$OH) in water (0.1% NH$_4$OH) 50 mL/min, 8 min run time] to provide the Examples 136-144.

TABLE 7

Parallel preparation of Examples 136-144.

| Example | Structure | LCMS data m/z | Ret time (min) | method | LRRK2 IC$_{50}$ (nM) |
|---|---|---|---|---|---|
| 136 | 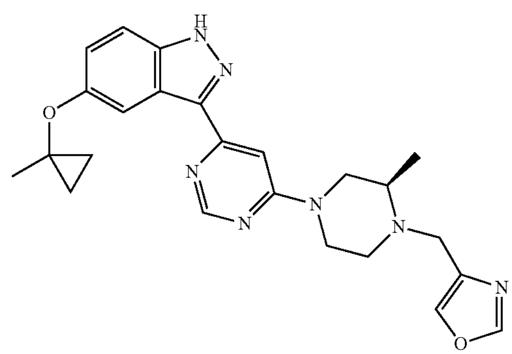 [SMILES: C[C@@H]1CN(c2cc(-c3n[nH]c4ccc(OC5(C)CC5)cc34)ncn2)CCN1Cc1cocn1] | 446.53 | 0.93 | D | 0.7 |
| 137 | 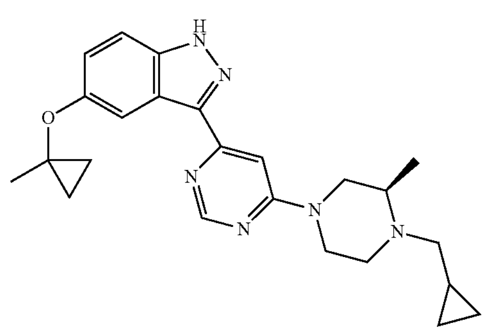 [SMILES: C[C@@H]1CN(c2cc(-c3n[nH]c4ccc(OC5(C)CC5)cc34)ncn2)CCN1CC1CC1] | 419.55 | 1.11 | D | 1.7 |

TABLE 7-continued

Parallel preparation of Examples 136-144.

| Example | Structure | LCMS data m/z | Ret time (min) | method | LRRK2 IC$_{50}$ (nM) |
|---|---|---|---|---|---|
| 138 | | 423.53 | 0.98 | D | 2.3 |
| 139 | | 437.56 | 1.07 | D | 0.6 |
| 140 | | 443.52 | 1.15 | D | 1.8 |
| 141 | | 447.60 | 1.32 | D | 2.5 |
| 142 | | 393.51 | 1.02 | D | 0.8 |

TABLE 7-continued

Parallel preparation of Examples 136-144.

| Example | Structure | LCMS data m/z | Ret time (min) | method | LRRK2 IC$_{50}$ (nM) |
|---|---|---|---|---|---|
| 143 | 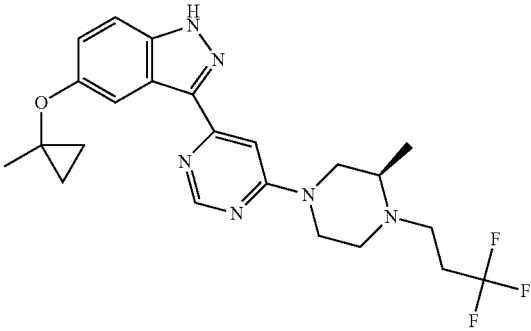 [SMILES: C[C@@H]1CN(c2cc(-c3n[nH]c4ccc(OC5(C)CC5)cc34)ncn2)CCN1CCC(F)(F)F] | 461.51 | 1.15 | D | 0.9 |
| 144 | 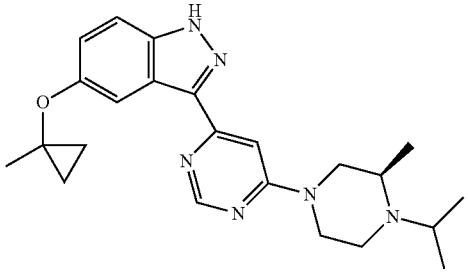 [SMILES: CC(C)N1CCN(c2cc(-c3n[nH]c4ccc(OC5(C)CC5)cc34)ncn2)C[C@H]1C] | 407.54 | 1.10 | D | 0.8 |

Scheme G:

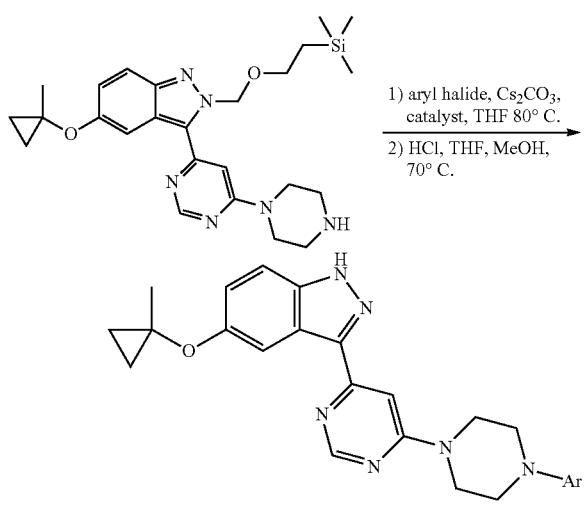

Examples 145-148

Parallel preparation of Examples 145-148: To a set of vials individually containing requisite aryl chloride or bromide (0.063 mmol) and Cs$_2$CO$_3$ (51 mg, 0.16 mmol) was added a solution of the piperazine from Scheme C (25 mg, 0.052 mmol) in THF (1 mL). The vials were capped and transferred to a glove box under an atmosphere of nitrogen. To each vial was added chloro(2-dicyclohexylphosphino-2', 6'-di-i-propoxy-1,1'-biphenyl)[2-(2-aminoethylphenyl)]palladium(II), methyl-t-butylether adduct (Strem) (2.1 mg, 0.0026 mmol). The vials were capped and heated at 80° C. overnight. The vials were cooled to RT and removed from the glove box. To each vial was added water. The mixtures were extracted with CH$_2$Cl$_2$ and the organic layers were transferred into a new set of vials. The organic layers were dried in vacuo. To each vial was then added THF:MeOH (1:3, 1 mL) followed by HCl (4 N in dioxane, 0.20 mL, 0.80 mmol). The vials were capped and the solutions were heated to 70° C. for 0.5 h. The solutions were allowed to cool to RT and the solvent was then removed in vacuo. Each crude product was redissolved in 1 mL of DMSO and filtered. The crude products were purified by mass triggered HPLC. Examples 145-146 were purified using the following conditions: [Waters Sunfire C18 column, 5 µm, 19×100 mm, gradient 10% to 60% MeCN (0.1% formic acid) in water (0.1% formic acid) 50 mL/min, 8 min run time] Examples 147-148 were purified using the following conditions: [Waters XBridge C18 column, 5 µm, 19×100 mm, gradient ranges from 10% initial to 70-76% MeCN (0.1% NH$_4$OH) in water (0.1% NH$_4$OH) 50 mL/min, 8 min run time].

TABLE 8

Parallel preparation of Examples 145-148.

| Example | Structure | LCMS data m/z | Ret time (min) | method | LRRK2 IC$_{50}$ (nM) |
|---------|-----------|-----|---------|--------|------|
| 145 | | 435.16 | 0.98 | D | 1.5 |
| 146 | | 454.20 | 1.04 | D | 1.8 |
| 147 | | 486.25 | 1.00 | D | 1.5 |
| 148 | | 443.22 | 1.11 | D | 1.9 |

Scheme H:

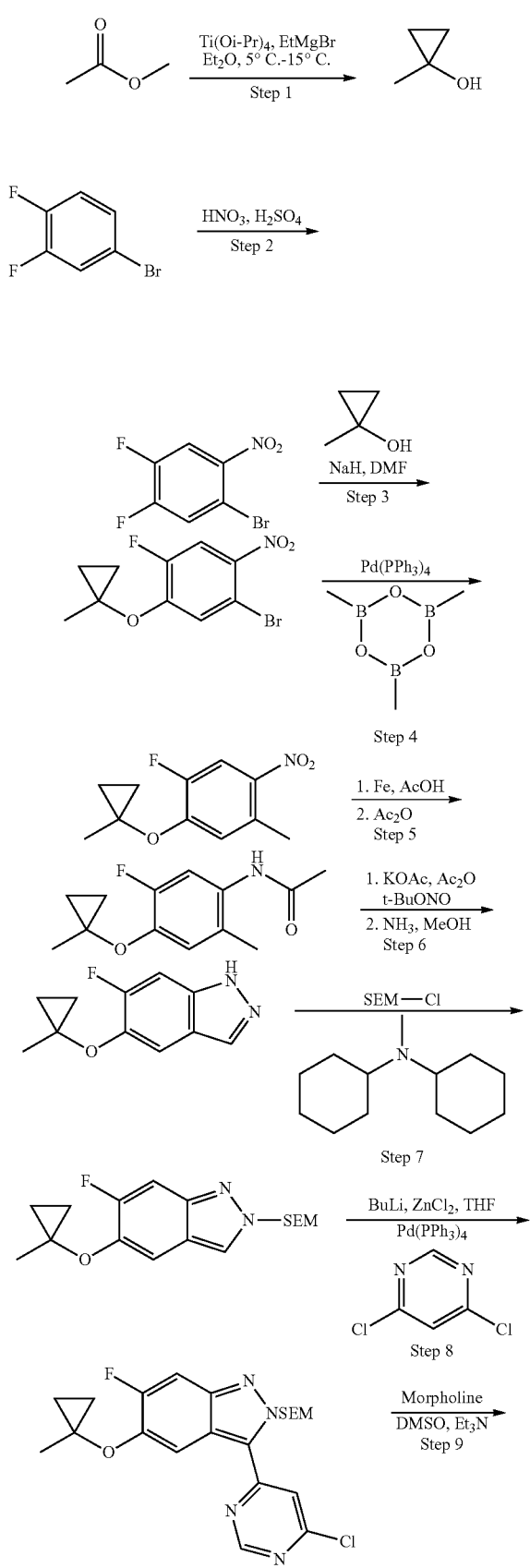

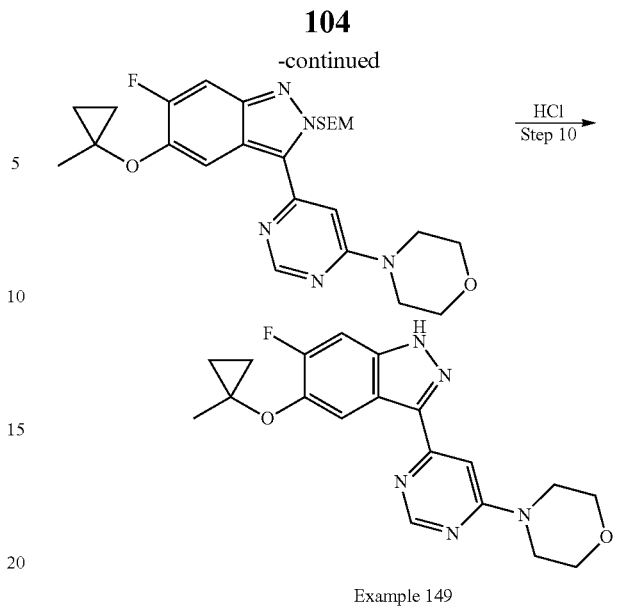

Example 149

Step 1:

To an ice-cooled solution of methyl acetate (55 mL, 69 mmol) and (i-PrO)$_4$Ti (21 mL, 71 mmol) in Et$_2$O (900 mL) was added a solution of EtMgBr in Et$_2$O (3.0 M, 500 mL, 1.5 mol) dropwise. After the addition, the reaction mixture was stirred at 5-15° C. for a further 1 h, and then quenched by pouring into a cold H$_2$SO$_4$ aqueous (9%, 1.1 L). The organic layer was separated and the aqueous was extracted with Et$_2$O (3×400 mL). The combined organic layers were washed with water (2×400 mL), and brine (2×400 mL), dried over Na$_2$SO$_4$ and filtered. The volatiles were distilled off under atmospheric pressure to afford the alcohol as the fraction collected at 105° C. GCMS: MS=72.1.

Step 2:

To a stirred solution of fuming HNO$_3$ (60 mL) and conc. H$_2$SO$_4$ (250 mL) was added compound 4-bromo-1,2-difluorobenzene (28 mL, 0.248 mol) dropwise while the temperature was kept <30° C. The mixture was stirred at room temperature for 2 h. The reaction was quenched by pouring into ice/water (1.2 L), followed by extraction with EtOAc (3×400 mL). The combined organic layers were washed with water (2×400 mL), and brine (2×400 mL), dried over Na$_2$SO$_4$ and filtered to afford the product. GCMS: MS=236.9

Step 3:

To an ice-cooled solution of 1-methylcyclopropanol (17 g, 236 mmol) and 1-bromo-4,5-difluoro-2-nitrobenzene (40 g, 168 mmol) in DMF (200 mL) was added NaH (60% in oil, 10 g, 250 mmol) portionwise. The mixture was stirred at room temperature for 3 h, quenched with water (600 mL), adjusted to pH 7-8 with H$_2$SO$_4$ (10%) and extracted with EtOAc (3×300 mL). The combined organic layers were washed with water (2×300 mL), and brine (300 mL), dried over Na$_2$SO$_4$, and evaporated. The residue was purified with flash chromatography (SiO$_2$: eluted with PE/EtOAc=20/1). The product was obtained as yellow solid. MS (ESI): m/z=292.0 [M+H]$^+$.

Step 4:

The bromide from step 3 (42.5 g, 146.6 mmol), 2,4,6-trimethyl-1,3,5,2,4,6-trioxatriborinane (50% w/w in THF, 45 mL, 161.6 mmol), Pd(PPh$_3$)$_4$ (4.00 g, 3.46 mmol), K$_2$CO$_3$ (40.0 g, 290 mmol) and Cs$_2$CO$_3$ (48.0 g, 147 mmol) were taken up into a mixture of dioxane (600 mL) and water (60 mL). After being degassed and recharged with argon, the mixture was heated at 90° C. overnight. The mixture was then filtered. The filtrate was concentrated, and diluted with EtOAc (600 mL) and the layers were separated. The organic phase was washed with water (300 mL), and brine (300 mL), dried over Na$_2$SO$_4$, filtered and concentrated under reduced pressure to leave a residue was purified via flash chromatography (elution with petroleum ether:EtOAc 10:1) to afford the product. MS (ESI): m/z=226.1 [M+H]$^+$.

Step 5:

To a stirred solution of the nitro compound (26.5 g, 118 mmol) in AcOH (200 mL) was added iron powder (32 g, 571 mmol) portionwise. The reaction mixture was stirred for 1 h, and evaporated under reduced pressure. The residue was suspended in EtOAc (500 mL), and then filtered. The filtrate was evaporated to afford the crude aniline. MS (ESI): m/z=196.2 [M+1]$^+$.

To an ice-cooled solution of the above aniline (24 g, crude, 118 mmol) and TEA (33 mL, 237 mmol) in DCM (200 mL) was added Ac$_2$O (14 mL, 148.5 mmol) dropwise. The mixture was stirred at room temperature for 3 h. The reaction mixture was washed with H$_2$O (100 mL). The DCM layer was dried over Na$_2$SO$_4$, filtered and evaporated to obtain the crude product.

Step 6:

To a stirred solution of the acetamide from step 5 (30 g, crude, 118 mmol) in toluene (400 mL) was added KOAc (20 g, 204 mmol) and Ac$_2$O (35 ml, 371 mmol). The mixture was heated to 60° C., after which time tert-butyl nitrite (42 mL, 354 mmol) was added dropwise and the resulting mixture was heated at 60° C. overnight. The reaction mixture was cooled to room temperature and washed with brine (2×100 mL). The organic layer was then dried over Na$_2$SO$_4$, filtered and evaporated. The residue was purified with flash chromatography (SiO$_2$:gradient elution:Petroleum ether: EtOAc=20:1-4:1) to afford the acyl indazole. MS (ESI): m/z=249.1 [M+1]$^+$.

To a stirred suspension of the above material (15 g, 60.5 mmol) in MeOH (60 mL) was added a solution of NH$_3$ in MeOH (60 mL of 7M solution in MeOH) and the mixture was stirred at room temperature for 1 h. The reaction mixture was concentrated to leave the crude indazole which was used in the next step without further purification. MS (ESI): m/z=207.1 [M+1]$^+$.

Step 7:

To a solution of the indazole from step 6 (16 g, 60.5 mmol) and N,N-dicyclohexyl methylamine (23 ml, 108.5 mmol) in THF (200 mL) was added SEMCl (16 mL, 90.5 mmol) dropwise. The resulting mixture was stirred at room temperature overnight. The reaction mixture was then washed with H$_2$O (100 mL) and brine (100 mL). The organic layer was dried over Na$_2$SO$_4$, filtered and concentrated under reduced pressure to leave a residue which was purified by flash chromatography (SiO$_2$:gradient elution petroleum ether:EtOAc 100:1-4:1) to afford the product. MS (ESI): m/z=337.2 [M+1]$^+$.

Step 8:

To a cold (−65° C.), stirred solution of the SEM protected indazole from step 7 (18.4 g, 54.8 mmol) in THF (300 mL) was added n-BuLi (1.6M in hexane, 70 mL, 112 mmol). The mixture was then slowly warmed to −30° C., recooled to −65° C. again and stirred at −65° C. for 2 h. To the mixture was added ZnCl$_2$ (110 mL of 1M solution in Et$_2$O, 110 mmol) at −65° C., and the mixture and stirred for 1 h. The reaction was then warmed to −20° C. A suspension of 4,6-dichloropyrimidine (10 g, 67.1 mmol) and Pd(PPh$_3$)$_4$ (3 g, 2.6 mmol) in THF (50 mL) was added to the mixture by syringe. The resulting mixture was stirred at room temperature overnight. After that time, the mixture was washed with brine (2×100 mL). The organic layer was then dried over Na$_2$SO$_4$, filtered and concentrated under reduced pressure to leave a residue which was purified by flash chromatography (SiO$_2$: Petroleum ether:EtOAc 50:1-50:3) to afford the desired chloropyrimidine adduct. MS (ESI): m/z=449.1 [M+1]$^+$.

Step 9:

A solution of the chloropyrimidine (100 mg, 0.22 mmol), morpholine (150 mg, 1.7 mmol) in DMSO (2 mL) was stirred at 100° C. overnight. To the reaction mixture was added H$_2$O (50 mL), extracted with EtOAc (3×20 mL). The combined organic layers were dried over Na$_2$SO$_4$, filtered and concentrated under reduced pressure to afford a residue which was used in the next step without further purification. MS (ESI): m/z=500.1 [[M+1]$^+$.

To a solution of the crude material (180 mg, 0.22 mmol) in MeOH (6 mL) was added HCl (1.5 ml of 3.5M solution in 1,4-dioxane). The resultant mixture was stirred at 60° C. for 0.5 h. The mixture was then concentrated in vacuo. The residue was partitioned between EtOAc (15 mL) and K$_2$CO$_3$ aq. (10%, 15 mL). The aq. layer was extracted with EtOAc (3×15 mL). The combined organic layers were washed with water (30 mL), dried over Na$_2$SO$_4$, filtered and concentrated under reduced pressure to leave a residue which purified by flash chromatography (SiO$_2$:gradient elution petroleum ether:EtOAc 1:1-2:1) to afford Example 149.

TABLE 9

The following examples were prepared from the chloropyrimidine core in Scheme H using the appropriate amine using conditions similiar to those described in Scheme H step 9.

| | | LRRK2 | LCMS data | | |
| --- | --- | --- | --- | --- | --- |
| Ex | Structure | IC$_{50}$ (nM) | m/z | RT (min) | Method |
| 149 | 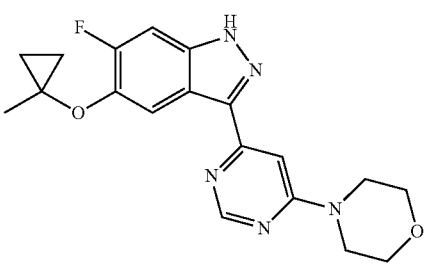 [SMILES: CC1(Oc2cc3c(-c4cc(N5CCOCC5)ncn4)n[nH]c3cc2F)CC1] | 0.71 | 370.2 | 1.87 | C2 |

TABLE 9-continued

The following examples were prepared from the chloropyrimidine core in Scheme H using the appropriate amine using conditions similiar to those described in Scheme H step 9.

| Ex | Structure | LRRK2 IC$_{50}$ (nM) | m/z | RT (min) | Method |
|---|---|---|---|---|---|
| 150 | 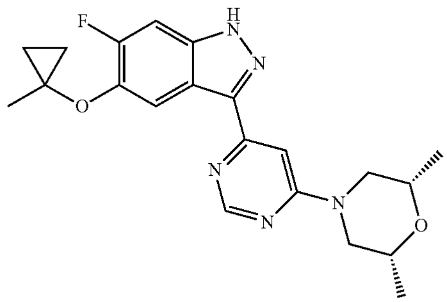 | 0.79 | 398.2 | 2.03 | C2 |
| 151 | 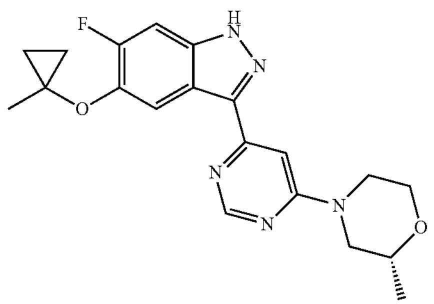 [SMILES: C[C@@H]1CN(c2cc(-c3n[nH]c4cc(F)c(OC5(C)CC5)cc34)ncn2)CCO1] | <0.6 | 384.2 | 1.95 | C2 |
| 152 | 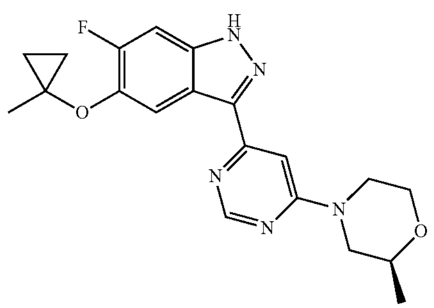 [SMILES: C[C@H]1CN(c2cc(-c3n[nH]c4cc(F)c(OC5(C)CC5)cc34)ncn2)CCO1] | 1.33 | 384.2 | 1.93 | C2 |
| 153 | 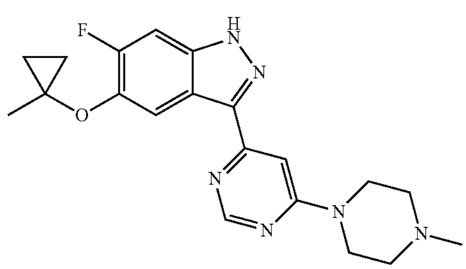 | <0.6 | 329.2 | 1.42 | C2 |
| 154 | 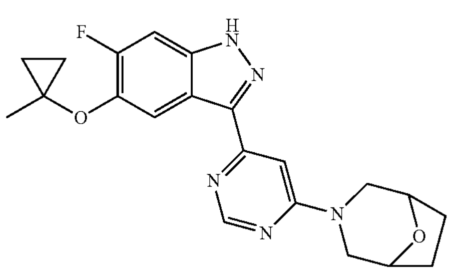 [SMILES: CC1(Oc2cc3c(-c4cc(N5CC6CCC(C5)O6)ncn4)n[nH]c3cc2F)CC1] | 1.93 | 396.2 | 1.92 | C2 |

TABLE 9-continued

The following examples were prepared from the chloropyrimidine core in Scheme H using the appropriate amine using conditions similiar to those described in Scheme H step 9.

| Ex | Structure | LRRK2 IC$_{50}$ (nM) | m/z | RT (min) | Method |
|---|---|---|---|---|---|
| 155 | 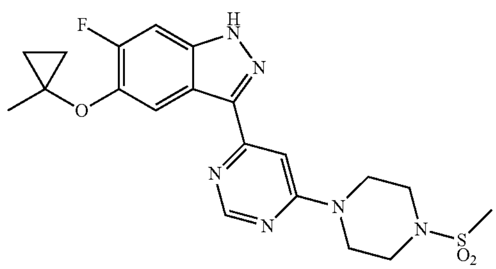 | <0.6 | 447.1 | 1.86 | C2 |
| 156 | 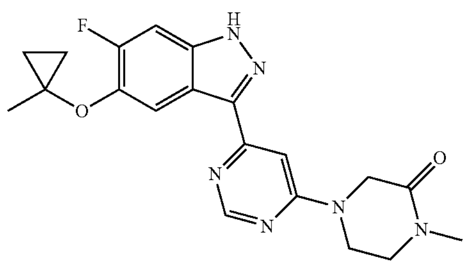 | <0.6 | 397.2 | 1.75 | C2 |
| 157 | 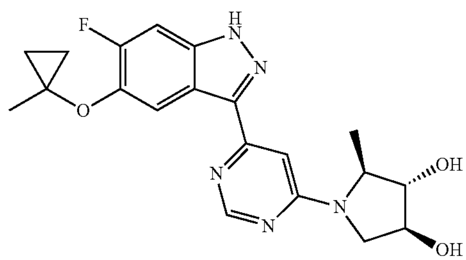 [SMILES: C[C@H]1[C@H](O)[C@@H](O)CN1c1cc(-c2n[nH]c3cc(F)c(OC4(C)CC4)cc23)ncn1] | 1.31 | 400.1 | 1.56 | C4 |
| 158 | 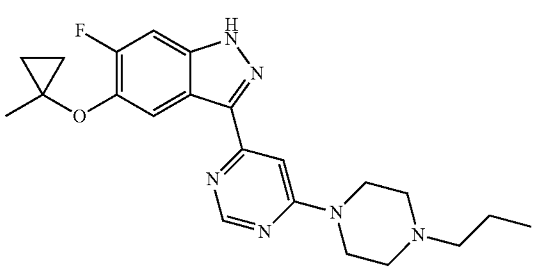 [SMILES: CCCN1CCN(c2cc(-c3n[nH]c4cc(F)c(OC5(C)CC5)cc34)ncn2)CC1] | 1.03 | 411.2 | 2.06 | C2 |
| 159 | 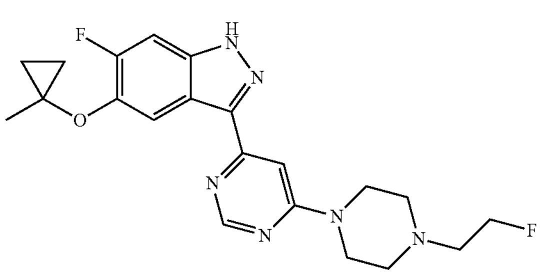 [SMILES: CC1(Oc2cc3c(-c4cc(N5CCN(CCF)CC5)ncn4)n[nH]c3cc2F)CC1] | 0.67 | 415.3 | 1.90 | C2 |

TABLE 9-continued

The following examples were prepared from the chloropyrimidine core in Scheme H using the appropriate amine using conditions similiar to those described in Scheme H step 9.

| Ex | Structure | LRRK2 IC$_{50}$ (nM) | LCMS data m/z | RT (min) | Method |
|---|---|---|---|---|---|
| 160 | 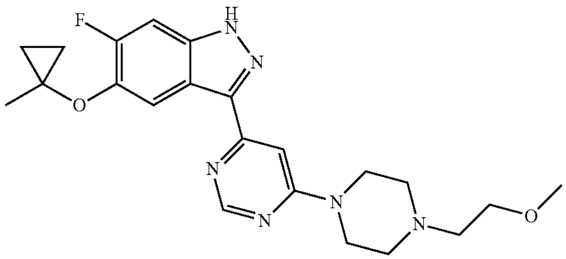 | <0.52 | 427.3 | 1.88 | C2 |

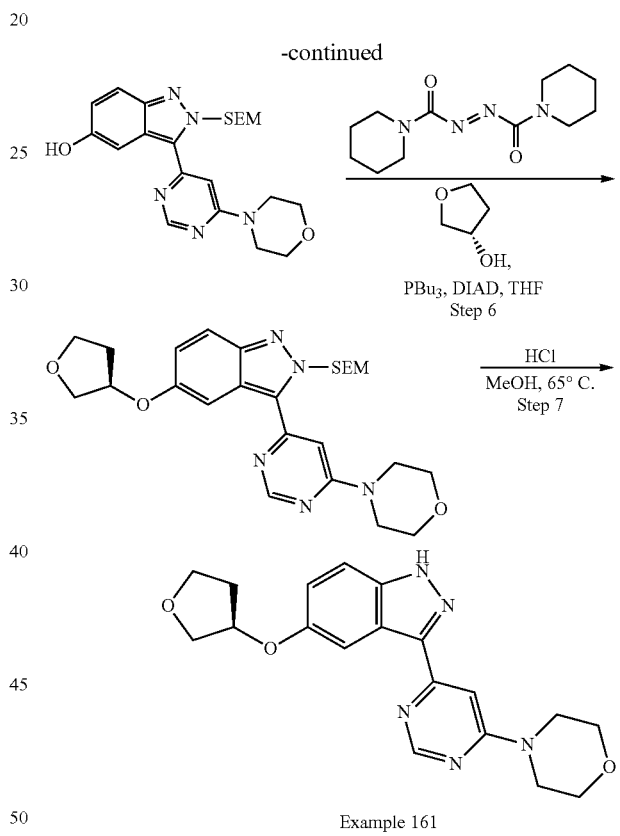

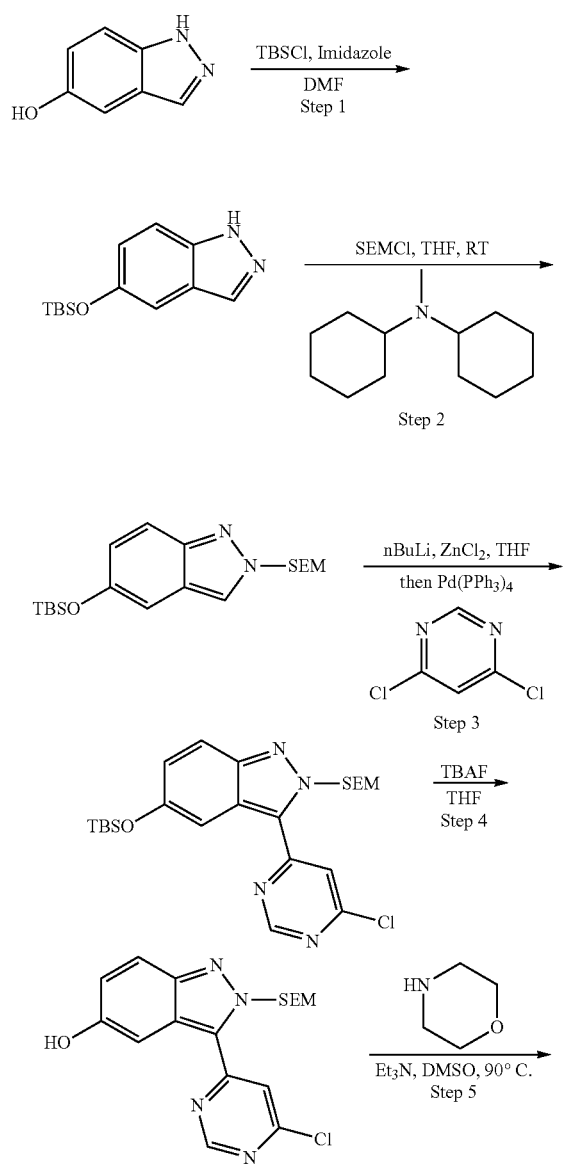

Example 161

Step 1:

To an ice-cooled mixture of 5-hydroxyindazole (53.6 g, 400 mmol) and imidazole (40.8 g, 600 mmol) in DMF (1 L) was added TBSCl (72 g, 480 mmol) over a period of 30 min. The ice-bath was removed and the reaction was stirred at RT overnight. Water (1 L) was added to the reaction slowly and the resultant mixture was extracted with EtOAc (2×500 mL). The combined organic layers were washed with water (2×500 mL) and brine (500 mL), dried over Na$_2$SO$_4$, filtered, and evaporated under reduced pressure to afford a residue which was purified by flash chromatography on silica gel (gradient elution with 6:1 to 2:1 petroleum ether: EtOAc) to afford the silyl ether: MS (ESI): m/z=249.1 [M+H]$^+$.

Step 2:

To a solution of above compound (92 g, 371 mmol) and N,N-dicyclohexyl methylamine (86.8 g, 445 mmol) in THF (600 mL) was slowly added SEMCl (68.2 g, 408 mmol). The resulting mixture was stirred at room temperature overnight and then filtered. The filtrate was concentrated in vacuo to give a residue which was purified by flash chromatography on silica gel (gradient elution with 60:1 to 10:1 petroleum ether:EtOAc) to afford the product: MS (ESI) m/z=379 [M+H]$^+$.

Step 3:

To a cold (−78° C.), stirred solution of SEM-protected indazole (60 g, 159 mmol) in THF (480 mL) was added n-BuLi (218 mL of 1.6M in hexane, 349 mmol) dropwise under N$_2$. The mixture was stirred for 2 h at −78° C. and then ZnCl$_2$ (280 mL of 1M solution in diethyl ether, 280 mmol) was added dropwise. After being stirred at −78° C. for an additional 1 h, the cooling bath was removed and the mixture was allowed to warm to room temperature. After that time, a degassed solution of 4,6-dichloropyrimidine (21 g, 173 mmol) and (Ph$_3$P)$_4$Pd (9.1 g, 7.9 mmol) in THF (120 mL) was then added under N$_2$. The reaction was stirred at room temperature overnight and then concentrated in vacuo to leave a residue which was purified by flash chromatography on silica gel (elution with 100:1 to 60:1 petroleum ether: EtOAc) to yield the chloropyrimidine. MS (ESI) m/z 491.1 [M]$^+$.

Step 4:

The chloropyrimidine (28 g, 57 mmol) and TBAF (22.4 g, 86 mmol) were mixed in THF (300 mL) and stirred at room temperature for 2 h. The THF was removed under reduced pressure and the residue was purified by flash chromatography on silica gel (elution with petroleum ether:EtOAc 3:1-1:1) to yield the hydroxyindazole. MS (ESI) m/z=377.1 [M+H]$^+$.

Step 5:

The chloropyrimidine from step 4 (5 g, 13.27 mmol), morpholine (3.48 ml, 39.8 mmol) and Et$_3$N (11.09 ml, 80 mmol) were dissolved in DMSO (40 ml). The mixture was heated at 90° C. in a sealed flask for 1 h. The mixture was diluted with EtOAc, washed with water and brine, dried over MgSO$_4$, filtered, and concentrated under reduced pressure to leave a residue which was purified by flash column chromatography on silica gel (gradient elution with 15-70% EtOAc in hexane) to afford the desired morpholine adduct. LCMS 428.2 [M+H]$^+$.

Step 6:

To a mixture of (S)-(+)-3-hydroxytetrahydrofuran (330 mg, 3.74 mmol), the phenol from step 5 (400 mg, 0.936 mmol) and nBu$_3$P (0.935 ml, 3.74 mmol) in THF (10 ml) was added 1,1'-(azodicarbonyl)dipiperidine (944 mg, 3.74 mmol) under N$_2$. The resulting mixture was stirred at room temperature overnight. The mixture was diluted with EtOAc, washed with water, dried over MgSO$_4$, filtered and concentrated under reduced pressure to leave a residue which was purified by flash column chromatography on silica gel (gradient elution with 20-50% EtOAc in hexane) to afford the product. LCMS 498.3 [M+H]$^+$.

Step 7:

The SEM protected indazole from step 6 (325 mg, 0.653 mmol) was dissolved in MeOH (6 ml) and HCl (4.90 ml of 4M solution in dioxane, 19.59 mmol) was added. After being heated at 65° C. in a sealed tube for 30 min the mixture was cooled to room temperature. The mixture was diluted with EtOAc, washed with a saturated aqueous solution of NaHCO$_3$, dried over MgSO$_4$, filtered and concentrated under reduced pressure to leave a residue which was purified by flash column chromatography on silica gel (gradient elution with 30-100% EtOAc in hexane) to afford Example 161.

TABLE 10

The following examples were prepared using similiar procedures to those described in Scheme I using the appropriate amine in step 5 and appropriate alcohol in step 6.

| Example | Structure | m/z | Ret time (min) | method | LRRK2 IC$_{50}$ (nM) |
|---|---|---|---|---|---|
| 161 | 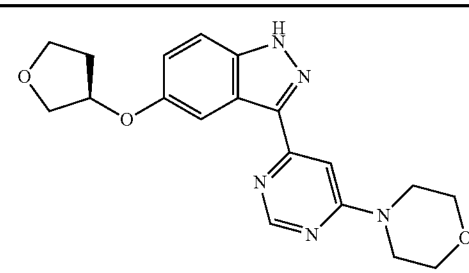 | 367.4 | 0.91 | A | 12.6 |
| 162 | 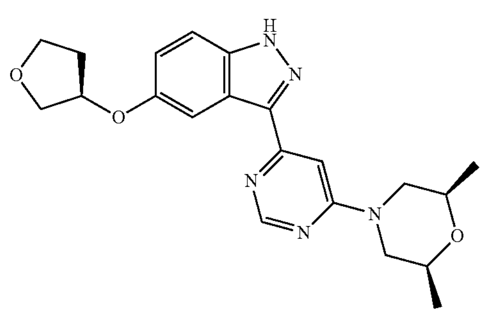 [SMILES: C[C@@H]1CN(c2cc(-c3n[nH]c4ccc(O[C@@H]5CCOC5)cc34)ncn2)C[C@H](C)O1] | 396.2 | 1.01 | A | 12.01 |

TABLE 10-continued

The following examples were prepared using similiar procedures to those described in Scheme I using the appropriate amine in step 5 and appropriate alcohol in step 6.

| Example | Structure | LCMS data m/z | Ret time (min) | method | LRRK2 IC$_{50}$ (nM) |
|---|---|---|---|---|---|
| 163 | 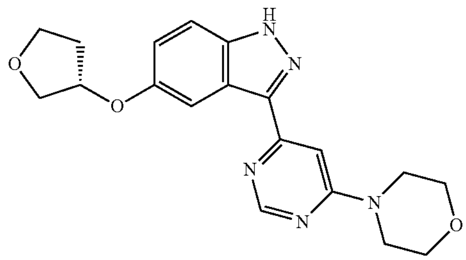 [SMILES: c1nc(-c2n[nH]c3ccc(O[C@H]4CCOC4)cc23)cc(N2CCOCC2)n1] | 367.4 | 0.93 | A | 12.1 |
| 164 | 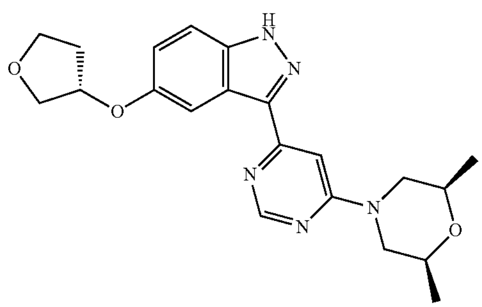 [SMILES: C[C@@H]1CN(c2cc(-c3n[nH]c4ccc(O[C@H]5CCOC5)cc34)ncn2)C[C@H](C)O1] | 396.2 | 0.96 | A | 6.86 |

Scheme J:

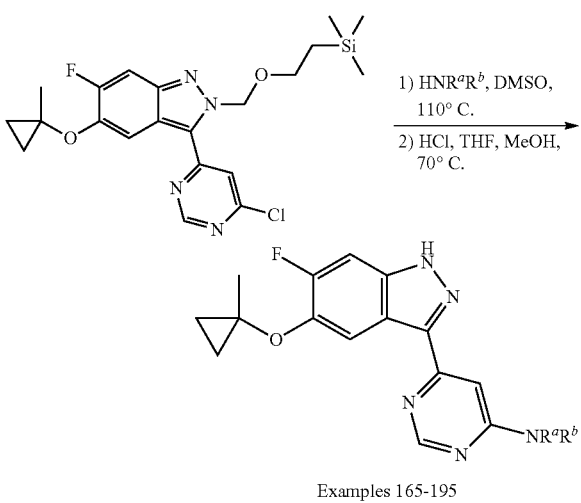

Examples 165-195

Parallel preparation of Examples 165-195: To a set of vials containing the chloropyrimidine core from Scheme H (25 mg, 0.056 mmol) in DMSO (0.3 mL) was individually added the requisite amine (0.067 mmol) and diisopropyl-ethylamine (0.039 mL, 0.223 mmol). The vials were capped and the mixtures were heated to 110° C. with stirring for 3 hours. The mixtures were cooled to RT. Water (2 mL) was added to each vial. The aqueous phase from each vial was extracted with DCM (2×1 mL). The organic layers from each vial were transferred to a clean vial and the solvent was removed in vacuo. To each vial was then added THF:MeOH (1:3, 1 mL) followed by HCl (4 N in dioxane, 0.20 mL, 0.80 mmol). The vials were capped and the solutions were heated to 70° C. for 0.5 h. The solutions were allowed to cool to RT and the solvent was then removed from the vials in vacuo. Each crude product was redissolved in 1 mL of DMSO and filtered. The crude products (excluding Example 195) were purified by mass triggered HPLC using the following conditions: [Waters XBridge C18 column, 5 μm, 19×100 mm, gradient ranges from 10 initial to 60-70% MeCN (0.1% NH$_4$OH) in water (0.1% NH$_4$OH) 25 mL/min, 8 min run time] to provide the Examples 165-190. Examples 191-194 were repurified using the following conditions: [Waters Sunfire C18 column, 19×100 mm, gradient ranges of 10% initial to 70-95% MeCN (0.1% TFA) in water (0.1% TFA) 25 mL/min, 8 min run time]. Example 195 was purified using the following condition: [Waters Sunfire C18 column, 5 μm, 19×100 mm, gradient 10% to 50% MeCN (0.1% formic acid) in water (0.1% formic acid) 25 mL/min, 8 min run time].

TABLE 11
Parallel preparation of Examples 165-195.
| Example | Structure | LCMS data | | | LRRK2 |
| --- | --- | --- | --- | --- | --- |
| | | m/z | Ret time (min) | method | IC$_{50}$ (nM) |
| 165 | 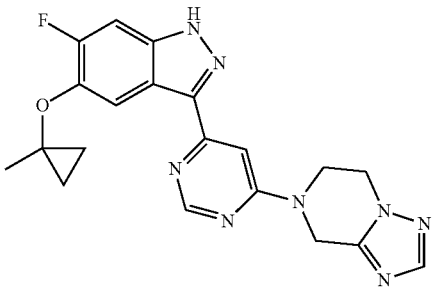 [SMILES: CC1(Oc2cc3c(-c4cc(N5CCn6ncnc6C5)ncn4)n[nH]c3cc2F)CC1] | 407.17 | 0.87 | D | 1.5 |
| 166 | 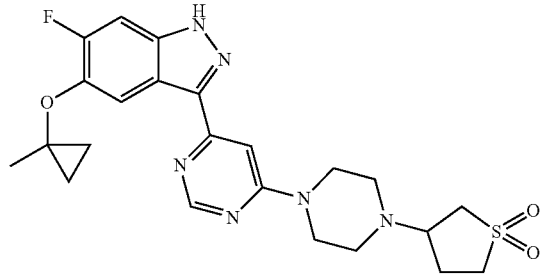 [SMILES: CC1(Oc2cc3c(-c4cc(N5CCN(C6CCS(=O)(=O)C6)CC5)ncn4)n[nH]c3cc2F)CC1] | 487.18 | 0.90 | D | 0.8 |
| 167 | 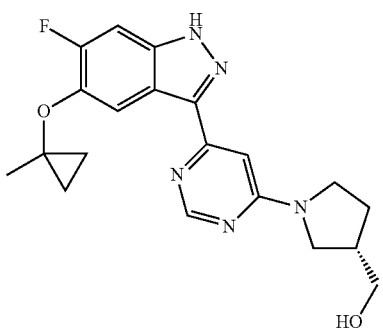 [SMILES: CC1(Oc2cc3c(-c4cc(N5CC[C@H](CO)C5)ncn4)n[nH]c3cc2F)CC1] | 384.18 | 0.84 | D | 1.1 |
| 168 | 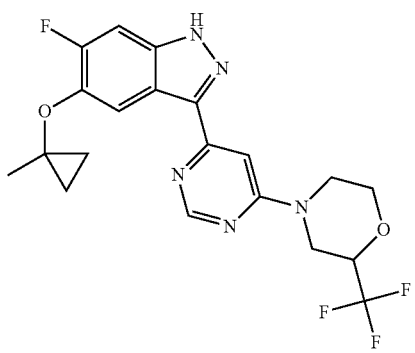 [SMILES: CC1(Oc2cc3c(-c4cc(N5CCOC(C(F)(F)F)C5)ncn4)n[nH]c3cc2F)CC1] | 475.23 | 1.16 | D | 1.9 |

TABLE 11-continued
Parallel preparation of Examples 165-195.
| Example | Structure | LCMS data m/z | Ret time (min) | method | LRRK2 IC$_{50}$ (nM) |
|---|---|---|---|---|---|
| 169 | 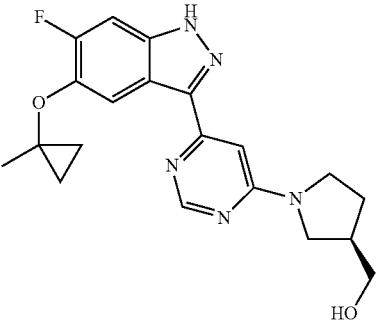 [SMILES: CC1(Oc2cc3c(-c4cc(N5CC[C@@H](CO)C5)ncn4)n[nH]c3cc2F)CC1] | 427.18 | 0.84 | D | 1.1 |
| 170 | 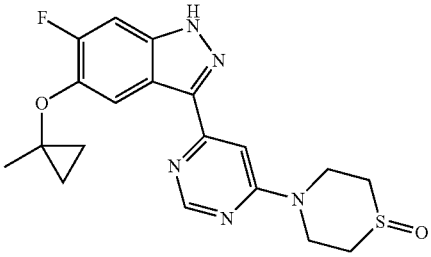 [SMILES: CC1(Oc2cc3c(-c4cc(N5CCS(=O)CC5)ncn4)n[nH]c3cc2F)CC1] | 453.15 | 0.94 | D | 0.6 |
| 171 | 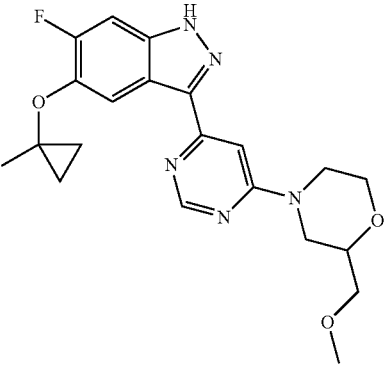 [SMILES: COCC1CN(c2cc(-c3n[nH]c4cc(F)c(OC5(C)CC5)cc34)ncn2)CCO1] | 447.2 | 0.95 | D | 1.6 |
| 172 | 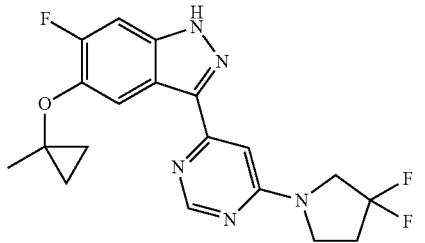 [SMILES: CC1(Oc2cc3c(-c4cc(N5CCC(F)(F)C5)ncn4)n[nH]c3cc2F)CC1] | 427.22 | 0.88 | D | 0.9 |

TABLE 11-continued

Parallel preparation of Examples 165-195.

| Example | Structure | LCMS data m/z | Ret time (min) | method | LRRK2 IC$_{50}$ (nM) |
|---|---|---|---|---|---|
| 173 | | 438.15 | 1.16 | D | 2.1 |
| 174 | | 384.18 | 0.84 | D | 0.6 |
| 175 | | 402.13 | 0.82 | D | 1.9 |
| 176 | | 414.19 | 1.00 | D | 0.7 |

TABLE 11-continued

Parallel preparation of Examples 165-195.

| Example | Structure | LCMS data | | | LRRK2 |
| --- | --- | --- | --- | --- | --- |
| | | m/z | Ret time (min) | method | IC$_{50}$ (nM) |
| 177 | 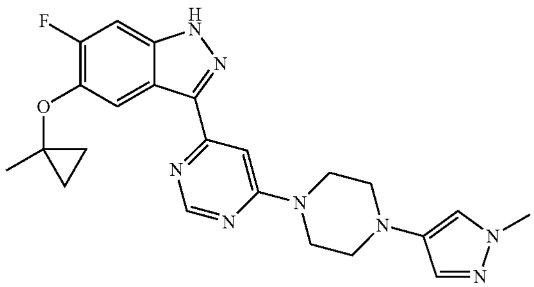 | 390.15 | 1.06 | D | 1.9 |
| 178 | 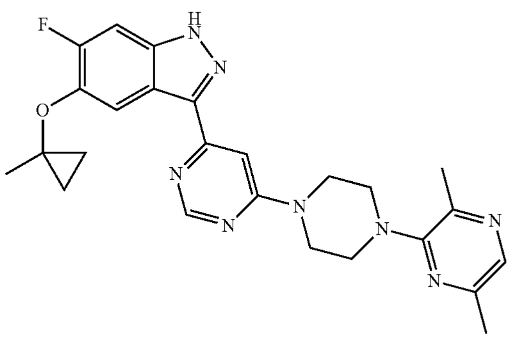 [SMILES: Cc1cnc(C)c(N2CCN(c3cc(-c4n[nH]c5cc(F)c(OC6(C)CC6)cc45)ncn3)CC2)n1] | 397.21 | 0.92 | D | 1.2 |
| 179 | 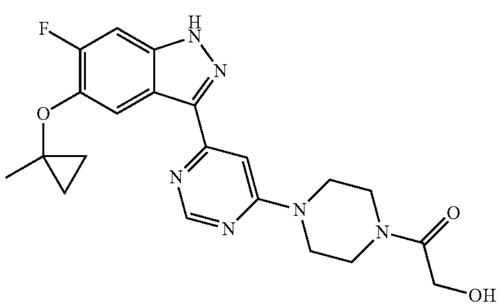 [SMILES: CC1(Oc2cc3c(-c4cc(N5CCN(C(=O)CO)CC5)ncn4)n[nH]c3cc2F)CC1] | 441.2 | 1.07 | D | 1.6 |
| 180 | 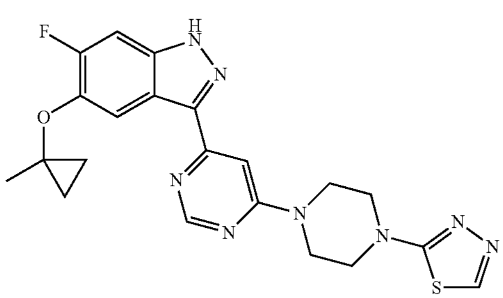 [SMILES: CC1(Oc2cc3c(-c4cc(N5CCN(c6nncs6)CC5)ncn4)n[nH]c3cc2F)CC1] | 416.18 | 0.93 | D | 0.7 |

TABLE 11-continued

Parallel preparation of Examples 165-195.

| Example | Structure | LCMS data m/z | Ret time (min) | method | LRRK2 IC$_{50}$ (nM) |
|---|---|---|---|---|---|
| 181 | | 418.13 | 0.92 | D | 3 |
| 182 | | 400.17 | 0.83 | D | 1.6 |
| 183 | | 421.17 | 1.03 | D | 2 |
| 184 | | 451.19 | 1.12 | D | 3.9 |

TABLE 11-continued

Parallel preparation of Examples 165-195.

| Example | Structure | LCMS data m/z | Ret time (min) | method | LRRK2 IC$_{50}$ (nM) |
|---|---|---|---|---|---|
| 185 | | 476.21 | 1.11 | D | 2.7 |
| 186 | | 453.23 | 1.05 | D | 0.6 |
| 187 | | 449.21 | 0.95 | D | 1.3 |
| 188 | | 418.17 | 0.96 | D | 1.4 |
| 189 | | 411.17 | 1.10 | D | 1.1 |

TABLE 11-continued

Parallel preparation of Examples 165-195.

| Example | Structure | LCMS data m/z | Ret time (min) | method | LRRK2 IC$_{50}$ (nM) |
|---|---|---|---|---|---|
| 190 | | 398.19 | 1.07 | D | 1.5 |
| 191 | | 398.19 | 1.06 | D | 13 |
| 192 | | 398.19 | 1.10 | D | 1.6 |
| 193 | | 489.17 | 1.14 | D | 16.8 |

TABLE 11-continued
Parallel preparation of Examples 165-195.
| Example | Structure | LCMS data m/z | Ret time (min) | method | LRRK2 IC$_{50}$ (nM) |
|---|---|---|---|---|---|
| 194 | 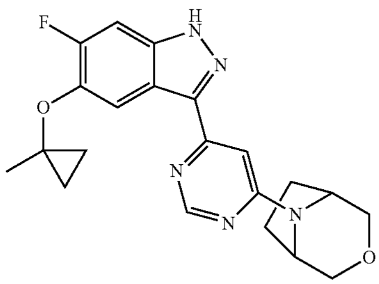 [SMILES: CC1(Oc2cc3c(-c4cc(N5C6CCC5COC6)ncn4)n[nH]c3cc2F)CC1] | 396.18 | 1.01 | D | 1.1 |
| 195 | 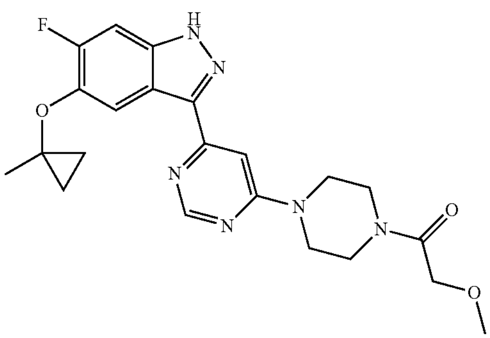 | 441.2 | 0.89 | D | 0.8 |
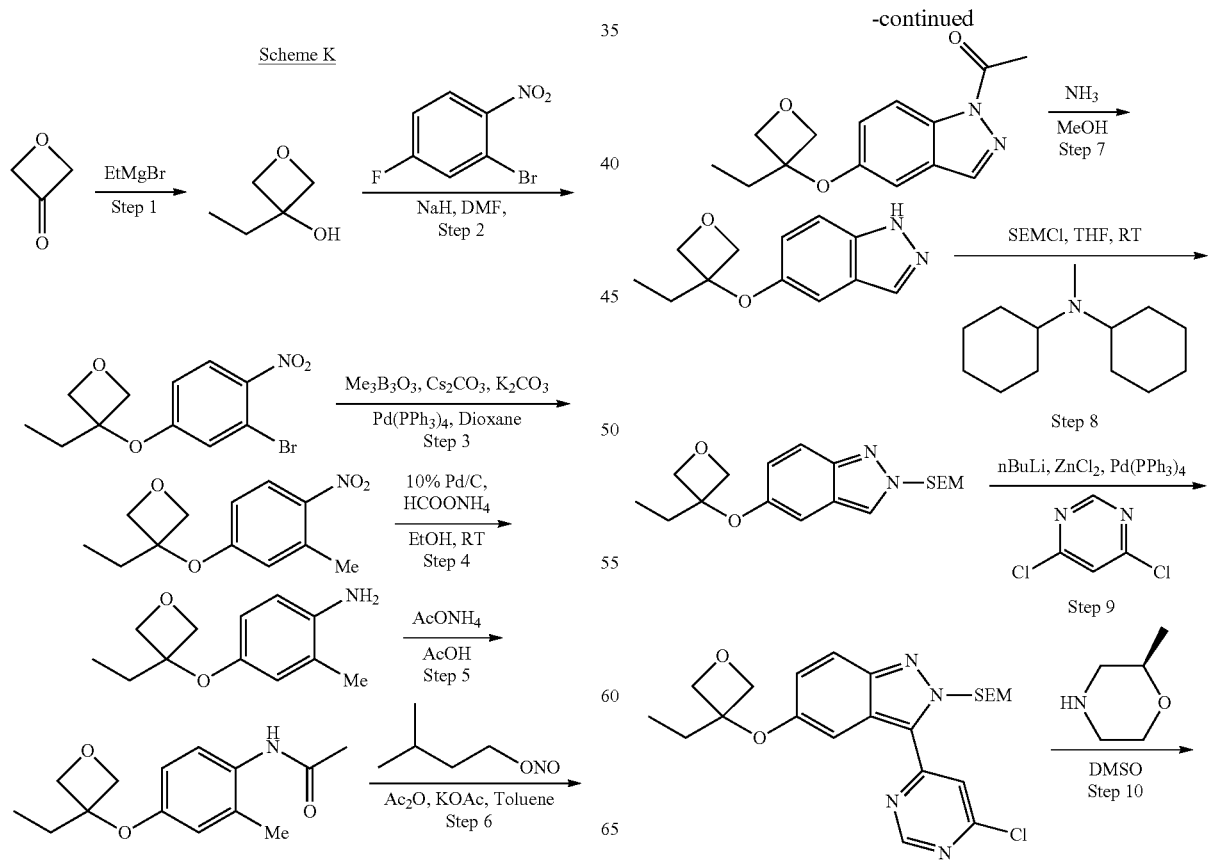

-continued

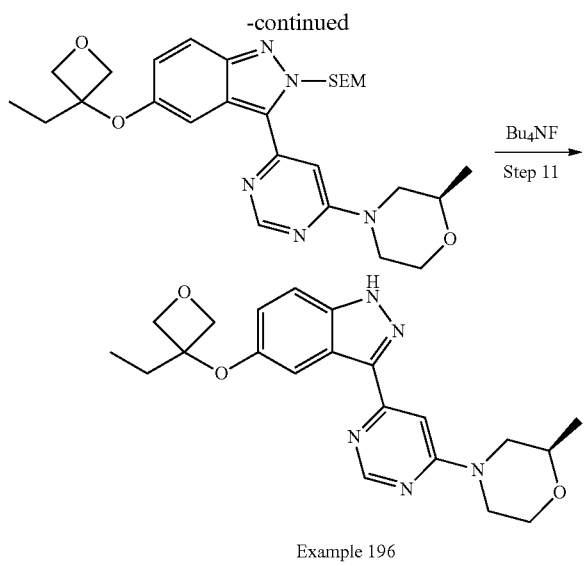

Example 196

Step 1:
To a cold (−78° C.), stirred solution of oxetan-3-one (25 g, 347 mmol) in Et$_2$O (300 mL) was added EtMgBr (140 mL of 3 M solution in Et$_2$O, 420 mmol) dropwise under N$_2$. After the addition was complete, the reaction mixture was allowed to warm to room temperature and stirred overnight. The reaction was quenched with a saturated aqueous solution of NH$_4$Cl (200 mL) and the resulting mixture was extracted with Et$_2$O (6×150 mL). The combined organic layers were washed with brine (400 mL), dried over Na$_2$SO$_4$, filtered and concentrated in vacuo to yield 3-ethyloxetan-3-ol.

Step 2:
To a cold (0° C.), stirred solution of 2-bromo-4-fluoro-1-nitrobenzene (8.8 g, 40 mmol) and 3-ethyloxetan-3-ol (4.5 g, 44 mmol) in DMF (100 mL) was added NaH (60%, 2.2 g, 44 mmol) in portions. The reaction mixture was then stirred at room temperature for 5 h, quenched with cold water (500 mL) and, extracted with EtOAc (2×150 mL). The combined organic layers were washed with water (200 mL), brine (200 mL), dried over Na$_2$SO$_4$, filtered and concentrated under reduced pressure to yield a residue which was purified by column chromatography on silica gel (gradient elution with petroleum ether:EtOAc 50:1 to 5:1) to afford the aryl ether. MS (ESI) m/z=304.0 [M+H]$^+$.

Step 3:
A stirred mixture of aryl ether (10 g, 33 mmol), 2,4,6-trimethyl-1,3,5,2,4,6-trioxatriborinane (50% w/w in THF, 10 mL, 36 mmol), Pd(PPh$_3$)$_4$ (3.8 g, 3.3 mmol), K$_2$CO$_3$ (4.6 g, 33 mmol) and Cs$_2$CO$_3$ (21.6 g, 66 mmol) in dioxane (200 ml)/H$_2$O (20 ml) was degassed with Ar. Then the mixture was heated at 100° C. overnight. The reaction mixture was cooled and dioxane was removed under reduced pressure. To the residue was added water (200 mL), extracted with EtOAc (3×200 mL). The combined organic layers were dried over Na$_2$SO$_4$, filtered and concentrated under reduced pressure to yield a residue which was purified by column chromatography on silica gel (gradient elution with petroleum ether:EtOAc 50:1 to 5:1) to afford the methylated product. MS (ESI) m/z=238.1 [M+H]$^+$.

Step 4:
A mixture of nitro derivative (5.1 g, 22 mmol), ammonium formate (16.3 g, 259 mol), 5% Pd—C (0.4 g) in EtOH (50 mL) was stirred at room temperature under N$_2$ for 5 h. The reaction mixture was filtered and the filtrate was concentrated under reduced pressure to yield the desired amino compound. MS (ESI) m/z=208.3 [M+H]$^+$.

Step 5:
A mixture of amino derivative (4 g, 19.3 mmol), ammonium acetate (1.49 g, 19.3 mmol) in AcOH (40 mL) was heated to reflux with stirring overnight. The reaction was concentrated under reduced pressure to yield a residue which was neutralized by a saturated aqueous solution of NaHCO$_3$. The resultant mixture was extracted with EtOAc (3×50 mL). The combined organic layers were dried over Na$_2$SO$_4$, filtered and concentrated under reduced pressure to yield a residue which was purified by column chromatography on silica gel (gradient elution with petroleum ether:EtOAc 10:1 to 1:1) to afford the acetamide. MS (ESI) m/z=250.1 [M+H]$^+$.

Step 6:
To a stirred solution of acetamide (4.3 g, 17 mmol) in toluene (40 mL) was added KOAc (2.54 g, 26 mmol) followed by Ac$_2$O (8.1 g, 79 mmol). The mixture was heated to 80° C. after which time, isopentyl nitrite (9.3 mL, 68 mmol) was added dropwise and the resulting mixture was heated at 80° C. overnight. Upon cooling to room temperature, the resulting mixture was washed with H$_2$O (30 mL) and the layers were separated. The organic layer was dried over Na$_2$SO$_4$, filtered and concentrated under reduced pressure to yield the indazole derivative. MS (ESI) m/z=261.2 [M+H]$^+$.

Step 7:
To a stirred suspension of above acyl indazole derivative (4 g, 15.4 mmol) in MeOH (40 mL) was added NH$_3$ (10 mL of 7.0 M solution in MeOH, 70 mmol) and the mixture was stirred at room temperature for 5 h. The reaction mixture was concentrated under reduced pressure to yield the indazole. MS (ESI) m/z=219.1 [M+H]$^+$.

Step 8:
To a stirred mixture of above indazole (3.2 g, 15 mmol) and N,N-dicyclohexyl methylamine (3.4 g, 18 mmol) in THF (40 mL) was slowly added SEMCl (2.7 g, 16 mmol). The resulting mixture was stirred at room temperature overnight and then filtered. The filtrate was concentrated in vacuo to yield a residue which was purified by flash chromatography on silica gel (gradient elution with petroleum ether:EtOAc 100:1 to 10:1) to afford the SEM-protected indazole. MS (ESI) m/z=349 [M+1]$^+$.

Step 9:
n-BuLi (1.6 M in hexane, 10 mL, 16 mmol) was added dropwise into a solution of above SEM-protected indazole (3.48 g, 10 mmol) in THF (50 mL) under N$_2$ at −78° C. The mixture was stirred for 2.0 h, and then ZnCl$_2$ (22 mL of 0.5 M solution in Et$_2$O, 11 mmol) was added dropwise. After being stirred at −78° C. for additional 2 h, the cooling bath was removed and the mixture was warmed to room temperature. A degassed solution of 4,6-dichloropyrimidine (1.64 g, 11 mmol) and (Ph$_3$P)$_4$Pd (1.16 g, 1 mmol) in THF (15 ml) was then added under N$_2$. The reaction was stirred at room temperature overnight and then concentrated in vacuo to yield a residue. Water (100 mL) was added and the resulting layer was extracted with EtOAc (2×150 mL). The combined organic layers were dried over Na$_2$SO$_4$, filtered and concentrated under reduced pressure to yield a residue which was purified by flash chromatography on silica gel (gradient elution with petroleum ether:EtOAc 100:1 to 10:1) to afford the desired chloropyrimidine. MS (ESI) m/z=461.2 [M+H]$^+$.

Step 10:

A mixture of the chloropyrimidine from step 9 (120 mg, 0.26 mmol), $^{i}Pr_2NEt$ (200 mg, 1.56 mmol) and (R)-2-methylmorpholine (79 mg, 0.78 mmol) in DMSO (3 mL) was stirred at 110° C. overnight. Upon cooling to room temperature, water (30 mL) was added and the resulting layer was extracted with EtOAc (30 mL). The organic layer was dried over $Na_2SO_4$, filtered and concentrated under reduced pressure to yield the product which was used in the next step without further purification. MS (ESI) m/z=526.2 $[M+H]^+$.

Step 11:

A mixture of the product from step 10 (130 mg, 0.25 mmol) and $Bu_4NF$. (259 mg, 1 mmol) in THF (5 mL) was heated to reflux with stirring overnight. The reaction mixture was evaporated to yield a residue which was purified by prep-HPLC (Column C18; Mobile phase: A: water, B: MeCN (20-70%) to afford Example 196. MS (ESI) m/z=396.2 $[M+H]^+$.

TABLE 12

The following examples were prepared by treating the intermediate from Scheme K step 9 with the appropriate amine using conditions similiar to those described in Scheme K steps 10-11.

| Ex | Structure | LRRK2 IC$_{50}$ (nM) | LCMS data m/z | RT (min) | Method |
|---|---|---|---|---|---|
| 196 | 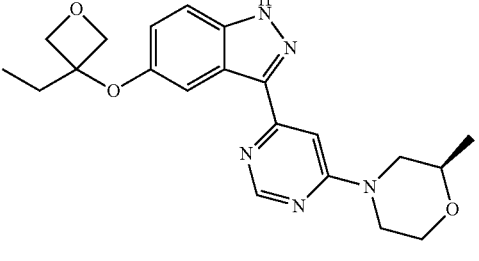 | 1.51 | 396.2 | 1.73 | C1 |
| 197 | 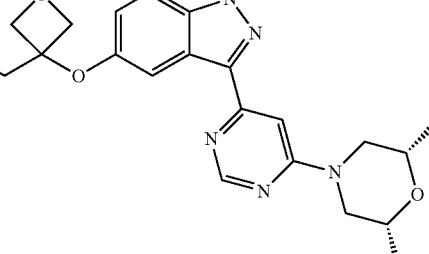 | 0.89 | 410.2 | 1.80 | C1 |
| 198 | 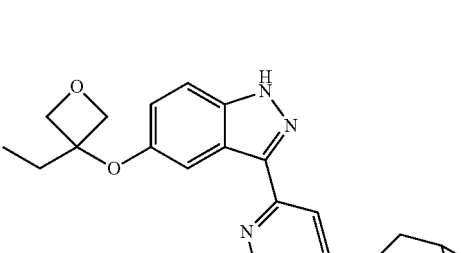 | 2.80 | 408.2 | 1.69 | C1 |

Scheme L

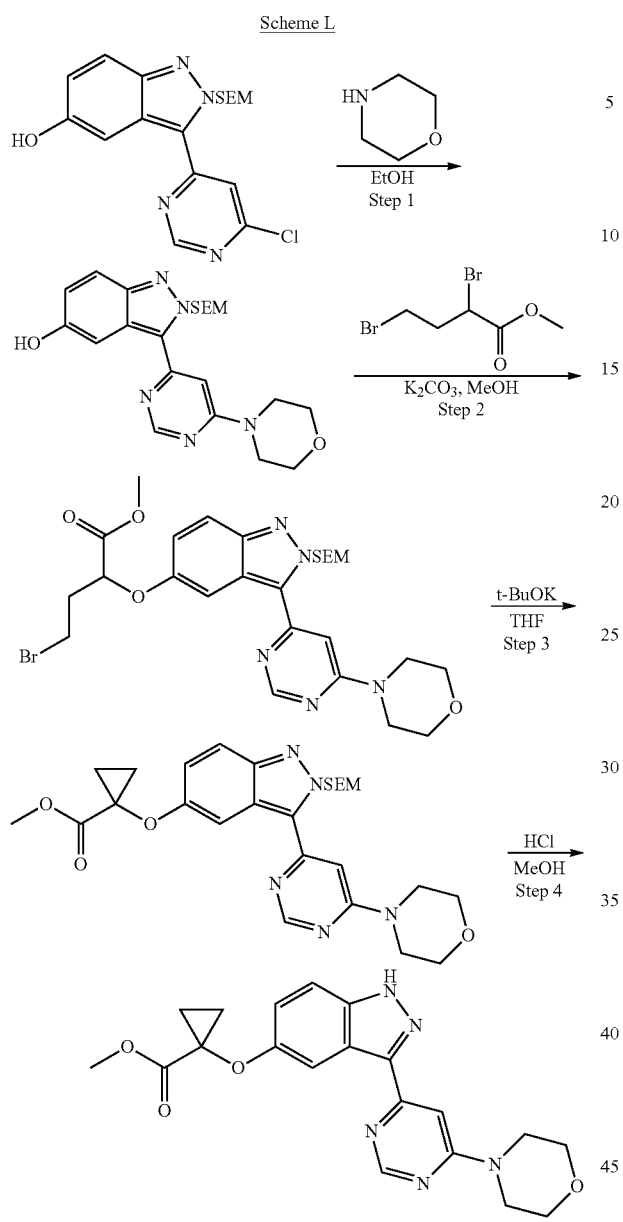

Example 199

Step 1:
To a solution of chloropyrimidine (1.5 g, 3.96 mmol), from Scheme I step 4, in ethanol (20 mL) was added morpholine (1.68 g, 19.3 mmol). The mixture was heated at 80° C. for 16 h. The volatiles were removed under reduced pressure to leave a residue which was purified with by column chromatography on silica gel chromatography (elution with 1:2 petroleum ether:EtOAc) to afford the morpholine-adduct.

Step 2:
To a solution of above adduct (0.10 g, 0.23 mmol) in MeCN (3 mL) was added methyl 2,4-dibromobutanoate (0.31 g, 1.19 mmol) and $K_2CO_3$ (0.17 g, 1.2 mmol). The mixture was heated at 75° C. for 16 h. The resulting mixture was cooled to room temperature, filtered and concentrated under reduced pressure to leave a residue was purified by Prep-TLC plate (elution with petroleum ether: EtOAc 1:1) to yield the aryl ether. MS (ESI) m/z=606.2 [M+1]$^+$.

Step 3:
To a cold (−78° C.), stirred solution of above aryl ether (156 mg, 0.257 mmol) in THF (2 mL) was added t-BuOK (37 mg, 0.334 mmol) under Ar. The cold bath was then removed and the reaction was stirred at room temperature overnight. The reaction was filtered and concentrated under reduced pressure to leave a residue which was purified by Prep-TLC plate to afford the desired cyclopropyl alkoxy compound. MS (ESI) m/z=526.1 [M+1]$^+$.

Step 4:
To a solution of compound prepared above (90 mg, 0.18 mmol) in methanol (10 mL) was added a solution of HCl (2 mL of 3.5 M solution in 1,4-dioxane). After being heated at 70° C. for 1 h the reaction was cooled to room temperature and extracted with EtOAc (3×20 mL). The combined organic layers were dried over $Na_2SO_4$, filtered and concentrated under reduced pressure to leave a residue which was purified by Prep-TLC plate (elution with 1:2 petroleum ether:EtOAc) to afford Example 199. MS (ESI) m/z=396.1 [M+1]$^+$ (ret. time=1.61 min, condition C4). LRRK2 IC$_{50}$: 21.7 nM.

Scheme M

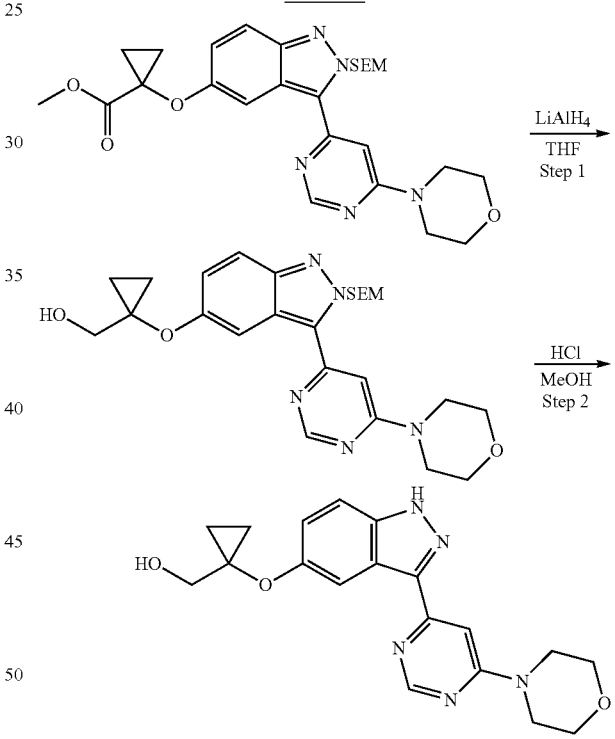

Example 200

Step 1:
To a cold (0° C.), stirred suspension of LiAlH$_4$ (4 mg, 0.085 mmol) in THF (2 mL) was added a solution of ester from step 3 in Scheme L (30 mg, 0.057 mmol) in THF (0.5 mL). The resulting mixture was stirred at 0° C. for 1 h and then at room temperature for additional 1 h. To this solution was carefully added water/EtOAc (0.5 mL/5 mL). The reaction was then stirred at room temperature for 0.5 h, and then concentrated under reduced pressure to leave a residue which was purified by Prep-TLC plate (elution with petroleum ether:EtOAc 1:1) to afford the alcohol. MS (ESI) m/z=498.1 [M+1]$^+$.

Step 2:

To a solution of above alcohol (4 mg, 0.0075 mmol) in methanol (2 mL) was added HCl (0.5 mL of 3.5 M solution in 1,4-dioxane). The resulting mixture was heated at 70° C. for 1 h. After being cooled to room temperature the layer was extracted with EtOAc (3×5 mL). The combined organic layers were dried over $Na_2SO_4$, filtered and concentrated under reduced pressure to leave a residue which was purified with Prep-TLC plate (elution with petroleum ether:EtOAc 1:1) to afford Example 200. MS (ESI) m/z=368.2 [M+1]+ (ret. time=1.50 min, condition C4). LRRK2 $IC_{50}$: 2.9 nM.

residue which was purified with Prep-TLC plate (elution with petroleum ether:EtOAc 1:3) to afford Example 201. MS (ESI) m/z=382.1 [M+1]+ (ret. time=1.62 min, condition C4). LRRK2 $IC_{50}$: 2.8 nM.

Example 202 was synthesized following the procedure similar to Scheme N employing EtI as the alkylating agent. MS (ESI) m/z=396.1 [M+1]+ (ret. time=1.65 min, condition C4). LRRK2 $IC_{50}$: 2.3 nM.

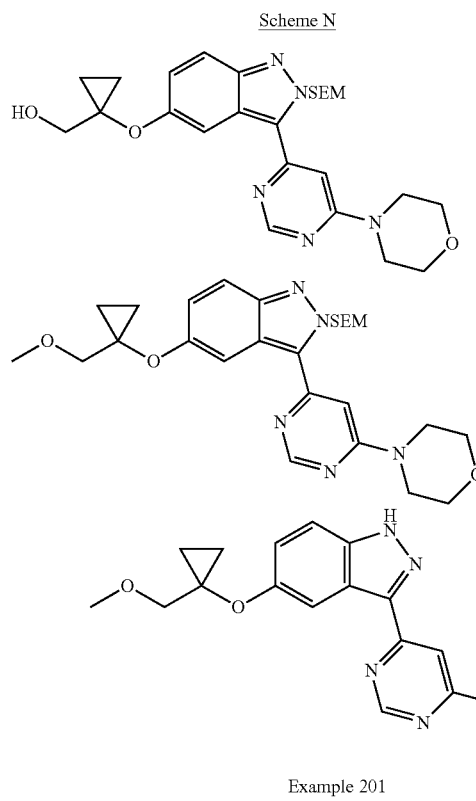

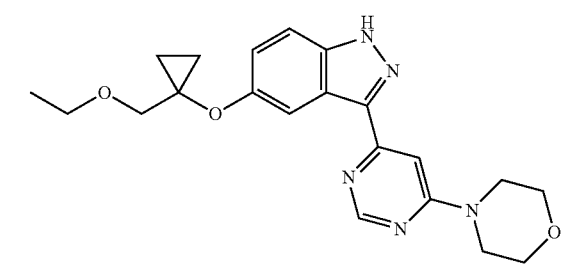 [SMILES: CCOCC1(Oc2ccc3[nH]nc(-c4cc(N5CCOCC5)ncn4)c3c2)CC1]

Example 202

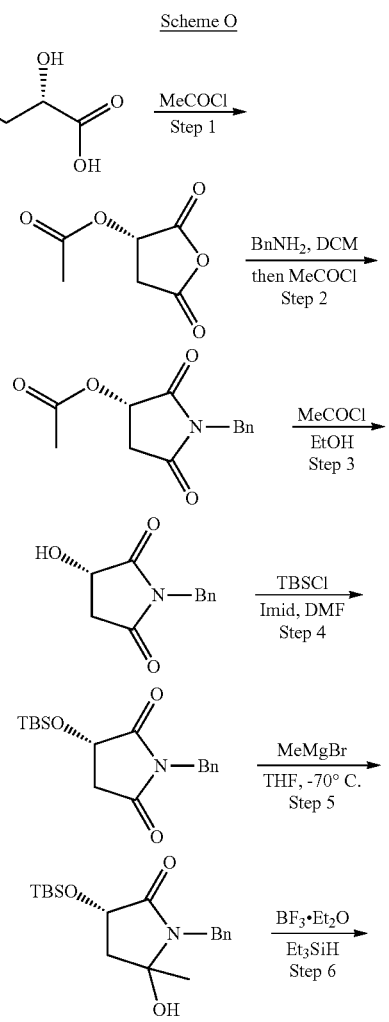

Step 1:

To a solution of alcohol from Scheme M Step 1 (8 mg, 0.016 mmol) in THF (1 mL) was added NaH (8 mg of 50% suspension in mineral oil, 0.16 mmol) and the mixture was stirred at room temperature for 1 h. The reaction was cooled to 0° C. at which time MeI (23 mg, 0.16 mmol) was added dropwise. After the addition was complete, the cold bath was removed and the reaction was stirred at room temperature for another 3 h. To this reaction was added EtOAc/water (5 mL/0.5 mL) and the resulting mixture was filtered and concentrated under reduced pressure to leave a residue which was purified with Prep-TLC plate (elution with petroleum ether:EtOAc 1:1) to afford the desired methyl ether. MS (ESI) m/z=512.1 [M+1]+.

Step 2:

To a solution of above methyl ether (8 mg, 0.016 mmol) in methanol (1 mL) was added HCl in dioxane (0.37 mL of 3.5 M solution in 1,4-dioxane). The resulting mixture was heated at 70° C. for 1 h. After being cooled to room temperature the reaction was extracted with EtOAc (3×5 mL). The combined organic layers were dried over $Na_2SO_4$, filtered and concentrated under reduced pressure to leave a

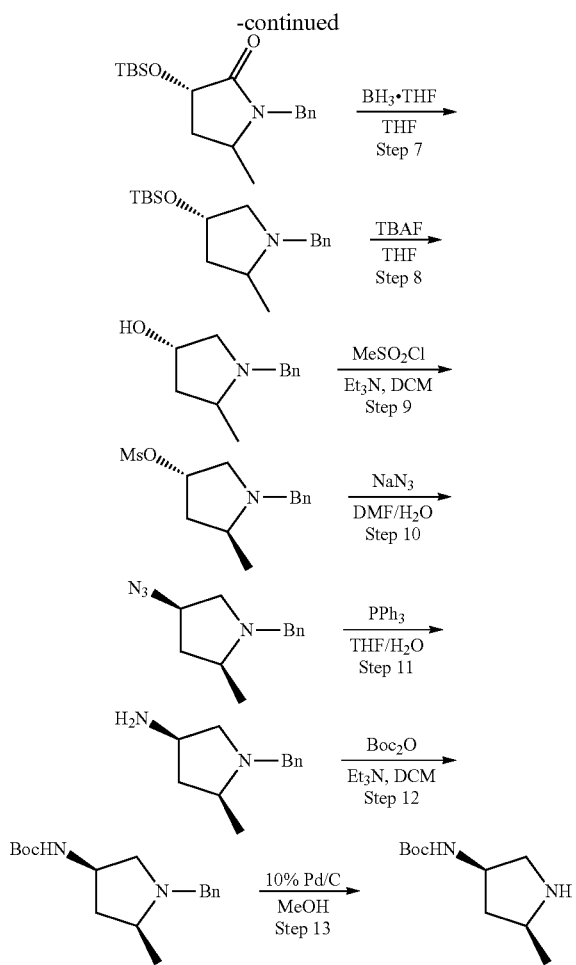

Step 1:

A mixture of L-(−)-malic acid (134 g) in 400 ml acetyl chloride was stirred at reflux for 5 h. The reaction mixture was cooled to room temperature and concentrated under reduced pressure to yield a residue which was directly used in the next step without further purification.

Step 2:

To a solution of compound from Step 1 (~1 mol) in DCM (2 L) was added BnNH$_2$ (350 mL) dropwise. After being stirred at rt overnight, acetyl chloride (350 mL) was added dropwise. The reaction was stirred at reflux for 5 h. The mixture was cooled to room temperature and concentrated under reduced pressure to yield a residue which was diluted with EtOAc and water. The organic layer was separated and the aqueous layer was extracted with EtOAc (×2). The combined organic layers were dried, filtered and concentrated under reduced pressure to leave residue which was purified by column chromatography on silica gel (elution with 3:1 petroleum ether:EtOAc) to afford the desired product.

Step 3:

To a stirred solution of compound from Step 2 (116 g, 0.47 mol) in EtOH (1.2 L) was added acetyl chloride (62 ml) dropwise at rt. After the addition was complete, the mixture was heated at 50° C. for 4 h. The reaction was cooled to rt and concentrated under reduced pressure to yield a residue. To this residue was added toluene and the resulting mixture was concentrated and dried to leave a residue which was recrystallized from toluene to afford the desired product.

Step 4:

To a stirred mixture of compound from Step 3 (86 g, 0.42 mol) and imidazole (43 g, 0.63 mol) in DMF (700 mL) was added TBSCl (75 g, 0.50 mol). The reaction was stirred at rt overnight. The reaction was diluted with EtOAc (2 L) and washed with water (2×500 ml) and brine (2×500 ml), dried, filtered and concentrated under reduced pressure to leave a residue which was purified by column chromatography on silica gel (elution with 30:1 petroleum ether:EtOAc) to afford the desired product.

Step 5:

To a cold (−70° C.), stirred solution of compound from Step 4 (160 g, 0.5 mol) in THF (1.5 L) was added MeMgBr (333 ml of 1.0 M solution in THF, 1.0 mol) dropwise. The reaction mixture was slowly warmed to −25° C. and then to −15° C. slowly before being quenched with a saturated aqueous solution of NH$_4$Cl. The organic layer was separated and the aqueous layer was extracted with EtOAc. The combined organic layers were dried, filtered and concentrated under reduced pressure to leave a residue which was purified by column chromatography on silica gel (elution with 30:1 petroleum ether:EtOAc) to afford the desired product.

Step 6:

To a cold (−70° C.), stirred solution of compound from Step 5 (67.5 g, 0.2 mol) in DCM (1 L) was added Et$_3$SiH (234 g, 2.0 mol) followed by BF$_3$.Et$_2$O (37 ml, 0.3 mol) dropwise. The cold bath was removed and the mixture was warmed to rt before being quenched by a saturated aqueous solution of NaHCO$_3$. The resulting layer was extracted with DCM, dried, filtered and concentrated under reduced pressure to leave a residue which was purified by column chromatography on silica gel (elution with 30:1 petroleum ether:EtOAc) to obtained the desired product.

Step 7:

A mixture of compound from Step 6 (62 g, 0.194 mol) and BH$_3$.THF (486 ml of 1.0 M solution in THF, 0.486 mol) in THF (100 mL) was stirred at reflux for 6 h. The reaction was cooled to rt and EtOH (100 ml) was added dropwise. The resulting mixture was stirred at reflux for additional 2 h. The reaction was cooled to rt and concentrated under reduced pressure to leave a residue which was redissolved in DCM and washed with a saturated aqueous solution of NaHCO$_3$. The organic layer was dried, filtered and concentrated under reduced pressure to yield the product which was used in the next step without further purification.

Step 8:

A mixture of compound from Step 7 (~60 g, 0.194 mol) and TBAF (76 g, 0.291 mol) in THF (600 mL) was stirred at rt overnight. The reaction mixture was concentrated under reduced pressure to leave a residue which was purified by column chromatography on silica gel (elution with 1:1 to 0:100 petroleum ether:EtOAc) to afford the desired product.

Step 9:

To a cold (0° C.), stirred solution of compound from Step 8 (36 g, 0.188 mol) in DCM (350 mL) was added Et$_3$N (40 ml, 0.28 mol) followed by MeSO$_2$Cl (25.8 g, 0.226 mol) dropwise. After being stirred at 0° C. for 2 h the mixture was washed with water and brine, dried, filtered and concentrated under reduced pressure to leave a residue which was purified by column chromatography on silica gel (gradient elution with 10:1 to 5:1 petroleum ether:EtOAc) to afford the desired product as a yellow oil.

Step 10:

A mixture of compound from Step 9 (25 g, 0.093 mol) and NaN$_3$ (18 g, 0.279 mol) in DMF (300 mL) and water (30 mL) was stirred at 100° C. overnight. The reaction mixture was cooled to rt and diluted with EtOAc. The resulting layer was washed with water and brine, dried, filtered and concentrated under reduced pressure to leave a residue which was used in the next step without further purification.

Step 11:

To a stirred mixture of compound from Step 10 (0.093 mol) and PPh$_3$ (73 g, 0.279 mol) in THF (300 mL) and water (30 mL) was stirred at 90° C. for 2 h. The reaction mixture was concentrated under reduced pressure to yield a residue which was diluted with water (200 mL) followed by 6N HCl until pH 1-2. The resulting layer extracted with EtOAc (×3). The aqueous layer was adjusted to pH 9-10 by using NaOH (10% aq.) which was then extracted with DCM (×5). The combined organic layers were washed with brine, dried, filtered and concentrated under reduced pressure to yield a residue which was used in the next step without further purification.

Step 12:

To a solution of compound amine from Step 11 (~0.093 mol) in DCM (250 mL) was added Et$_3$N (20 ml, 0.14 mol) followed by Boc$_2$O (24 g, 0.112 mol). After being stirred at rt for 2 h the mixture was washed with water and brine, dried, filtered and concentrated under reduced pressure to leave a residue which was purified by column chromatography on silica gel (gradient elution with 20:1 to 5:1 petroleum ether:EtOAc) to afford the desired product.

Step 13:

To a stirred solution of compound from Step 12 (36 g, 0.14 mol) in MeOH (500 mL) was added 10% wet Pd/C (5 g). The flask was evacuated and back-filled with H$_2$ (×2). The resulting mixture was then stirred at 45° C. for 20 h. The reaction was filtrated and the filtrate was concentrated to obtain the amine.

Scheme P

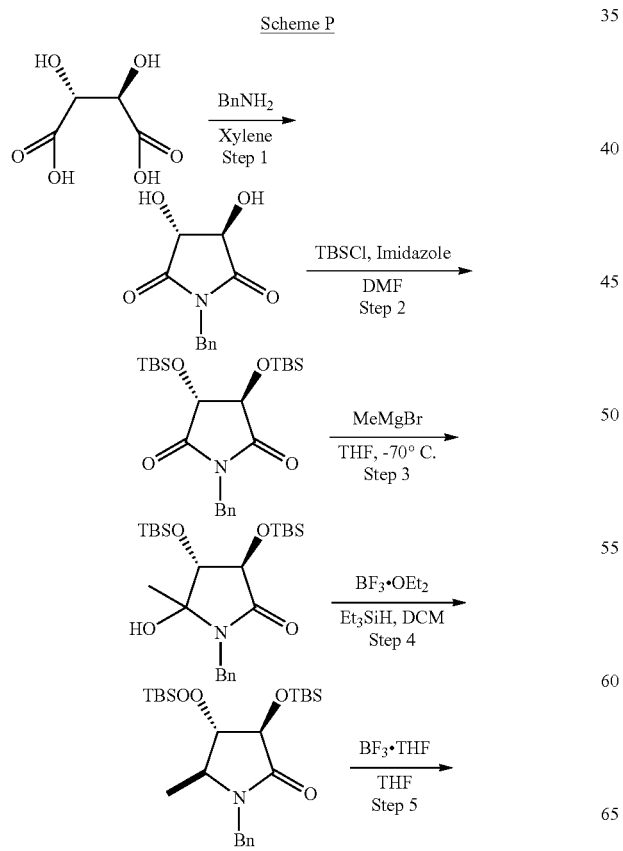

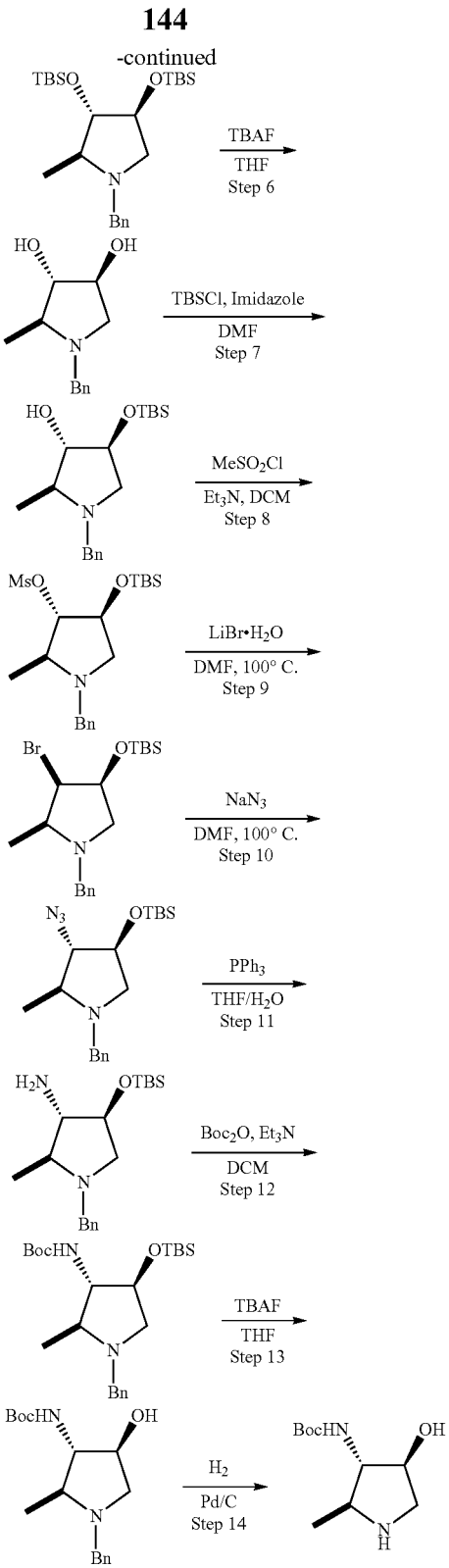

Step 1:

A mixture of L-tartaric acid (250 g, 1.67 mol) and BnNH$_2$ (178 g, 1.67 mol) in xylene (1.5 L) was stirred under reflux for 4 h using a Dean-Stark water separator. The reaction was cooled to room temperature with stirring and filtrated. The solid was washed with EtOH to afford the desired product.

Step 2:

To a stirred solution of diol from Step 1 (275 g, 1.24 mol) in DMF (1.8 L) was added imidazole (254 g, 3.73 mol) followed by TBSCl (467 g, 3.11 mol). The reaction mixture was stirred at rt overnight before being diluted with EtOAc. The resulting layer was washed with water and brine, dried, filtered and concentrated to leave a residue which was purified by column chromatography on silica gel (elution with petroleum ether:EtOAc 100:1) to afford the desired product.

Step 3:

To a cold (−70° C.), stirred solution of compound from Step 2 (270 g, 0.6 mol) in THF (3 L) was added MeMgBr (400 ml of 1.0 M solution in THF, 1.2 mol) dropwise. The reaction mixture was slowly warmed to −10° C. and then to rt before being quenched with a saturated aqueous solution of $NH_4Cl$. The organic layer was separated and the aqueous layer was extracted with EtOAc. The combined organic layers were dried, filtered and concentrated under reduced pressure to leave a residue which and purified by column chromatography on silica gel (elution with 50:1 to 10:1 petroleum ether:EtOAc) to afford the product.

Step 4:

To a cold (−70° C.), stirred solution of compound from Step 3 (350 g, 0.75 mol) in DCM (2 L) was added $Et_3SiH$ (870 g, 7.5 mol) followed by a solution of $BF_3.Et_2O$ (139 ml, 1.125 mol) dropwise. The reaction mixture was warmed up to rt before being quenched with a saturated aqueous solution of $NaHCO_3$. The organic layer was separated and the aqueous layer was extracted with DCM. The combined organic layers were dried, filtered and concentrated under reduced pressure to leave a residue which and purified by column chromatography on silica gel (elution with petroleum ether:EtOAc 10:1) to afford the product.

Step 5:

A mixture of compound from Step 4 (325 g, 0.72 mol) and $BH_3.THF$ (1800 mL of 1.0 M solution in THF, 1.8 mol) in THF (500 mL) was stirred at reflux for 6 h. The reaction was cooled and EtOH (300 ml) was added dropwise. The mixture was stirred at reflux for additional 2 h followed by cooling to rt. The reaction mixture was concentrated to leave a residue which was dissolved in DCM. The organic layer was washed with a saturated aqueous solution of $NaHCO_3$, dried, filtered and concentrated to afford the product.

Step 6:

To a stirred solution of compound from Step 5 (438 g, 1.0 mol) in THF (2.5 L) was added TBAF (657 g, 2.5 mol) and the resulting mixture was stirred at rt overnight. The reaction mixture concentrated under reduced pressure to leave a residue which was directly purified by column chromatography on silica gel (gradient elution with 1:1 to 0:100 petroleum ether:EtOAc) to afford the diol.

Step 7:

To a solution of diol from Step 6 (95 g, 0.46 mol) in DMF (1 L) was added imidazole (47 g, 0.69 mol) followed by TBSCl (76 g, 0.5 mol). The reaction was stirred at rt overnight. The reaction was diluted with EtOAc and the resulting layer was washed with water and brine, dried, filtered and concentrated under reduced pressure to leave a residue which was purified by column chromatography on silica gel (elution with 4:1 petroleum ether:EtOAc) to afford the desired product.

Step 8:

To a cold (0° C.), stirred solution of alcohol from Step 7 (75 g, 0.234 mol) in DCM (750 mL) was added $Et_3N$ (49 ml, 0.35 mol) followed by $MeSO_2Cl$ (32 g, 0.28 mol) dropwise. The resulting mixture was stirred at 0° C. for 2 h. The mixture was washed with water and brine, dried, filtered and concentrated to afford the desired mesylate which was directly used in the next step without further purification.

Step 9:

A mixture of mesylate from Step 8 (93 g, 0.233 mol) and $LiBr.H_2O$ (245 g, 2.33 mol) in DMF (1 L) was stirred at 100° C. overnight. After being cooled to room temperature the reaction was diluted with EtOAc. The resulting layer was washed with water and brine, dried, filtered and concentrated under reduced pressure to leave a residue which was purified by column chromatography on silica gel (elution with 50:1 petroleum ether:EtOAc) to afford the desired product Step 10:

A mixture of bromide from Step 9 (64 g, 0.167 mol) and $NaN_3$ (33 g, 0.5 mol) in DMF (600 mL) and water (50 mL) was stirred at 100° C. for 2 days. After being cooled to room temperature the reaction was diluted with EtOAc, washed with water and brine, dried, filtered and concentrated to afford the azide which was directly used in the next step without further purification.

Step 11:

A mixture of azide from Step 10 (0.344 mol) and $PPh_3$ (262 g, 1.0 mol) in THF (1.5 L) and water (150 mL) was stirred at 90° C. for 2 h. The reaction was concentrated under reduced pressure to leave a residue which was diluted with water (500 ml) followed by the addition of 6N HCl until pH 1-2. The aqueous layer was extracted with EtOAc. The aqueous phase was adjusted to pH 9-10 by adding an aqueous solution of NaOH (10%). The resulting layer was extracted with DCM. The organic layer was washed with brine, dried, filtered and concentrated under reduced pressure to afford the desired amine.

Step 12:

To a stirred solution of amine from Step 11 (156 g, 0.49 mol) in DCM (2 L) was added $Et_3N$ (103 ml, 0.73 mol) followed by $Boc_2O$ (128 g, 0.59 mol). After being stirred at rt for 2 h the reaction was washed with water and brine, dried, filtered and concentrated under reduced pressure to leave a residue which was purified by column chromatography on silica gel (elution with 20:1 petroleum ether:EtOAc) to afford the carbamate.

Step 13:

To a stirred solution of compound from Step 12 (60 g, 0.143 mol) in THF (1 L) was added TBAF (56 g, 0.214 mol) and the resulting mixture was stirred at room temperature overnight. The mixture was concentrated and the residue was purified by column chromatography on silica gel (gradient elution with 1:1 to 1:5 Petroleum ether:EtOAc) to afford the desired product.

Step 14:

To a stirred solution of compound from Step 13 (39 g, 0.127 mol) in MeOH (800 mL) was added 10% wet Pd/C (4 g). The flask was evacuated and back-filled with $H_2$ (×2). The resulting mixture was then stirred at 30° C. for 24 h. The reaction was filtrated and the filtrate was concentrated to obtain the desired amine.

TABLE 13

The following examples were prepared from the requisite amines and the chloropyrimidine described in Scheme H procedures similiar to those described in Scheme H.

| Ex | Structure | Amine | LRRK2 IC$_{50}$ (nM) | LCMS Data m/z | RT (min) | Method |
|---|---|---|---|---|---|---|
| 203 | 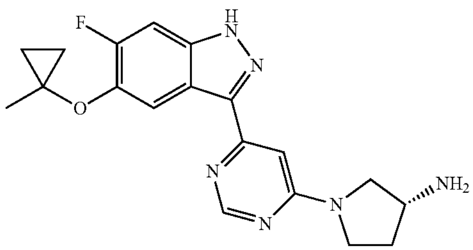 [SMILES: CC1(Oc2cc3c(-c4cc(N5CC[C@@H](N)C5)ncn4)n[nH]c3cc2F)CC1] | | 1.38 | 369.1 | 1.57 | C4 |
| 204 | 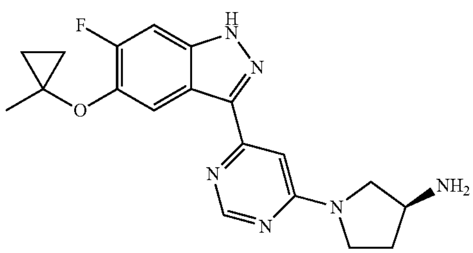 [SMILES: CC1(Oc2cc3c(-c4cc(N5CC[C@H](N)C5)ncn4)n[nH]c3cc2F)CC1] | | 1.59 | 369.2 | 1.59 | C4 |
| 205 | 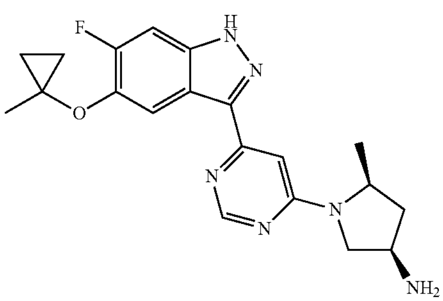 [SMILES: C[C@H]1C[C@@H](N)CN1c1cc(-c2n[nH]c3cc(F)c(OC4(C)CC4)cc23)ncn1] | | 1.29 | 383.1 | 1.50 | C4 |
| 206 | 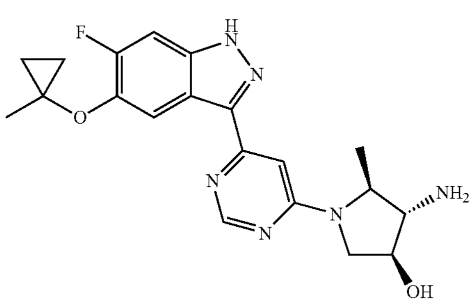 [SMILES: C[C@H]1[C@H](N)[C@@H](O)CN1c1cc(-c2n[nH]c3cc(F)c(OC4(C)CC4)cc23)ncn1] | | 0.99 | 399.1 | 1.51 | C4 |

In all cases, the Boc group was removed during the removal of SEM group in the final step.

Scheme Q

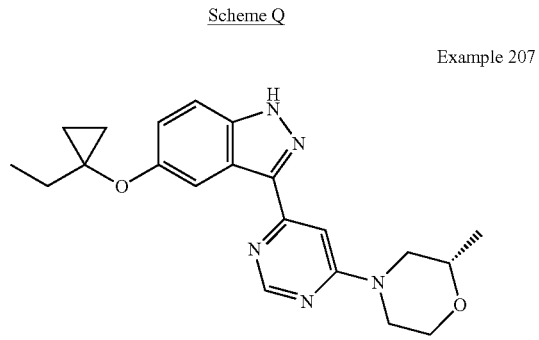 [SMILES: CCC1(Oc2ccc3[nH]nc(-c4cc(N5CCO[C@@H](C)C5)ncn4)c3c2)CC1]

Example 207

Example 207

Example 207 and analogs were synthesized following the same experimental procedure mentioned in Scheme A utilizing 1-ethylcyclopropanol as the starting alcohol.

TABLE 14

Examples 207-219 were prepared from the requisite amine and the chloropyrimidine described in Scheme Q.

| Ex | Structure | LRRK2 IC$_{50}$ (nM) | m/z | RT (min) | Method |
|---|---|---|---|---|---|
| 207 | 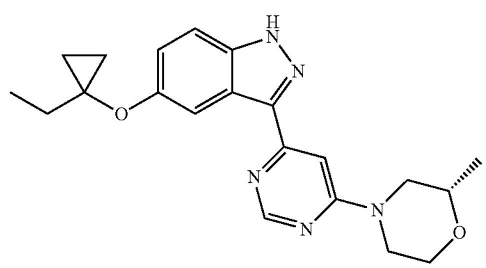 [SMILES: CCC1(Oc2ccc3[nH]nc(-c4cc(N5CCO[C@@H](C)C5)ncn4)c3c2)CC1] | 1.61 | 380.1 | 1.69 | C4 |
| 208 | 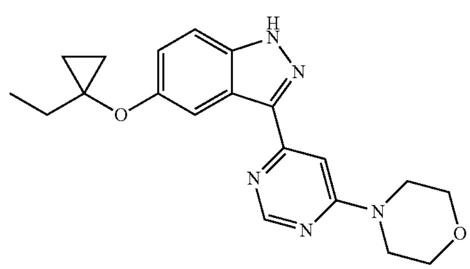 [SMILES: CCC1(Oc2ccc3[nH]nc(-c4cc(N5CCOCC5)ncn4)c3c2)CC1] | 0.95 | 366.2 | 1.66 | C4 |
| 209 | 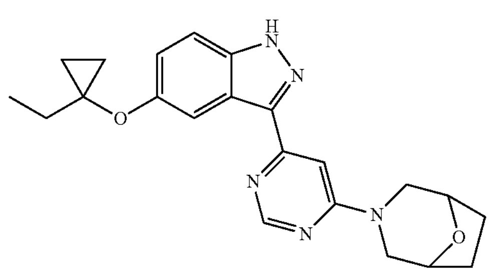 [SMILES: CCC1(Oc2ccc3[nH]nc(-c4cc(N5CC6CCC(C5)O6)ncn4)c3c2)CC1] | 3.2 | 392.2 | 1.70 | C4 |

TABLE 14-continued

*Examples 207-219 were prepared from the requisite amine and the chloropyrimidine described in Scheme Q.*

| Ex | Structure | LRRK2 IC₅₀ (nM) | LCMS Data m/z | RT (min) | Method |
|---|---|---|---|---|---|
| 210 | | 1.14 | 394.2 | 1.74 | C4 |
| 211 | | 0.99 | 380.2 | 1.70 | C4 |
| 212 | | 1.98 | 365.1 | 1.50 | C4 |
| 213 | | 3.43 | 365.2 | 1.49 | C4 |
| 214 | | 3.1 | 395.2 | 1.52 | C4 |

TABLE 14-continued

Examples 207-219 were prepared from the requisite amine and the chloropyrimidine described in Scheme Q.

| Ex | Structure | LRRK2 IC$_{50}$ (nM) | LCMS Data m/z | RT (min) | Method |
|---|---|---|---|---|---|
| 215 | 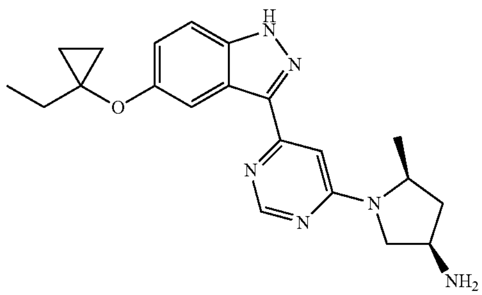 [SMILES: CCC1(Oc2ccc3[nH]nc(-c4cc(N5C[C@H](N)C[C@@H]5C)ncn4)c3c2)CC1] | 2.59 | 379.2 | 1.50 | C4 |
| 216 | 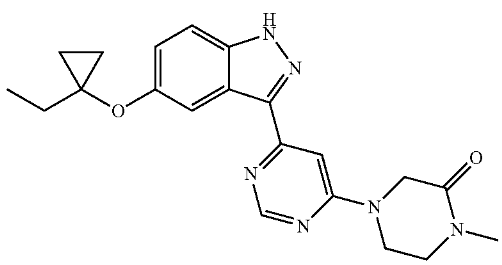 [SMILES: CCC1(Oc2ccc3[nH]nc(-c4cc(N5CCN(C)C(=O)C5)ncn4)c3c2)CC1] | 1.27 | 393.1 | 1.70 | C4 |
| 217 | 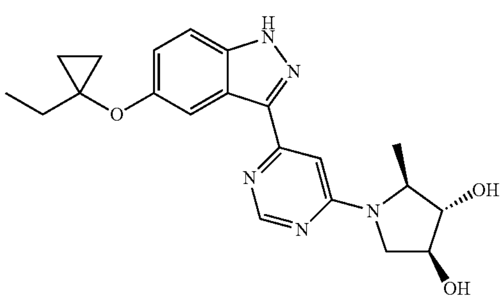 [SMILES: CCC1(Oc2ccc3[nH]nc(-c4cc(N5C[C@H](O)[C@@H](O)[C@@H]5C)ncn4)c3c2)CC1] | 1.63 | 396.1 | 1.58 | C4 |
| 218 | 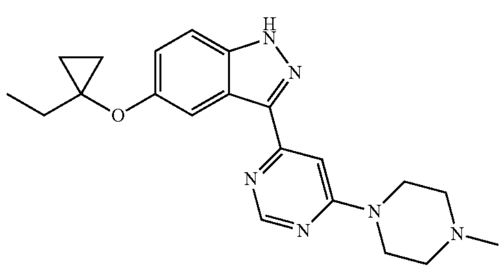 [SMILES: CCC1(Oc2ccc3[nH]nc(-c4cc(N5CCN(C)CC5)ncn4)c3c2)CC1] | 1.49 | 379.2 | 1.56 | C4 |
| 219 | 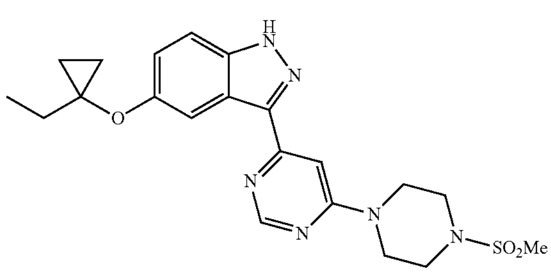 [SMILES: CCC1(Oc2ccc3[nH]nc(-c4cc(N5CCN(S(C)(=O)=O)CC5)ncn4)c3c2)CC1] | 0.67 | 443.0 | 1.74 | C4 |

In examples 212, 213, 214 and 215 the primary amines were protected with a Boc group which was removed during the final treatment with acid.
TABLE 15
The following examples were prepared from the requisite amines and the chloropyrimidine following procedures similiar to those described in Scheme A.
| Ex | Structure | LRRK2 IC$_{50}$ (nM) | m/z | RT (min) | Method |
|---|---|---|---|---|---|
| 220 | 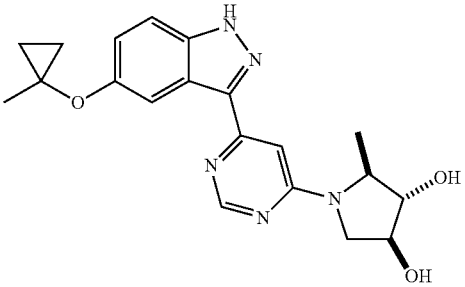 [SMILES: C[C@H]1[C@H](O)[C@@H](O)CN1c1cc(-c2n[nH]c3ccc(OC4(C)CC4)cc23)ncn1] | 1.77 | 382.1 | 1.60 | C1 |
| 221 | 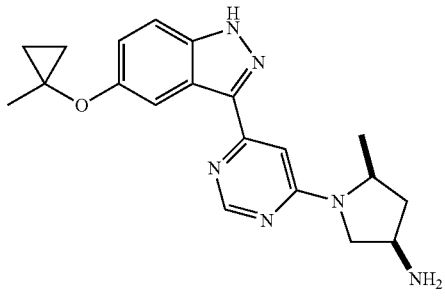 [SMILES: C[C@H]1C[C@@H](N)CN1c1cc(-c2n[nH]c3ccc(OC4(C)CC4)cc23)ncn1] | 1.54 | 365.2 | 1.68 | C1 |
| 222 | 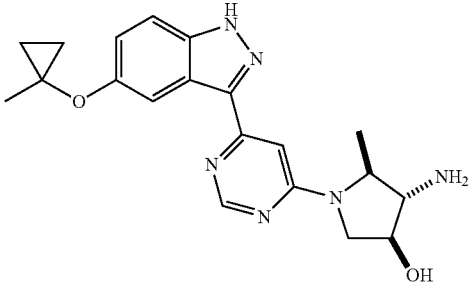 [SMILES: C[C@H]1[C@H](N)[C@@H](O)CN1c1cc(-c2n[nH]c3ccc(OC4(C)CC4)cc23)ncn1] | 2.33 | 381.1 | 1.58 | C1 |
| 223 | 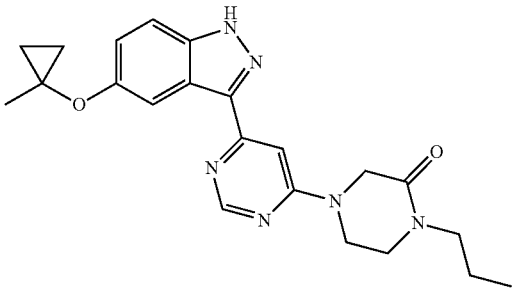 [SMILES: CCCN1CCN(c2cc(-c3n[nH]c4ccc(OC5(C)CC5)cc34)ncn2)CC1=O] | 1.04 | 407.2 | 1.06 | C3 |

TABLE 15-continued

The following examples were prepared from the requisite amines and the chloropyrimidine following procedures similiar to those described in Scheme A.

| Ex | Structure | LRRK2 IC$_{50}$ (nM) | LCMS Data m/z | RT (min) | Method |
|---|---|---|---|---|---|
| 224 | 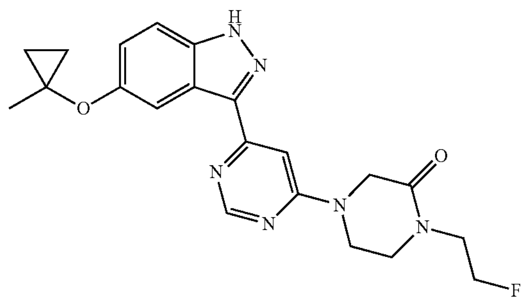 [SMILES: CC1(Oc2ccc3[nH]nc(-c4cc(N5CCN(CCF)C(=O)C5)ncn4)c3c2)CC1] | 1.81 | 411.2 | 1.75 | C1 |
| 227 | 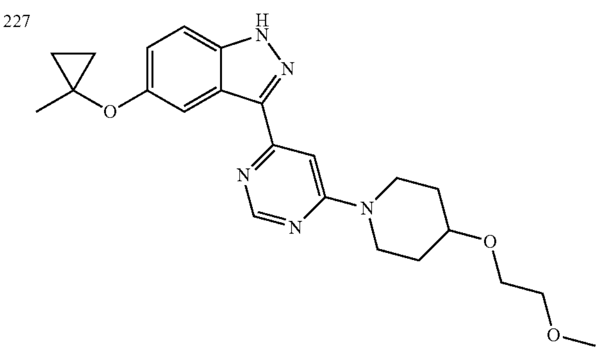 | 0.94 | 424.3 | 1.88 | C2 |
| 228 | 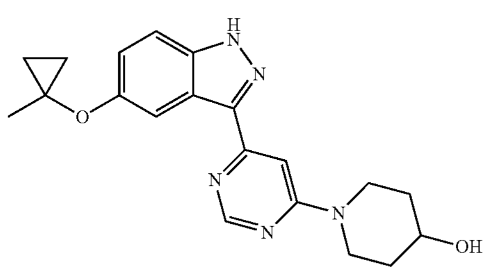 [SMILES: CC1(Oc2ccc3[nH]nc(-c4cc(N5CCC(O)CC5)ncn4)c3c2)CC1] | 0.79 | 366.3 | 1.69 | C2 |
| 229 | 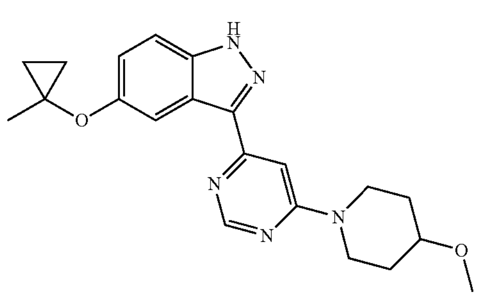 | 1.03 | 380.2 | 1.90 | C2 |

TABLE 15-continued

The following examples were prepared from the requisite amines and the chloropyrimidine following procedures similiar to those described in Scheme A.

| Ex | Structure | LRRK2 IC$_{50}$ (nM) | m/z | RT (min) | Method |
|---|---|---|---|---|---|
| 230 | 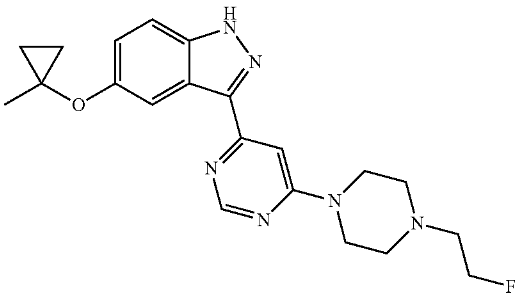 [SMILES: CC1(Oc2ccc3[nH]nc(-c4cc(N5CCN(CCF)CC5)ncn4)c3c2)CC1] | 0.45 | 397.2 | 1.91 | C1 |
| 231 | 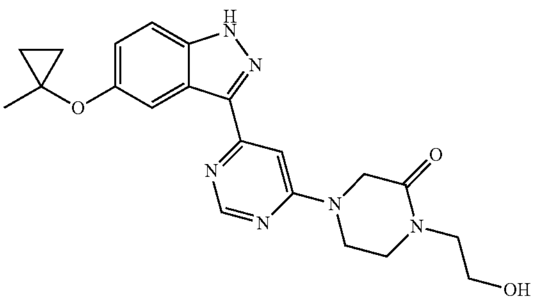 [SMILES: CC1(Oc2ccc3[nH]nc(-c4cc(N5CCN(CCO)C(=O)C5)ncn4)c3c2)CC1] | 0.73 | 409.2 | 1.66 | C1 |
| 232 | 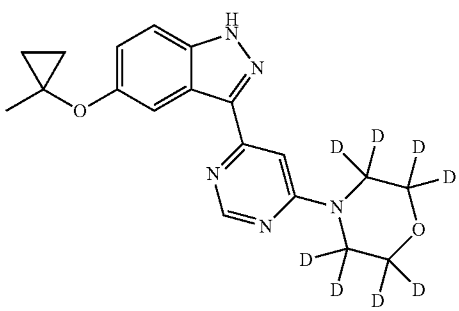 [SMILES: [2H]C1([2H])OC([2H])([2H])C([2H])([2H])N(c2cc(-c3n[nH]c4ccc(OC5(C)CC5)cc34)ncn2)C1([2H])[2H]] | 0.6 | 359.2 | 0.67 | A |
| 233 | 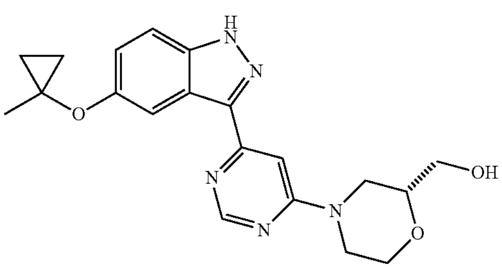 [SMILES: CC1(Oc2ccc3[nH]nc(-c4cc(N5CCO[C@@H](CO)C5)ncn4)c3c2)CC1] | 0.75 | 382.2 | 0.62 | A |
| 234 | 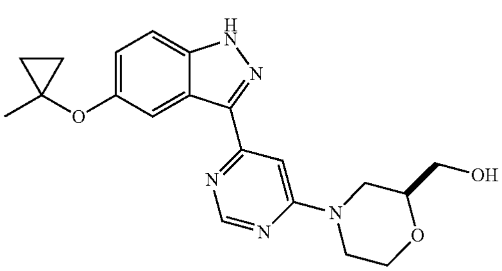 [SMILES: CC1(Oc2ccc3[nH]nc(-c4cc(N5CCO[C@H](CO)C5)ncn4)c3c2)CC1] | 0.78 | 382.1 | 0.83 | A |

TABLE 15-continued

The following examples were prepared from the requisite amines and the chloropyrimidine following procedures similiar to those described in Scheme A.

| Ex | Structure | LRRK2 IC$_{50}$ (nM) | m/z | RT (min) | Method |
|---|---|---|---|---|---|
| 235 | 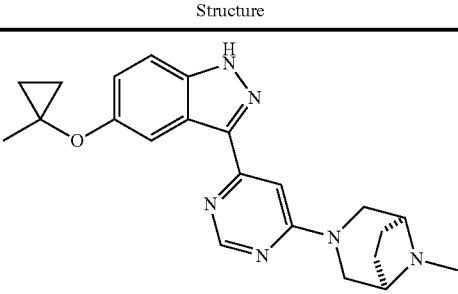 | 4.44 | 391.2 | 0.91 | A |
| 236 | 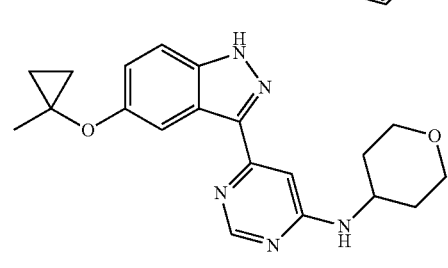 | 1.71 | 366.2 | 0.85 | A |
| 237 | 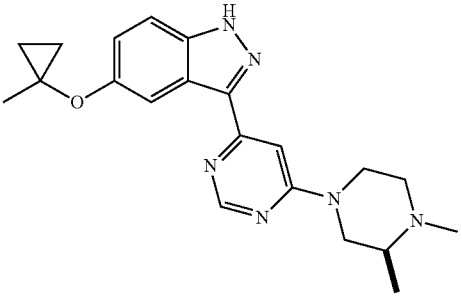 | 0.6 | 379.06 | 0.92 | A |

In examples 221 and 222 the primary amines were protected with a Boc group which was removed during the final treatment with acid.

Scheme R

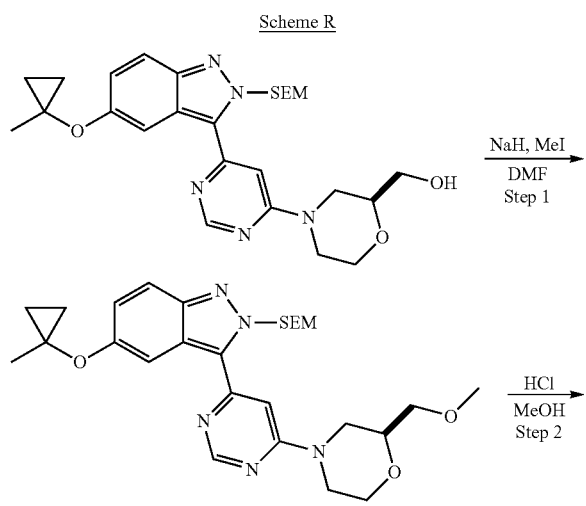

-continued

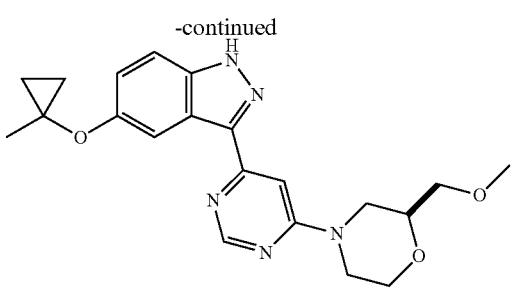

Example R1

Step 1:

To a cold (0° C.), stirred solution of the alcohol (225 mg, 0.440 mmol), (prepared following the method described in Scheme A) in DMF (1.5 mL) was added NaH (21.10 mg of 60% in oil, 0.528 mmol) and the mixture was stirred for 15 min. After that time, iodomethane (55.0 μl, 0.879 mmol) was added and the reaction mixture was slowly warmed to room temperature and stirred at that temperature overnight. The reaction was quenched with water and the mixture was extracted with EtOAc (×3). The combined organic layers were dried over MgSO$_4$, filtered, and concentrated under reduced pressure to leave a residue which was purified by Prep-TLC (elution with 2:1 DCM:EtOAc) to afford the desired methyl ether as a colorless oil.

Step 2:

Example R1 was prepared by the removal of SEM group as described by method 2 in Scheme A. LCMS 396.2 [M+1]$^+$ (ret. time=0.93 min, condition A). LRRK2 IC$_{50}$: 1.9 nM.

Example R2 was synthesized using the procedure described in Scheme R. LCMS 396.1 [M+1]$^+$ (ret. time=0.98 min, condition A). LRRK2 IC$_{50}$: 0.8 nM.

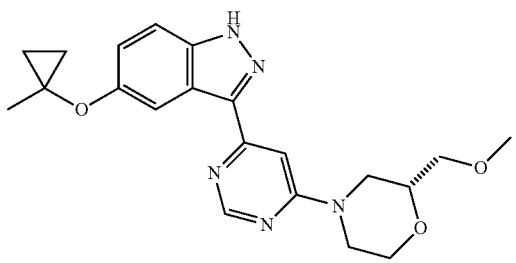

Example R2

Scheme S

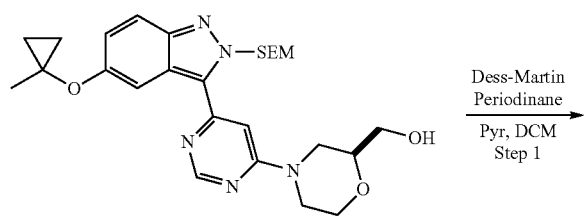

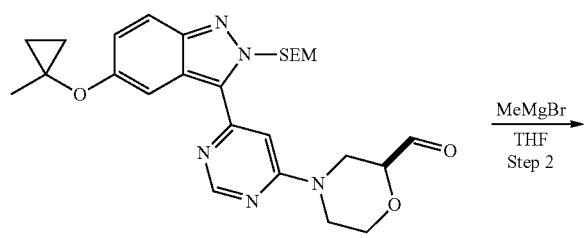

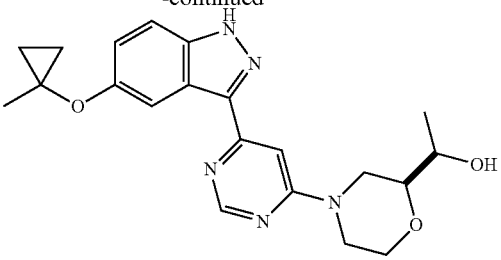

Example S1

Step 1:

To a cold (0° C.), stirred solution of alcohol (850 mg, 1.661 mmol) in DCM (5.5 mL) was added pyridine (134 μl, 1.661 mmol) followed by Dess-Martin Periodinane (740 mg, 1.744 mmol). The reaction mixture was slowly warmed to room temperature and stirred overnight. The reaction was quenched with a saturated aqueous solution of Na$_2$S$_2$O$_3$ and the resultant mixture was extracted with DCM (×3). The combined organic layers were dried over MgSO$_4$, filtered, and concentrated under reduced pressure to leave a residue which was used directly in the next step without further purification.

Step 2:

To a cold (0° C.), stirred solution of above aldehyde in THF (10.5 mL) was added MeMgBr (2.1 mL of 3.0 M solution in diethylether, 6.28 mmol) dropwise over 5 min. After being stirred at room temperature overnight, the reaction was quenched with a saturated aqueous solution of NH$_4$Cl and the resulting layer was extracted with EtOAc (×3). The combined organic layers were dried over MgSO$_4$, filtered, and concentrated under reduced pressure to leave a residue which was purified by flash chromatography on silica (elution with 5:1 DCM:MeOH) to yield the desired alcohol as a yellow solid.

Step 3:

Example S1 was prepared by the removal of SEM group as described by method 2 in Scheme A. LCMS 396.3 [M+1]$^+$ (ret. time=0.66 min, condition A). LRRK2 IC$_{50}$: 0.7 nM.

Scheme T:

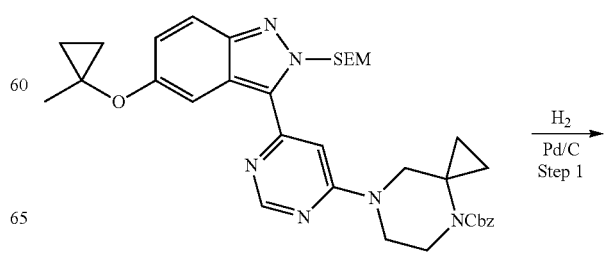

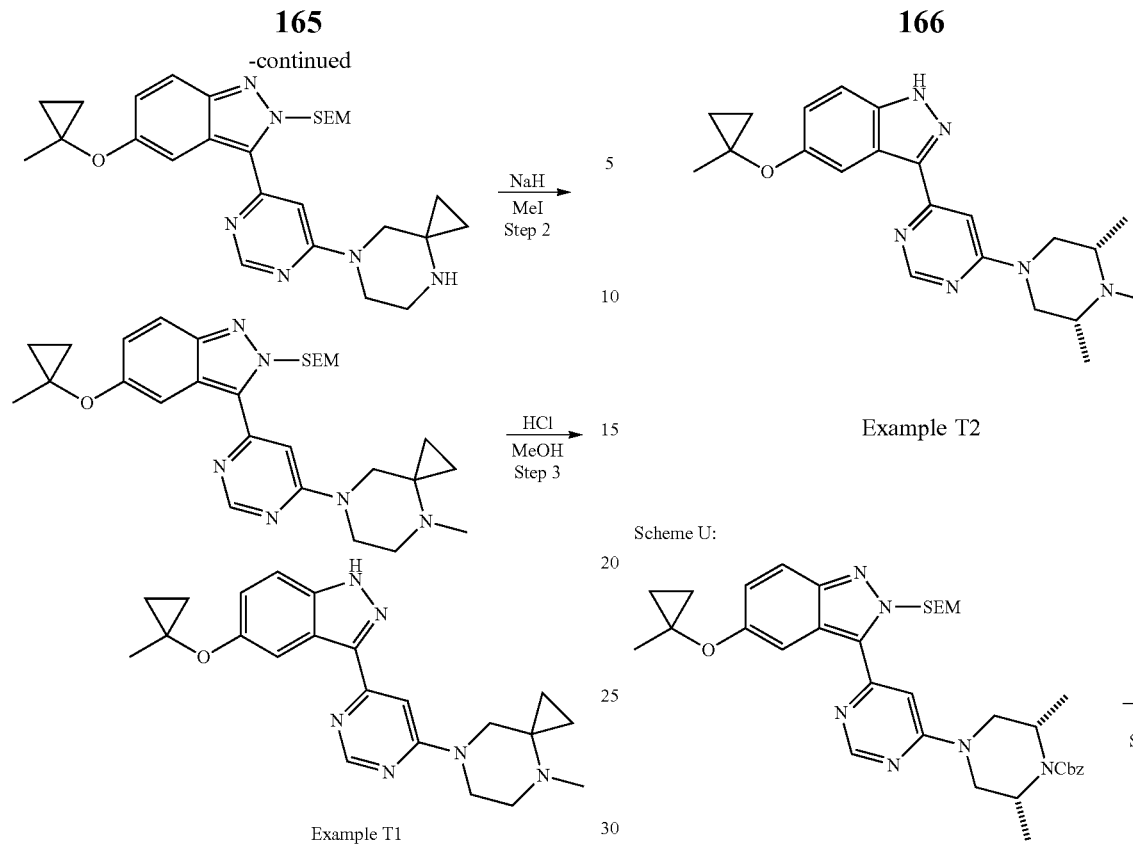

Example T1

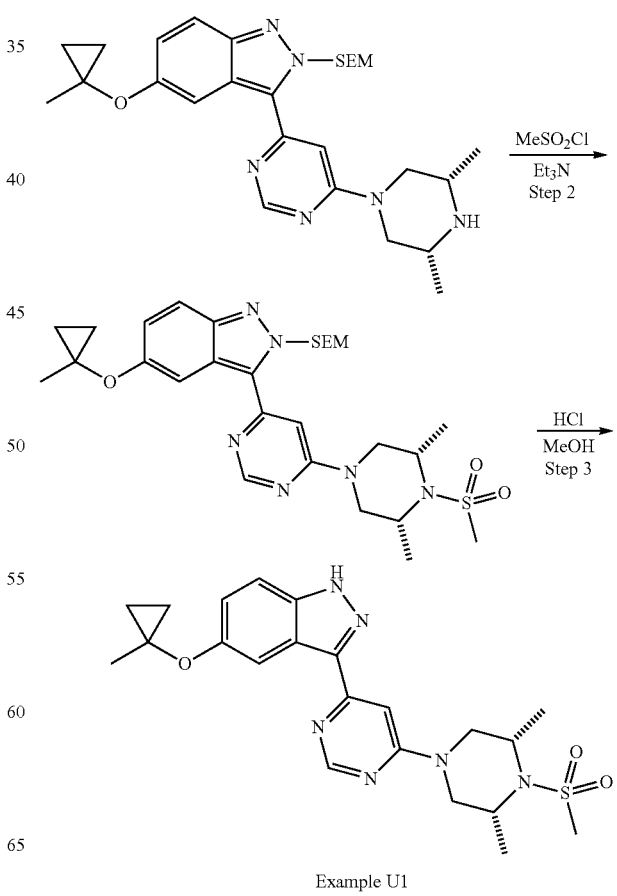

Example T2

Scheme U:

Example U1

Step 1:

To a stirred solution of the Cbz-protected piperazine (584 mg, 0.911 mmol) in EtOH (4.6 mL) was added 10% Pd/C (48.5 mg, 0.046 mmol). The flask was evacuated and backfilled with $H_2$ (×2). The reaction mixture was stirred under $H_2$ overnight before being filtered through a pad of celite. The filtrate was concentrated under reduced pressure to leave a residue which was purified by flash chromatography on silica (elution with 20:1 DCM:MeOH) to yield the desired piperazine compound.

Step 2:

To a cold (0° C.), stirred solution of above piperazine (409 mg, 0.807 mmol) in DMF (2.7 mL) was added NaH (58.1 mg of 60% in oil, 1.453 mmol). After 5 min the mixture was warmed to room temperature followed by addition of MeI (202 μl, 3.23 mmol). After being stirred at room temperature overnight the reaction was quenched with water and the resultant mixture was extracted with DCM (×3). The combined organic layers were dried over MgSO4, filtered, and concentrated under reduced pressure to leave a residue which was purified by flash chromatography on silica (elution with 20:1 DCM:MeOH) to yield the desired N-methylpiperazine.

Step 3:

Example T1 was prepared by the removal of SEM group as described by method 2 in Scheme A. LCMS 391.2 $[M+1]^+$ (ret. time=0.95 min, condition A). LRRK2 $IC_{50}$: 0.6 nM.

Example T2 was synthesized using the similar procedure described in Scheme T. LCMS 393.3 $[M+1]^+$ (ret. time=0.98 min, condition A). LRRK2 $IC_{50}$: 0.8 nM.

167

Step 1:
The hydrogenation was carried out using similar method described in step 1 of Scheme T to provide the dimethylpiperazine intermediate.

Step 2:
To a stirred solution of above dimethylpiperazine (370 mg, 0.727 mmol) in DCM (7.3 mL) was added Et₃N (203 μl, 1.455 mmol) followed by MeSO₂Cl (68.0 μl, 0.873 mmol). After being stirred at room temperature for 18 h the reaction was quenched with a saturated aqueous solution of NaHCO₃ and the resultant mixture was extracted DCM (×3). The combined organic layers were dried over MgSO₄, filtered, and concentrated under reduced pressure to leave a residue which was purified by flash chromatography on silica (elution with 5:1 DCM:MeOH) to afford the desired product as a light brown oil.

Step 3:
Example U1 was prepared by the removal of SEM group as described by method 2 in Scheme A. LCMS 457.3 [M+1]⁺ (ret. time=0.97 min, condition A). LRRK2 IC₅₀: 5.2 nM.

168

-continued

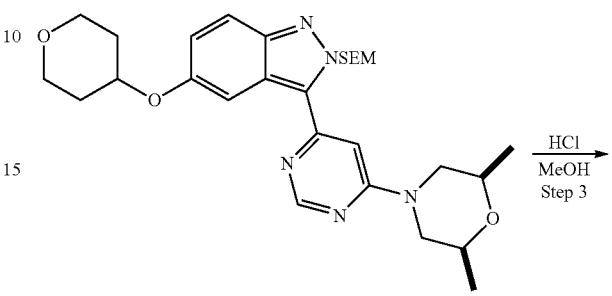

TABLE U

The following examples were prepared following the procedure similiar to that described in Scheme U.

| Ex | Structure | LRRK2 IC$_{50}$ (nM) | LCMS Data m/z | RT (min) | Method |
|---|---|---|---|---|---|
| U2 | 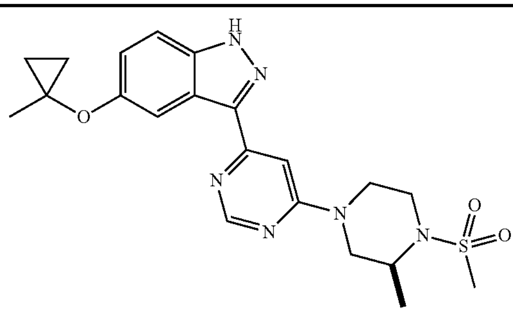 | 1.18 | 443.2 | 0.92 | A |

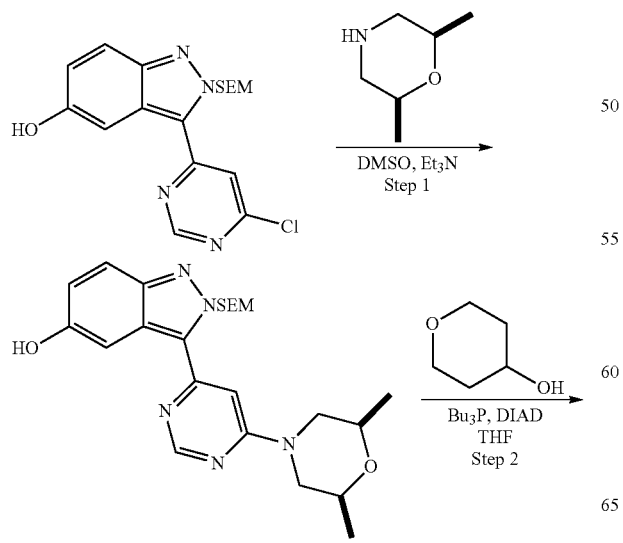

Scheme V:

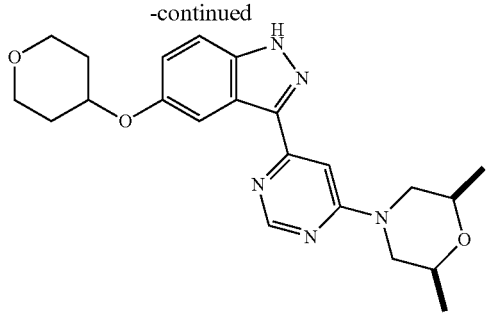

Example V1

Step 1:
A mixture of chloropyrimidine (5 g, 13.27 mmol), from Scheme I step 4, cis-dimethylmorpholine (4.90 mL, 39.8 mmol) and Et₃N (11.09 ml, 80 mmol) in DMSO (40 ml) was heated at 90° C. in a sealed flask for 1 h. After being cooled to room temperature the mixture was diluted with EtOAc, washed with water and brine, dried over MgSO₄, filtered and concentrated under reduced pressure to leave a residue which was purified by flash column chromatography on silica (elution with 1560% EtOAc in hexane) to afford the desired dimethylmorpholine adduct.
Step 2:
This step was carried out following the procedure described in Scheme I for step 6.
Step 3:
Example V1 was prepared by the removal of SEM group as described by method 2 in Scheme A. LCMS 410.09 [M+H]$^+$ (ret. time=1.05 min, condition A). LRRK2 IC$_{50}$: 24 nM.

Example V2 was synthesized using the similar procedure described in Scheme W. LCMS 382.2 [M+H]$^+$ (ret. time=0.91 min, condition A). LRRK2 IC$_{50}$: 28.6 nM.

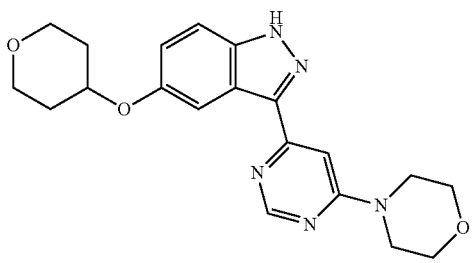

Example V2

LCMS Conditions

Condition A:
Column: SUPELCO Ascentis Express C18, 3×50 mm, 2.7 um, Mobile phase: A: Water (0.05% TFA) B: Acetonitrile (0.05% TFA), UV: 200-400 nm

| [Gradient Table] | | | |
|---|---|---|---|
| Time (min) | Flow Rate | % A | % B |
| Initial | 1.25 | 90 | 10 |
| 0.8 | 1.25 | 1 | 99 |
| 1.99 | 1.25 | 1 | 99 |
| 2.00 | 1.25 | 90 | 10 |

Condition B:
Agilent 6140 Quadruple Easy Access LC/MS; Column: Agilent Zorbax SB-C18, 3.0×50 mm, 1.8 µm; Solvent A: Water with 0.1% TFA; Solvent B: acetonitrile with 0.1% TFA; Flow Rate: 1 mL/min; Dual wavelength UV Detection at 220 nm and 254 nm; Gradient: 10% Solvent B to 95% Solvent B over 1.5 min., isocratic at 95% Solvent B for 1.2 min., gradient to 10% Solvent B over 0.1 min., isocratic at 10% Solvent B for 0.8 min.
Condition C1:
Mobile Phase: A: Water (10 mM NH$_4$HCO$_3$) B: Acetonitrile, Gradient: 5%-95% B in 1.5 min, Flow Rate: 1.8 mL/min, Column: XBridge C18, 4.6*50 mm, 3.5 um.
Condition C2:
Mobile Phase: A: Water (10 mM NH$_4$HCO$_3$) B: Acetonitrile, Gradient: 5% B for 0.2 min, increase to 95% B within 1.5 min, 95% B for 1.5 min, back to 5% B within 0.01 min., Flow Rate: 1.8 mL/min, Column: XBridge C18, 4.6*50 mm, 3.5 urn.
Condition C3:
Mobile Phase: A: Water (0.01% TFA) B: MeCN (0.01% TFA), Gradient: 5%-95% B in 1.2 min, Flow Rate: 2.0 ml/min, Column: Merck C18, 50 mm, 3 mm.

Condition C4:
Mobile Phase: A: Water (0.01% TFA) B: MeCN (0.01% TFA), Gradient: 5%-95% B in 1.5 min, Flow Rate: 1.8 ml/min, Column: Sunfire C18, 4.6*50 mm, 3.5 um.
Condition C5:
Mobile Phase: A: Water (0.01% TFA) B: MeCN (0.01% TFA), Gradient: 5%-95% B in 1.5 min, Flow Rate: 2.0 ml/min, Column: XBridge C18, 4.6*50 mm, 3.5 um.
Condition C6:
Column: SunFire C18, 4.6×50 mm, 3.5 urn, Mobile phase: H$_2$O (0.05% TFA) (A)/MeCN (0.05% TFA) (B), Elution program: Gradient from 5 to 95% of B in 1.2 min at 2 ml/min.
Condition D:
Waters Acquity UPLC/MS, Electrospray positive ion mode; Column: Waters Acquity UPLC BEH C18, 2.1×50 mm, 1.7 micron; Gradient elution 5:95 to 100:0 MeCN (0.1% NH$_4$OH): water (0.1% NH$_4$OH) over 1.4 min 0.8 mL/min; UV: 220 nm.

Biological Assays

The data presented for the 5 mM and Km ATP LanthaScreen™ Assay represents mean IC$_{50}$ values based on several test results and may have reasonable deviations depending on the specific conditions and reagents used. Reagents for the LRRK2 5 mM and Km ATP LanthaScreen™ Assay were purchased from Life Technologies Corporation.

LRRK2 5 mM ATP LanthaScreen™ Assay
  a) 400 nl of a 1:2.15 serial dilution of test compound (98 µM top assay concentration) is spotted via Labcyte Echo to certain wells in a 384 well black, untreated plate. Control wells contain 400 nl of either DMSO or 400 nl of a known inhibitor in DMSO.
  b) 10 µl of a 2.5 nM LRRK2(G2019S mutation, GST-LRRK2(amino acids 970-2527)) enzyme solution in 1× assay buffer (50 mM Tris pH 8.5, 10 mM MgCl$_2$, 0.01% Brij-35, 1.0 mM EGTA, 2 mM DTT, 0.05 mM NaVO$_4$) is added to all wells.
  c) A 30 minute room temperature incubation is followed by addition of 10 µl of 800 nM fluorescein labeled LRRKtide peptide substrate and 10 mM ATP solution in 1× assay buffer to all wells.
  d) After a 35 minute room temperature incubation, 20 µl of TR-FRET Dilution Buffer (Invitrogen PV3756B) containing 4 nM Tb-labeled anti-phospho LRRKtide antibody and 20 mM EDTA is added to all wells.
  e) Plates are incubated at room temperature for 1 hour and read on an Envision™ multi-mode plate reader with LanthaScreen™ settings. Results are analysed using Assay Data Analyzer.

LRRK2 Km ATP LanthaScreen™ Assay
  a) 400 nl of a 1:2.15 serial dilution of test compound (98 µM top assay concentration) is spotted via Labcyte Echo to certain wells in a 384 well black, untreated plate. Control wells contain 400 nl of either DMSO or 400 nl of a known inhibitor in DMSO.
  b) 10 µl of a 2.5 nM LRRK2(G2019S mutation, GST-LRRK2(amino acids 970-2527)) enzyme solution in 1× assay buffer (50 mM Tris pH 8.5, 10 mM MgCl$_2$, 0.01% Brij-35, 1 mM EGTA, 2 mM DTT, 0.05 mM NaVO$_4$) is added to all wells.
  c) A 30 minute room temperature incubation is followed by addition of 10 µl of 800 nM fluorescein labeled LRRKtide peptide substrate and 186 µM ATP solution in 1× assay buffer to all wells.
  d) After a 60 minute room temperature incubation, 20 µl of TR-FRET Dilution Buffer (Invitrogen PV3756B)

containing 4 nM Tb-labeled anti-phospho LRRKtide antibody and 20 mM EDTA is added to all wells.

e) Plates are incubated at room temperature for 1 hour and read on an Envision™ multi-mode plate reader with LanthaScreen™ settings. Results are analysed using Assay Data Analyzer.

TABLE A 5 mM ATP LanthaScreen ™ Assay Data of representative compounds
In the table below, representative examples are provided with their respective $IC_{50}$ in the 5 mM ATP LanthaScreen ™ Assay. Preferred compounds would have an $IC_{50}$ less than 1 μM in the 5 mM ATP LanthaScreen Assay.

| Example | $IC_{50}$ (nM) |
| --- | --- |
| 3 | 11 |
| 38 | 5.1 |
| T2 | 0.49 |
| 51 | 6.4 |
| 36 | 3.7 |
| 47 | 10 |
| 11 | 12 |
| 40 | 9.0 |
| 25 | 2.4 |
| 10 | 8.8 |
| 75 | 14 |

TABLE B

Kinase selectivity of representative compounds
Kinase selectivity were performed using Z'-LYTE ™ or Adapta ® assay platforms available from Life Technologies Corporation. Values in Table B are percent inhibition in the prescence of 1 μM of the representative Example.

| Kinase | Assay Platform | Ex 1 | Ex 51 | Ex. 12 | Ex 55 |
| --- | --- | --- | --- | --- | --- |
| AURKB (Aurora B) | A | 28 | 16 | 37 | 33 |
| BRAF V599E | A | 24 | 10 | 11 | 17 |
| CDK1/cyclin B | A | 10 | 1 | 43 | 6 |
| CHEK2 (CHK2) | A | 21 | 15 | 17 | 19 |
| CLK2 | A | 57 | 55 | 53 | 69 |
| DYRK1A | A | 16 | 4 | 5 | 13 |
| IRAK1 | B | 23 | -15 | 31 | 0 |
| JAK3 | A | 7 | 7 | 12 | 5 |
| MAPK1 (ERK2) | A | 8 | -4 | 10 | 3 |
| MAPK8 (JNK1) | A | 56 | 0 | 40 | 33 |

A - Z-LYTE ™;
B - Adapta ®

The invention claimed is:

1. A compound of the formula:

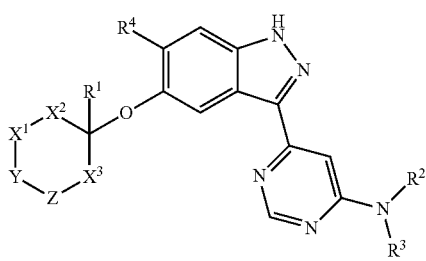

wherein $X^1$, $X^2$ and $X^3$ are each independently selected from the group consisting of a bond or $CR^eR^f$;
Y is O, $CR^aR^b$ or $NR^c$;
Z is O, $CR^aR^b$ or $NR^c$;
$R^1$ is selected from the group consisting of hydrogen and $C_{1-6}$ alkyl, which is optionally substituted with one to three substitutents independently selected from the group consisting of halo, cyano, hydroxyl, $NR^cR^d$, $OR^5$ and $(C=O)OR^5$;

$R^2$ is selected from the group consisting of hydrogen and $C_{1-6}$ alkyl, which is optionally substituted with one to three substitutents independently selected from the group consisting of:
a) halo,
b) cyano,
c) $R^5$,
d) $R^7$,
e) $OR^5$, and
f) $NR^cR^d$;

$R^3$ is selected from the group consisting of:
a) hydrogen,
b) $C_{1-6}$ alkyl, which is optionally substituted with one to three substitutents independently selected from the group consisting of halo, cyano, $OR^5$ and $NR^cR^d$,
c) $C_{3-8}$ cycloalkyl, which is optionally substituted with one to three substitutents independently selected from the group consisting of halo, cyano, $OR^5$ and $NR^cR^d$,
d) heterocyclyl, which is optionally substituted with one to three substitutents independently selected from the group consisting of halo, cyano, oxo, $R^5$, $OR^5$ and $NR^cR^d$,
e) heteroaryl, which is optionally substituted with one to three substitutents independently selected from the group consisting of halo, cyano, oxo, $R^5$, $OR^5$ and $NR^cR^d$;
f) $C_{4-8}$cycloalkenyl, which is optionally substituted with one to three substitutents independently selected from the group consisting of halo, cyano, $OR^5$ and $NR^cR^d$,
g) $(C=O)R^7$,
h) $(C=O)R^5$,
i) $S(O)_mR^5$, and
j) $S(O)_mR^7$;
or $R^2$ and $R^3$ can be taken together with the atoms to which they are attached to form a 3 to 8 membered heterocyclic ring, wherein said ring may contain from one to three heteroatoms selected from N, O and S, wherein the sulfur is optionally oxidized to the sulfone or sulfoxide, and which ring is optionally substituted with one to four substituents each independently selected from the group consisting of:
a) halo,
b) oxo,
c) cyano,
d) $OR^5$,
e) $NR^cR^d$,
f) $SO_3H$,
g) $S(O)_mR^5$,
h) $S(O)_mR^7$
i) $R^5$,
j) $R^6$,
k) $R^7$,
l) $(C=O)R^5$,
m) $(C=O)OR^5$,
n) $(C=O)R^7$, and
o) $(C=O)NR^cR^d$;

$R^4$ is selected from the group consisting of hydrogen, halo, cyano, $OR^5$, aryl, heteroaryl, $C_{3-8}$ cycloalkyl, $C_{4-8}$ cycloalkenyl, $C_{4-8}$ heterocyclyl and $C_{1-6}$ alkyl, which is optionally substituted with one to three substitutents independently selected from the group consisting of halo, cyano, $OC_{1-3}$alkyl, $NR^cR^d$ and hydroxyl;

$R^5$ is selected from the group consisting of hydrogen and $C_{1-6}$ alkyl, which is optionally substituted with one to three substituents independently selected from the group consisting of:
a) halo,
b) hydroxyl,
c) $OC_{1-6}$alkyl,
d) $NR^cR^d$,
e) $(C=O)NR^cR^d$,
f) $S(O)_m$,
g) $S(O)_mR^8$,
h) $S(O)_mR^7$,
i) $R^7$, and
j) $OR^7$;

$R^6$ is $C_{1-6}$alkyl, which is optionally substituted with one to three substituents independently selected from the group consisting of halo and hydroxyl;

or $R^5$ and $R^6$ can be taken together with the atoms to which they are attached to form a 4 to 8 membered heterocyclic, 3 to 8 membered carbocyclic, aryl or heteroaryl ring, wherein said heterocyclic and heteroaryl rings may contain from one to three heteroatoms selected from N, O and S, wherein said heterocyclic, carbocyclic, aryl and heteroaryl rings are optionally substituted with one to three substituents independently selected from the group consisting of:
a) halo,
b) oxo,
c) cyano,
d) hydroxyl,
e) $C_{1-3}$ alkyl, which is optionally substituted with one to three halo,
f) $C_{3-8}$ cycloalkyl,
g) $OC_{1-3}$alkyl, which is optionally substituted with one to three halo, and
h) $OC_{3-8}$cycloalkyl;

$R^7$ is selected from the group consisting of $C_{4-8}$ heterocyclyl, $C_{3-8}$ cycloalkyl, $C_{4-8}$ cycloalkenyl, aryl or heteroaryl, wherein said heterocyclyl, cycloalkyl, cycloalkenyl, aryl and heteroaryl groups are optionally substituted with one to three substituents independently selected from the group consisting of:
a) halo,
b) cyano,
c) hydroxyl,
d) oxo,
e) $C_{1-3}$alkyl, which is optionally substituted with one to four substituents independently selected from the group consisting of hydroxyl, halo, cyano, heterocyclyl, $OC_{1-3}$ alkyl and $NR^cR^d$,
f) $OC_{1-3}$alkyl, which is optionally substituted with one to four substituents independently selected from the group consisting of hydroxyl, halo, cyano, heterocyclyl, $OC_{1-3}$ alkyl $NR^cR^d$ and aryl,
g) $C_{3-8}$ cycloalkyl, which is optionally substituted with one to four substituents independently selected from the group consisting of hydroxyl, halo, cyano, heterocyclyl, $OC_{1-3}$alkyl and $NR^cR^d$,
h) aryl, which is optionally substituted with one to four substituents independently selected from the group consisting of hydroxyl, halo, cyano, heterocyclyl, $OC_{1-3}$ alkyl, $S(O)_mNR^cR^d$, $C(O)NR^cR^d$ and $NR^cR^d$,
i) heterocyclyl, which is optionally substituted with one to four substituents independently selected from the group consisting of hydroxyl, halo, cyano, heterocyclyl, $OC_{1-3}$ alkyl, $S(O)_mNR^cR^d$, $C(O)NR^cR^d$ and $NR^cR^d$,
j) heterocyclyl, which is optionally substituted with one to four substituents independently selected from the group consisting of hydroxyl, halo, cyano, $OC_{1-3}$alkyl and $NR^cR^d$,
k) $C_{4-8}$ cycloalkenyl, which is optionally substituted with one to four substituents independently selected from the group consisting of hydroxyl, halo, cyano, heterocyclyl, $OC_{1-3}$ alkyl and $NR^cR^d$;

$R^8$ is hydrogen or $C_{1-6}$alkyl, which is optionally substituted with one to three substituents independently selected from the group consisting of:
a) halo,
b) cyano,
c) hydroxyl,
d) $OC_{1-3}$alkyl, which is optionally substituted with one to four substituents independently selected from the group consisting of hydroxyl, halo and $NR^cR^d$, and
e) $C_{3-8}$ cycloalkyl;

$R^a$ is selected from the group consisting of hydrogen and $C_{1-6}$ alkyl;

$R^b$ is selected from the group consisting of hydrogen and $C_{1-6}$ alkyl;

$R^c$ is selected from the group consisting of:
a) hydrogen and
b) $C_{1-3}$ alkyl, which is optionally substituted with one to three substituents independently selected from the group consisting of halo, hydroxyl, cyano, heteroaryl, aryl, $NH(C_{1-3}alkyl)$, $N(C_{1-3}alkyl)_2$, $OC_{1-6}$ alkyl, and $C_{3-8}$ cycloalkyl;

$R^d$ is selected from the group consisting of:
a) hydrogen,
b) $C_{3-8}$ cycloalkyl,
c) $C_{3-6}$ heterocyclyl,
d) $C_{1-3}$ alkyl,
e) $(C=O)C_{1-3}$alkyl,
f) aryl, and
g) heteroaryl;

wherein said cycloalkyl, heterocyclyl, alkyl, aryl and heteroaryl groups are each optionally substituted with one to three substituents independently selected from the group consisting of halo, hydroxyl, cyano, $R^8$, $SO_2R^8$, $OC_{1-6}$alkyl and $C_{3-8}$ cycloalkyl, or $R^e$ and $R^d$ can be taken together with the atoms to which they are attached to form a 3 to 8 membered heterocyclic ring, wherein said ring may contain from one to three heteroatoms selected from N, O and S, wherein the sulfur is optionally oxidized to the sulfone or sulfoxide, and which ring is optionally substituted with one to four substituents each independently selected from the group consisting of halo, cyano, hydroxyl, $C_{1-3}$ alkyl and $OC_{1-3}$alkyl;

$R^e$ is selected from the group consisting of hydrogen and $C_{1-3}$alkyl;

$R^f$ is selected from the group consisting of hydrogen and $C_{1-3}$ alkyl;

m is an integer from zero to two,
or a pharmaceutically acceptable salt thereof.

2. The compound of claim 1 wherein $X^1$, $X^2$ and $X^3$ are each a bond, or a pharmaceutically acceptable salt thereof.

3. The compound of claim 2 wherein Y is O or $CR^aR^b$ and Z is O or $CR^aR^b$; or a pharmaceutically acceptable salt thereof.

4. The compound of claim 3 wherein $R^1$ is selected from the group consisting of hydrogen and $C_{1-3}$ alkyl, or a pharmaceutically acceptable salt thereof.

5. The compound of claim 4 wherein $R^4$ is selected from the group consisting of hydrogen and halo, or a pharmaceutically acceptable salt thereof.

6. The compound of claim 5 wherein $R^2$ and $R^3$ can be taken together with the atoms to which they are attached to form a 3 to 8 membered heterocyclic ring, wherein said ring may contain from one to three heteroatoms selected from N, O and S, wherein the sulfur is optionally oxidized to the sulfone or sulfoxide, and which ring is optionally substituted with one to four substituents each independently selected from the group consisting of:

a) halo,
b) oxo,
c) cyano,
d) $OR^5$,
e) $NR^cR^d$,
f) $SO_3H$,
g) $S(O)_mR^5$,
h) $S(O)_mR^7$,
i) $R^5$,
j) $R^6$,
k) $R^7$,
l) (C=O)$R^5$,
m) (C=O)O$R^5$,
n) (C=O)$R^7$, and
o) (C=O)N$R^cR^d$;

or a pharmaceutically acceptable salt thereof.

7. The compound of claim 6 wherein $R^2$ and $R^3$ can be taken together with the atoms to which they are attached to form a 6 membered heterocyclic ring, wherein said ring may contain from one to three heteroatoms selected from N, O and S, wherein the sulfur is optionally oxidized to the sulfone or sulfoxide, and which ring is optionally substituted with one to four substituents each independently selected from the group consisting of:

a) halo,
b) oxo,
c) $OR^5$,
d) $NR^cR^d$,
e) $S(O)_mR^5$,
f) $R^5$,
g) $R^6$,
h) $R^7$,
i) (C=O)$R^5$,
j) (C=O)O$R^5$, and
k) (C=O)$R^7$, or a pharmaceutically acceptable salt thereof.

8. A compound selected from

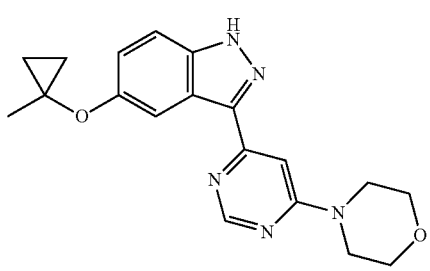

-continued

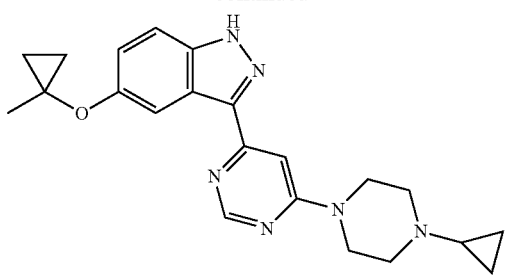

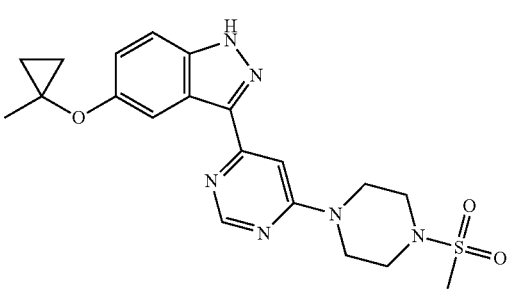

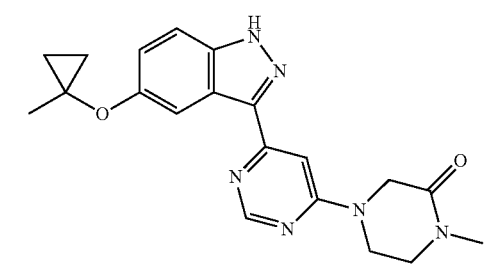

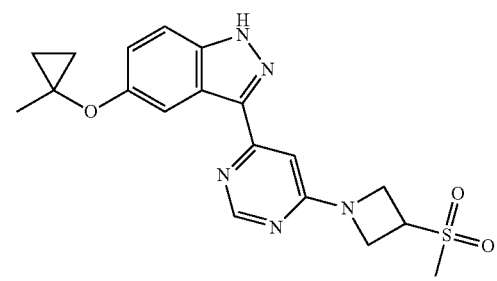

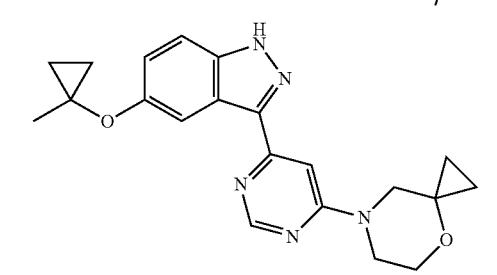

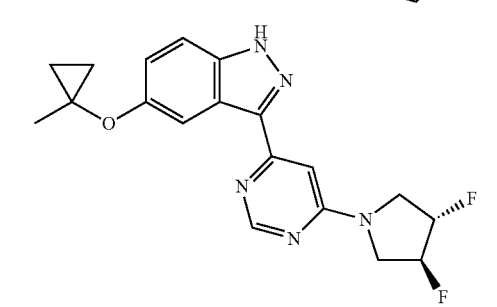

177
-continued
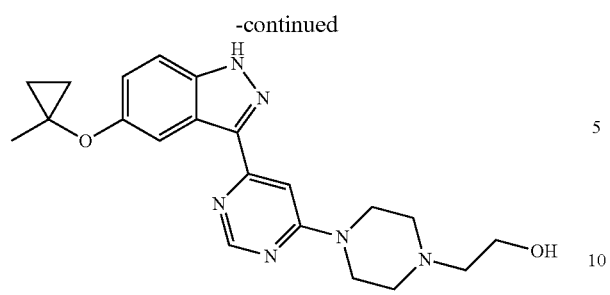
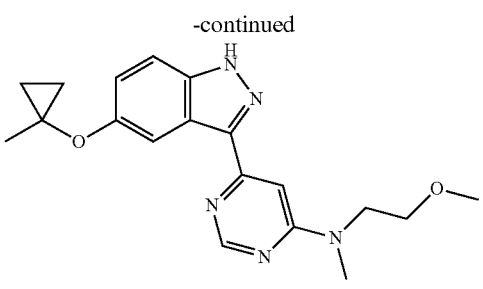
178
-continued
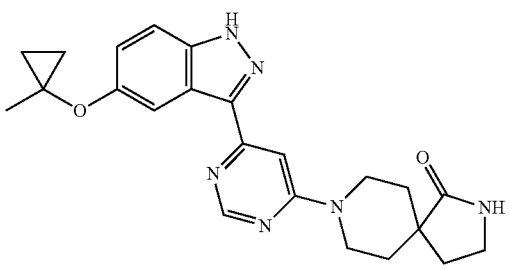
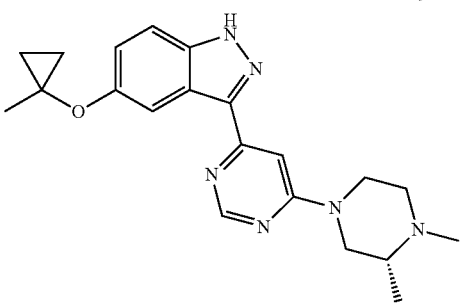
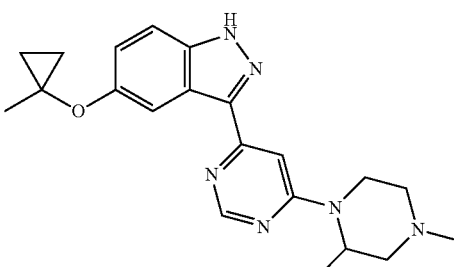
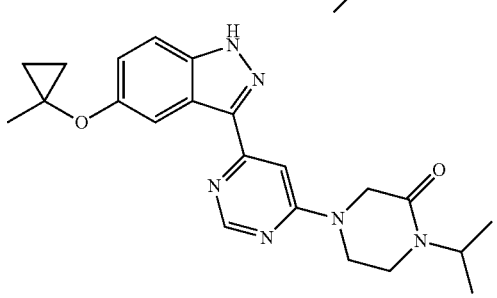
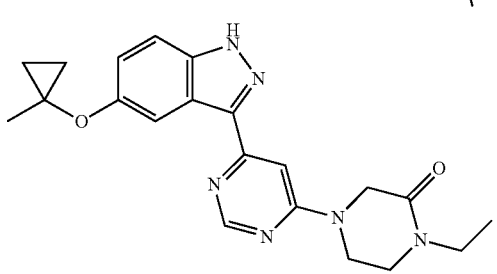

-continued
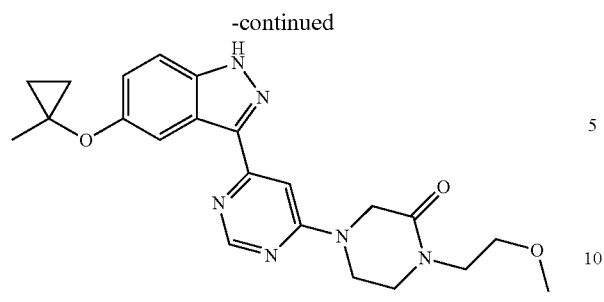
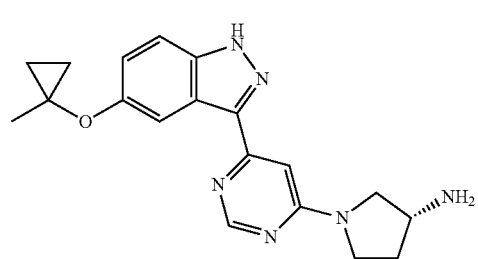
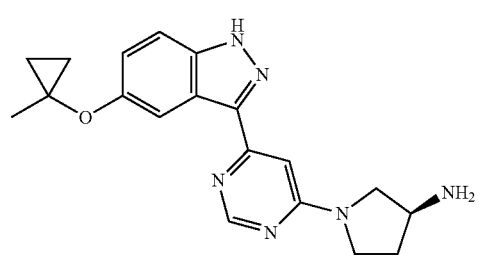
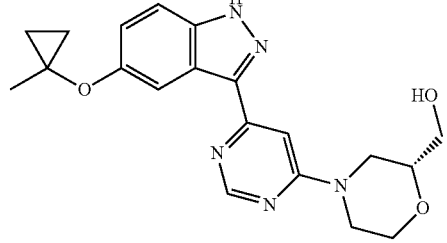
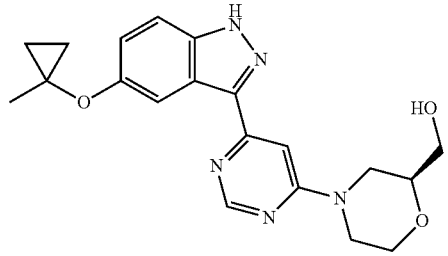
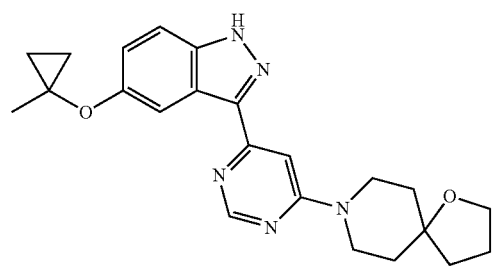
-continued
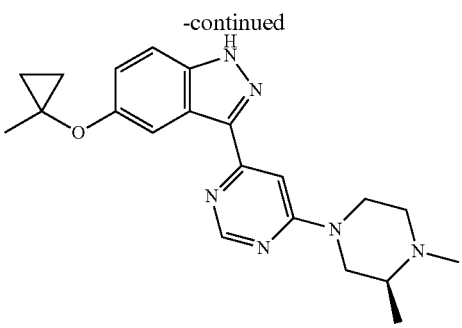
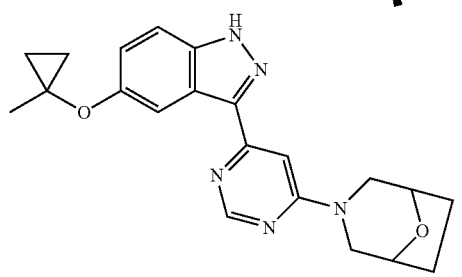
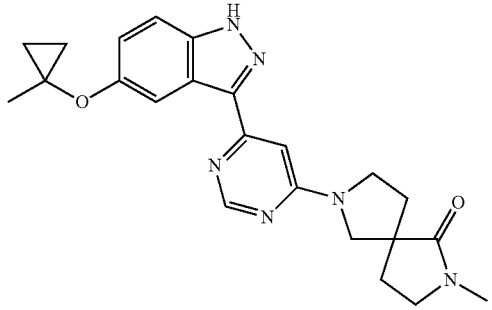
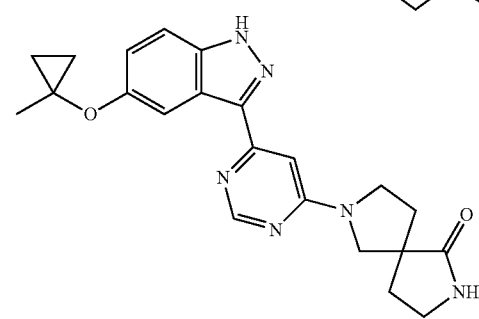
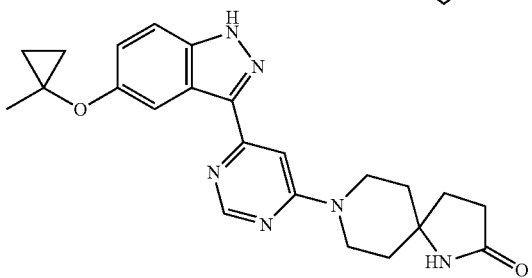
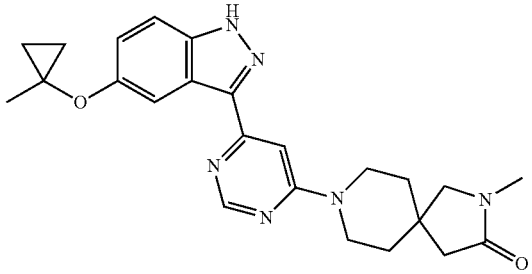

181
-continued
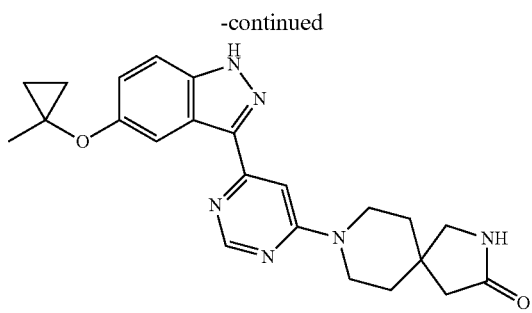
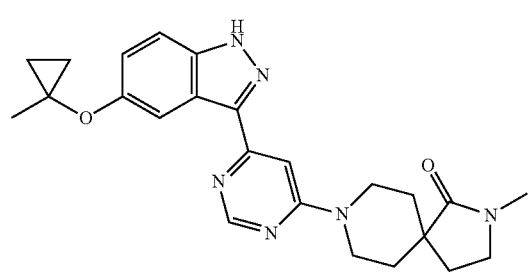
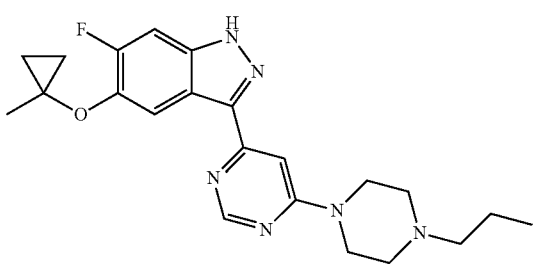
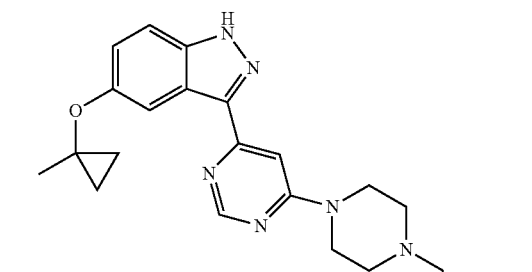
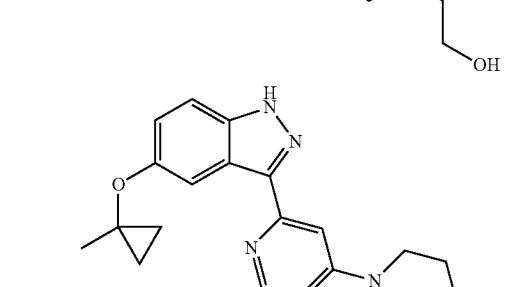
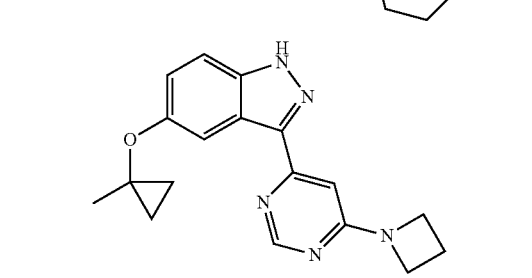
182
-continued
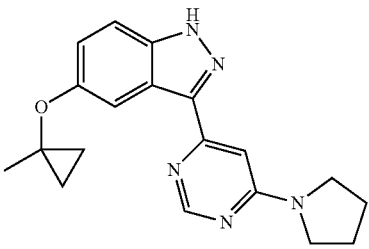
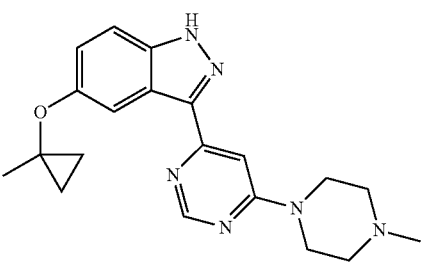
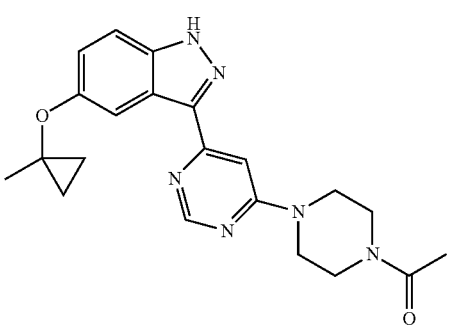
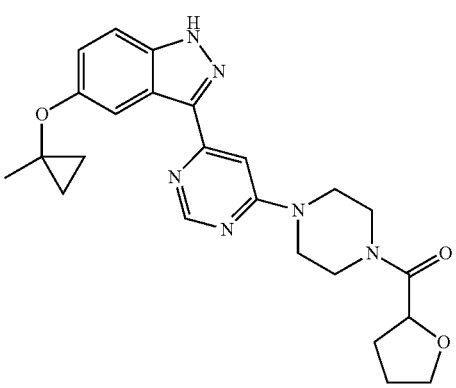
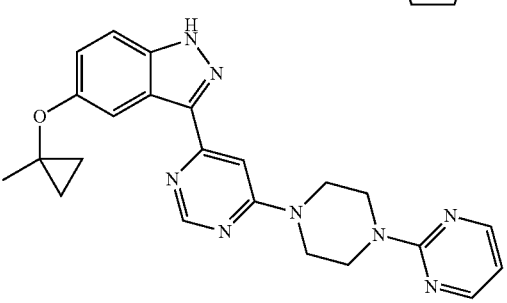

-continued
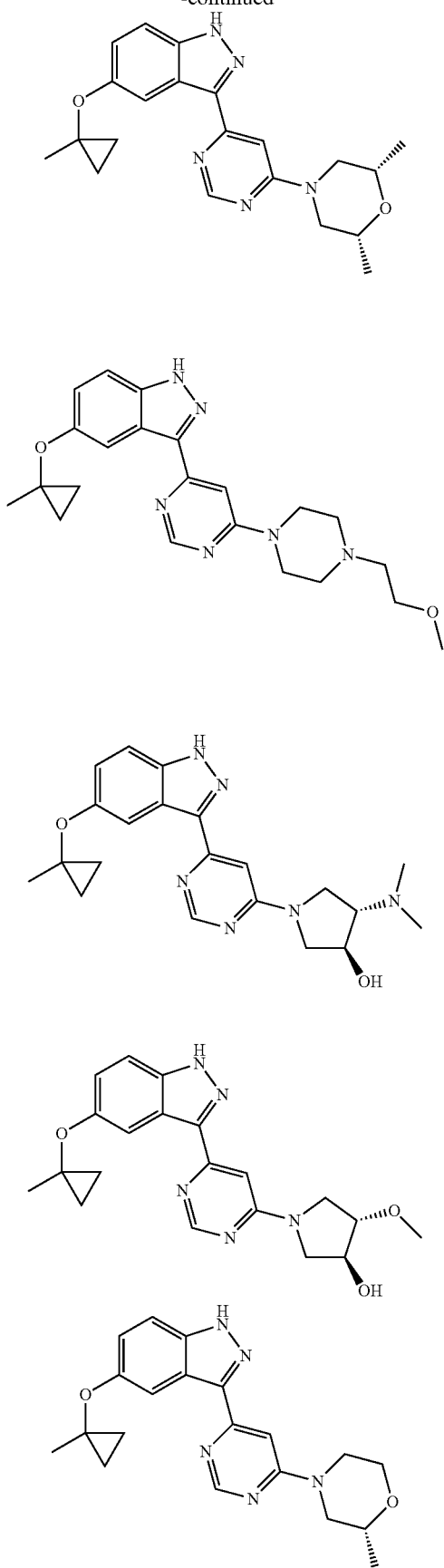
-continued
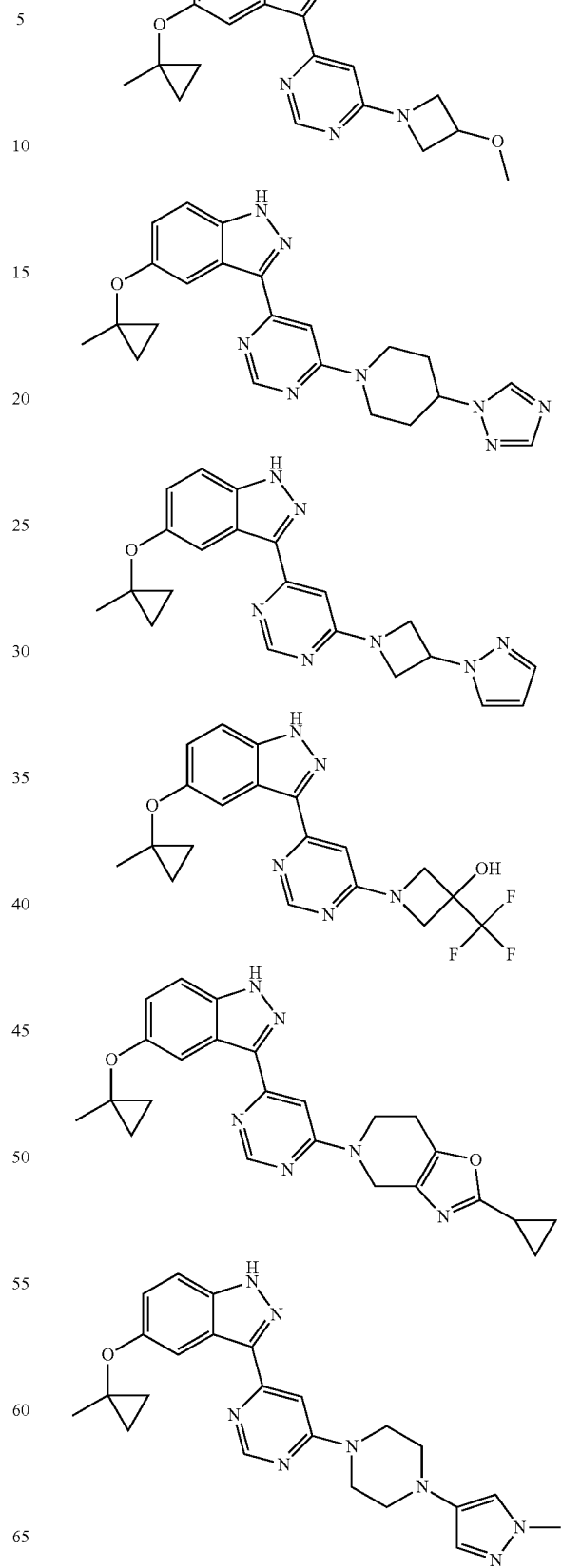

185
-continued
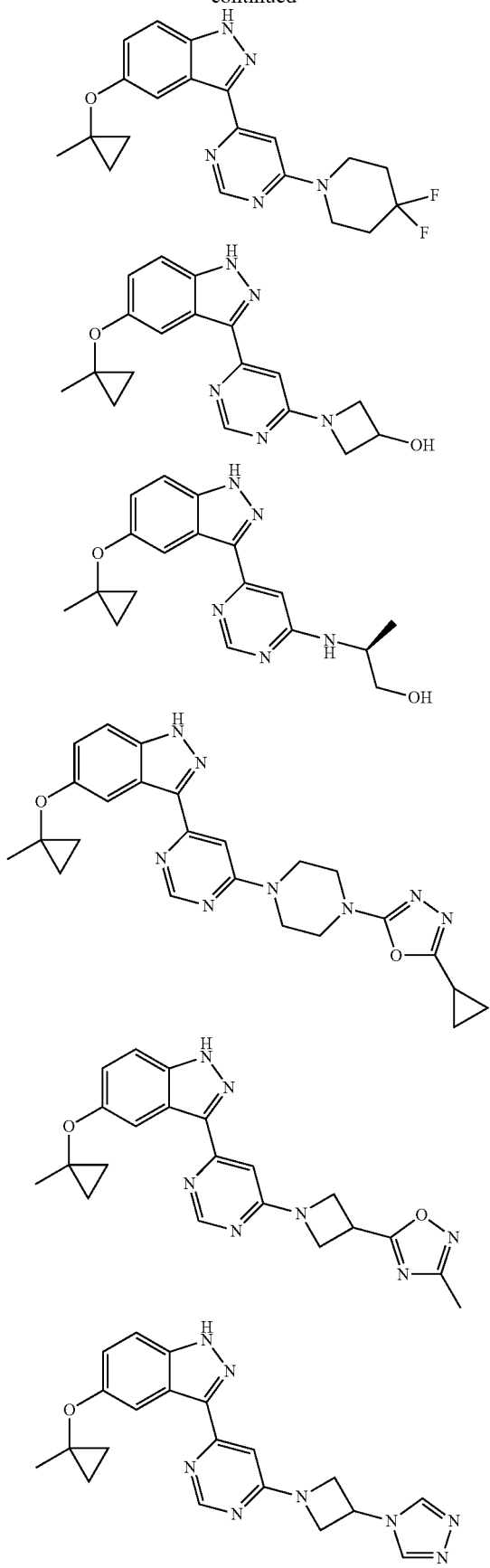
186
-continued
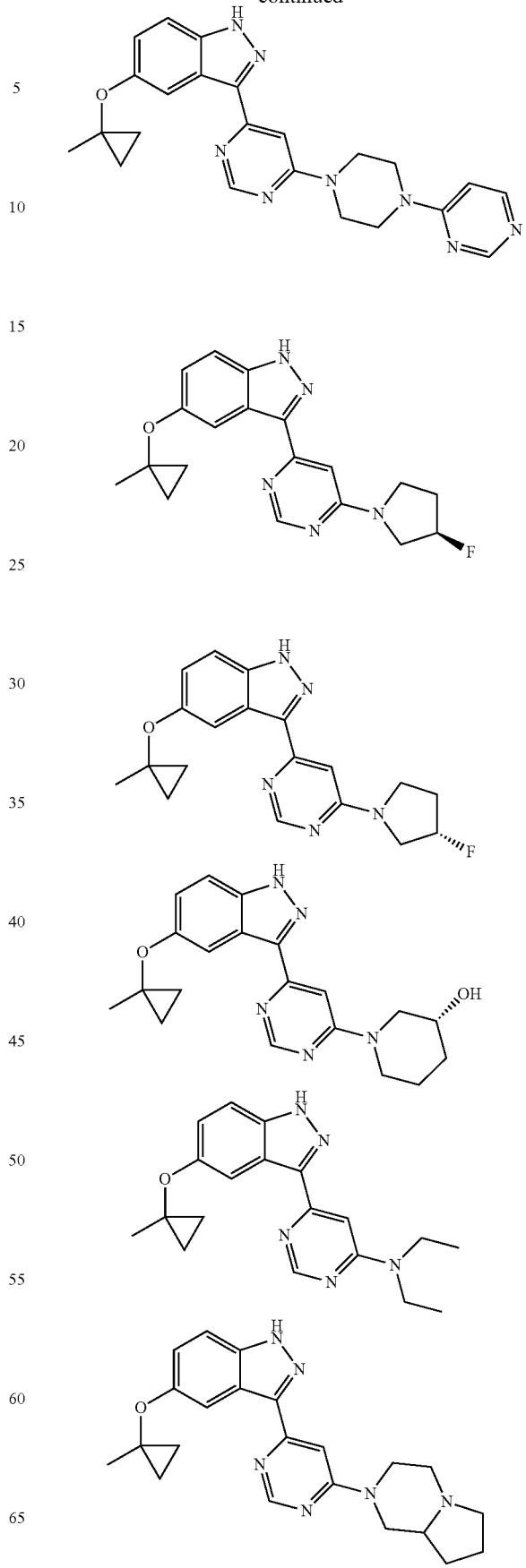

187
-continued
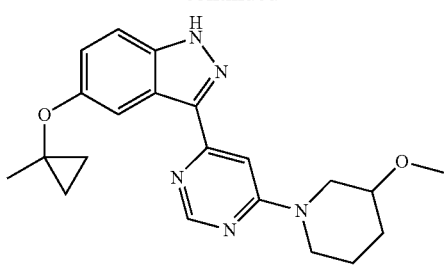
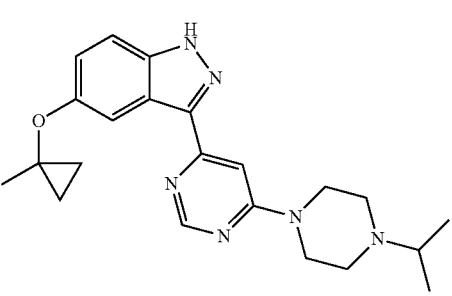
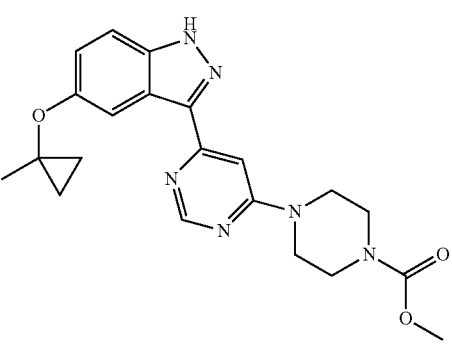
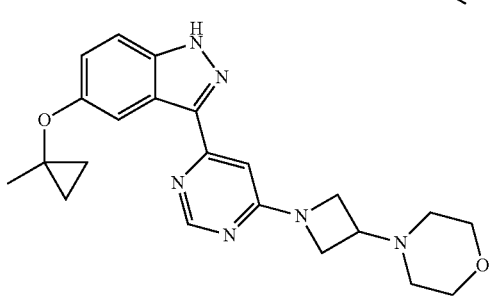
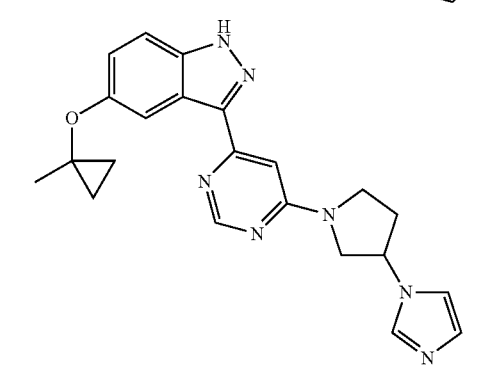
188
-continued
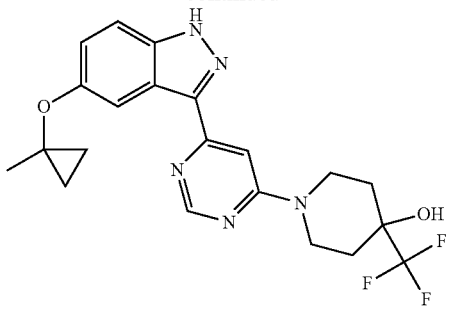
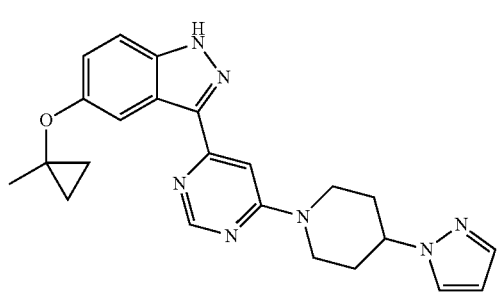
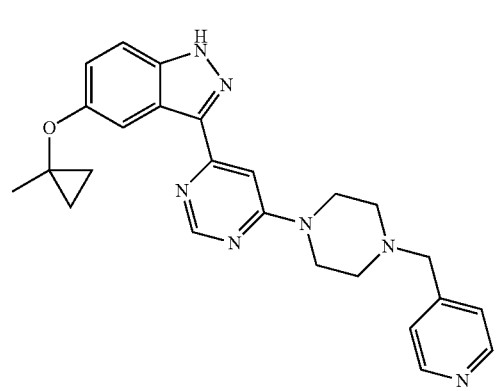
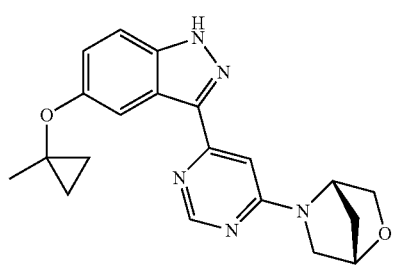
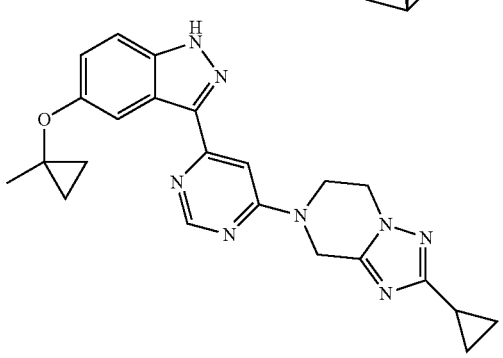

| 189 -continued | 190 -continued |
|---|---|
| 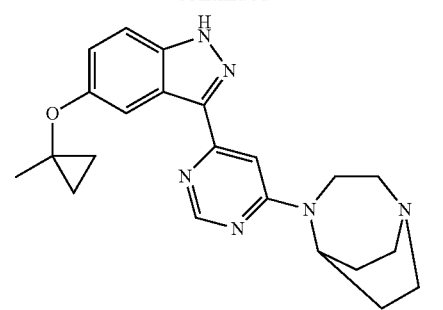 | 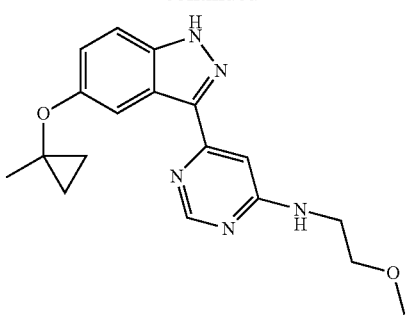 |
| 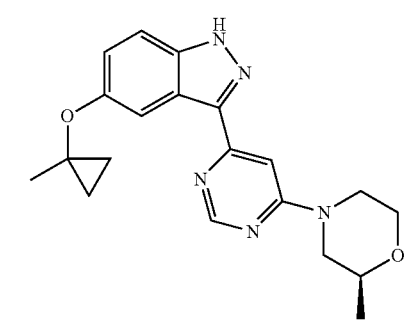 | 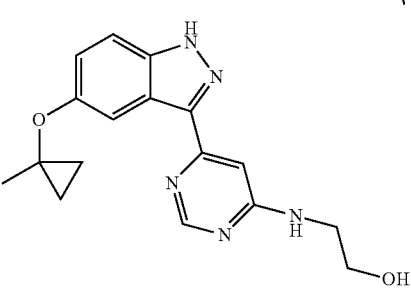 |
| 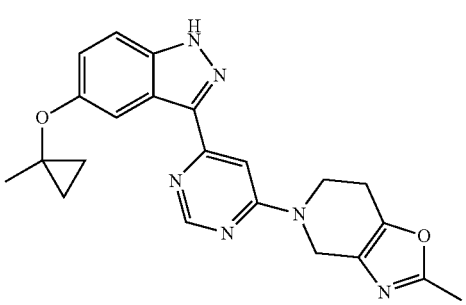 | 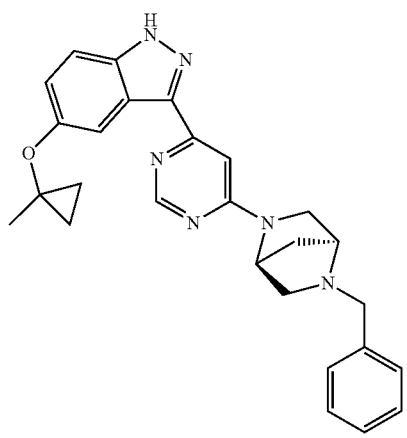 |
| 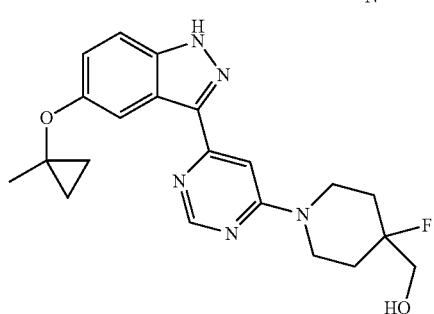 | 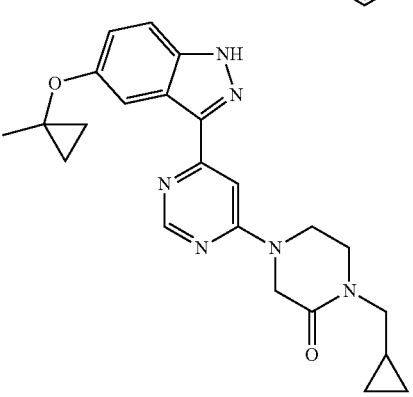 |
| 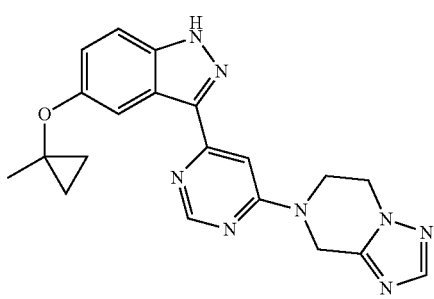 | 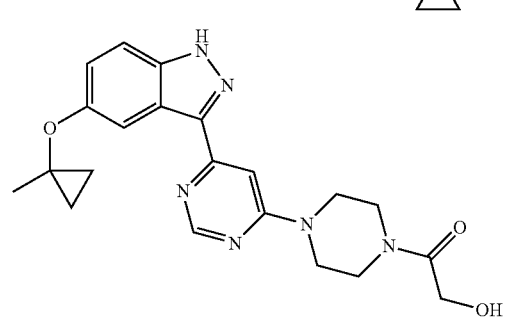 |

191
-continued
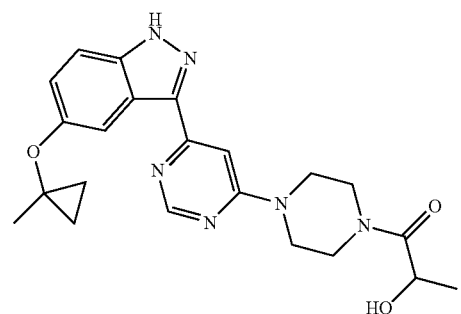
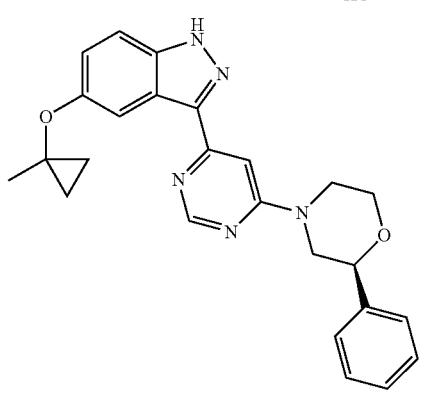
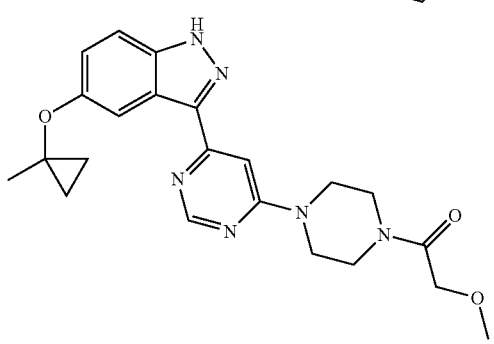
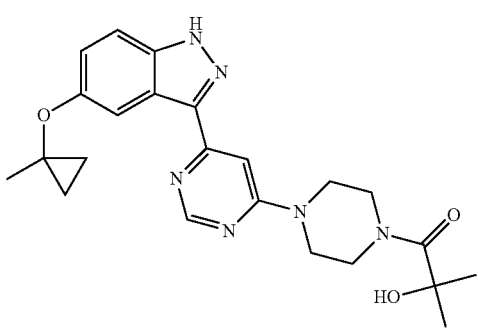
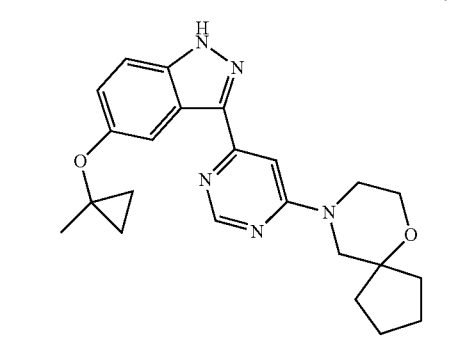
192
-continued
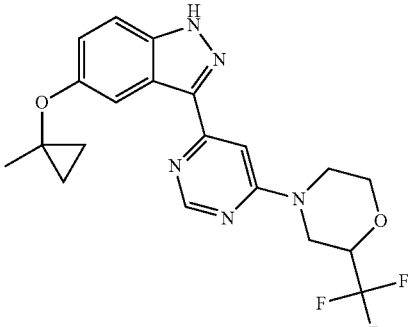
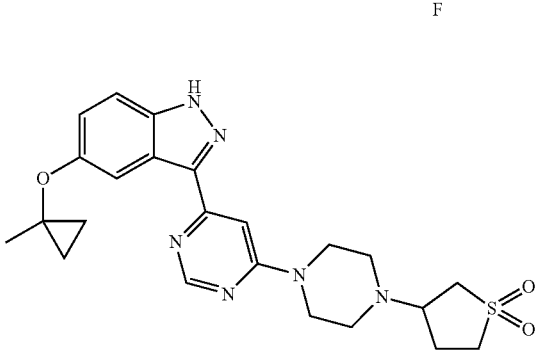
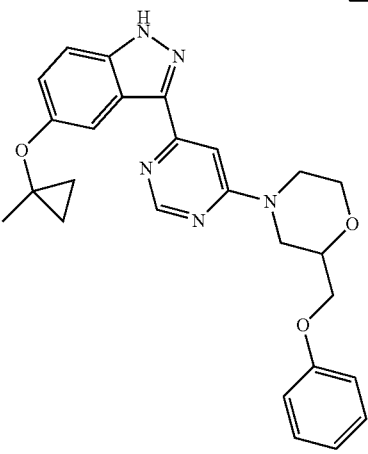
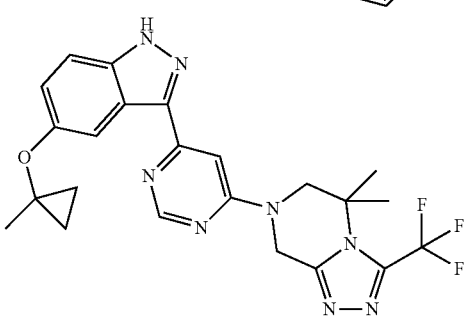
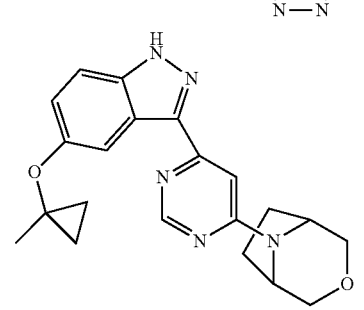

193
-continued
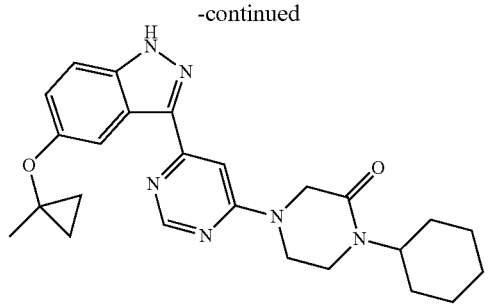
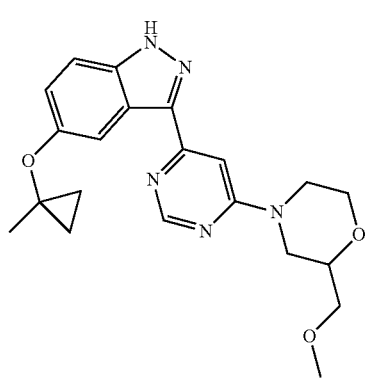
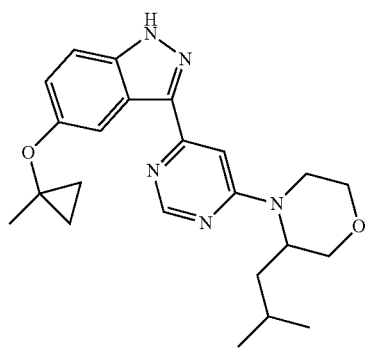
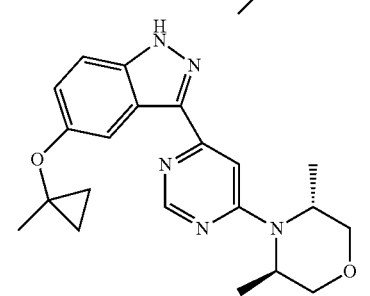
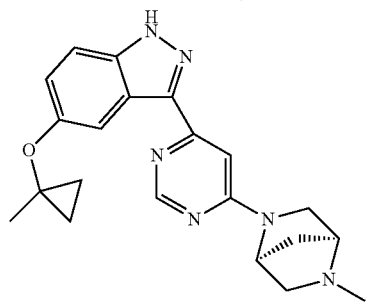
194
-continued
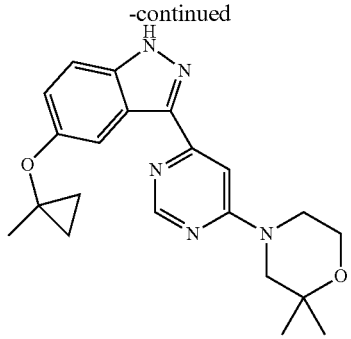
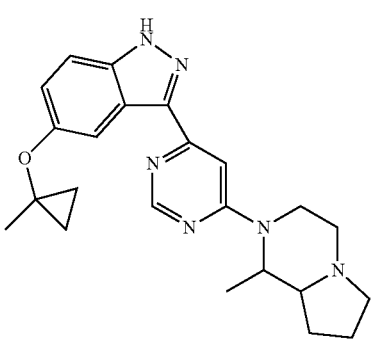
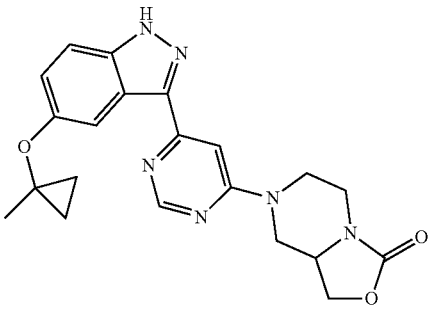
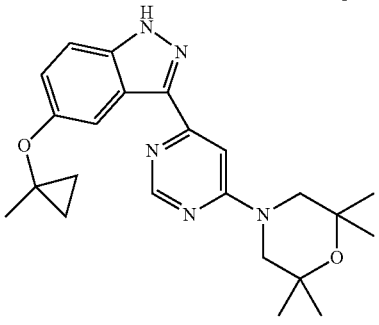
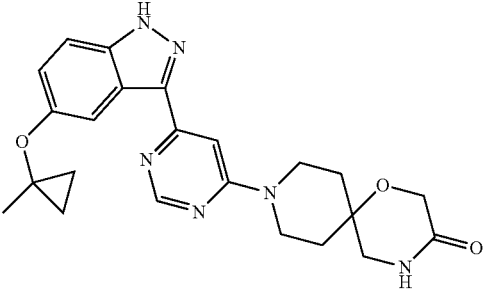

195
-continued
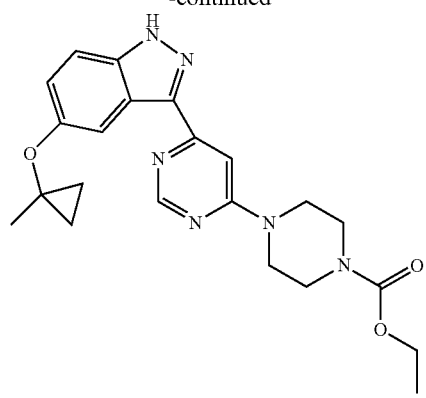
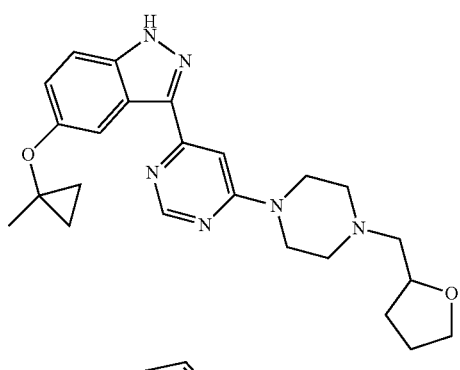
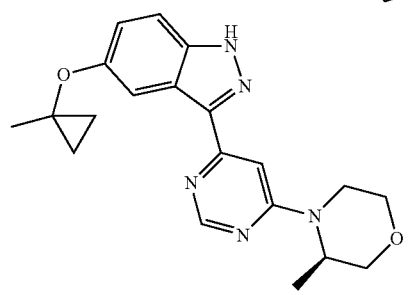
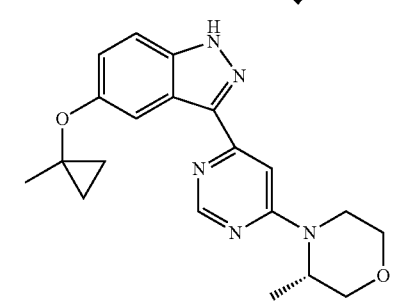
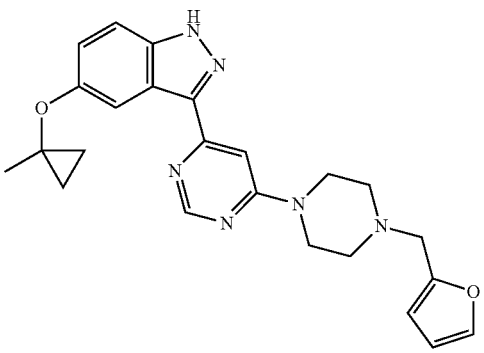
196
-continued
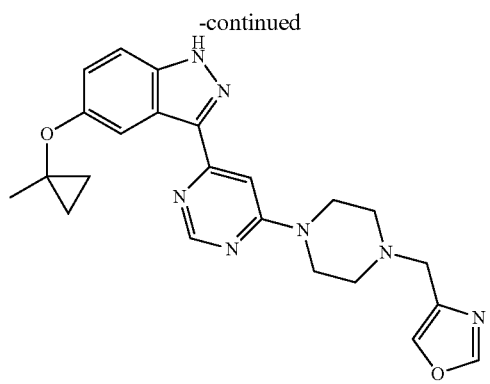
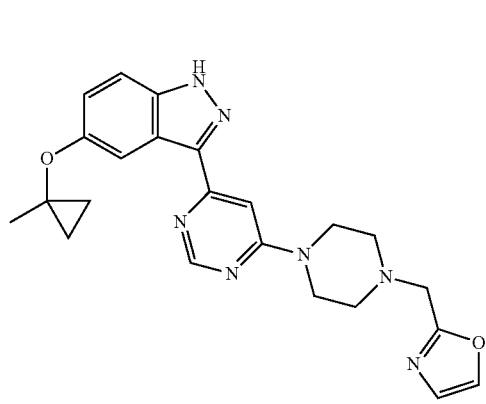
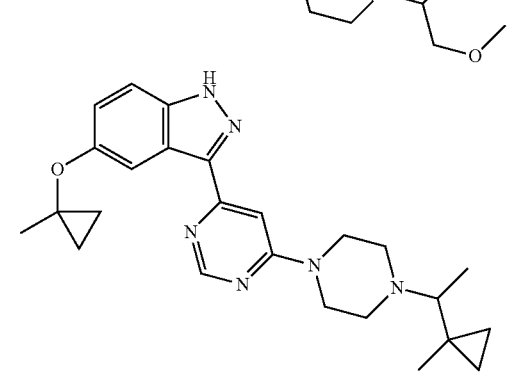
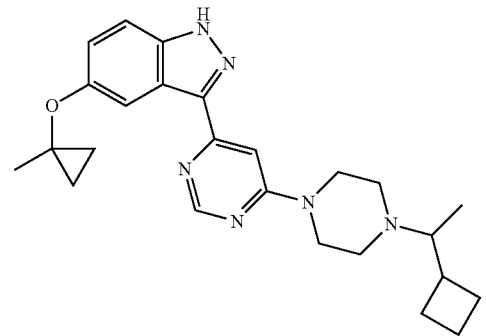

197
-continued
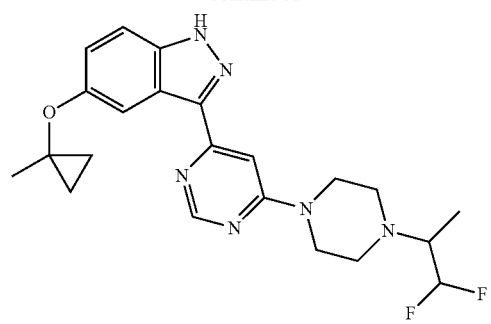
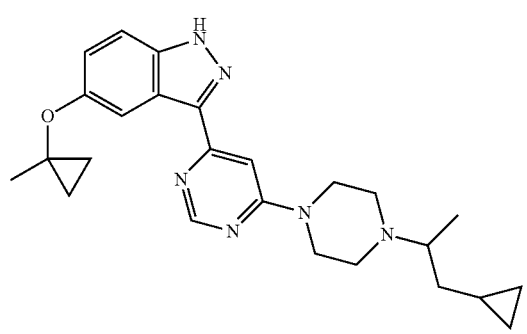
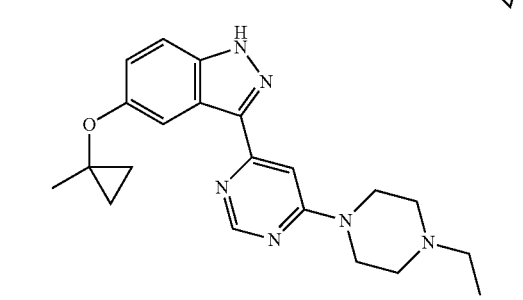
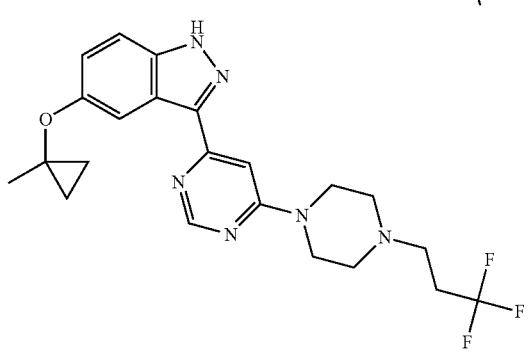
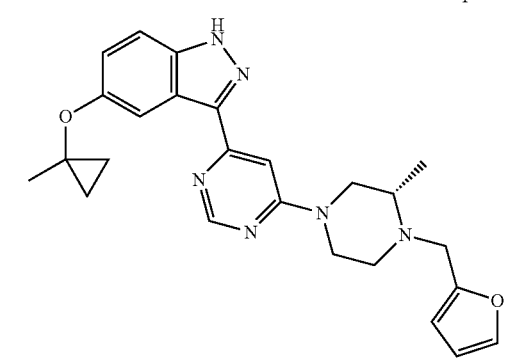
198
-continued
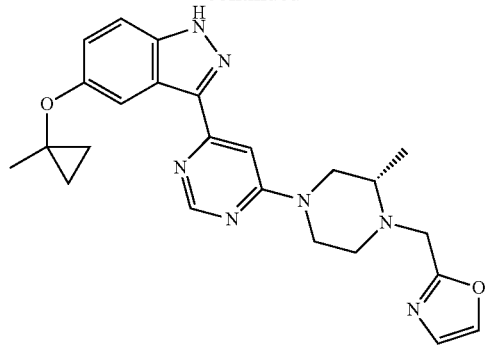
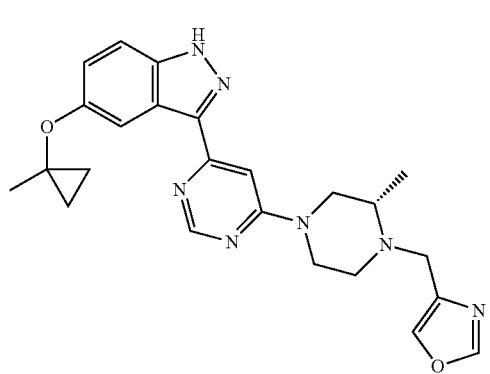
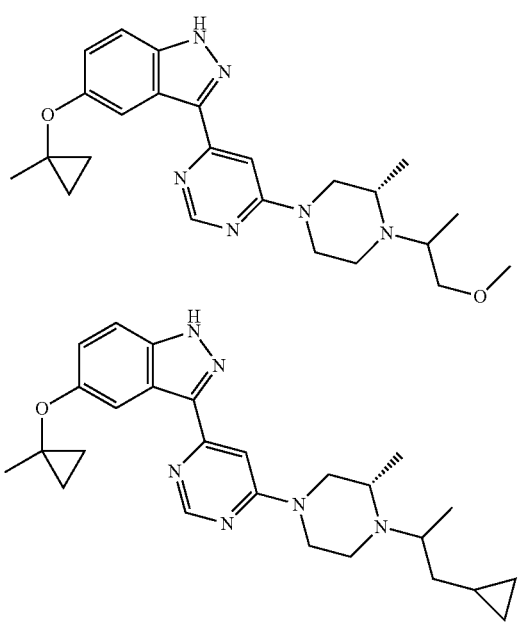
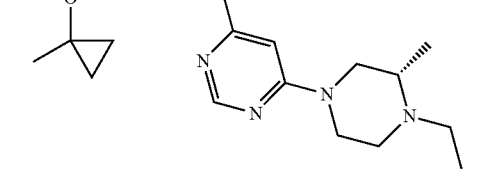

199
-continued
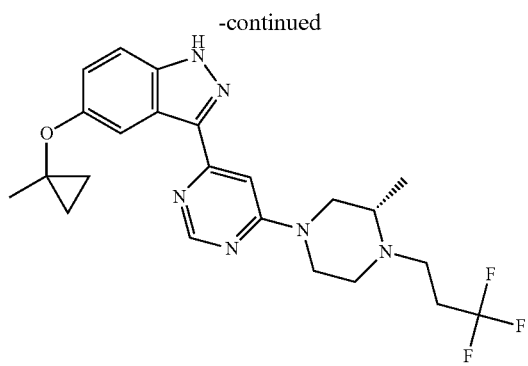
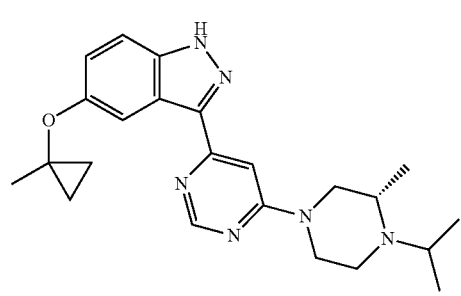
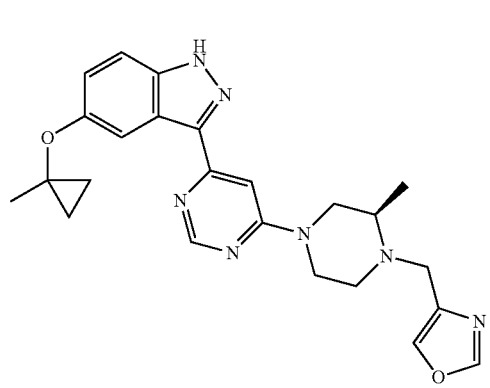
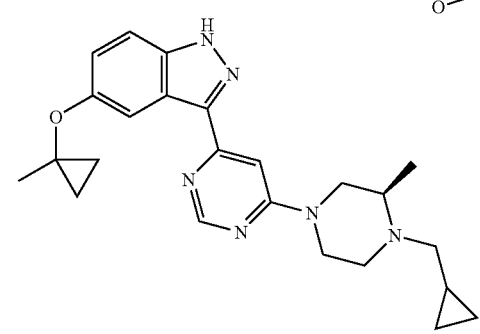
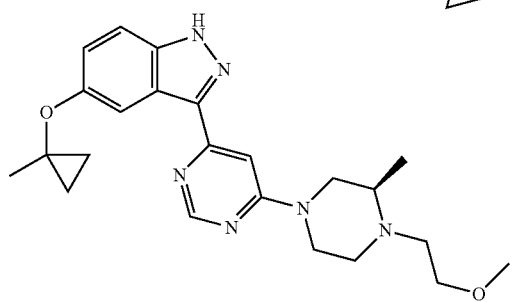
200
-continued
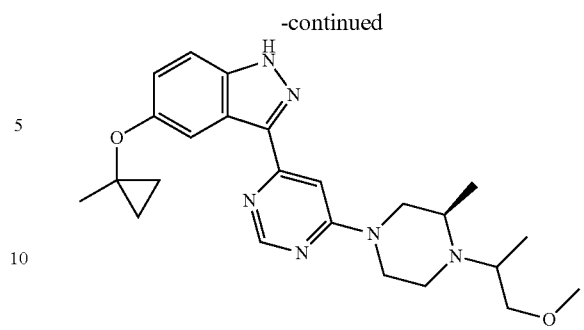
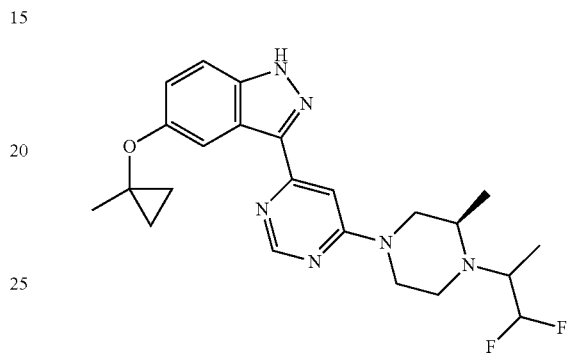
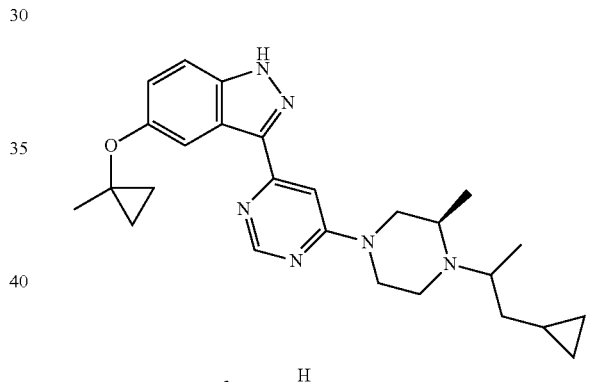
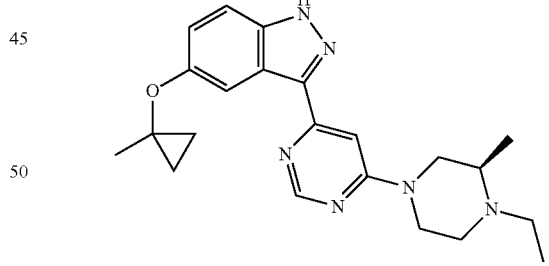
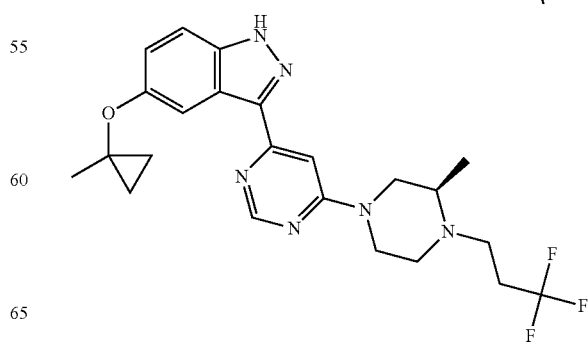

201
-continued
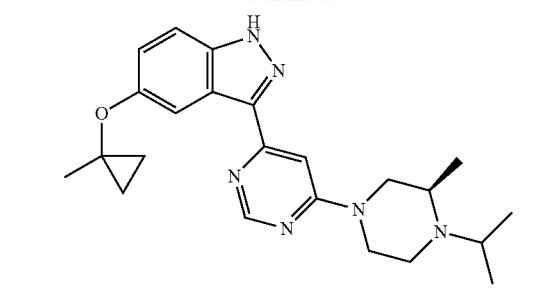
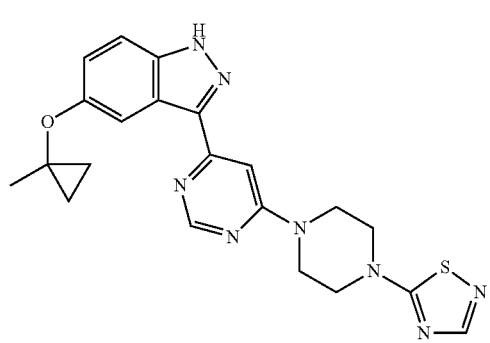
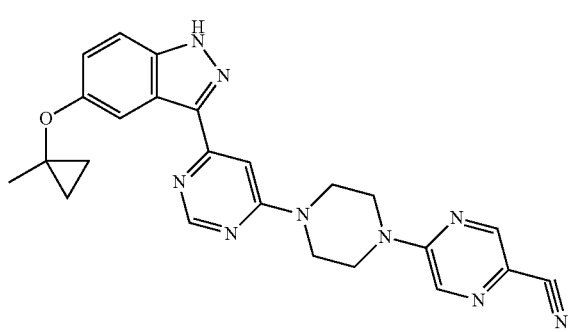
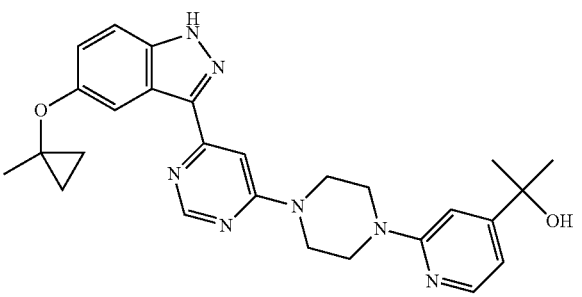
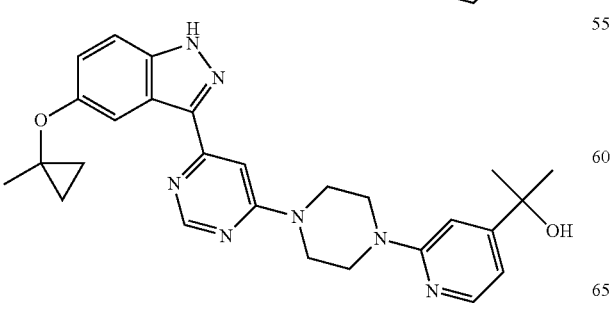
202
-continued
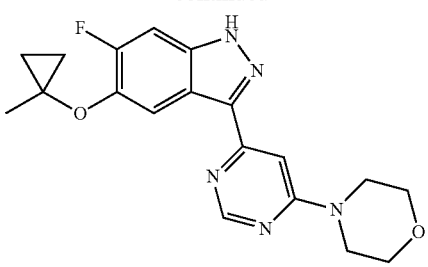
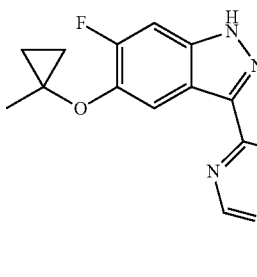
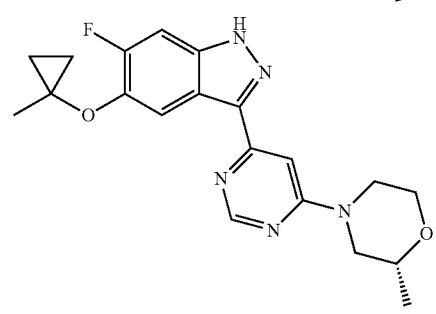
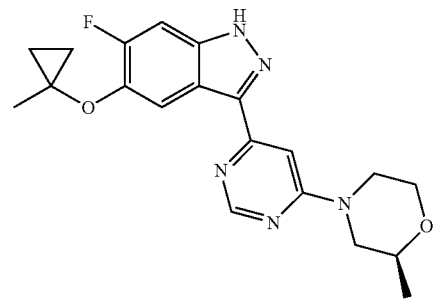
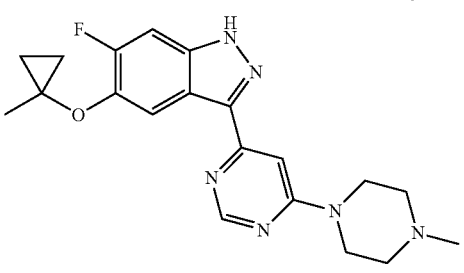
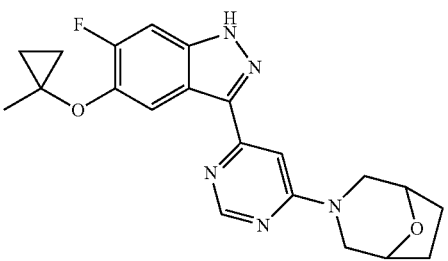

203
-continued
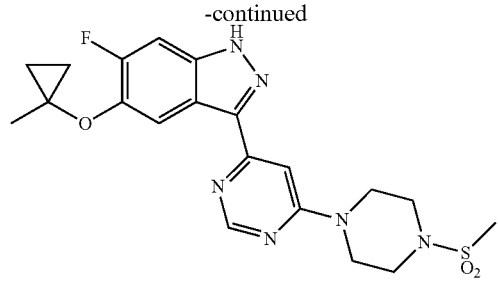
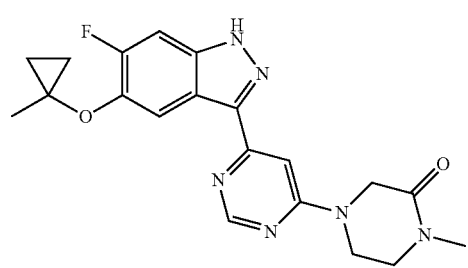
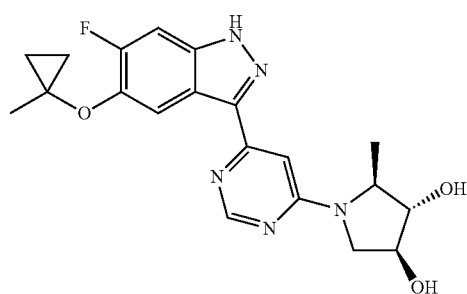
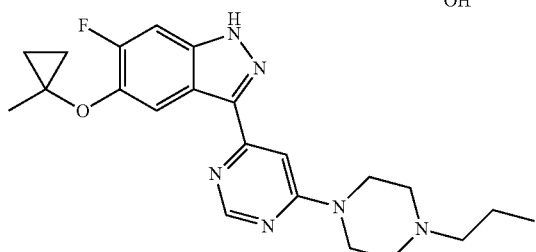
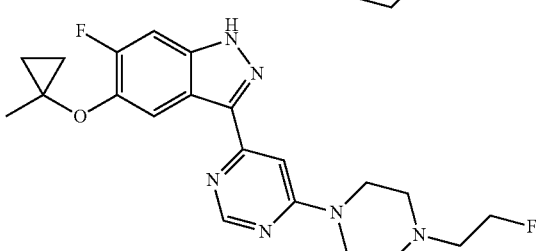
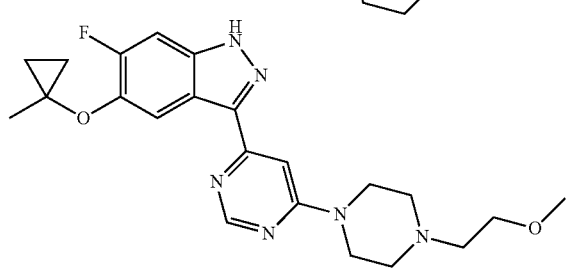
204
-continued
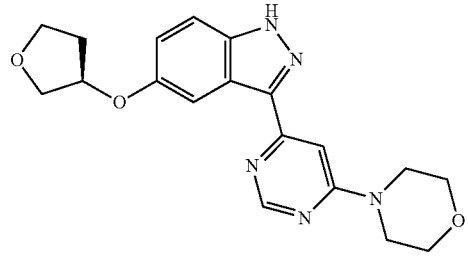
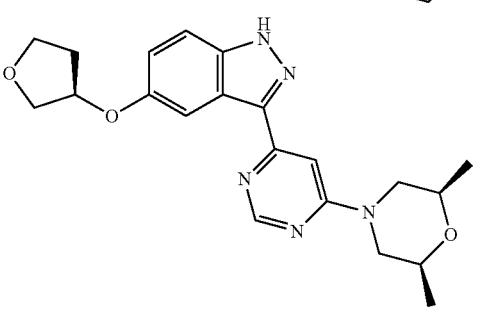
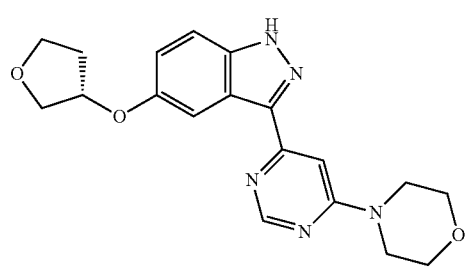
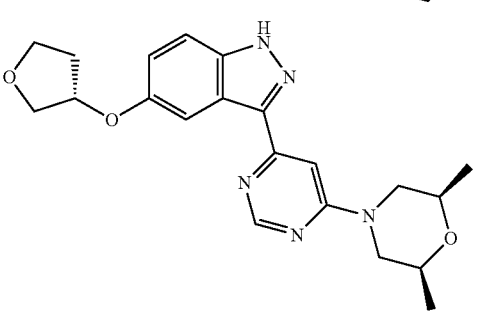
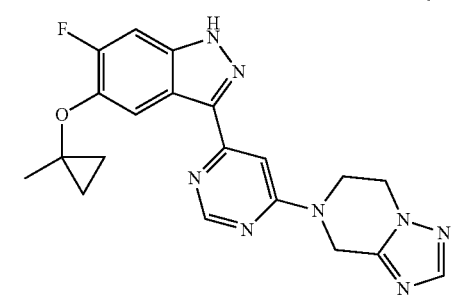
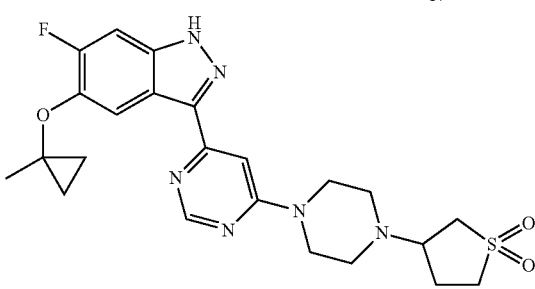

205
-continued
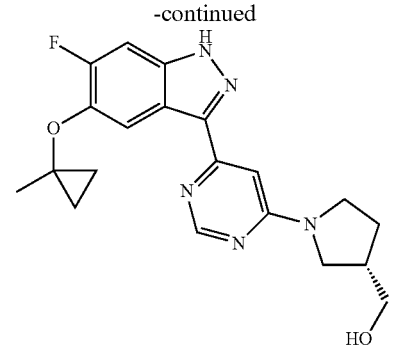
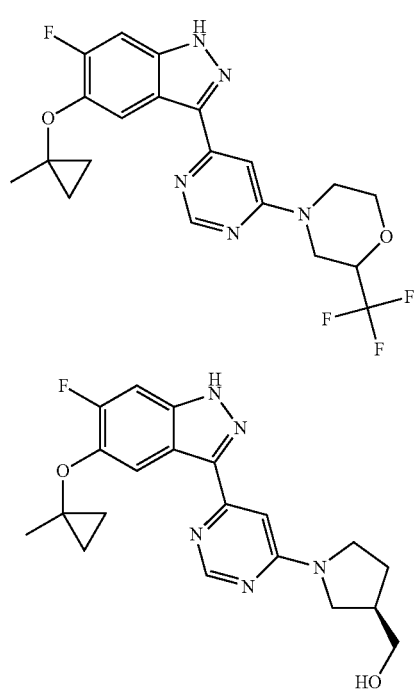
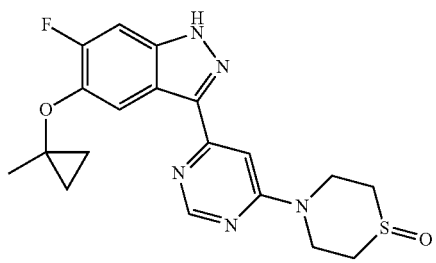
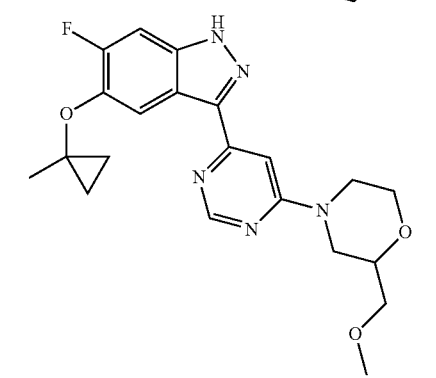
206
-continued
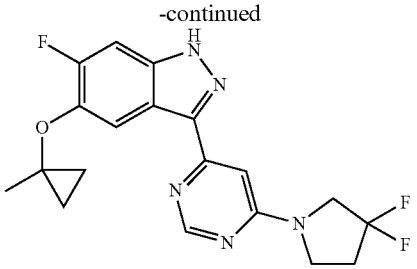
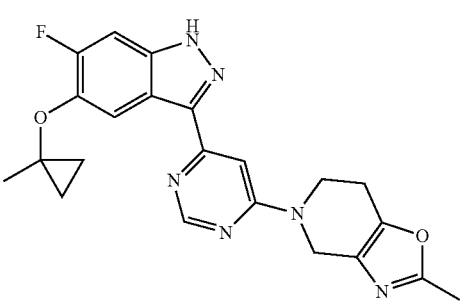
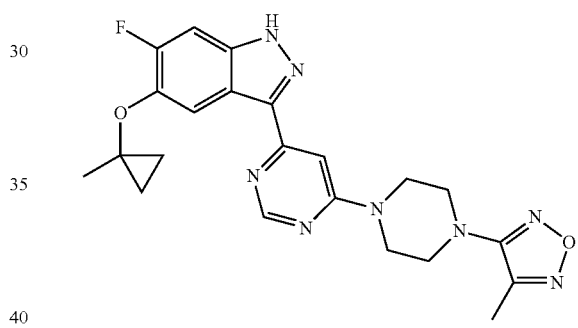
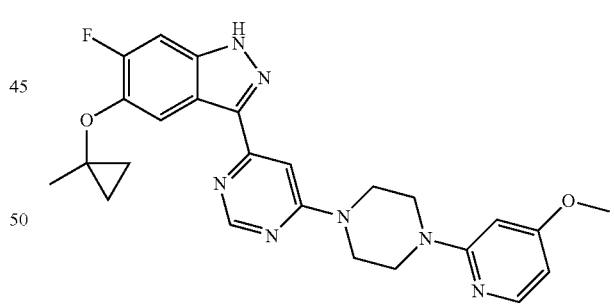
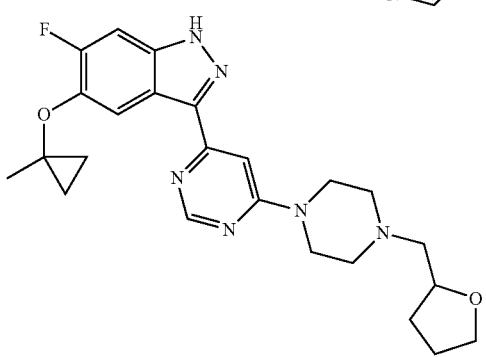

207
-continued
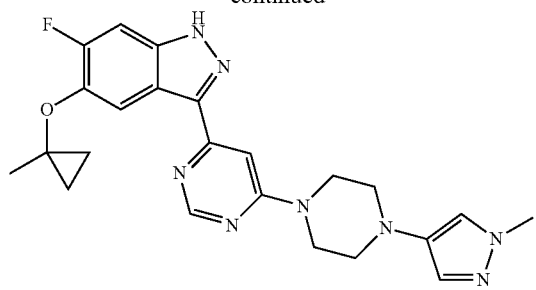
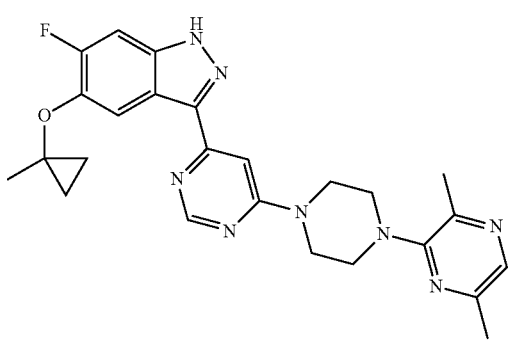
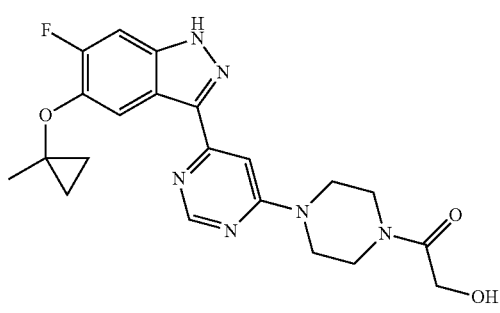
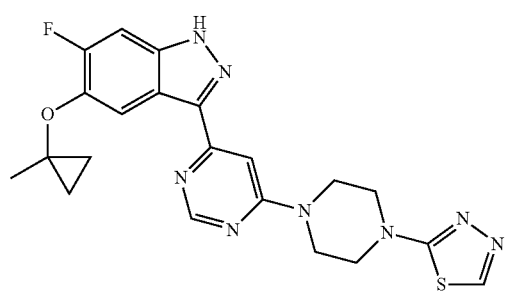
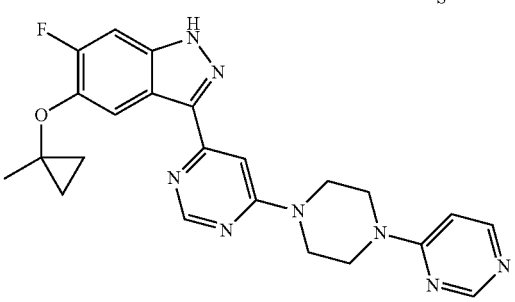
208
-continued
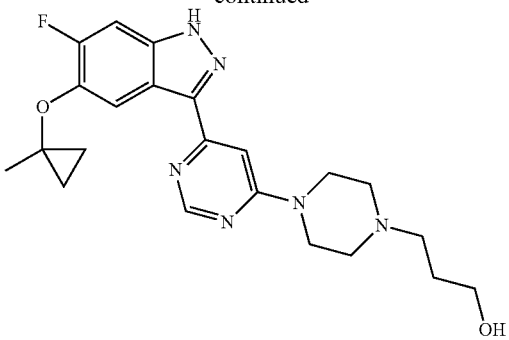
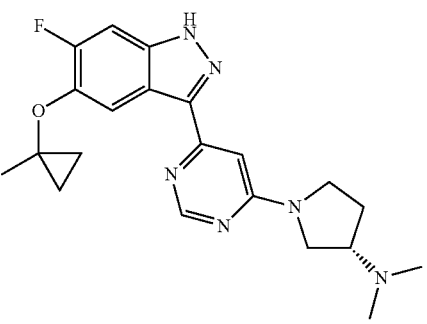
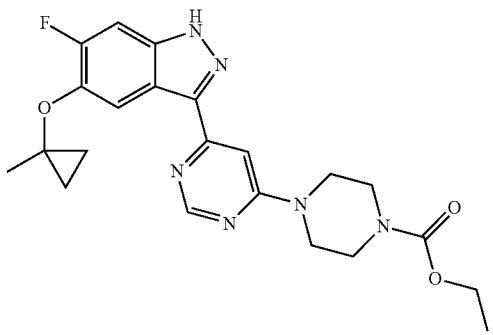
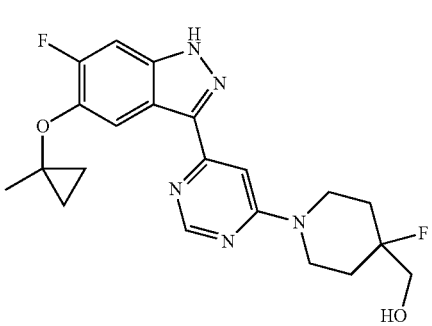
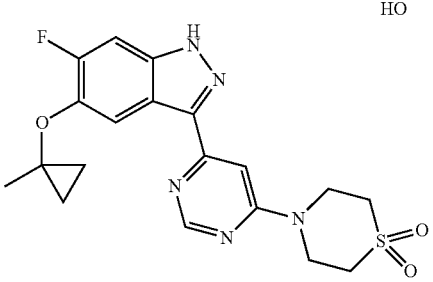

209
-continued
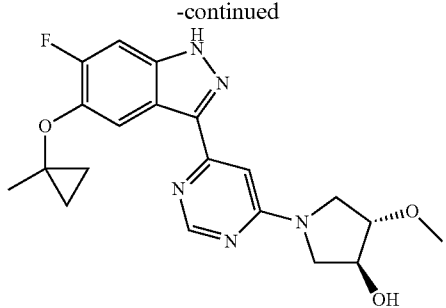
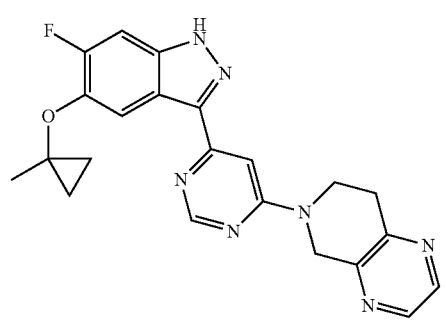
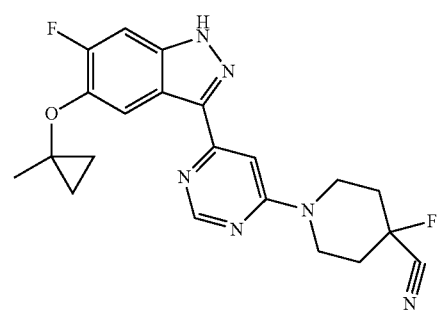
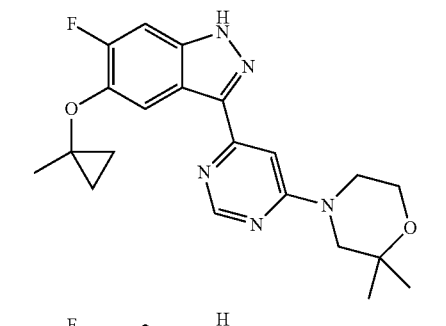
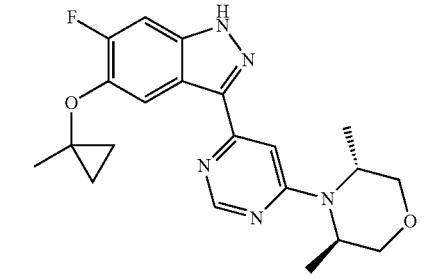
210
-continued
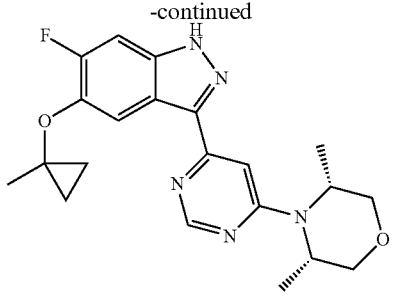
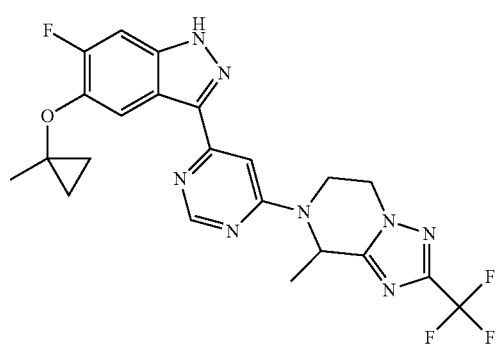
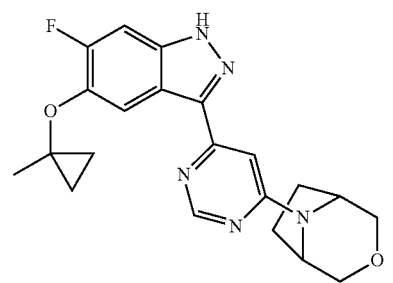
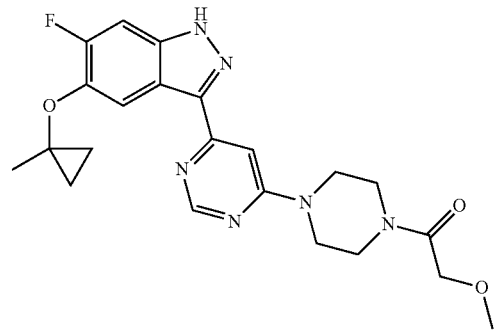
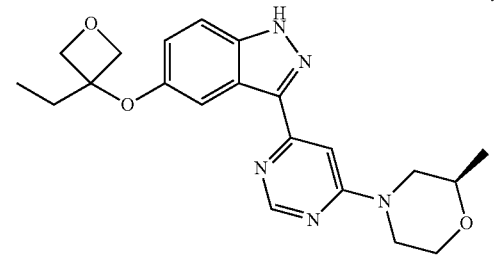

211
-continued
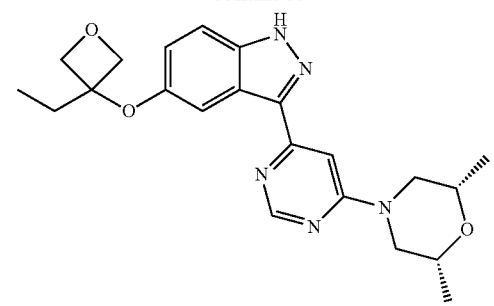
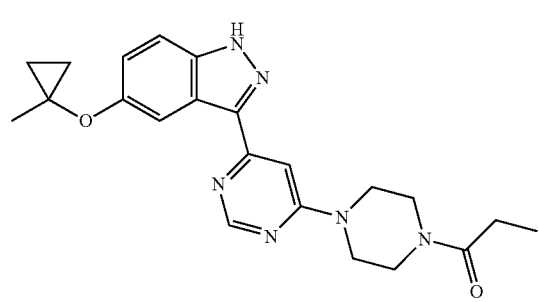
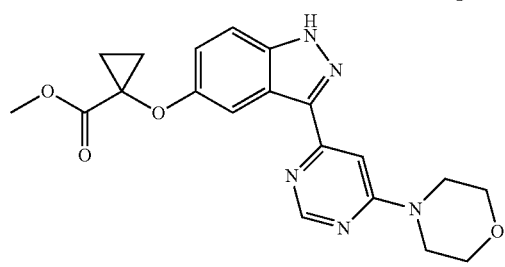
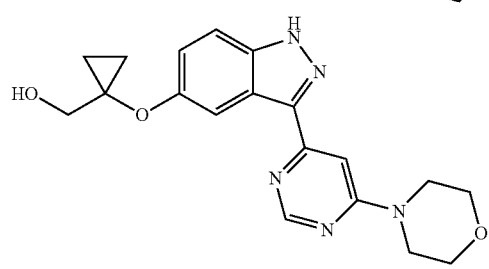
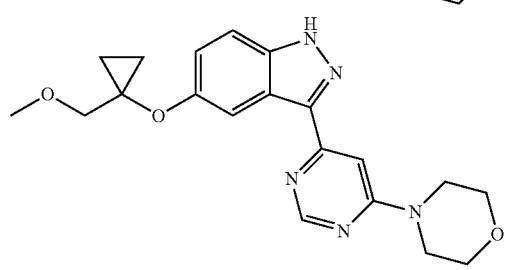
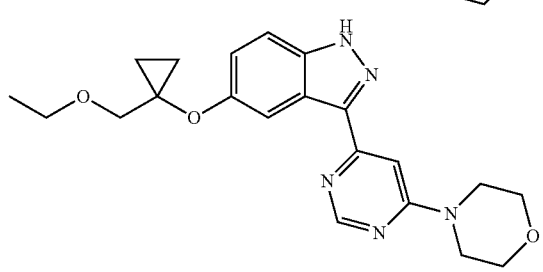
212
-continued
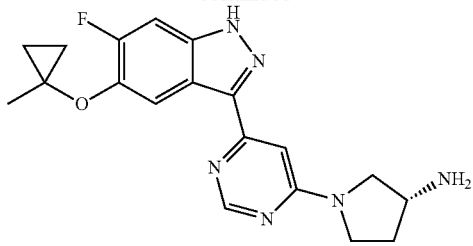
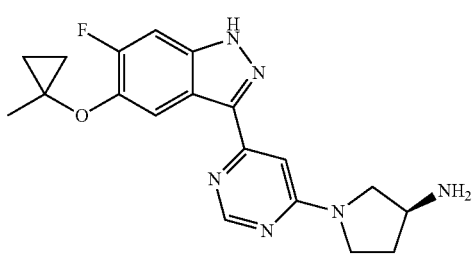
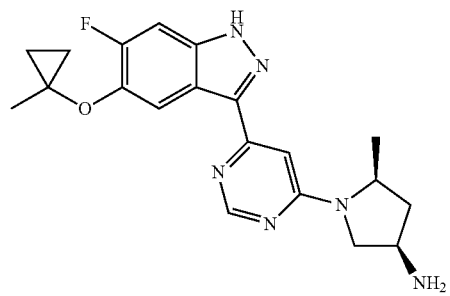
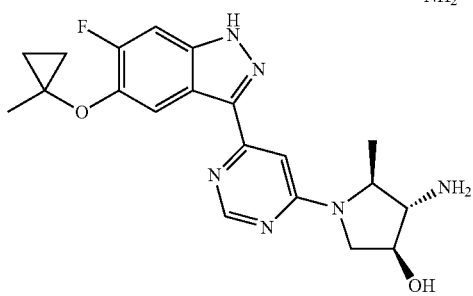
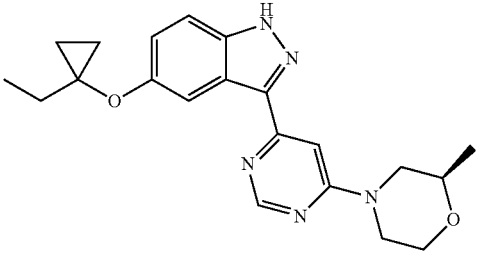
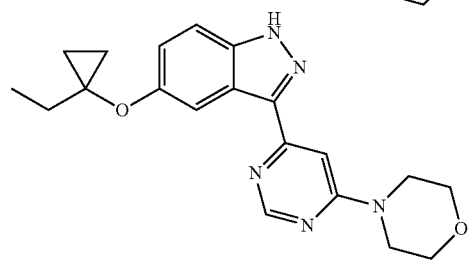

213
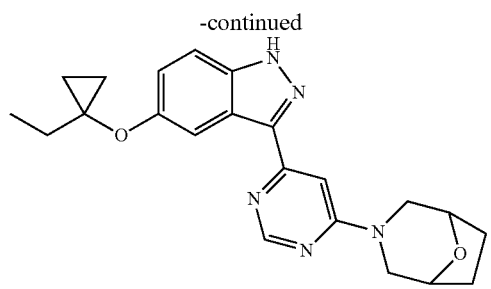
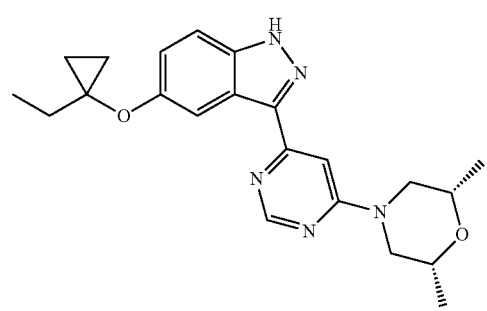
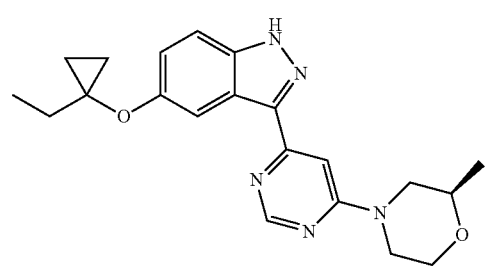
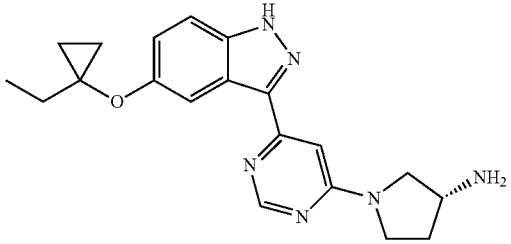
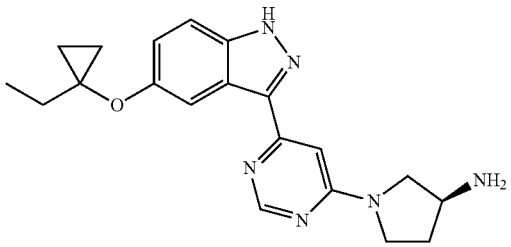
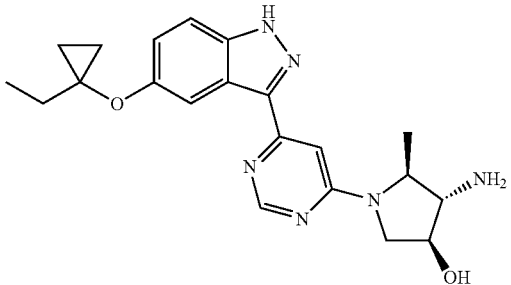
214
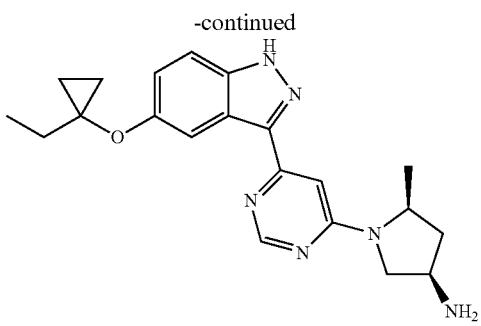
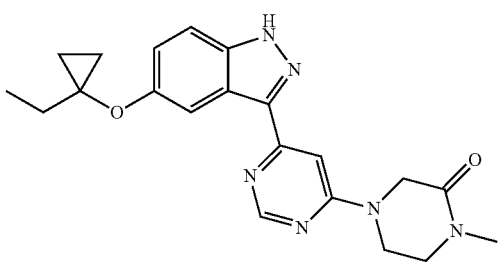
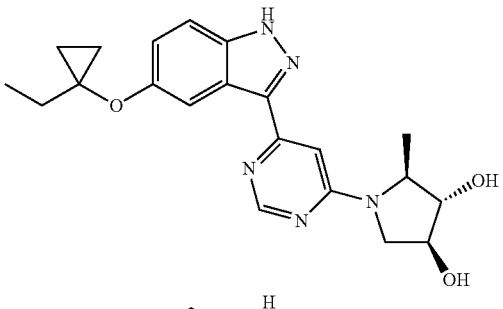
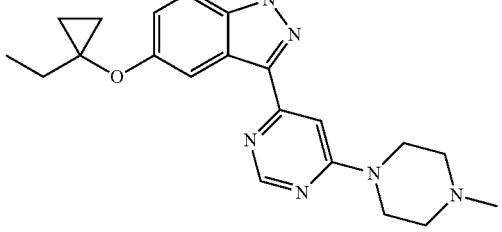
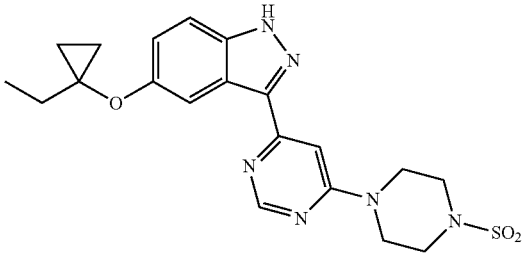
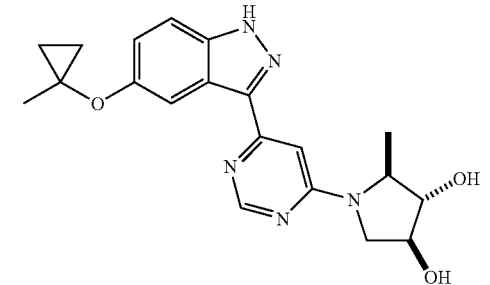

| 215 | 216 |
|---|---|
| -continued | -continued |
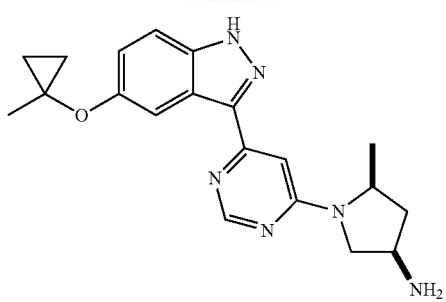
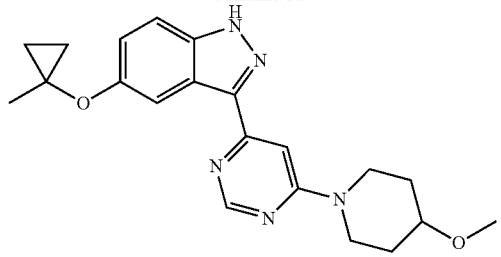
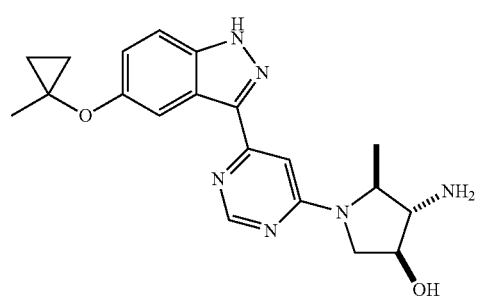
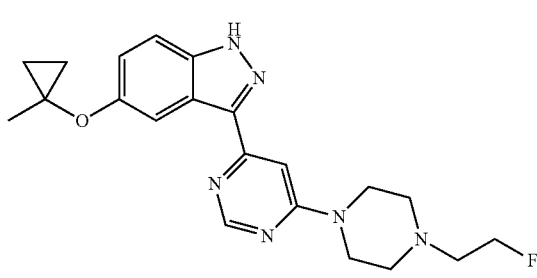
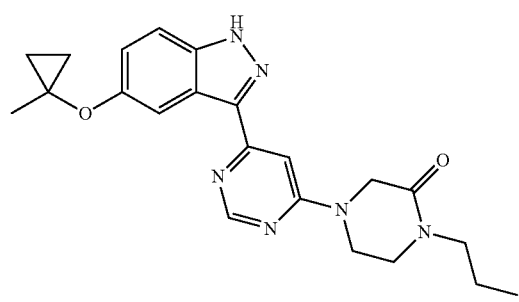
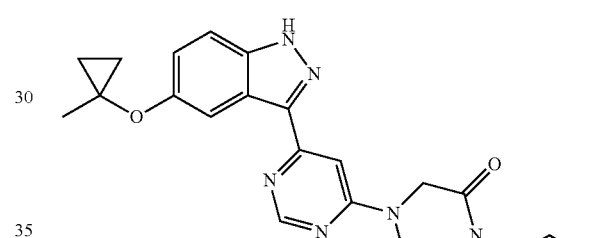
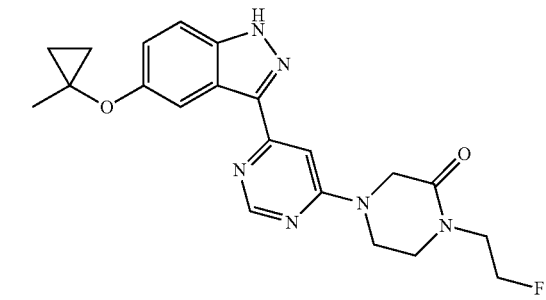
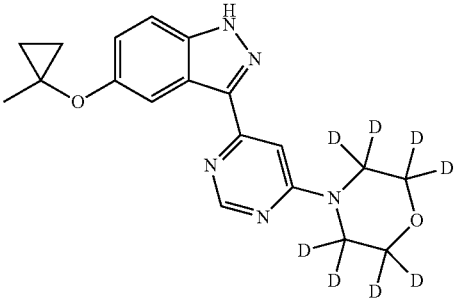
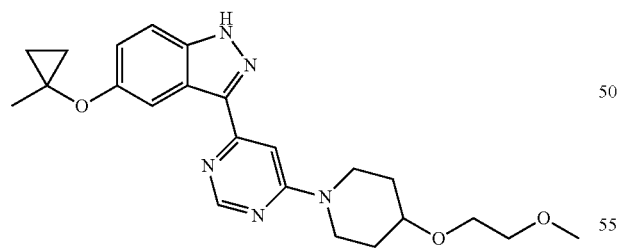
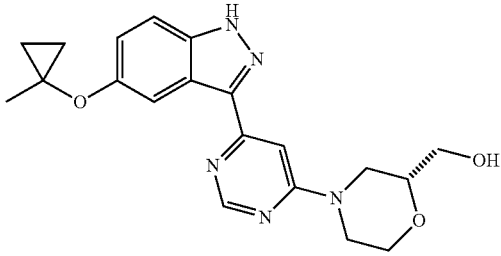
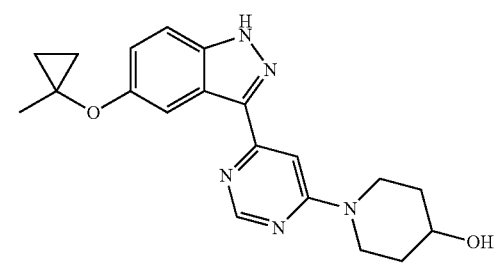
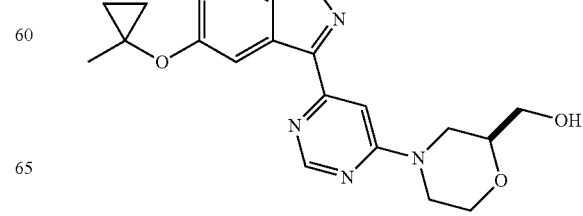

217
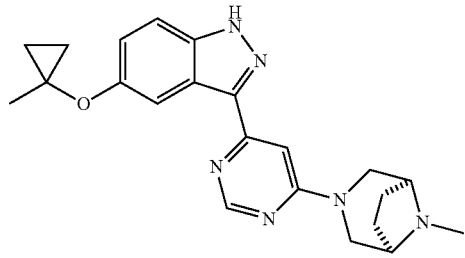
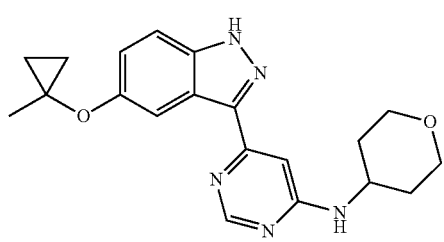 [SMILES: CC1(Oc2ccc3[nH]nc(-c4cc(NC5CCOCC5)ncn4)c3c2)CC1]
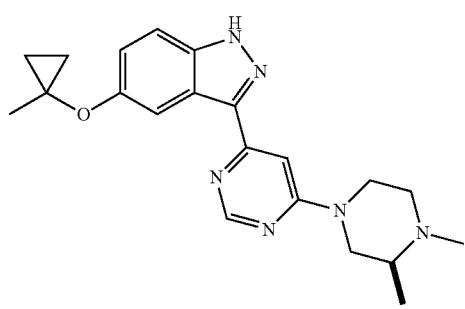
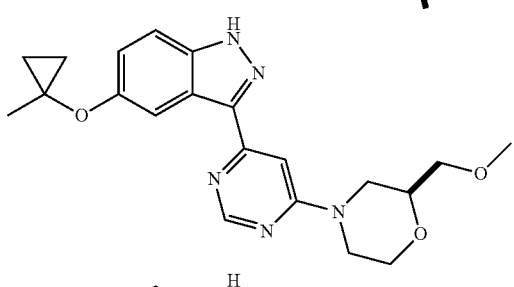
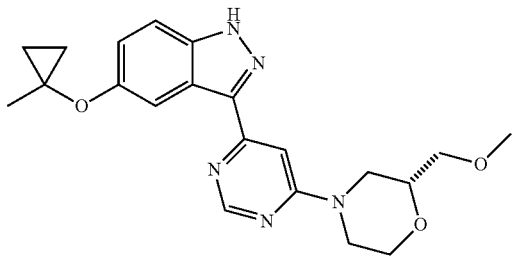
218
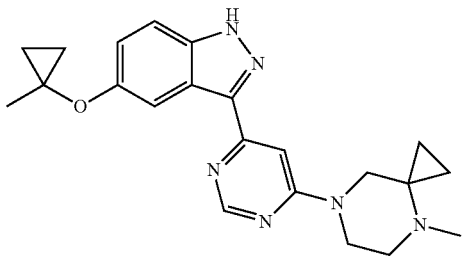
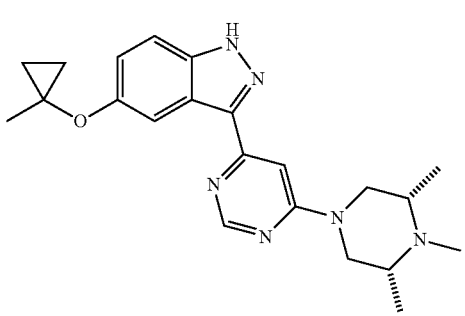
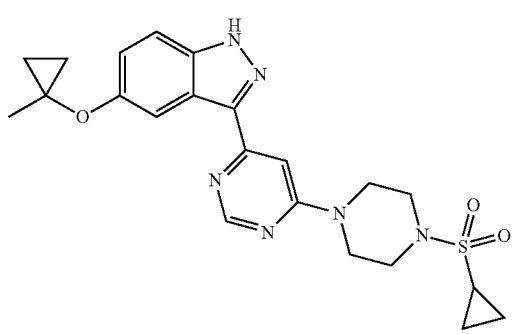
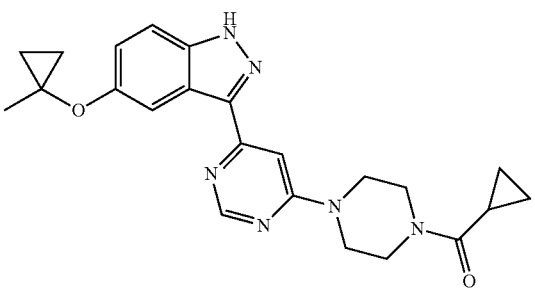
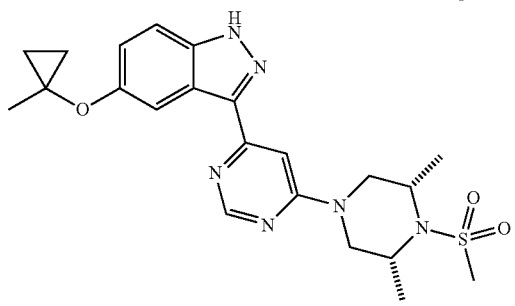

219
-continued
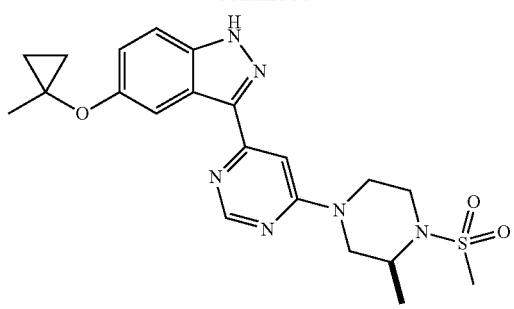 [SMILES: C[C@H]1CN(c2cc(-c3n[nH]c4ccc(OC5(C)CC5)cc34)ncn2)CCN1S(C)(=O)=O]
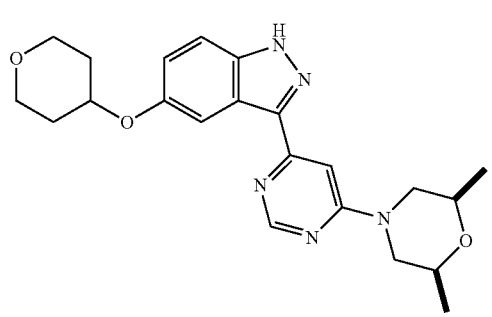
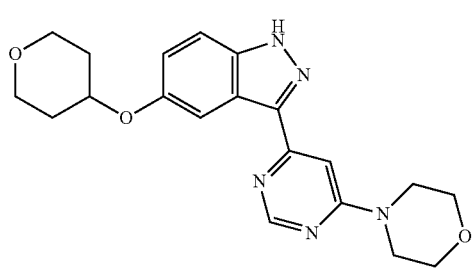 [SMILES: c1nc(-c2n[nH]c3ccc(OC4CCOCC4)cc23)cc(N2CCOCC2)n1]
or a pharmaceutically acceptable salt thereof.
9. The compound of claim 8 selected from
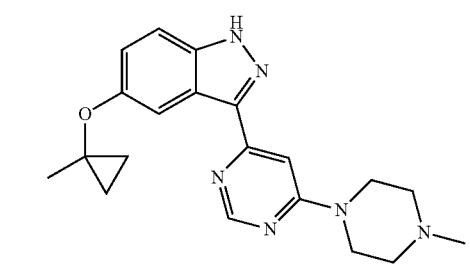
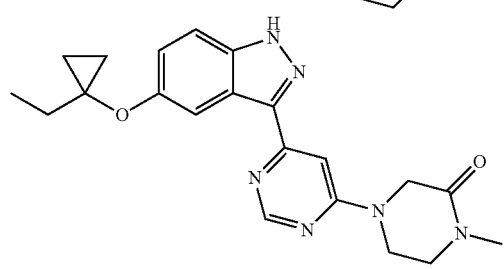
220
-continued
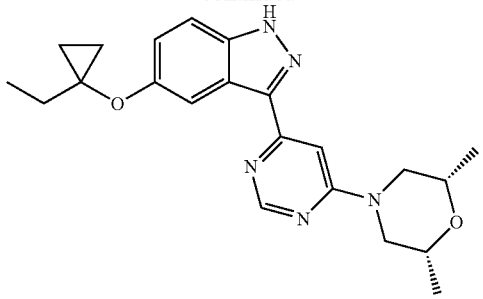

10. The compound of claim 9 selected from

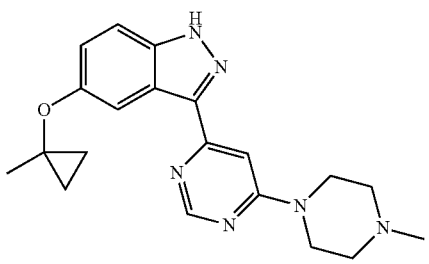

or a pharmaceutically acceptable salt thereof.

11. The compound of claim 9 selected from

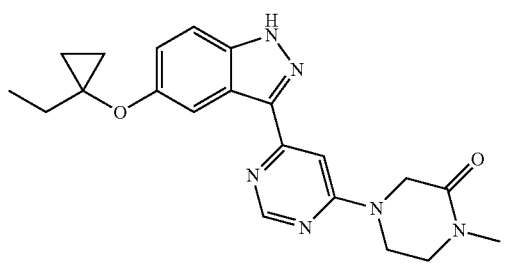 [SMILES: CCC1(Oc2ccc3[nH]nc(-c4cc(N5CCN(C)C(=O)C5)ncn4)c3c2)CC1]

or a pharmaceutically acceptable salt thereof.

12. The compound of claim 9 selected from

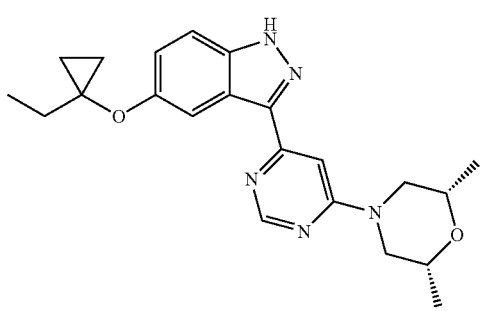 [SMILES: CCC1(Oc2ccc3[nH]nc(-c4cc(N5C[C@@H](C)O[C@@H](C)C5)ncn4)c3c2)CC1]

or a pharmaceutically acceptable salt thereof.

13. The compound of claim 9 selected from

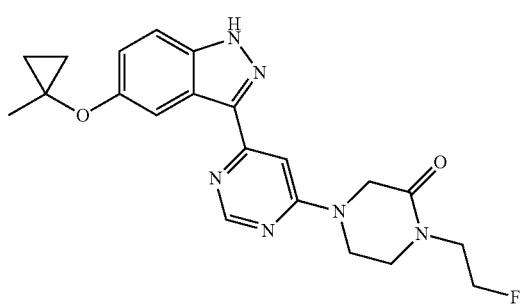 [SMILES: CC1(Oc2ccc3[nH]nc(-c4cc(N5CCN(CCF)C(=O)C5)ncn4)c3c2)CC1]

or a pharmaceutically acceptable salt thereof.

14. The compound of claim 9 selected from

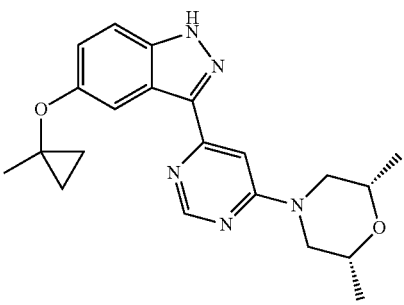

or a pharmaceutically acceptable salt thereof.

15. The compound of claim 9 selected from

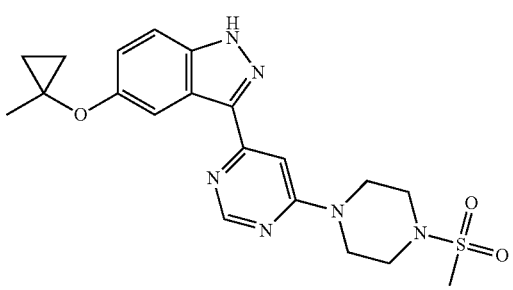 [SMILES: CC1(Oc2ccc3[nH]nc(-c4cc(N5CCN(S(C)(=O)=O)CC5)ncn4)c3c2)CC1]

or a pharmaceutically acceptable salt thereof.

16. The compound of claim 9 selected from

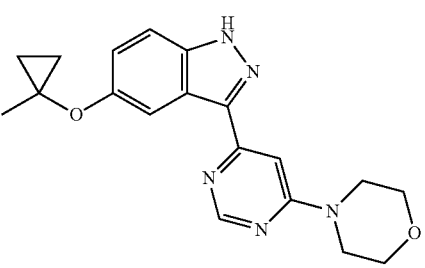 [SMILES: CC1(Oc2ccc3[nH]nc(-c4cc(N5CCOCC5)ncn4)c3c2)CC1]

or a pharmaceutically acceptable salt thereof.

17. The compound of claim 9 selected from

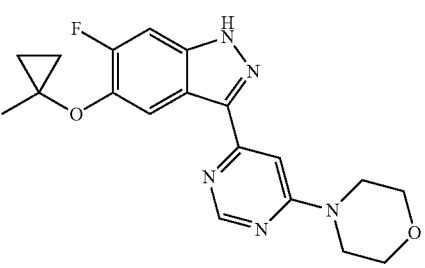 [SMILES: CC1(Oc2cc3c(-c4cc(N5CCOCC5)ncn4)n[nH]c3cc2F)CC1]

or a pharmaceutically acceptable salt thereof.

18. A pharmaceutical composition comprising a compound of claim 1, and a pharmaceutically acceptable carrier.

* * * * *

UNITED STATES PATENT AND TRADEMARK OFFICE
CERTIFICATE OF CORRECTION

PATENT NO. : 9,493,440 B2
APPLICATION NO. : 14/772295
DATED : November 15, 2016
INVENTOR(S) : Michael Miller et al.

It is certified that error appears in the above-identified patent and that said Letters Patent is hereby corrected as shown below:

On the Title Page

Under item (72) Inventors:
Replace: "Marc Poirer, Stewartsville, NJ (US);"
With: "Marc Poirier, Stewartsville, NJ (US);"

Signed and Sealed this
Fourteenth Day of March, 2017

Michelle K. Lee
*Director of the United States Patent and Trademark Office*